(12) United States Patent
Anderson et al.

(10) Patent No.: US 9,676,810 B2
(45) Date of Patent: Jun. 13, 2017

(54) NEUROPROTECTIVE MOLECULES AND METHODS OF TREATING NEUROLOGICAL DISORDERS AND INDUCING STRESS GRANULES

(75) Inventors: Paul Anderson, Belmont, MA (US);
Pavel Ivanov, Brighton, MA (US);
Mohammed Emara, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/808,863

(22) PCT Filed: Jul. 8, 2011

(86) PCT No.: PCT/US2011/043400
§ 371 (c)(1),
(2), (4) Date: Mar. 29, 2013

(87) PCT Pub. No.: WO2012/006551
PCT Pub. Date: Jan. 12, 2012

(65) Prior Publication Data
US 2013/0197067 A1      Aug. 1, 2013

Related U.S. Application Data

(60) Provisional application No. 61/362,526, filed on Jul. 8, 2010.

(51) Int. Cl.
*C07H 21/02* (2006.01)
*C12N 15/11* (2006.01)

(52) U.S. Cl.
CPC ............ *C07H 21/02* (2013.01); *C12N 15/11* (2013.01); *C12N 2310/18* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan | |
| 5,432,272 A | 7/1995 | Benner | |
| 6,043,060 A | 3/2000 | Imanishi | |
| 6,268,490 B1 | 7/2001 | Imanishi | |
| 8,173,616 B2 * | 5/2012 | Anderson et al. | 514/44 A |
| 2002/0115080 A1 | 8/2002 | Skouv | |
| 2002/0128381 A1 | 9/2002 | Jakobsen | |
| 2003/0092905 A1 | 5/2003 | Kochkine | |
| 2005/0085555 A1 | 4/2005 | Murphy et al. | |
| 2006/0134748 A1 * | 6/2006 | RajBhandary et al. | 435/69.1 |
| 2007/0203079 A1 | 8/2007 | Caldwell et al. | |
| 2008/0096191 A1 | 4/2008 | Kauppinen | |
| 2009/0023594 A1 | 1/2009 | Mouritzen | |
| 2009/0286753 A1 | 11/2009 | Kauppinen | |
| 2010/0035968 A1 | 2/2010 | Rasmussen | |
| 2010/0261175 A1 | 10/2010 | Rasmussen | |
| 2010/0267018 A1 | 10/2010 | Wengel | |
| 2010/0279895 A1 | 11/2010 | Wengel | |
| 2010/0286044 A1 | 11/2010 | Litman | |
| 2011/0046209 A1 | 2/2011 | Anderson | |
| 2011/0076675 A1 | 3/2011 | Jacobsen | |
| 2012/0263648 A1 * | 10/2012 | Shapiro et al. | 424/9.1 |

FOREIGN PATENT DOCUMENTS

WO    WO2009134443 A2 * 11/2009

OTHER PUBLICATIONS

Phizicky et al. Roles of tRNA Modifications in tRNA Turnover. In Grosjean H. Ed., DNA and RNA Modification Enzymes: Structure, Mechanism, Function and Evolution. 2009. pp. 564-576.*
(Grewal, Savraj s. Why Should Cancer Biologists Care About tRNAs? tRNA Synthesis, mRNA Translation and Control of Growth. Biochimica et Biophysica Acta, 2015. http://dx.doi.org/10.1016/j.bbagrm.2014.12.005. 10 pages).*
Junghee Lee et al., "Mitochondrial Nuclear Receptors and Transcription Factors; Who's Minding the Cell?," Journal of Neuroscience Research, vol. 86, pp. 961-971 (2008).
Yoshihiko Suzuki et al., "A Case of Diabetic Amyotrophy Associated with 3243 Mitochondrial tRNA (leu: UUR) Mutation and Successful Therapy with Coenzyme QIO," Endocrine Journal, vol. 42(2), pp. 141-145 (1995).
International Search Report and Written Opinion of the International Searching Authority, mailed Feb. 9, 201, in International Application No. PCT/US2011/043400, 12 pgs.
Bochkov et al., Translational efficiency of EMCV IRES in bicistronic vectors is dependent upon IRES sequence and gene location, BioTechniques, vol. 41, pp. 283-284, 286, 288, and 290, 2006.
Buchan et al., Eukaryotic Stress Granules: The Ins and Out of Translation Mol., Cell vol. 36 No. 6, pp. 932, 2009.
De Gregorio et al., Translational activation of uncapped mRNAs by the central part of human eIF4G is 5' end-dependent, RNA, vol. 4, pp. 828-836, 1998.

(Continued)

*Primary Examiner* — Christopher M Babic
*Assistant Examiner* — Kimberly A Aron
(74) *Attorney, Agent, or Firm* — Fish & Richardson P.C.

(57) ABSTRACT

Provided herein are neuroprotective molecules containing a sequence of 25-35 contiguous nucleotides that is at least 80% identical to a contiguous sequence between nucleotide 1 and nucleotide 50 of a mature human tRNA and at least four contiguous guanosine-containing nucleotides, where the sequence of 25-35 contiguous nucleotides contains a D-loop stem structure, the at least four contiguous guanosine-containing nucleotides are located at the 5' end of the neuroprotective molecule, and the neuroprotective molecule contains at least one deoxyribonucleotide. Also provided are methods of inducing or increasing stress granule formation in a cell, decreasing protein translation in a cell, decreasing stress-induced cell death, or treating a neurological disorder associated with neuron death in a subject using at least one of these neuroprotective molecules.

12 Claims, 17 Drawing Sheets

(56) References Cited

OTHER PUBLICATIONS

Emara et al., Angiogenin-induced tRNA-derived Stress-induced RNAs Promote Stress-induced Stress Granule Assembly, J. Biol. Chem., vol. 285, pp. 10959-10968, 2010.
Freier et al., The ups and downs of nucleic acid duplex stability: structure-stability studies on chemically-modified DNA:RNA duplexes, Nucleic Acid Res. 25: No. 22, pp. 4429-4443, 1997.
International Preliminary Report on Patentability for PCT/US/2011/043400 dated Jan. 8, 2013, 7 pages.
Kaminski et al., Translation of encephalomyocarditis virus RNA: parameters influencing the selection of the internal initiation site, EMBO J., vol. 13, pp. 1673-1681, 1998.
Kedersha et al., Real-time and quantitative imaging of mammalian stress granules and processing bodies, Methods Enzymol. vol. 448, pp. 521-552, 2008 (Abstract).
Yamasaki et al., Angiogenin cleaves tRNA and promotes stress-induced translational repression, J Cell Biol., vol. 185, No. 1, pp. 35-42, 2009.
Darby and Joho, "Differential Binding of Zinc Fingers from Xenopus TFIIIA and p43 to 5S RNA and the 5S RNA Gene," Mollecular and Cellular Biology, Jul. 1992, 12(7): 3155-3164.

* cited by examiner (SEQ ID NO: 37)

G-rich ODNs

* 5'Ala tiDNA
    GGGGGTGTAGCTCAGTGGTAGAGCGCGTGC (SEQ ID NO: 32)
* Tel4
    TTAGGGTTAGGGTTAGGGTTAGGG (SEQ ID NO: 33)
* AS1411
    GGTGGTGGTGGTTGTGGTGGTGGTGG (SEQ ID NO: 34)
* GT-oligo
    TGTTTGTTTGTTTGTTTGTTTGTTTGT (SEQ ID NO: 35)
* C-myc-oligo
    GGGGAGGGTGGGGAGGGTGGGG (SEQ ID NO: 36)

SEQUENCE LISTING

<160> NUMBER OF SEQ ID NOS: 796

<210> SEQ ID NO 1
<211> LENGTH: 30
<212> TYPE: RNA
<213> ORGANISM: Artificial Sequence
<220> FEATURE:
<223> OTHER INFORMATION: Description of Artificial Sequence: Synthetic
      Ctrl1 tiRNA oligonucleotide

<400> SEQUENCE: 1
ugaaggguuu uuugugucuc uauuuccuuc                                           30

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      Ctrl2 tiRNA oligonucleotide

<400> SEQUENCE: 2
ugugagucac gugagggcag aaucugcuc                                            29

<210> SEQ ID NO 3
<211> LENGTH: 31
<212> TYPE: RNA
<213> ORGANISM: Artificial Sequence
<220> FEATURE:
<223> OTHER INFORMATION: Description of Artificial Sequence: Synthetic
      Ctrl3 tiRNA oligonucleotide

<400> SEQUENCE: 3
gcauucacuu ggauaguaaa uccaagcuga a                                         31

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence: Synthetic
    5' Ala tiRNA oligonucleotide

<400> SEQUENCE: 4
ggggguguag cucaguggua gagcgcgugc                                30

<210> SEQ ID NO 5
<211> LENGTH: 32
<212> TYPE: RNA
<213> ORGANISM: Artificial Sequence
<220> FEATURE:
<223> OTHER INFORMATION: Description of Artificial Sequence: Synthetic
    5' Val tiRNA oligonucleotide

<400> SEQUENCE: 5
guuuccguag uguagugguu aucacguucg cc                             32

<210> SEQ ID NO 6
<211> LENGTH: 30
<212> TYPE: RNA
<213> ORGANISM: Artificial Sequence
<220> FEATURE:
<223> OTHER INFORMATION: Description of Artificial Sequence: Synthetic
    5'-Gly-GCC tiRNA oligonucleotide

<400> SEQUENCE: 6
gcaugggugg uucaguggua gaauucucgc                                30

<210> SEQ ID NO 7
<211> LENGTH: 31
<212> TYPE: RNA
<213> ORGANISM: Artificial Sequence
<220> FEATURE:
<223> OTHER INFORMATION: Description of Artificial Sequence: Synthetic
    5'-GlyCCC tiRNA oligonucleotide

<400> SEQUENCE: 7
gcgccgcugg uguagugguu ucaugcaaga u                              31

<210> SEQ ID NO 8
<211> LENGTH: 30
<212> TYPE: RNA
<213> ORGANISM: Artificial Sequence
<220> FEATURE:
<223> OTHER INFORMATION: Description of Artificial Sequence: Synthetic
    5'-Pro tiRNA oligonucleotide

<400> SEQUENCE: 8
ggcucguugg ucuagggua ugauucucgg                                 30

<210> SEQ ID NO 9
<211> LENGTH: 29
<212> TYPE: RNA
<213> ORGANISM: Artificial Sequence
<220> FEATURE:
<223> OTHER INFORMATION: Description of Artificial Sequence: Synthetic
    5'-Gln tiRNA oligonucleotide

<400> SEQUENCE: 9
gguuccaugg uguaaugguu agcacucug                                 29

<210> SEQ ID NO 10
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Cys tiRNA oligonucleotide

<400> SEQUENCE: 10
ggggguauag cucaguggua gagcauuuga                                    30

<210> SEQ ID NO 11
<211> LENGTH: 31
<212> TYPE: RNA
<213> ORGANISM: Artificial Sequence
<220> FEATURE:
<223> OTHER INFORMATION: Description of Artificial Sequence: Synthetic
      5'-Met tiRNA oligonucleotide

<400> SEQUENCE: 11
gccucguuag cgcaguaggu agcgcgucag u                                  31

<210> SEQ ID NO 12
<211> LENGTH: 29
<212> TYPE: RNA
<213> ORGANISM: Artificial Sequence
<220> FEATURE:
<223> OTHER INFORMATION: Description of Artificial Sequence: Synthetic
      5'-Met-I tiRNA oligonucleotide

<400> SEQUENCE: 12
agcagagugg cgcagcggaa gcgugcugg                                     29

<210> SEQ ID NO 13
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Ala oligonucleotide

<400> SEQUENCE: 13
cuuagcaugc acgaggcccc ggguucaauc cccggcaccu cca                     43

<210> SEQ ID NO 14
<211> LENGTH: 38
<212> TYPE: RNA
<213> ORGANISM: Artificial Sequence
<220> FEATURE:
<223> OTHER INFORMATION: Description of Artificial Sequence: Synthetic
      3'-Arg tiRNA oligonucleotide

<400> SEQUENCE: 14
ggaucagaag auugagggu cgggucccuu cguggucg                            38

<210> SEQ ID NO 15
<211> LENGTH: 38
<212> TYPE: RNA
<213> ORGANISM: Artificial Sequence
<220> FEATURE:
<223> OTHER INFORMATION: Description of Artificial Sequence: Synthetic
      3'-Gly tiRNA oligonucleotide

<400> SEQUENCE: 15
ccacgcggga ggcccggguu cgauucccgg ccaaugca                           38

-continued

```
<210> SEQ ID NO 16
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Gln tiRNA oligonucleotide

<400> SEQUENCE: 16
gacucugaau ccagcgaucc gaguucaaau cucgguggaa ccu                    43

<210> SEQ ID NO 17
<211> LENGTH: 42
<212> TYPE: RNA
<213> ORGANISM: Artificial Sequence
<220> FEATURE:
<223> OTHER INFORMATION: Description of Artificial Sequence: Synthetic
      3'-Pro tiRNA oligonucleotide

<400> SEQUENCE: 17
uuaggaugcg agagguccecg gguucaaauc ccggacgagc cc                     42

<210> SEQ ID NO 18
<211> LENGTH: 30
<212> TYPE: RNA
<213> ORGANISM: Artificial Sequence
<220> FEATURE:
<223> OTHER INFORMATION: Description of Artificial Sequence: Synthetic
      U4G tiRNA oligonucleotide

<400> SEQUENCE: 18 uggggguguag cucagugguua gagcgcgugc                                  30

<210> SEQ ID NO 19
<211> LENGTH: 29
<212> TYPE: RNA
<213> ORGANISM: Artificial Sequence
<220> FEATURE:
<223> OTHER INFORMATION: Description of Artificial Sequence: Synthetic
      4G tiRNA oligonucleotide

<400> SEQUENCE: 19 ggggguguagc ucagugguag agcgcgugc                                    29

<210> SEQ ID NO 20
<211> LENGTH: 30
<212> TYPE: RNA
<213> ORGANISM: Artificial Sequence
<220> FEATURE:
<223> OTHER INFORMATION: Description of Artificial Sequence: Synthetic
      UU3G tiRNA oligonucleotide

<400> SEQUENCE: 20
uuggguguag cucagugguua gagcgcgugc                                   30

<210> SEQ ID NO 21
<211> LENGTH: 28
<212> TYPE: RNA
<213> ORGANISM: Artificial Sequence
<220> FEATURE:
<223> OTHER INFORMATION: Description of Artificial Sequence: Synthetic
      3G tiRNA oligonucleotide

<400> SEQUENCE: 21
ggguguagcu cagugguaga gcgcgugc                                      28

<210> SEQ ID NO 22
```

```
<211> LENGTH: 30
<212> TYPE: RNA
<213> ORGANISM: Artificial Sequence
<220> FEATURE:
<223> OTHER INFORMATION: Description of Artificial Sequence: Synthetic
      GG-UU tiRNA oligonucleotide

<400> SEQUENCE: 22 gggggugugag cucaguuuua gagcgcgugc                                            30

<210> SEQ ID NO 23
<211> LENGTH: 27
<212> TYPE: RNA
<213> ORGANISM: Artificial Sequence
<220> FEATURE:
<223> OTHER INFORMATION: Description of Artificial Sequence: Synthetic
      27-mer tiRNA oligonucleotide

<400> SEQUENCE: 23 gggggugugag cucaguggua gagcgcg                                               27

<210> SEQ ID NO 24
<211> LENGTH: 24
<212> TYPE: RNA
<213> ORGANISM: Artificial Sequence
<220> FEATURE:
<223> OTHER INFORMATION: Description of Artificial Sequence: Synthetic
      24-mer tiRNA oligonucleotide

<400> SEQUENCE: 24 gggggugugag cucaguggua gagc                                                  24

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      21-mer tiRNA oligonucleotide

<400> SEQUENCE: 25 gggggugugag cucaguggua g                                                     21

<210> SEQ ID NO 26
<211> LENGTH: 31
<212> TYPE: RNA
<213> ORGANISM: Artificial Sequence
<220> FEATURE:
<223> OTHER INFORMATION: Description of Artificial Sequence: Synthetic
      Modified 5'-tiRNAMet oligonucleotide

<400> SEQUENCE: 26 gggggguuuag cgcaguaggu agcgcgucag u                                          31

<210> SEQ ID NO 27
<211> LENGTH: 30
<212> TYPE: RNA
<213> ORGANISM: Artificial Sequence
<220> FEATURE:
<223> OTHER INFORMATION: Description of Artificial Sequence: Synthetic
      Ctrl1-biotinylated tiRNA oligonucleotide
<220> FEATURE:
<223> OTHER INFORMATION: 3' Biotin

<400> SEQUENCE: 27
ugaaggguuu uuguguccuc uauuuccuuc                                             30
```

<210> SEQ ID NO 28
<211> LENGTH: 29
<212> TYPE: RNA
<213> ORGANISM: Artificial Sequence
<220> FEATURE:
<223> OTHER INFORMATION: Description of Artificial Sequence: Synthetic
      Ctrl2-biotinylated tiRNA oligonucleotide
<220> FEATURE:
<223> OTHER INFORMATION: 3' Biotin

<400> SEQUENCE: 28
ugugagucac gugagggcag aaucugcuc                                    29

<210> SEQ ID NO 29
<211> LENGTH: 31
<212> TYPE: RNA
<213> ORGANISM: Artificial Sequence
<220> FEATURE:
<223> OTHER INFORMATION: Description of Artificial Sequence: Synthetic
      Ctrl3-biotinylated tiRNA oligonucleotide
<220> FEATURE:
<223> OTHER INFORMATION: 3' Biotin

<400> SEQUENCE: 29
gcauucacuu ggauaguaaa uccaagcuga a                                 31

<210> SEQ ID NO 30
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Ala-biotinylated tiRNA oligonucleotide
<220> FEATURE:
<223> OTHER INFORMATION: 3' Biotin

<400> SEQUENCE: 30 gggggguguag cucaguggua gagcgcgugc                                  30

<210> SEQ ID NO 31
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Ala-biotinylated tiRNA oligonucleotide
<220> FEATURE:
<223> OTHER INFORMATION: 3' Biotin

<400> SEQUENCE: 31
cuuagcaugc acgaggcccc ggguucaauc cccggcaccu cca                    43

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      5'-Ala tiDNA oligonucleotide

<400> SEQUENCE: 32
gggggtgtag ctcagtggta gagcgcgtgc                                   30

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic

```
                    Tel4 oligonucleotide

<400> SEQUENCE: 33
ttagggttag ggttagggtt aggg                                           24

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      AS1411 oligonucleotide

<400> SEQUENCE: 34
ggtggtggtg gttgtggtgg tggtgg                                         26

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      GT-oligonucleotide

<400> SEQUENCE: 35
tgtttgtttg tttgtttgtt tgtttgt                                        27

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      C-myc oligonucleotide

<400> SEQUENCE: 36
ggggagggtg gggagggtgg gg                                             22

<210> SEQ ID NO 37
<211> LENGTH: 75
<212> TYPE: RNA
<213> ORGANISM: Artificial Sequence
<220> FEATURE:
<223> OTHER INFORMATION: Description of Artificial Sequence: Synthetic
      5'-tiRNAAla oligonucleotide

<400> SEQUENCE: 37 gggggguguag cucaguggua gagcgcgugc uuagcaugca cgaggccccg gguucaaucc   60
ccggcaccuc caccc                                                     75

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      Ctrl 25 oligonucleotide

<400> SEQUENCE: 38
aaaaaactcg agatggcgca cgctg                                          25

<210> SEQ ID NO 39
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      CRO26 oligonucleotide

<400> SEQUENCE: 39
cctcctcctc cttctcctcc tcctcc                                          26

<210> SEQ ID NO 40
<211> LENGTH: 32
<212> TYPE: RNA
<213> ORGANISM: Homo sapiens

<400> SEQUENCE: 40 gggggugüag cucaguggua gagcgcgugc uu                                   32

<210> SEQ ID NO 41
<211> LENGTH: 31
<212> TYPE: RNA
<213> ORGANISM: Homo sapiens

<400> SEQUENCE: 41 gggggugüag cucaguggua gagcgcgugc u                                    31

<210> SEQ ID NO 42
<211> LENGTH: 32
<212> TYPE: RNA
<213> ORGANISM: Homo sapiens

<400> SEQUENCE: 42 gggggggugüa gcucaguggu agagcgcgug cu                                  32
```

```
<210> SEQ ID NO 42
<211> LENGTH: 32
<212> TYPE: RNA
<213> ORGANISM: Homo sapiens

<400> SEQUENCE: 42
ggggggugua gcucaguggu agagcgcgug cu                                   32

<210> SEQ ID NO 43
<211> LENGTH: 30
<212> TYPE: RNA
<213> ORGANISM: Homo sapiens

<400> SEQUENCE: 43 gggggugüag cucaguggua gagcgcgugc                                      30

<210> SEQ ID NO 44
<211> LENGTH: 31
<212> TYPE: RNA
<213> ORGANISM: Homo sapiens

<400> SEQUENCE: 44
ggggggugua gcucaguggu agagcgcgug c                                    31

<210> SEQ ID NO 45
<211> LENGTH: 32
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 45
gggggunuag cucaguggua gagcgcgugc uu                                   32

<210> SEQ ID NO 46
<211> LENGTH: 29
<212> TYPE: RNA
<213> ORGANISM: Homo sapiens

<400> SEQUENCE: 46
``` gggggguguag cucaguggua gagcgcgug    29

<210> SEQ ID NO 47
<211> LENGTH: 31
<212> TYPE: RNA
<213> ORGANISM: Homo sapiens

<400> SEQUENCE: 47
guguagcuca gugguagagc gcgugcuucg c    31

<210> SEQ ID NO 48
<211> LENGTH: 31
<212> TYPE: RNA
<213> ORGANISM: Homo sapiens
<220> FEATURE:
<221> NAME/KEY: modified_base
<222> LOCATION: (6)..(6)
<223> OTHER INFORMATION: a, c, g or u

<400> SEQUENCE: 48
ggggunuagc ucagugguag agcgcgugcu u    31

<210> SEQ ID NO 49
<211> LENGTH: 32
<212> TYPE: RNA
<213> ORGANISM: Homo sapiens
<220> FEATURE:
<221> NAME/KEY: modified_base
<222> LOCATION: (8)..(8)
<223> OTHER INFORMATION: a, c, g or u

<400> SEQUENCE: 49 gggggggunua gcucaguggu agagcgcgug cu    32

<210> SEQ ID NO 50
<211> LENGTH: 31
<212> TYPE: RNA
<213> ORGANISM: Homo sapiens

<400> SEQUENCE: 50 ggggguguagc ucaguggguag agagcgugcu u    31

<210> SEQ ID NO 51
<211> LENGTH: 30
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 51 ggggunuag cucaguggua gagcgcgugc    30

<210> SEQ ID NO 52
<211> LENGTH: 31
<212> TYPE: RNA
<213> ORGANISM: Homo sapiens

<400> SEQUENCE: 52 gggggguguag cucaguggua gagagcgugc u    31

<210> SEQ ID NO 53
<211> LENGTH: 31
<212> TYPE: RNA
<213> ORGANISM: Homo sapiens -continued

<400> SEQUENCE: 53
ggggauguag cucaguggua gagcgcaugc u                                    31

<210> SEQ ID NO 54
<211> LENGTH: 30
<212> TYPE: RNA
<213> ORGANISM: Homo sapiens

<400> SEQUENCE: 54
gggggauuag cucaaauggu agagcgcucg                                      30

<210> SEQ ID NO 55
<211> LENGTH: 31
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 55
ggggaunuag cucaguggua gagcgcaugc u                                    31

<210> SEQ ID NO 56
<211> LENGTH: 27
<212> TYPE: RNA
<213> ORGANISM: Homo sapiens

<400> SEQUENCE: 56
ggcucuguug cgcaauggau agcgcau                                         27

<210> SEQ ID NO 57
<211> LENGTH: 28
<212> TYPE: RNA
<213> ORGANISM: Homo sapiens

<400> SEQUENCE: 57
uccucauuag uauaguggug aguauccc                                        28

<210> SEQ ID NO 58
<211> LENGTH: 30
<212> TYPE: RNA
<213> ORGANISM: Homo sapiens

<400> SEQUENCE: 58 gggggurag cucaguggua gagcauuuga                                       30

<210> SEQ ID NO 59
<211> LENGTH: 29
<212> TYPE: RNA
<213> ORGANISM: Homo sapiens

<400> SEQUENCE: 59 gggggurag cucaguggua gagcauuug                                        29

<210> SEQ ID NO 60
<211> LENGTH: 28
<212> TYPE: RNA
<213> ORGANISM: Homo sapiens

<400> SEQUENCE: 60 gggggurag cucaguggua gagcauuu                                         28

```
<210> SEQ ID NO 61
<211> LENGTH: 27
<212> TYPE: RNA
<213> ORGANISM: Homo sapiens

<400> SEQUENCE: 61 gggggguauag cucagugggu agagcau                                          27

<210> SEQ ID NO 62
<211> LENGTH: 30
<212> TYPE: RNA
<213> ORGANISM: Homo sapiens

<400> SEQUENCE: 62 gggggguguaa cucaguggua gagcauuuga                                       30

<210> SEQ ID NO 63
<211> LENGTH: 29
<212> TYPE: RNA
<213> ORGANISM: Homo sapiens

<400> SEQUENCE: 63 gguccaugg uguaaugguu agcacucug                                          29

<210> SEQ ID NO 64
<211> LENGTH: 32
<212> TYPE: RNA
<213> ORGANISM: Homo sapiens

<400> SEQUENCE: 64
uuggugguuc agugguagaa uucucgccug cc                                     32

<210> SEQ ID NO 65
<211> LENGTH: 31
<212> TYPE: RNA
<213> ORGANISM: Homo sapiens

<400> SEQUENCE: 65
uuggugguuc agugguagaa uucucgccug c                                      31

<210> SEQ ID NO 66
<211> LENGTH: 30
<212> TYPE: RNA
<213> ORGANISM: Homo sapiens

<400> SEQUENCE: 66
uuggugguuc agugguagaa uucucgccug                                        30

<210> SEQ ID NO 67
<211> LENGTH: 29
<212> TYPE: RNA
<213> ORGANISM: Homo sapiens

<400> SEQUENCE: 67
uggugguuca gugguagaau ucucgccug                                         29

<210> SEQ ID NO 68
<211> LENGTH: 31
<212> TYPE: RNA
<213> ORGANISM: Homo sapiens

<400> SEQUENCE: 68
auuggugguu cagugguaga auucucgccu g                                      31
```

<210> SEQ ID NO 69
<211> LENGTH: 29
<212> TYPE: RNA
<213> ORGANISM: Homo sapiens

<400> SEQUENCE: 69
uuggugguuc agugguagaa uucucgccu                                    29

<210> SEQ ID NO 70
<211> LENGTH: 31
<212> TYPE: RNA
<213> ORGANISM: Homo sapiens

<400> SEQUENCE: 70
ggcauuggug guucaguggu agaauucucg c                                 31

<210> SEQ ID NO 71
<211> LENGTH: 29
<212> TYPE: RNA
<213> ORGANISM: Homo sapiens

<400> SEQUENCE: 71
auuggugguu cagugguaga auucucgcc                                    29

<210> SEQ ID NO 72
<211> LENGTH: 31
<212> TYPE: RNA
<213> ORGANISM: Homo sapiens

<400> SEQUENCE: 72
agcauuggug guucaguggu agaauucucg c                                 31

<210> SEQ ID NO 73
<211> LENGTH: 29
<212> TYPE: RNA
<213> ORGANISM: Homo sapiens

<400> SEQUENCE: 73
cauugguggu ucagugguag aauucucgc                                    29

<210> SEQ ID NO 74
<211> LENGTH: 32
<212> TYPE: RNA
<213> ORGANISM: Homo sapiens

<400> SEQUENCE: 74
gggaggcccg gguucguuuc ccggccaaug ca                                32

<210> SEQ ID NO 75
<211> LENGTH: 30
<212> TYPE: RNA
<213> ORGANISM: Homo sapiens

<400> SEQUENCE: 75
gcauuggugg uucaguggua gaauucucac                                   30

<210> SEQ ID NO 76
<211> LENGTH: 32
<212> TYPE: RNA
<213> ORGANISM: Homo sapiens

<400> SEQUENCE: 76
cgggaggccc ggguucgguu cccggccaau gc        32

<210> SEQ ID NO 77
<211> LENGTH: 27
<212> TYPE: RNA
<213> ORGANISM: Homo sapiens

<400> SEQUENCE: 77
uuggugguuc aguaggtagaa uucucgc        27

<210> SEQ ID NO 78
<211> LENGTH: 28
<212> TYPE: RNA
<213> ORGANISM: Homo sapiens

<400> SEQUENCE: 78
gacauuggug guucaguggu agaauucu        28

<210> SEQ ID NO 79
<211> LENGTH: 27
<212> TYPE: RNA
<213> ORGANISM: Homo sapiens

<400> SEQUENCE: 79
ugguucagug guagaauucu cgccucc        27

<210> SEQ ID NO 80
<211> LENGTH: 27
<212> TYPE: RNA
<213> ORGANISM: Homo sapiens

<400> SEQUENCE: 80
gcauugguau aguguauca ugcaaga        27

<210> SEQ ID NO 81
<211> LENGTH: 32
<212> TYPE: RNA
<213> ORGANISM: Homo sapiens

<400> SEQUENCE: 81
agcguuggug guauaguggu gagcauagcu gc        32

<210> SEQ ID NO 82
<211> LENGTH: 30
<212> TYPE: RNA
<213> ORGANISM: Homo sapiens

<400> SEQUENCE: 82
ggccgugauc guauaguggu uaguacucug        30

<210> SEQ ID NO 83
<211> LENGTH: 31
<212> TYPE: RNA
<213> ORGANISM: Homo sapiens

<400> SEQUENCE: 83
ucgccgugau cguauagugg uuaguacucu g        31

<210> SEQ ID NO 84
<211> LENGTH: 28
<212> TYPE: RNA
<213> ORGANISM: Homo sapiens

<400> SEQUENCE: 84

-continued

| | |
|---|---|
| ggccgugauc guauagtggu uaguacuc | 28 |

<210> SEQ ID NO 85
<211> LENGTH: 29
<212> TYPE: RNA
<213> ORGANISM: Homo sapiens

<400> SEQUENCE: 85

| | |
|---|---|
| aggccgugau cguauagugg uuaguacuc | 29 |

<210> SEQ ID NO 86
<211> LENGTH: 27
<212> TYPE: RNA
<213> ORGANISM: Homo sapiens

<400> SEQUENCE: 86

| | |
|---|---|
| ggccgugauc guauaguggu uaguacu | 27 |

<210> SEQ ID NO 87
<211> LENGTH: 26
<212> TYPE: RNA
<213> ORGANISM: Homo sapiens

<400> SEQUENCE: 87

| | |
|---|---|
| ggccgugauc guauaguggu uaguac | 26 |

<210> SEQ ID NO 88
<211> LENGTH: 26
<212> TYPE: RNA
<213> ORGANISM: Homo sapiens

<400> SEQUENCE: 88

| | |
|---|---|
| ggccgguuag cucaguuggu uagagc | 26 |

<210> SEQ ID NO 89
<211> LENGTH: 26
<212> TYPE: RNA
<213> ORGANISM: Homo sapiens

<400> SEQUENCE: 89

| | |
|---|---|
| ggccgguuag cucaguuggu cagagc | 26 |

<210> SEQ ID NO 90
<211> LENGTH: 31
<212> TYPE: RNA
<213> ORGANISM: Homo sapiens

<400> SEQUENCE: 90

| | |
|---|---|
| ggccgguuag cucaguuggu aagagcuugg u | 31 |

<210> SEQ ID NO 91
<211> LENGTH: 31
<212> TYPE: RNA
<213> ORGANISM: Homo sapiens

<400> SEQUENCE: 91

| | |
|---|---|
| ggggcggccg guuagcucag uugguaagag c | 31 |

<210> SEQ ID NO 92
<211> LENGTH: 26
<212> TYPE: RNA
<213> ORGANISM: Homo sapiens

```
<400> SEQUENCE: 92
ggccgguuag cucaguuggu aagagc                                          26

<210> SEQ ID NO 93
<211> LENGTH: 26
<212> TYPE: RNA
<213> ORGANISM: Homo sapiens

<400> SEQUENCE: 93
gguagugugg ccgagcgguc uaaggc                                          26

<210> SEQ ID NO 94
<211> LENGTH: 31
<212> TYPE: RNA
<213> ORGANISM: Homo sapiens

<400> SEQUENCE: 94
guagucgugg ccgagugguu aaggcuaugg a                                    31

<210> SEQ ID NO 95
<211> LENGTH: 32
<212> TYPE: RNA
<213> ORGANISM: Homo sapiens

<400> SEQUENCE: 95
gacgaggugg ccgagugguu aaggcuaugg au                                   32

<210> SEQ ID NO 96
<211> LENGTH: 32
<212> TYPE: RNA
<213> ORGANISM: Homo sapiens

<400> SEQUENCE: 96
gacgaggugg ccgagugguu aaggcuaugg ac                                   32

<210> SEQ ID NO 97
<211> LENGTH: 31
<212> TYPE: RNA
<213> ORGANISM: Homo sapiens

<400> SEQUENCE: 97
gacgaggugg ccgagugguu aaggcuaugg a                                    31

<210> SEQ ID NO 98
<211> LENGTH: 30
<212> TYPE: RNA
<213> ORGANISM: Homo sapiens

<400> SEQUENCE: 98
gacgaggugg ccgagugguu aaggcuaugg                                      30

<210> SEQ ID NO 99
<211> LENGTH: 31
<212> TYPE: RNA
<213> ORGANISM: Homo sapiens

<400> SEQUENCE: 99
gacgaggugg ccgagugguu aaggcaaugg a                                    31

<210> SEQ ID NO 100
<211> LENGTH: 30
<212> TYPE: RNA
<213> ORGANISM: Homo sapiens
```

<400> SEQUENCE: 100
gacgaggugg ccgagugguu aaggcaaugg                                          30

<210> SEQ ID NO 101
<211> LENGTH: 26
<212> TYPE: RNA
<213> ORGANISM: Homo sapiens

<400> SEQUENCE: 101
uguagucgug gccgaguggu uaaggc                                              26

<210> SEQ ID NO 102
<211> LENGTH: 31
<212> TYPE: RNA
<213> ORGANISM: Homo sapiens

<400> SEQUENCE: 102
gccuggauag cucaguuggu agagcaucag a                                        31

<210> SEQ ID NO 103
<211> LENGTH: 29
<212> TYPE: RNA
<213> ORGANISM: Homo sapiens

<400> SEQUENCE: 103
gccuggauag cucaguuggu agagcauca                                           29

<210> SEQ ID NO 104
<211> LENGTH: 32
<212> TYPE: RNA
<213> ORGANISM: Homo sapiens

<400> SEQUENCE: 104
gccuggguag cucagucggu agagcaucag ac                                       32

<210> SEQ ID NO 105
<211> LENGTH: 31
<212> TYPE: RNA
<213> ORGANISM: Homo sapiens

<400> SEQUENCE: 105
gccuggguag cucagucggu agagcaucag a                                        31

<210> SEQ ID NO 106
<211> LENGTH: 30
<212> TYPE: RNA
<213> ORGANISM: Homo sapiens

<400> SEQUENCE: 106
gccuggguag cucagucggu agagcaucag                                          30

<210> SEQ ID NO 107
<211> LENGTH: 32
<212> TYPE: RNA
<213> ORGANISM: Homo sapiens

<400> SEQUENCE: 107
gcagaguggc gcagcggaag cgugcugggc cc                                       32

<210> SEQ ID NO 108
<211> LENGTH: 32
<212> TYPE: RNA

```
<213> ORGANISM: Homo sapiens

<400> SEQUENCE: 108
ggcagagugg cgcagcggaa gcgugcuggg cc                          32

<210> SEQ ID NO 109
<211> LENGTH: 28
<212> TYPE: RNA
<213> ORGANISM: Homo sapiens

<400> SEQUENCE: 109
gcagaguggc gcagcggaag cgugcugg                               28

<210> SEQ ID NO 110
<211> LENGTH: 29
<212> TYPE: RNA
<213> ORGANISM: Homo sapiens

<400> SEQUENCE: 110
ugcagagugg cgcagcggaa gcgugcugg                              29

<210> SEQ ID NO 111
<211> LENGTH: 29
<212> TYPE: RNA
<213> ORGANISM: Homo sapiens

<400> SEQUENCE: 111
gcaguggcgc agcggaagcg ugcugggcc                              29

<210> SEQ ID NO 112
<211> LENGTH: 27
<212> TYPE: RNA
<213> ORGANISM: Homo sapiens

<400> SEQUENCE: 112
gcagaguggc gcagcggaag cgugcug                                27

<210> SEQ ID NO 113
<211> LENGTH: 32
<212> TYPE: RNA
<213> ORGANISM: Homo sapiens

<400> SEQUENCE: 113
cgcagagucg cgcagcggaa gcgugcuggg cc                          32

<210> SEQ ID NO 114
<211> LENGTH: 31
<212> TYPE: RNA
<213> ORGANISM: Homo sapiens

<400> SEQUENCE: 114
cagagucgcg cagcggaagc gugcugggcc c                           31

<210> SEQ ID NO 115
<211> LENGTH: 31
<212> TYPE: RNA
<213> ORGANISM: Homo sapiens

<400> SEQUENCE: 115
agaguugcgc agcggaagcg ugcugggccc a                           31

<210> SEQ ID NO 116
<211> LENGTH: 27
```

```
<212> TYPE: RNA
<213> ORGANISM: Homo sapiens

<400> SEQUENCE: 116
gagauagcag aguggcgcag cggaagc                                           27

<210> SEQ ID NO 117
<211> LENGTH: 30
<212> TYPE: RNA
<213> ORGANISM: Homo sapiens

<400> SEQUENCE: 117
ggcucguugg ucuaggggua ugauucucgg                                        30

<210> SEQ ID NO 118
<211> LENGTH: 30
<212> TYPE: RNA
<213> ORGANISM: Homo sapiens

<400> SEQUENCE: 118
aggcucguug gucuaguggu augauucucg                                        30

<210> SEQ ID NO 119
<211> LENGTH: 30
<212> TYPE: RNA
<213> ORGANISM: Homo sapiens

<400> SEQUENCE: 119
gcccggauga uccucagugg ucuggggugc                                        30

<210> SEQ ID NO 120
<211> LENGTH: 26
<212> TYPE: RNA
<213> ORGANISM: Homo sapiens

<400> SEQUENCE: 120
uguagucgug gccgaguggu uaaggc                                            26

<210> SEQ ID NO 121
<211> LENGTH: 32
<212> TYPE: RNA
<213> ORGANISM: Homo sapiens

<400> SEQUENCE: 121
gacgaggugg ccgagugguu aaggcuaugg ac                                     32

<210> SEQ ID NO 122
<211> LENGTH: 32
<212> TYPE: RNA
<213> ORGANISM: Homo sapiens

<400> SEQUENCE: 122
gacgaggugg ccgagugguu aaggcuaugg au                                     32

<210> SEQ ID NO 123
<211> LENGTH: 31
<212> TYPE: RNA
<213> ORGANISM: Homo sapiens

<400> SEQUENCE: 123
gacgaggugg ccgagugguu aaggcuaugg a                                      31

<210> SEQ ID NO 124
```

```
<210> SEQ ID NO 124
<211> LENGTH: 31
<212> TYPE: RNA
<213> ORGANISM: Homo sapiens

<400> SEQUENCE: 124
gacgaggugg ccgagugguu aaggcaaugg a                              31

<210> SEQ ID NO 125
<211> LENGTH: 30
<212> TYPE: RNA
<213> ORGANISM: Homo sapiens

<400> SEQUENCE: 125
gacgaggugg ccgagugguu aaggcuaugg                                30

<210> SEQ ID NO 126
<211> LENGTH: 30
<212> TYPE: RNA
<213> ORGANISM: Homo sapiens

<400> SEQUENCE: 126
gacgaggugg ccgagugguu aaggcaaugg                                30

<210> SEQ ID NO 127
<211> LENGTH: 31
<212> TYPE: RNA
<213> ORGANISM: Homo sapiens

<400> SEQUENCE: 127
gccuggauag cucaguuggu agagcaucag a                              31

<210> SEQ ID NO 128
<211> LENGTH: 29
<212> TYPE: RNA
<213> ORGANISM: Homo sapiens

<400> SEQUENCE: 128
gccuggauag cucaguuggu agagcauca                                 29

<210> SEQ ID NO 129
<211> LENGTH: 32
<212> TYPE: RNA
<213> ORGANISM: Homo sapiens

<400> SEQUENCE: 129
ggcagagugg cgcagcggaa gcgugcuggg cc                             32

<210> SEQ ID NO 130
<211> LENGTH: 32
<212> TYPE: RNA
<213> ORGANISM: Homo sapiens

<400> SEQUENCE: 130
gcagaguggc gcagcggaag cgugcugggc cc                             32

<210> SEQ ID NO 131
<211> LENGTH: 28
<212> TYPE: RNA
<213> ORGANISM: Homo sapiens

<400> SEQUENCE: 131
gcagaguggc gcagcggaag cgugcugg                                  28
```

```
<210> SEQ ID NO 132
<211> LENGTH: 28
<212> TYPE: RNA
<213> ORGANISM: Homo sapiens

<400> SEQUENCE: 132
cggaagcgug cugggcccau aacccaga                                        28

<210> SEQ ID NO 133
<211> LENGTH: 29
<212> TYPE: RNA
<213> ORGANISM: Homo sapiens

<400> SEQUENCE: 133
ugcagagugg cgcagcggaa gcgugcugg                                       29

<210> SEQ ID NO 134
<211> LENGTH: 29
<212> TYPE: RNA
<213> ORGANISM: Homo sapiens

<400> SEQUENCE: 134
gcaguggcgc agcggaagcg ugcugggcc                                       29

<210> SEQ ID NO 135
<211> LENGTH: 27
<212> TYPE: RNA
<213> ORGANISM: Homo sapiens

<400> SEQUENCE: 135
gcagaguggc gcagcggaag cgugcug                                         27

<210> SEQ ID NO 136
<211> LENGTH: 32
<212> TYPE: RNA
<213> ORGANISM: Homo sapiens

<400> SEQUENCE: 136
cgcagagucg cgcagcggaa gcgugcuggg cc                                   32

<210> SEQ ID NO 137
<211> LENGTH: 31
<212> TYPE: RNA
<213> ORGANISM: Homo sapiens

<400> SEQUENCE: 137
cagagucgcg cagcggaagc gugcugggcc c                                    31

<210> SEQ ID NO 138
<211> LENGTH: 31
<212> TYPE: RNA
<213> ORGANISM: Homo sapiens

<400> SEQUENCE: 138
agaguugcgc agcggaagcg ugcugggccc a                                    31

<210> SEQ ID NO 139
<211> LENGTH: 31
<212> TYPE: RNA
<213> ORGANISM: Homo sapiens

<400> SEQUENCE: 139
gccuggauag cucaguuggu agagcaucag a                                    31
```

```
<210> SEQ ID NO 140
<211> LENGTH: 29
<212> TYPE: RNA
<213> ORGANISM: Homo sapiens

<400> SEQUENCE: 140
gccuggauag cucaguuggu agagcauca                                29

<210> SEQ ID NO 141
<211> LENGTH: 32
<212> TYPE: RNA
<213> ORGANISM: Homo sapiens

<400> SEQUENCE: 141
uuccguagug uagugguuau cacguucgcc uc                            32

<210> SEQ ID NO 142
<211> LENGTH: 30
<212> TYPE: RNA
<213> ORGANISM: Homo sapiens

<400> SEQUENCE: 142
uuccguagug uagugguuau cacguucgcc                               30

<210> SEQ ID NO 143
<211> LENGTH: 32
<212> TYPE: RNA
<213> ORGANISM: Homo sapiens

<400> SEQUENCE: 143
uccguagugu agugguuauc acguucgccu ga                            32

<210> SEQ ID NO 144
<211> LENGTH: 31
<212> TYPE: RNA
<213> ORGANISM: Homo sapiens

<400> SEQUENCE: 144
uccguagugu agugguuauc acguucgccu g                             31

<210> SEQ ID NO 145
<211> LENGTH: 32
<212> TYPE: RNA
<213> ORGANISM: Homo sapiens

<400> SEQUENCE: 145
uccguagugu agugguuauc acguucgccu ca                            32

<210> SEQ ID NO 146
<211> LENGTH: 30
<212> TYPE: RNA
<213> ORGANISM: Homo sapiens

<400> SEQUENCE: 146
uccguagugu agugguuauc acguucgccu                               30

<210> SEQ ID NO 147
<211> LENGTH: 32
<212> TYPE: RNA
<213> ORGANISM: Homo sapiens

<400> SEQUENCE: 147 guuccguag uguaguggguc aucacguucg cc                            32
```

<210> SEQ ID NO 148
<211> LENGTH: 28
<212> TYPE: RNA
<213> ORGANISM: Homo sapiens

<400> SEQUENCE: 148
ccguagugua gugguuauca cguucgcc					28

<210> SEQ ID NO 149
<211> LENGTH: 30
<212> TYPE: RNA
<213> ORGANISM: Homo sapiens

<400> SEQUENCE: 149
guuuccguag uguagugguc aucacguucg					30

<210> SEQ ID NO 150
<211> LENGTH: 27
<212> TYPE: RNA
<213> ORGANISM: Homo sapiens

<400> SEQUENCE: 150
cguaguguag ugguuaucac guucgcc					27

<210> SEQ ID NO 151
<211> LENGTH: 30
<212> TYPE: RNA
<213> ORGANISM: Homo sapiens

<400> SEQUENCE: 151
uccguagugu aguggguauc acuuucgccu					30

<210> SEQ ID NO 152
<211> LENGTH: 31
<212> TYPE: RNA
<213> ORGANISM: Homo sapiens

<400> SEQUENCE: 152
uccguagugu acugguuauc acguucgccu g					31

<210> SEQ ID NO 153
<211> LENGTH: 28
<212> TYPE: RNA
<213> ORGANISM: Homo sapiens

<400> SEQUENCE: 153
cguaguguag uggucaucac guucgccu					28

<210> SEQ ID NO 154
<211> LENGTH: 32
<212> TYPE: RNA
<213> ORGANISM: Homo sapiens

<400> SEQUENCE: 154 gggggguguag cucaguggua gagcgcgugc uu				32

<210> SEQ ID NO 155
<211> LENGTH: 31
<212> TYPE: RNA
<213> ORGANISM: Homo sapiens

<400> SEQUENCE: 155

```
gggggguguag cucaguggua gagcgcgugc u                              31

<210> SEQ ID NO 156
<211> LENGTH: 30
<212> TYPE: RNA
<213> ORGANISM: Homo sapiens

<400> SEQUENCE: 156 gggggguguag cucaguggua gagcgcgugc                                30

<210> SEQ ID NO 157
<211> LENGTH: 29
<212> TYPE: RNA
<213> ORGANISM: Homo sapiens

<400> SEQUENCE: 157 gggggguguag cucaguggua gagcgcgug                                 29

<210> SEQ ID NO 158
<211> LENGTH: 32
<212> TYPE: RNA
<213> ORGANISM: Homo sapiens

<400> SEQUENCE: 158
ggggggugua gcucaguggu agagcgcgug cu                              32

<210> SEQ ID NO 159
<211> LENGTH: 32
<212> TYPE: RNA
<213> ORGANISM: Homo sapiens

<400> SEQUENCE: 159
uuggugguuc aguguagaa uucucgccug cc                               32

<210> SEQ ID NO 160
<211> LENGTH: 31
<212> TYPE: RNA
<213> ORGANISM: Homo sapiens

<400> SEQUENCE: 160
uuggugguuc aguguagaa uucucgccug c                                31

<210> SEQ ID NO 161
<211> LENGTH: 30
<212> TYPE: RNA
<213> ORGANISM: Homo sapiens

<400> SEQUENCE: 161
uuggugguuc aguguagaa uucucgccug                                  30

<210> SEQ ID NO 162
<211> LENGTH: 29
<212> TYPE: RNA
<213> ORGANISM: Homo sapiens

<400> SEQUENCE: 162
uuggugguuc aguguagaa uucucgccu                                   29

<210> SEQ ID NO 163
<211> LENGTH: 29
<212> TYPE: RNA
<213> ORGANISM: Homo sapiens

<400> SEQUENCE: 163
```
uggugguuca gugguagaau ucucgccug 29

<210> SEQ ID NO 164
<211> LENGTH: 31
<212> TYPE: RNA
<213> ORGANISM: Homo sapiens

<400> SEQUENCE: 164
auuggugguu cagugguaga auucucgccu g 31

<210> SEQ ID NO 165
<211> LENGTH: 29
<212> TYPE: RNA
<213> ORGANISM: Homo sapiens

<400> SEQUENCE: 165
auuggugguu cagugguaga auucucgcc 29

<210> SEQ ID NO 166
<211> LENGTH: 31
<212> TYPE: RNA
<213> ORGANISM: Homo sapiens

<400> SEQUENCE: 166
ggcauuggug guucaguggu agaauucucg c 31

<210> SEQ ID NO 167
<211> LENGTH: 27
<212> TYPE: RNA
<213> ORGANISM: Homo sapiens

<400> SEQUENCE: 167
uuggugguuc agugguagaa uucucgc 27

<210> SEQ ID NO 168
<211> LENGTH: 27
<212> TYPE: RNA
<213> ORGANISM: Homo sapiens

<400> SEQUENCE: 168
ugguucagug guagaauucu cgccucc 27

<210> SEQ ID NO 169
<211> LENGTH: 29
<212> TYPE: RNA
<213> ORGANISM: Homo sapiens

<400> SEQUENCE: 169
cauugguggu ucaguggaug aauucucgc 29

<210> SEQ ID NO 170
<211> LENGTH: 31
<212> TYPE: RNA
<213> ORGANISM: Homo sapiens

<400> SEQUENCE: 170
agcauuggug guucaguggu agaauucucg c 31

<210> SEQ ID NO 171
<211> LENGTH: 30
<212> TYPE: RNA
<213> ORGANISM: Homo sapiens

<400> SEQUENCE: 171
gcauuggugg uucaguggua gaauucucac                                  30

<210> SEQ ID NO 172
<211> LENGTH: 40
<212> TYPE: DNA
<213> ORGANISM: Homo sapiens

<400> SEQUENCE: 172
gtctctgtgg cgcaatcggt tagcgcgttc ggctgttaac                       40

<210> SEQ ID NO 173
<211> LENGTH: 40
<212> TYPE: DNA
<213> ORGANISM: Homo sapiens

<400> SEQUENCE: 173
gccgaaatag ctcagttggg agagcgttag actgaagatc                       40

<210> SEQ ID NO 174
<211> LENGTH: 21
<212> TYPE: DNA
<213> ORGANISM: Homo sapiens

<400> SEQUENCE: 174
gggagggtgg ggagggtggg g                                           21

<210> SEQ ID NO 175
<211> LENGTH: 32
<212> TYPE: DNA
<213> ORGANISM: Artificial Sequence
<220> FEATURE:
<223> OTHER INFORMATION: Description of Artificial Sequence: Synthetic
      ME8 probe

<400> SEQUENCE: 175
ctttatgttt ttggcgtctt ccatctcgag gc                               32

<210> SEQ ID NO 176
<211> LENGTH: 73
<212> TYPE: DNA
<213> ORGANISM: Homo sapiens

<400> SEQUENCE: 176
ggggaattag ctcaagcggt agagcgctcc cttagcatgc gagaggtagc gggatcgacg  60
cccccattct cta                                                    73

<210> SEQ ID NO 177
<211> LENGTH: 73
<212> TYPE: DNA
<213> ORGANISM: Homo sapiens

<400> SEQUENCE: 177
gggggattag ctcaagcggt agggtgcctg cttagcatgc aagaggtagc aggatcgacg  60
cctgcattct cca                                                    73

<210> SEQ ID NO 178
<211> LENGTH: 71
<212> TYPE: DNA
<213> ORGANISM: Homo sapiens

<400> SEQUENCE: 178

```
gggggtgtag atcagtggta gggcgcacgc ttagcatgca tgaggccctg ggtcaatccc    60
cagcacctcc a                                                         71
```

<210> SEQ ID NO 179
<211> LENGTH: 73
<212> TYPE: DNA
<213> ORGANISM: Homo sapiens

<400> SEQUENCE: 179

```
ggggattag ctcaagcggt agagcgcctg cttagcatgc aagaggtagc aggatcgatg     60
cctgcattct cca                                                       73
```

<210> SEQ ID NO 180
<211> LENGTH: 73
<212> TYPE: DNA
<213> ORGANISM: Homo sapiens

<400> SEQUENCE: 180

```
ggggaattgg ctcaagcggt agagcgcttg cttagcatgc aagaggtagc aggatcgacg    60
cctgcactct cca                                                       73
```

<210> SEQ ID NO 181
<211> LENGTH: 73
<212> TYPE: DNA
<213> ORGANISM: Homo sapiens

<400> SEQUENCE: 181

```
ggggaattgg ctcaagcggt agagcgcttg cttagcatgc aagaggtagc aggatcgacg    60
cctgcactct cca                                                       73
```

<210> SEQ ID NO 182
<211> LENGTH: 73
<212> TYPE: DNA
<213> ORGANISM: Homo sapiens

<400> SEQUENCE: 182

```
ggggaattag cgcaagtggt agagtgcttg cttagcatgc aagaggtagt gggatcgatg    60
cccacattct cca                                                       73
```

<210> SEQ ID NO 183
<211> LENGTH: 73
<212> TYPE: DNA
<213> ORGANISM: Homo sapiens

<400> SEQUENCE: 183

```
ggggaattag cccaagtggt agagcgcttg cttagcatgc aagaggtagt gggatcgatg    60
cccacattct cca                                                       73
```

<210> SEQ ID NO 184
<211> LENGTH: 73
<212> TYPE: DNA
<213> ORGANISM: Homo sapiens

<400> SEQUENCE: 184

```
ggggaattag ctcaagtggt agagcgctcg cttagcatgc gagaggtagt gggatcgatg    60
cccgcattct cca                                                       73
```

<210> SEQ ID NO 185
<211> LENGTH: 73

```
<212> TYPE: DNA
<213> ORGANISM: Homo sapiens

<400> SEQUENCE: 185
ggggaattag ctcaagtggt agagcgcttg cttagcatgc aagaggtagt gggatcaatg    60
cccacattct cca                                                       73

<210> SEQ ID NO 186
<211> LENGTH: 73
<212> TYPE: DNA
<213> ORGANISM: Homo sapiens

<400> SEQUENCE: 186
ggggaattag ctcaagcggt agagcgcttg cttagcatgc aagaggtagt gggatcgatg    60
cccacattct cca                                                       73

<210> SEQ ID NO 187
<211> LENGTH: 73
<212> TYPE: DNA
<213> ORGANISM: Homo sapiens

<400> SEQUENCE: 187
ggggaattag ctcaagcggt agagcgcttg cttagcatgc aagaggtagt gggatcgatg    60
cccacattct cca                                                       73

<210> SEQ ID NO 188
<211> LENGTH: 73
<212> TYPE: DNA
<213> ORGANISM: Homo sapiens

<400> SEQUENCE: 188
ggggaattag ctcaagtggt agagcgcttg cttagcatgc aagaggtagt gggatcgatg    60
cccacattct cca                                                       73

<210> SEQ ID NO 189
<211> LENGTH: 73
<212> TYPE: DNA
<213> ORGANISM: Homo sapiens

<400> SEQUENCE: 189
ggggaattag ctcaagtggt agagcgcttg cttagcatgc aagaggtagt gggatcgatg    60
cccacattct cca                                                       73

<210> SEQ ID NO 190
<211> LENGTH: 73
<212> TYPE: DNA
<213> ORGANISM: Homo sapiens

<400> SEQUENCE: 190
ggggaattag ctcaagtggt agagcgcttg cttagcatgc aagaggtagt gggatcgatg    60
cccacattct cca                                                       73

<210> SEQ ID NO 191
<211> LENGTH: 73
<212> TYPE: DNA
<213> ORGANISM: Homo sapiens

<400> SEQUENCE: 191
ggggaattag ctcaaatggt agagcgctcg cttagcatgc gagaggtagc gggatcgatg    60
```
cccgcattct cca						73

<210> SEQ ID NO 192
<211> LENGTH: 73
<212> TYPE: DNA
<213> ORGANISM: Homo sapiens

<400> SEQUENCE: 192
ggggaattag ctcaagtggt agagcgcttg cttagcacgc aagaggtagt gggatcgatg		60 cccacattct cca						73

<210> SEQ ID NO 193
<211> LENGTH: 73
<212> TYPE: DNA
<213> ORGANISM: Homo sapiens

<400> SEQUENCE: 193
ggggaattag ctcaggcggt agagcgctcg cttagcatgc gagaggtagc gggatcgacg		60 cccgcattct cca						73

<210> SEQ ID NO 194
<211> LENGTH: 73
<212> TYPE: DNA
<213> ORGANISM: Homo sapiens

<400> SEQUENCE: 194
ggggaattag ctcaggcggt agagcgctcg cttagcatgc gagaggtagc gggatcgacg		60 cccgcattct cca						73

<210> SEQ ID NO 195
<211> LENGTH: 73
<212> TYPE: DNA
<213> ORGANISM: Homo sapiens

<400> SEQUENCE: 195
gggggattag ctcaaatggt agagcgctcg cttagcatgc gagaggtagc gggatcgatg		60 cccgcatcct cca						73

<210> SEQ ID NO 196
<211> LENGTH: 73
<212> TYPE: DNA
<213> ORGANISM: Homo sapiens

<400> SEQUENCE: 196
gggggattag ctcaaatggt agagcgctcg cttagcatgc gagaggtagc gggatcgatg		60 cccgcatcct cca						73

<210> SEQ ID NO 197
<211> LENGTH: 72
<212> TYPE: DNA
<213> ORGANISM: Homo sapiens

<400> SEQUENCE: 197
gggggtgtag ctcagtggta gagcgcgtgc ttagcatgca cgaggccccg ggttcaatcc		60 ctggcacctc ca						72

<210> SEQ ID NO 198
<211> LENGTH: 72
<212> TYPE: DNA
<213> ORGANISM: Homo sapiens

<400> SEQUENCE: 198
gggggtatag ctcagcggta gagcgcgtgc ttagcatgca cgaggtcctg ggttcaatcc    60
ccaatacctc ca                                                        72

<210> SEQ ID NO 199
<211> LENGTH: 72
<212> TYPE: DNA
<213> ORGANISM: Homo sapiens

<400> SEQUENCE: 199
gggggtgtag ctcagtggta gagcgcgtgc ttagcatgca cgaggccctg ggttcaatcc    60
ccagcacctc ca                                                        72

<210> SEQ ID NO 200
<211> LENGTH: 72
<212> TYPE: DNA
<213> ORGANISM: Homo sapiens

<400> SEQUENCE: 200
ggggatgtag ctcagtggta gagcgcatgc ttagcatgca tgaggtcccg ggttcgatcc    60
ccagcatctc ca                                                        72

<210> SEQ ID NO 201
<211> LENGTH: 72
<212> TYPE: DNA
<213> ORGANISM: Homo sapiens

<400> SEQUENCE: 201
gggggtgtag ctcagtggta gagcgcgtgc ttagcatgta cgaggtcccg ggttcaatcc    60
ccggcacctc ca                                                        72

<210> SEQ ID NO 202
<211> LENGTH: 72
<212> TYPE: DNA
<213> ORGANISM: Homo sapiens

<400> SEQUENCE: 202
gggggtgtag ctcagtggta gagcgcgtgc ttagcatgca cgaggccccg ggttcaatcc    60
ccggcacctc ca                                                        72

<210> SEQ ID NO 203
<211> LENGTH: 72
<212> TYPE: DNA
<213> ORGANISM: Homo sapiens

<400> SEQUENCE: 203
gggggtgtag ctcagtggta gagcgcgtgc ttagcatgca cgaggccccg ggttcaatcc    60
ccggcacctc ca                                                        72

<210> SEQ ID NO 204
<211> LENGTH: 72
<212> TYPE: DNA
<213> ORGANISM: Homo sapiens

<400> SEQUENCE: 204
gggggtatag ctcagtggta gagcgcgtgc ttagcatgca cgaggtcctg ggttcgatcc    60
ccagtacctc ca                                                        72

<210> SEQ ID NO 205
<211> LENGTH: 72
<212> TYPE: DNA
<213> ORGANISM: Homo sapiens

<400> SEQUENCE: 205
gggggtgtag atcagtggta gagcgcatgc ttcgcatgta cgaggtccct ggttcaatcc    60
ctggtacctc ca    72

<210> SEQ ID NO 206
<211> LENGTH: 72
<212> TYPE: DNA
<213> ORGANISM: Homo sapiens

<400> SEQUENCE: 206
gggggtgtag ctcagtggta gagcgcgtgc ttcgcatgta cgaggccccg ggttcgaccc    60
ccggctcctc ca    72

<210> SEQ ID NO 207
<211> LENGTH: 72
<212> TYPE: DNA
<213> ORGANISM: Homo sapiens

<400> SEQUENCE: 207
ggggatgtag ctcagtggta gagcgcgcgc ttcgcatgtg tgaggtcccg ggttcaatcc    60
ccggcatctc ca    72

<210> SEQ ID NO 208
<211> LENGTH: 72
<212> TYPE: DNA
<213> ORGANISM: Homo sapiens

<400> SEQUENCE: 208
ggggatgtag ctcagtggta gagcgcatgc ttcgcatgta tgaggccccg ggttcgatcc    60
ccggcatctc ca    72

<210> SEQ ID NO 209
<211> LENGTH: 72
<212> TYPE: DNA
<213> ORGANISM: Homo sapiens

<400> SEQUENCE: 209
ggggatgtag ctcagtggta gagcgcatgc ttcgcatgta tgaggtcccg ggttcgatcc    60
ccggcatctc ca    72

<210> SEQ ID NO 210
<211> LENGTH: 72
<212> TYPE: DNA
<213> ORGANISM: Homo sapiens

<400> SEQUENCE: 210
gggggtgtag ctcagtggta gagcggatgc tttgcatgta tgagactttg ggttggatcc    60
ccagcacctc ca    72

<210> SEQ ID NO 211
<211> LENGTH: 71
<212> TYPE: DNA
<213> ORGANISM: Homo sapiens

<400> SEQUENCE: 211

-continued

```
gggggtgtag ctcagtggta gagcgcatgc tttgcatgta tgaggcctcg gttcgatccc    60
cgacacctcc a                                                         71

<210> SEQ ID NO 212
<211> LENGTH: 72
<212> TYPE: DNA
<213> ORGANISM: Homo sapiens

<400> SEQUENCE: 212
gggggtgtag ctcagtggta gagcacatgc tttgcatgtg tgaggccccg ggttcgatcc    60
ccggcacctc ca                                                        72

<210> SEQ ID NO 213
<211> LENGTH: 72
<212> TYPE: DNA
<213> ORGANISM: Homo sapiens

<400> SEQUENCE: 213
gggggtgtag ctcagtggta gagcgcatgc tttgcatgta tgaggcctcg ggttcgatcc    60
ccgacacctc ca                                                        72

<210> SEQ ID NO 214
<211> LENGTH: 72
<212> TYPE: DNA
<213> ORGANISM: Homo sapiens

<400> SEQUENCE: 214
ggggatgtag ctcagtggta gagcgcatgc tttgcacgta tgaggccccg ggttcaatcc    60
ccggcatctc ca                                                        72

<210> SEQ ID NO 215
<211> LENGTH: 72
<212> TYPE: DNA
<213> ORGANISM: Homo sapiens

<400> SEQUENCE: 215
ggggatgtag ctcagtggta gagcgcatgc tttgcatgta tgaggccccg ggttcgatcc    60
ccggcatctc ca                                                        72

<210> SEQ ID NO 216
<211> LENGTH: 72
<212> TYPE: DNA
<213> ORGANISM: Homo sapiens

<400> SEQUENCE: 216
ggggatgtag ctcagtggta gagcgcatgc tttgcatgta tgaggccccg ggttcgatcc    60
ccggcatctc ca                                                        72

<210> SEQ ID NO 217
<211> LENGTH: 72
<212> TYPE: DNA
<213> ORGANISM: Homo sapiens

<400> SEQUENCE: 217
ggggatgtag ctcagtggta gagcgcatgc tttgcatgta tgaggtcccg ggttcgatcc    60
ccggcatctc ca                                                        72

<210> SEQ ID NO 218
```

```
<211> LENGTH: 72
<212> TYPE: DNA
<213> ORGANISM: Homo sapiens

<400> SEQUENCE: 218
gggggtgtag ctcagtggta gagcgcatgc tttgcatgta tgaggtcccg ggttcgatcc    60
ccggcacctc ca                                                        72

<210> SEQ ID NO 219
<211> LENGTH: 73
<212> TYPE: DNA
<213> ORGANISM: Homo sapiens

<400> SEQUENCE: 219
gggccagtgg cgcaatggat aacgcgtctg actacggatc agaagattct aggttcgact    60
cctggctggc tcg                                                       73

<210> SEQ ID NO 220
<211> LENGTH: 73
<212> TYPE: DNA
<213> ORGANISM: Homo sapiens

<400> SEQUENCE: 220
gggccagtgg cgcaatggat aacgcgtctg actacggatc agaagattct aggttcgact    60
cctggctggc tcg                                                       73

<210> SEQ ID NO 221
<211> LENGTH: 73
<212> TYPE: DNA
<213> ORGANISM: Homo sapiens

<400> SEQUENCE: 221
gggccagtgg cgcaatggat aacgcgtctg actacggatc agaagattct aggttcgact    60
cctggctggc tcg                                                       73

<210> SEQ ID NO 222
<211> LENGTH: 73
<212> TYPE: DNA
<213> ORGANISM: Homo sapiens

<400> SEQUENCE: 222
gggccagtgg cgcaatggat aacgcgtctg actacggatc agaagattct aggttcgact    60
cctggctggc tcg                                                       73

<210> SEQ ID NO 223
<211> LENGTH: 73
<212> TYPE: DNA
<213> ORGANISM: Homo sapiens

<400> SEQUENCE: 223
gggccagtgg cgcaatggat aacgcgtctg actacggatc agaagattcc aggttcgact    60
cctggctggc tcg                                                       73

<210> SEQ ID NO 224
<211> LENGTH: 73
<212> TYPE: DNA
<213> ORGANISM: Homo sapiens

<400> SEQUENCE: 224
gggccagtgg cgcaatggat aacgcgtctg actacggatc agaagattcc aggttcgact    60
```
cctggctggc tcg                                                            73

<210> SEQ ID NO 225
<211> LENGTH: 73
<212> TYPE: DNA
<213> ORGANISM: Homo sapiens

<400> SEQUENCE: 225
gggccagtgg cgcaatggat aacgcgtctg actacggatc agaagattcc aggttcgact        60
cctggctggc tcg                                                            73

<210> SEQ ID NO 226
<211> LENGTH: 73
<212> TYPE: DNA
<213> ORGANISM: Homo sapiens

<400> SEQUENCE: 226
gacccagtgg cctaatggat aaggcatcag cctccggagc tggggattgt gggttcgagt        60
cccatctggg tcg                                                            73

<210> SEQ ID NO 227
<211> LENGTH: 73
<212> TYPE: DNA
<213> ORGANISM: Homo sapiens

<400> SEQUENCE: 227
gacccagtgg cctaatggat aaggcatcag cctccggagc tggggattgt gggttcgagt        60
cccatctggg tcg                                                            73

<210> SEQ ID NO 228
<211> LENGTH: 73
<212> TYPE: DNA
<213> ORGANISM: Homo sapiens

<400> SEQUENCE: 228
ggccgcgtgg cctaatggat aaggcgtctg attccggatc agaagattga gggttcgagt        60
cccttcgtgg tcg                                                            73

<210> SEQ ID NO 229
<211> LENGTH: 73
<212> TYPE: DNA
<213> ORGANISM: Homo sapiens

<400> SEQUENCE: 229
ggccgcgtgg cctaatggat aaggcgtctg attccggatc agaagattga gggttcgagt        60
cccttcgtgg tcg                                                            73

<210> SEQ ID NO 230
<211> LENGTH: 73
<212> TYPE: DNA
<213> ORGANISM: Homo sapiens

<400> SEQUENCE: 230
ggccgcgtgg cctaatggat aaggcgtctg attccggatc agaagattga gggttcgagt        60
cccttcgtgg tcg                                                            73

<210> SEQ ID NO 231
<211> LENGTH: 73
<212> TYPE: DNA

<213> ORGANISM: Homo sapiens

<400> SEQUENCE: 231
gccccagtgg cctgatggat aaggtactgg cctcctaagc cagggattgt gggttcgagt    60
tccacctggg gta                                                      73

<210> SEQ ID NO 232
<211> LENGTH: 73
<212> TYPE: DNA
<213> ORGANISM: Homo sapiens

<400> SEQUENCE: 232
gccccagtgg cctaatggat aaggcattgg cctcctaagc cagggattgt gggttcgagt    60
cccatctggg gtg                                                      73

<210> SEQ ID NO 233
<211> LENGTH: 73
<212> TYPE: DNA
<213> ORGANISM: Homo sapiens

<400> SEQUENCE: 233
gccccggtgg cctaatggat aaggcattgg cctcctaagc cagggattgt gggttcgagt    60
cccacccggg gta                                                      73

<210> SEQ ID NO 234
<211> LENGTH: 73
<212> TYPE: DNA
<213> ORGANISM: Homo sapiens

<400> SEQUENCE: 234
gccccagtgg cctaatggat aaggcactgg cctcctaagc cagggattgt gggttcgagt    60
cccacctggg gtg                                                      73

<210> SEQ ID NO 235
<211> LENGTH: 73
<212> TYPE: DNA
<213> ORGANISM: Homo sapiens

<400> SEQUENCE: 235
gccccagtgg cctaatggat aaggcactgg cctcctaagc cagggattgt gggttcgagt    60
cccacctggg gta                                                      73

<210> SEQ ID NO 236
<211> LENGTH: 73
<212> TYPE: DNA
<213> ORGANISM: Homo sapiens

<400> SEQUENCE: 236
ggccgtgtgg cctaatggat aaggcgtctg acttcggatc aaaagattgc aggtttgagt    60
tctgccacgg tcg                                                      73

<210> SEQ ID NO 237
<211> LENGTH: 73
<212> TYPE: DNA
<213> ORGANISM: Homo sapiens

<400> SEQUENCE: 237
gaccacgtgg cctaatggat aaggcgtctg acttcggatc agaagattga gggttcgaat    60
cccttcgtgg ttg                                                      73

<210> SEQ ID NO 238
<211> LENGTH: 73
<212> TYPE: DNA
<213> ORGANISM: Homo sapiens

<400> SEQUENCE: 238
gaccacgtgg cctaatggat aaggcgtctg acttcggatc agaagattga gggttcgaat      60
cccttcgtgg tta                                                        73

<210> SEQ ID NO 239
<211> LENGTH: 73
<212> TYPE: DNA
<213> ORGANISM: Homo sapiens

<400> SEQUENCE: 239
gaccgcgtgg cctaatggat aaggcgtctg acttcggatc agaagattga gggttcgagt      60
cccttcgtgg tcg                                                        73

<210> SEQ ID NO 240
<211> LENGTH: 73
<212> TYPE: DNA
<213> ORGANISM: Homo sapiens

<400> SEQUENCE: 240
gaccacgtgg cctaatggat aaggcgtctg acttcggatc agaagattga gggttcgaat      60
ccctccgtgg tta                                                        73

<210> SEQ ID NO 241
<211> LENGTH: 73
<212> TYPE: DNA
<213> ORGANISM: Homo sapiens

<400> SEQUENCE: 241
ggccgcgtgg cctaatggat aaggcgtctg acttcggatc agaagattgc aggttcgagt      60
cctgccgcgg tcg                                                        73

<210> SEQ ID NO 242
<211> LENGTH: 74
<212> TYPE: DNA
<213> ORGANISM: Homo sapiens

<400> SEQUENCE: 242
gtctctgtgg cgcaatggac gagcgcgctg gacttctaat ccagaggttc cgggttcgag      60
tcccggcaga gatg                                                       74

<210> SEQ ID NO 243
<211> LENGTH: 91
<212> TYPE: DNA
<213> ORGANISM: Homo sapiens

<400> SEQUENCE: 243
ggctctgtgg cgcaatggat agcgcattgg acttctagct gagcctagtg tggtcattca      60
aaggttgtgg gttcgagtcc caccagagtc g                                    91

<210> SEQ ID NO 244
<211> LENGTH: 87
<212> TYPE: DNA
<213> ORGANISM: Homo sapiens

<400> SEQUENCE: 244
ggctctgtgg cgcaatggat agcgcattgg acttctagcc taaatcaaga gattcaaagg    60
ttgcgggttc gagtccctcc agagtcg    87

<210> SEQ ID NO 245
<211> LENGTH: 86
<212> TYPE: DNA
<213> ORGANISM: Homo sapiens

<400> SEQUENCE: 245
ggctctgtgg cgcaatggat agcgcattgg acttctagat agttagagaa attcaaaggt    60
tgtgggttcg agtcccacca gagtcg    86

<210> SEQ ID NO 246
<211> LENGTH: 88
<212> TYPE: DNA
<213> ORGANISM: Homo sapiens

<400> SEQUENCE: 246
ggctctgtgg cgcaatggat agcgcattgg acttctagtg acgaatagag caattcaaag    60
gttgtgggtt cgaatcccac cagagtcg    88

<210> SEQ ID NO 247
<211> LENGTH: 85
<212> TYPE: DNA
<213> ORGANISM: Homo sapiens

<400> SEQUENCE: 247
ggctccgtgg cgcaatggat agcgcattgg acttctagag gctgaaggca ttcaaaggtt    60
ccgggttcga gtcccggcgg agtcg    85

<210> SEQ ID NO 248
<211> LENGTH: 74
<212> TYPE: DNA
<213> ORGANISM: Homo sapiens

<400> SEQUENCE: 248
gtctctgtgg cgcaatcggt cagagcgttc ggctattaac cgaacggtga gtagttcaag    60
accacccagg gacg    74

<210> SEQ ID NO 249
<211> LENGTH: 76
<212> TYPE: DNA
<213> ORGANISM: Homo sapiens

<400> SEQUENCE: 249
gtctctgtgg cgccatcggt tagtgccttc ggctgtttga accgaaaggc tggtggttca    60
agcccaccca gagatg    76

<210> SEQ ID NO 250
<211> LENGTH: 74
<212> TYPE: DNA
<213> ORGANISM: Homo sapiens

<400> SEQUENCE: 250
atctccgtgg agcaattggt tagcgcgttc ggccgttaac cggaaagttg gtggttcgag    60
cctacccagg gacg    74

```
<210> SEQ ID NO 251
<211> LENGTH: 74
<212> TYPE: DNA
<213> ORGANISM: Homo sapiens

<400> SEQUENCE: 251
gtctctgtgg tgcaatcggt tagcgcgttc ggctgttaac cataaggttg gtggttacag    60
accacccagg gacg                                                      74

<210> SEQ ID NO 252
<211> LENGTH: 74
<212> TYPE: DNA
<213> ORGANISM: Homo sapiens

<400> SEQUENCE: 252
gtttctgtag cgcgatcggt tagcgccttc ggctgttaaa cgaaaggttg gtggttcgtt    60 cccacccgg gaca                                                       74

<210> SEQ ID NO 253
<211> LENGTH: 74
<212> TYPE: DNA
<213> ORGANISM: Homo sapiens

<400> SEQUENCE: 253
gtctctgtgg cgcaatcggt tagcgcgttt gactgttaac tgaaaggttg gtggtgcaag    60
cccatccagg gatg                                                      74

<210> SEQ ID NO 254
<211> LENGTH: 74
<212> TYPE: DNA
<213> ORGANISM: Homo sapiens

<400> SEQUENCE: 254
gtctctgtgg cgcaatcggt tagcgcgttt gactgttaac tgaaaggttg gtggtgcaag    60
cccatccagg gatg                                                      74

<210> SEQ ID NO 255
<211> LENGTH: 74
<212> TYPE: DNA
<213> ORGANISM: Homo sapiens

<400> SEQUENCE: 255
gtctctgtgg cgcaatcggt tagcgcgttt gactgttaac tgaaaggttg gtggtgcaag    60
cccatccagg gatg                                                      74

<210> SEQ ID NO 256
<211> LENGTH: 74
<212> TYPE: DNA
<213> ORGANISM: Homo sapiens

<400> SEQUENCE: 256
gtctctgtgg cgcaatcggt tagcgcgttt gactgttaac tgaaaggttg gtggtgcaag    60
cccatccagg gatg                                                      74

<210> SEQ ID NO 257
<211> LENGTH: 74
<212> TYPE: DNA
<213> ORGANISM: Homo sapiens

<400> SEQUENCE: 257
```

```
gtctctgtgg cgcaatcggt tagcgcgttt gactgttaac tgaaaggttg gtggtgcaag    60
cccatccagg gatg                                                      74
```

<210> SEQ ID NO 258
<211> LENGTH: 74
<212> TYPE: DNA
<213> ORGANISM: Homo sapiens

<400> SEQUENCE: 258

```
atctccgtgg agcaattggt tagcgcgttc ggctgttaac cggaaagttg gtggttcgag    60
cctacccagg gacg                                                      74
```

<210> SEQ ID NO 259
<211> LENGTH: 74
<212> TYPE: DNA
<213> ORGANISM: Homo sapiens

<400> SEQUENCE: 259

```
gtctctgtgg tgcaatcggt tagcgcgttc cgctgttaac cgaaagcttg gtggtttgag    60
cccacccagg gatg                                                      74
```

<210> SEQ ID NO 260
<211> LENGTH: 74
<212> TYPE: DNA
<213> ORGANISM: Homo sapiens

<400> SEQUENCE: 260

```
gtctctgtgg tgcaatcggt tagcgcgttc ggctgttaac cataaggttg gtggttagag    60
accacccagg gacg                                                      74
```

<210> SEQ ID NO 261
<211> LENGTH: 74
<212> TYPE: DNA
<213> ORGANISM: Homo sapiens

<400> SEQUENCE: 261

```
gtctctgtgg cgcaatcggc tagcgcgttt ggctgttaac taaaaagttg gtggttcgaa    60
cacacccaga ggcg                                                      74
```

<210> SEQ ID NO 262
<211> LENGTH: 74
<212> TYPE: DNA
<213> ORGANISM: Homo sapiens

<400> SEQUENCE: 262

```
gtctctgtgg tgcaatcggt tagcgcgttc cgctgttaac cgaaagcttg gtggttcgag    60
cccacccagg gatg                                                      74
```

<210> SEQ ID NO 263
<211> LENGTH: 74
<212> TYPE: DNA
<213> ORGANISM: Homo sapiens

<400> SEQUENCE: 263

```
gtctctgtgg tgcaatcggt tagcgcgttc cgctgttaac cgaaagcttg gtggttcgag    60
cccacccagg gatg                                                      74
```

<210> SEQ ID NO 264
<211> LENGTH: 74

```
<212> TYPE: DNA
<213> ORGANISM: Homo sapiens

<400> SEQUENCE: 264
gtctctgtgg cgcaatcggc tagcgcgttt ggctgttaac taaaaggttg gcggttcgaa    60
cccacccaga ggcg                                                      74

<210> SEQ ID NO 265
<211> LENGTH: 74
<212> TYPE: DNA
<213> ORGANISM: Homo sapiens

<400> SEQUENCE: 265
gtctctgtgg cgcaatcggt tagcgcgttc ggctgttaac tgaaaggtta gtggttcgag    60
cccacccggg gacg                                                      74

<210> SEQ ID NO 266
<211> LENGTH: 74
<212> TYPE: DNA
<213> ORGANISM: Homo sapiens

<400> SEQUENCE: 266
gtctctgtgg cgcaatcggt tagcgcgttc ggctgttaac tgaaaggtta gtggttcgag    60
cccacccggg gacg                                                      74

<210> SEQ ID NO 267
<211> LENGTH: 74
<212> TYPE: DNA
<213> ORGANISM: Homo sapiens

<400> SEQUENCE: 267
gtctctgtgg cgcaatcggc tagcgcgttt ggctgttaac taaaaggttg gtggttcgaa    60
cccacccaga ggcg                                                      74

<210> SEQ ID NO 268
<211> LENGTH: 74
<212> TYPE: DNA
<213> ORGANISM: Homo sapiens

<400> SEQUENCE: 268
gtctctgtgg cgtagtcggt tagcgcgttc ggctgttaac cgaaaagttg gtggttcgag    60
cccacccagg aacg                                                      74

<210> SEQ ID NO 269
<211> LENGTH: 74
<212> TYPE: DNA
<213> ORGANISM: Homo sapiens

<400> SEQUENCE: 269
gtctctgtgg cgcaatgggt tagcgcgttc ggctgttaac cgaaaggttg gtggttcgag    60
cccatccagg gacg                                                      74

<210> SEQ ID NO 270
<211> LENGTH: 74
<212> TYPE: DNA
<213> ORGANISM: Homo sapiens

<400> SEQUENCE: 270
gtctctgtgg cgcaatcggt tagcgcgttc ggctgttaac tgaaaggttg gtggttcgag    60
```

```
cccacccagg gacg                                                    74

<210> SEQ ID NO 271
<211> LENGTH: 74
<212> TYPE: DNA
<213> ORGANISM: Homo sapiens

<400> SEQUENCE: 271
gtctctgtgg cgcaatcggt tagcgcgttc ggctgttaac cgaaagattg gtggttcgag  60
cccacccagg gacg                                                    74

<210> SEQ ID NO 272
<211> LENGTH: 74
<212> TYPE: DNA
<213> ORGANISM: Homo sapiens

<400> SEQUENCE: 272
gtctctgtgg cgcaatcggt tagcgcattc ggctgttaac cgaaaggttg gtggttcgag  60
cccacccagg gacg                                                    74

<210> SEQ ID NO 273
<211> LENGTH: 74
<212> TYPE: DNA
<213> ORGANISM: Homo sapiens

<400> SEQUENCE: 273
gtctctgtgg cgcaatcggt tagcgcattc ggctgttaac cgaaaggttg gtggttcgag  60
cccacccagg gacg                                                    74

<210> SEQ ID NO 274
<211> LENGTH: 74
<212> TYPE: DNA
<213> ORGANISM: Homo sapiens

<400> SEQUENCE: 274
gtctctgtgg cgcaatcggt tagcgcgttc ggctgttaac cgaaaggttg gtggttcgag  60
cccacccagg gacg                                                    74

<210> SEQ ID NO 275
<211> LENGTH: 74
<212> TYPE: DNA
<213> ORGANISM: Homo sapiens

<400> SEQUENCE: 275
gtctctgtgg cgcaatcggt tagcgcgttc ggctgttaac cgaaaggttg gtggttcgag  60
cccacccagg gacg                                                    74

<210> SEQ ID NO 276
<211> LENGTH: 74
<212> TYPE: DNA
<213> ORGANISM: Homo sapiens

<400> SEQUENCE: 276
gtctctgtgg cgcaatcggt tagcgcgttc ggctgttaac cgaaaggttg gtggttcgag  60
cccacccagg gacg                                                    74

<210> SEQ ID NO 277
<211> LENGTH: 74
<212> TYPE: DNA
<213> ORGANISM: Homo sapiens
```

<400> SEQUENCE: 277
gtctctgtgg cgcaatcggt tagcgcgttc ggctgttaac cgaaaggttg gtggttcgag    60
cccacccagg gacg    74

<210> SEQ ID NO 278
<211> LENGTH: 74
<212> TYPE: DNA
<213> ORGANISM: Homo sapiens

<400> SEQUENCE: 278
gtctctgtgg cgcaatcggt tagcgcgttc ggctgttaac cgaaaggttg gtggttcgag    60
cccacccagg gacg    74

<210> SEQ ID NO 279
<211> LENGTH: 74
<212> TYPE: DNA
<213> ORGANISM: Homo sapiens

<400> SEQUENCE: 279
gtctctgtgg cgcaatcggt tagcgcgttc ggctgttaac cgaaaggttg gtggttcgag    60
cccacccagg gacg    74

<210> SEQ ID NO 280
<211> LENGTH: 74
<212> TYPE: DNA
<213> ORGANISM: Homo sapiens

<400> SEQUENCE: 280
gtctctgtgg cgcaatcggt tagcgcgttc ggctgttaac cgaaaggttg gtggttcgat    60
cccacccagg gacg    74

<210> SEQ ID NO 281
<211> LENGTH: 72
<212> TYPE: DNA
<213> ORGANISM: Homo sapiens

<400> SEQUENCE: 281
tccttgttac tatagtggta agtatctctg cctgtcatgc atgagagagg gggtcgattc    60
cctgacgggg ag    72

<210> SEQ ID NO 282
<211> LENGTH: 71
<212> TYPE: DNA
<213> ORGANISM: Homo sapiens

<400> SEQUENCE: 282
tccttgttag tatagtggtg agtgtttctg cctgtcatgt ggagactgga gtttgagtcc    60
ccaacaggga g    71

<210> SEQ ID NO 283
<211> LENGTH: 72
<212> TYPE: DNA
<213> ORGANISM: Homo sapiens

<400> SEQUENCE: 283
tactcgttag tatagtggtg cgtatccccg tctgtcacgc gggagagcgg ggttcgctct    60
cccgacgggg ag    72

<210> SEQ ID NO 284
<211> LENGTH: 71
<212> TYPE: DNA
<213> ORGANISM: Homo sapiens

<400> SEQUENCE: 284
ttcttgttaa tatagtggtg agtattccca cctgtcatgc gggagacggg gttcaattcc    60
ctgatgggga g                                                         71

<210> SEQ ID NO 285
<211> LENGTH: 72
<212> TYPE: DNA
<213> ORGANISM: Homo sapiens

<400> SEQUENCE: 285
tcctcatcag tatagtggtg agtatccccg cctgtcacgc gggagactgg ggttcgattc    60
cctgaggagg ag                                                        72

<210> SEQ ID NO 286
<211> LENGTH: 72
<212> TYPE: DNA
<213> ORGANISM: Homo sapiens

<400> SEQUENCE: 286
tcctcgttag tatggtggtg agtatccctg cctgtcacgc gggagaccgg ggttcgattc    60
cccaacgggg ag                                                        72

<210> SEQ ID NO 287
<211> LENGTH: 72
<212> TYPE: DNA
<213> ORGANISM: Homo sapiens

<400> SEQUENCE: 287
tcctcgttag tatagtggtg agtgtccccg tctgtcacgc gggagaccgg ggttcgattc    60
cccgacgggg ag                                                        72

<210> SEQ ID NO 288
<211> LENGTH: 72
<212> TYPE: DNA
<213> ORGANISM: Homo sapiens

<400> SEQUENCE: 288
tcctcgttag tatagtggtg agtatccccg cctgtcacgc gggagaccgg ggttcgattc    60
cccgacgggg ag                                                        72

<210> SEQ ID NO 289
<211> LENGTH: 72
<212> TYPE: DNA
<213> ORGANISM: Homo sapiens

<400> SEQUENCE: 289
tcctcgttag tatagtggtg agtatccccg cctgtcacgc gggagaccgg ggttcgattc    60
cccgacgggg ag                                                        72

<210> SEQ ID NO 290
<211> LENGTH: 72
<212> TYPE: DNA
<213> ORGANISM: Homo sapiens

<400> SEQUENCE: 290

-continued tcctcgttag tatagtggtg agtatccccg cctgtcacgc gggagaccgg ggttcgattc    60
cccgacgggg ag                                                       72

<210> SEQ ID NO 291
<211> LENGTH: 72
<212> TYPE: DNA
<213> ORGANISM: Homo sapiens

<400> SEQUENCE: 291
tcctcgttag tatagtggtg agtatccccg cctgtcacgc gggagaccgg ggttcgattc    60
cccgacgggg ag                                                       72

<210> SEQ ID NO 292
<211> LENGTH: 72
<212> TYPE: DNA
<213> ORGANISM: Homo sapiens

<400> SEQUENCE: 292
tcctcgttag tatagtggtg agtatccccg cctgtcacgc gggagaccgg ggttcgattc    60
cccgacgggg ag                                                       72

<210> SEQ ID NO 293
<211> LENGTH: 72
<212> TYPE: DNA
<213> ORGANISM: Homo sapiens

<400> SEQUENCE: 293
tcctcgttag tatagtggtg agtatccccg cctgtcacgc gggagaccgg ggttcgattc    60
cccgacgggg ag                                                       72

<210> SEQ ID NO 294
<211> LENGTH: 72
<212> TYPE: DNA
<213> ORGANISM: Homo sapiens

<400> SEQUENCE: 294
tcctcgttag tatagtggtg agtatccccg cctgtcacgc gggagaccgg ggttcgattc    60
cccgacgggg ag                                                       72

<210> SEQ ID NO 295
<211> LENGTH: 72
<212> TYPE: DNA
<213> ORGANISM: Homo sapiens

<400> SEQUENCE: 295
tcctcgttag tatagtggtg agtatccccg cctgtcacgc gggagaccgg ggttcgattc    60
cccgacgggg ag                                                       72

<210> SEQ ID NO 296
<211> LENGTH: 72
<212> TYPE: DNA
<213> ORGANISM: Homo sapiens

<400> SEQUENCE: 296
tcctcgttag tatagtggtg agtatccccg cctgtcacgc gggagaccgg ggttcgattc    60
cccgacgggg ag                                                       72

<210> SEQ ID NO 297

```
<211> LENGTH: 72
<212> TYPE: DNA
<213> ORGANISM: Homo sapiens

<400> SEQUENCE: 297
tcctcgttag tatagtggtg agtatccccg cctgtcacgc gggagaccgg ggttcgattc    60
cccgacgggg ag                                                       72

<210> SEQ ID NO 298
<211> LENGTH: 72
<212> TYPE: DNA
<213> ORGANISM: Homo sapiens

<400> SEQUENCE: 298
tcctcgttag tatagtggtg agtatccccg cctgtcacgc gggagaccgg ggttcgattc    60
cccgacgggg ag                                                       72

<210> SEQ ID NO 299
<211> LENGTH: 72
<212> TYPE: DNA
<213> ORGANISM: Homo sapiens

<400> SEQUENCE: 299
tcctcgttag tatagtggtt agtatccccg cctgtcacgc gggagaccgg ggttcaattc    60
cccgacgggg ag                                                       72

<210> SEQ ID NO 300
<211> LENGTH: 72
<212> TYPE: DNA
<213> ORGANISM: Homo sapiens

<400> SEQUENCE: 300
gggggtaggg ctcagggata gagcatttga ctgcagatca agaggtcccc ggttcgaatc    60
taggtgcccc ct                                                       72

<210> SEQ ID NO 301
<211> LENGTH: 72
<212> TYPE: DNA
<213> ORGANISM: Homo sapiens

<400> SEQUENCE: 301
gggggtatag ctcacaggta gagcatttga ctgcagatca agaggtcccc ggttcaaatc    60
cggttactcc ct                                                       72

<210> SEQ ID NO 302
<211> LENGTH: 72
<212> TYPE: DNA
<213> ORGANISM: Homo sapiens

<400> SEQUENCE: 302
gggcgtatag ctcaggggta gagcatttga ctgcagatca agaggtcccc agttcaaatc    60
tgggtgccca ct                                                       72

<210> SEQ ID NO 303
<211> LENGTH: 72
<212> TYPE: DNA
<213> ORGANISM: Homo sapiens

<400> SEQUENCE: 303
gggggtatag ctcacaggta gagcatttga ctgcagatca agaggtcccc ggttcaaatc    60
```
tgggtgcccc ct                                                          72

<210> SEQ ID NO 304
<211> LENGTH: 72
<212> TYPE: DNA
<213> ORGANISM: Homo sapiens

<400> SEQUENCE: 304
gggcgtatag ctcaggggta gagcatttga ctgcagatca agaggtcccc agttcaaatc      60
tgggtgcccc ct                                                          72

<210> SEQ ID NO 305
<211> LENGTH: 72
<212> TYPE: DNA
<213> ORGANISM: Homo sapiens

<400> SEQUENCE: 305
gggggtatag ctcaggggta gagcatttga ctgcaaatca agaggtccct gattcaaatc      60
caggtgcccc ct                                                          72

<210> SEQ ID NO 306
<211> LENGTH: 72
<212> TYPE: DNA
<213> ORGANISM: Homo sapiens

<400> SEQUENCE: 306
gggggtatag ttcaggggta gagcatttga ctgcagatca agaggtccct ggttcaaatc      60
caggtgcccc ct                                                          72

<210> SEQ ID NO 307
<211> LENGTH: 72
<212> TYPE: DNA
<213> ORGANISM: Homo sapiens

<400> SEQUENCE: 307
ggggatatag ctcaggggta gagcatttga ctgcagatca agaggtcccc ggttcaaatc      60
cgggtgcccc cc                                                          72

<210> SEQ ID NO 308
<211> LENGTH: 72
<212> TYPE: DNA
<213> ORGANISM: Homo sapiens

<400> SEQUENCE: 308
gggggtatag ctcaggggta gagcacttga ctgcagatca agaagtcctt ggttcaaatc      60
caggtgcccc ct                                                          72

<210> SEQ ID NO 309
<211> LENGTH: 72
<212> TYPE: DNA
<213> ORGANISM: Homo sapiens

<400> SEQUENCE: 309
gggggtatag ctcaggggta gagcatttga ctgcagatca agaggtctct ggttcaaatc      60
caggtgcccc ct                                                          72

<210> SEQ ID NO 310
<211> LENGTH: 72
<212> TYPE: DNA

<213> ORGANISM: Homo sapiens

<400> SEQUENCE: 310
gggggtatag ctcaggggta gagcatttga ctgcagatca agaagtcccc ggttcaaatc    60
cgggtgcccc ct    72

<210> SEQ ID NO 311
<211> LENGTH: 72
<212> TYPE: DNA
<213> ORGANISM: Homo sapiens

<400> SEQUENCE: 311
gggggtatag ctcaggggta gagcatttga ctgcagatca agaggtcccc agttcaaatc    60
tgggtgcccc ct    72

<210> SEQ ID NO 312
<211> LENGTH: 72
<212> TYPE: DNA
<213> ORGANISM: Homo sapiens

<400> SEQUENCE: 312
gggggtatag cttaggggta gagcatttga ctgcagatca aaaggtccct ggttcaaatc    60
caggtgcccc tt    72

<210> SEQ ID NO 313
<211> LENGTH: 72
<212> TYPE: DNA
<213> ORGANISM: Homo sapiens

<400> SEQUENCE: 313
gggggtatag cttagcggta gagcatttga ctgcagatca agaggtcccc ggttcaaatc    60
cgggtgcccc ct    72

<210> SEQ ID NO 314
<211> LENGTH: 72
<212> TYPE: DNA
<213> ORGANISM: Homo sapiens

<400> SEQUENCE: 314
gggggtatag ctcaggggta gagcatttga ctgcagatca agaggtccct ggttcaaatc    60
caggtgcccc cc    72

<210> SEQ ID NO 315
<211> LENGTH: 72
<212> TYPE: DNA
<213> ORGANISM: Homo sapiens

<400> SEQUENCE: 315
gggggtatag ctcaggggta gagcatttga ctgcagatca agaggtccct ggttcaaatc    60
caggtgcccc ct    72

<210> SEQ ID NO 316
<211> LENGTH: 72
<212> TYPE: DNA
<213> ORGANISM: Homo sapiens

<400> SEQUENCE: 316
gggggtatag ctcaggggta gagcatttga ctgcagatca agaggtccct ggttcaaatc    60
caggtgcccc ct    72

<210> SEQ ID NO 317
<211> LENGTH: 72
<212> TYPE: DNA
<213> ORGANISM: Homo sapiens

<400> SEQUENCE: 317
gggggtatag ctcaggggta gagcatttga ctgcagatca agaggtccct ggttcaaatc    60
caggtgcccc ct                                                       72

<210> SEQ ID NO 318
<211> LENGTH: 72
<212> TYPE: DNA
<213> ORGANISM: Homo sapiens

<400> SEQUENCE: 318
gggggtatag ctcaggggta gagcatttga ctgcagatca agaggtccct ggttcaaatc    60
caggtgcccc ct                                                       72

<210> SEQ ID NO 319
<211> LENGTH: 72
<212> TYPE: DNA
<213> ORGANISM: Homo sapiens

<400> SEQUENCE: 319
gggggtatag ctcaggggta gagcatttga ctgcagatca agaggtcccc ggttcaaatc    60
cgggtgcccc ct                                                       72

<210> SEQ ID NO 320
<211> LENGTH: 73
<212> TYPE: DNA
<213> ORGANISM: Homo sapiens

<400> SEQUENCE: 320
gggggtatag ctcaggtggt agagcatttg actgcagatc aagaggtccc cggttcaaat    60
ccgggtgccc cct                                                      73

<210> SEQ ID NO 321
<211> LENGTH: 72
<212> TYPE: DNA
<213> ORGANISM: Homo sapiens

<400> SEQUENCE: 321
gggggtgtag ctcagtggta gagcatttga ctgcagatca agaggtccct ggttcaaatc    60
caggtgcccc ct                                                       72

<210> SEQ ID NO 322
<211> LENGTH: 73
<212> TYPE: DNA
<213> ORGANISM: Homo sapiens

<400> SEQUENCE: 322
gggggtatag ctcagtgggt agagcatttg actgcagatc aagaggtccc cggttcaaat    60
ccgggtgccc cct                                                      73

<210> SEQ ID NO 323
<211> LENGTH: 72
<212> TYPE: DNA
<213> ORGANISM: Homo sapiens -continued

<400> SEQUENCE: 323
gggggtatag ctcagtggta gagcatttga ctgcagatca agaggtccct ggttcaaatc     60
cgggtgcccc ct     72

<210> SEQ ID NO 324
<211> LENGTH: 72
<212> TYPE: DNA
<213> ORGANISM: Homo sapiens

<400> SEQUENCE: 324
gggggtatag ctcaggggta gagcacttga ctgcagatca agaggtccct ggttcaaatc     60
caggtgcccc ct     72

<210> SEQ ID NO 325
<211> LENGTH: 72
<212> TYPE: DNA
<213> ORGANISM: Homo sapiens

<400> SEQUENCE: 325
gggggtatag ctcagtggta gagcatttga ctgcagatca agaggtcccc ggttcaaatc     60
cgggtgcccc ct     72

<210> SEQ ID NO 326
<211> LENGTH: 72
<212> TYPE: DNA
<213> ORGANISM: Homo sapiens

<400> SEQUENCE: 326
gggggtatag ctcagtggta gagcatttga ctgcagatca agaggtcccc ggttcaaatc     60
cgggtgcccc ct     72

<210> SEQ ID NO 327
<211> LENGTH: 72
<212> TYPE: DNA
<213> ORGANISM: Homo sapiens

<400> SEQUENCE: 327
gggggtatag ctcagtggta gagcatttga ctgcagatca agaggtcccc ggttcaaatc     60
cgggtgcccc ct     72

<210> SEQ ID NO 328
<211> LENGTH: 72
<212> TYPE: DNA
<213> ORGANISM: Homo sapiens

<400> SEQUENCE: 328
gggggtatag ctcagtggta gagcatttga ctgcagatca agaggtcccc ggttcaaatc     60
cgggtgcccc ct     72

<210> SEQ ID NO 329
<211> LENGTH: 72
<212> TYPE: DNA
<213> ORGANISM: Homo sapiens

<400> SEQUENCE: 329 ggggcatag ctcagtggta gagcatttga ctgcagatca agaggtccct ggttcaaatc     60
caggtgcccc ct     72

```
<210> SEQ ID NO 330
<211> LENGTH: 74
<212> TYPE: DNA
<213> ORGANISM: Homo sapiens

<400> SEQUENCE: 330
ggcagtatgg tagagtggtt aagatcatga actctgaagt cagagatact tgaatttgaa    60
tgctggttct gtca                                                      74

<210> SEQ ID NO 331
<211> LENGTH: 78
<212> TYPE: DNA
<213> ORGANISM: Homo sapiens

<400> SEQUENCE: 331
ggcagtgtag cccagaggtt caagggcatt cgctctggta tcagaagggt ctgggttcaa    60
atcccttgtg cactgctt                                                  78

<210> SEQ ID NO 332
<211> LENGTH: 73
<212> TYPE: DNA
<213> ORGANISM: Homo sapiens

<400> SEQUENCE: 332
gagctgtagc atagtgatta gggacatgga ctctggagcc aaatctgcct gggttctagt    60
cccagctgtc tca                                                       73

<210> SEQ ID NO 333
<211> LENGTH: 73
<212> TYPE: DNA
<213> ORGANISM: Homo sapiens

<400> SEQUENCE: 333
ggttccatgg tgtaatggta agcaccctgg actctgaatc cagcaaccag agttccagtc    60
tcagcgtgga cct                                                       73

<210> SEQ ID NO 334
<211> LENGTH: 72
<212> TYPE: DNA
<213> ORGANISM: Homo sapiens

<400> SEQUENCE: 334
ggttccatgg tgtaatggtg accactttgg actctgaata cagtgatcag agttcaagtc    60
tcactggaac ct                                                        72

<210> SEQ ID NO 335
<211> LENGTH: 72
<212> TYPE: DNA
<213> ORGANISM: Homo sapiens

<400> SEQUENCE: 335
ggttccatgg tgtaatggtg agcactttgg actctgaata cagtgatcag agttcaagtc    60
tcactgggac ct                                                        72

<210> SEQ ID NO 336
<211> LENGTH: 72
<212> TYPE: DNA
<213> ORGANISM: Homo sapiens

<400> SEQUENCE: 336
```

```
ggttccatgg tgtaatggtg agcactttgg actctgaata cagtgatcag agttcaagtc    60
tcactgggac ct                                                        72

<210> SEQ ID NO 337
<211> LENGTH: 72
<212> TYPE: DNA
<213> ORGANISM: Homo sapiens

<400> SEQUENCE: 337
ggttccatgg tgtaatggtg agcactttgg actctgaata cagtgatcag agttcaagtc    60
tcactgggac ct                                                        72

<210> SEQ ID NO 338
<211> LENGTH: 72
<212> TYPE: DNA
<213> ORGANISM: Homo sapiens

<400> SEQUENCE: 338
ggttccatgg tgtaatggta agcactctgg actctgaatc cagccatctg agttcgagtc    60
tctgtggaac ct                                                        72

<210> SEQ ID NO 339
<211> LENGTH: 72
<212> TYPE: DNA
<213> ORGANISM: Homo sapiens

<400> SEQUENCE: 339
ggccccatgg tgtaatggtc agcactctgg actctgaatc cagcgatccg agttcaaatc    60
tcggtgggac cc                                                        72

<210> SEQ ID NO 340
<211> LENGTH: 72
<212> TYPE: DNA
<213> ORGANISM: Homo sapiens

<400> SEQUENCE: 340
ggttccatgg tgtaatggtt agcactctgg actctgaatc cggtaatccg agttcaaatc    60
tcggtggaac ct                                                        72

<210> SEQ ID NO 341
<211> LENGTH: 72
<212> TYPE: DNA
<213> ORGANISM: Homo sapiens

<400> SEQUENCE: 341
ggttccatgg tgtaatggta agcactctgg actctgaatc cagcgatccg agttcgagtc    60
tcggtggaac ct                                                        72

<210> SEQ ID NO 342
<211> LENGTH: 72
<212> TYPE: DNA
<213> ORGANISM: Homo sapiens

<400> SEQUENCE: 342
ggttccatgg tgtaatggta agcactctgg actctgaatc cagcgatccg agttcgagtc    60
tcggtggaac ct                                                        72

<210> SEQ ID NO 343
<211> LENGTH: 72
```

```
<212> TYPE: DNA
<213> ORGANISM: Homo sapiens

<400> SEQUENCE: 343
ggttccatgg tgtaatggtg agcactctgg actctgaatc cagcgatccg agttcgagtc      60
tcggtggaac ct                                                         72

<210> SEQ ID NO 344
<211> LENGTH: 72
<212> TYPE: DNA
<213> ORGANISM: Homo sapiens

<400> SEQUENCE: 344
ggttccatgg tgtaatggtg agcactctgg actctgaatc cagcgatccg agttcgagtc      60
tcggtggaac ct                                                         72

<210> SEQ ID NO 345
<211> LENGTH: 72
<212> TYPE: DNA
<213> ORGANISM: Homo sapiens

<400> SEQUENCE: 345
ggttccatgg tgtaatggtt agcactctgg actctgaatc cagcgatccg agttcaagtc      60
tcggtggaac ct                                                         72

<210> SEQ ID NO 346
<211> LENGTH: 72
<212> TYPE: DNA
<213> ORGANISM: Homo sapiens

<400> SEQUENCE: 346
ggttccatgg tgtaatggtt agcactctgg actctgaatc cagcgatccg agttcaaatc      60
tcggtggaac ct                                                         72

<210> SEQ ID NO 347
<211> LENGTH: 72
<212> TYPE: DNA
<213> ORGANISM: Homo sapiens

<400> SEQUENCE: 347
ggttccatgg tgtaatggtt agcactctgg actctgaatc cagcgatccg agttcaaatc      60
tcggtggaac ct                                                         72

<210> SEQ ID NO 348
<211> LENGTH: 72
<212> TYPE: DNA
<213> ORGANISM: Homo sapiens

<400> SEQUENCE: 348
ggttccatgg tgtaatggtt agcactctgg actctgaatc cagcgatccg agttcaaatc      60
tcggtggaac ct                                                         72

<210> SEQ ID NO 349
<211> LENGTH: 72
<212> TYPE: DNA
<213> ORGANISM: Homo sapiens

<400> SEQUENCE: 349
ggttccatgg tgtaatggtt agcactctgg actctgaatc cagcgatccg agttcaaatc      60
```

```
tcggtggaac ct                                                          72

<210> SEQ ID NO 350
<211> LENGTH: 72
<212> TYPE: DNA
<213> ORGANISM: Homo sapiens

<400> SEQUENCE: 350
ggttccatgg tgtaatggtt agcactctgg actctgaatc cagcgatccg agttcaaatc      60
tcggtggaac ct                                                          72

<210> SEQ ID NO 351
<211> LENGTH: 73
<212> TYPE: DNA
<213> ORGANISM: Homo sapiens

<400> SEQUENCE: 351
gtgcagagta gtacagtggt taaaccatgg tctttggagc cagactgcct ggggtcggat      60
cccagctctc aca                                                         73

<210> SEQ ID NO 352
<211> LENGTH: 72
<212> TYPE: DNA
<213> ORGANISM: Homo sapiens

<400> SEQUENCE: 352
taggacttgg tgtaatgggt agcacagaga attttggatt ctcaggggtg ggttcaattc      60
ctttcgtcct ag                                                          72

<210> SEQ ID NO 353
<211> LENGTH: 73
<212> TYPE: DNA
<213> ORGANISM: Homo sapiens

<400> SEQUENCE: 353
gaccatgtgg cctaagggaa aagacatctc actttgggtc agaagattga gggttcaagt     60
cctttcatgg tca                                                         73

<210> SEQ ID NO 354
<211> LENGTH: 72
<212> TYPE: DNA
<213> ORGANISM: Homo sapiens

<400> SEQUENCE: 354
taggacatgg tgtaataggt agaatggaga attttgaatt ctcaggggta ggttcaattc      60
ctatagttct ag                                                          72

<210> SEQ ID NO 355
<211> LENGTH: 72
<212> TYPE: DNA
<213> ORGANISM: Homo sapiens

<400> SEQUENCE: 355
ggtcccatgg tgtaatggtt agcactctgg gctttgaatc cagcaatccg agttcgaatc      60
ttggtgggac ct                                                          72

<210> SEQ ID NO 356
<211> LENGTH: 72
<212> TYPE: DNA
<213> ORGANISM: Homo sapiens
```

```
<400> SEQUENCE: 356
ggccccatgg tgtaatggtt agcactctgg actttgaatc cagcgatccg agttcaaatc    60
tcggtgggac ct                                                       72

<210> SEQ ID NO 357
<211> LENGTH: 72
<212> TYPE: DNA
<213> ORGANISM: Homo sapiens

<400> SEQUENCE: 357
ggccccatgg tgtaatggtt agcactctgg actttgaatc cagcgatccg agttcaaatc    60
tcggtgggac ct                                                       72

<210> SEQ ID NO 358
<211> LENGTH: 72
<212> TYPE: DNA
<213> ORGANISM: Homo sapiens

<400> SEQUENCE: 358
ggccccatgg tgtaatggtt agcactctgg actttgaatc cagcgatccg agttcaaatc    60
tcggtgggac ct                                                       72

<210> SEQ ID NO 359
<211> LENGTH: 72
<212> TYPE: DNA
<213> ORGANISM: Homo sapiens

<400> SEQUENCE: 359
ggtcccatgg tgtaatggtt agcactctgg actttgaatc cagcgatccg agttcaaatc    60
tcggtgggac ct                                                       72

<210> SEQ ID NO 360
<211> LENGTH: 69
<212> TYPE: DNA
<213> ORGANISM: Homo sapiens

<400> SEQUENCE: 360
tccctggtag tctagtggct aaagtttggc gctctcaccg ccgggactgg ttgattccag    60
atcaggga                                                            69

<210> SEQ ID NO 361
<211> LENGTH: 72
<212> TYPE: DNA
<213> ORGANISM: Homo sapiens

<400> SEQUENCE: 361
cccctggtgg tctatcggtt aggattcaga cctctcacca ctgctaccca tgctcgattc    60
ctggtcaggg aa                                                       72

<210> SEQ ID NO 362
<211> LENGTH: 72
<212> TYPE: DNA
<213> ORGANISM: Homo sapiens

<400> SEQUENCE: 362
ccccgggtgg tgtagtggat gggatttggc gctctcacca ccatggcccg gatttgattc    60
ccggtcaggg aa                                                       72
```

```
<210> SEQ ID NO 363
<211> LENGTH: 71
<212> TYPE: DNA
<213> ORGANISM: Homo sapiens

<400> SEQUENCE: 363
tccttgatgt ctagtggtta ggatttggtg ctctcactgc agcagcctgg gttcatttct    60
cagtcaggga a                                                         71

<210> SEQ ID NO 364
<211> LENGTH: 72
<212> TYPE: DNA
<213> ORGANISM: Homo sapiens

<400> SEQUENCE: 364
cccctggtgg tctagtgctt aggattcggt gctctcaccg ctgctgcctg cgttcgattc    60
ccggtcaggg aa                                                        72

<210> SEQ ID NO 365
<211> LENGTH: 72
<212> TYPE: DNA
<213> ORGANISM: Homo sapiens

<400> SEQUENCE: 365
tccctggtgg tctagtggtt aggattcggc gctctcaccg ccgcggcccg ggttcgattc    60
ccggtcagga aa                                                        72

<210> SEQ ID NO 366
<211> LENGTH: 72
<212> TYPE: DNA
<213> ORGANISM: Homo sapiens

<400> SEQUENCE: 366
tccctggtgg tctagtggtt aggattcggc gctctcaccg ccgcggcccg ggttcgattc    60
ccggtcaggg aa                                                        72

<210> SEQ ID NO 367
<211> LENGTH: 72
<212> TYPE: DNA
<213> ORGANISM: Homo sapiens

<400> SEQUENCE: 367
tccctggtgg tctagtggtt aggattcggc gctctcaccg ccgcggcccg ggttcgattc    60
ccggtcaggg aa                                                        72

<210> SEQ ID NO 368
<211> LENGTH: 72
<212> TYPE: DNA
<213> ORGANISM: Homo sapiens

<400> SEQUENCE: 368
tccctggtgg tctagtggtt aggattcggc gctctcaccg ccgcggcccg ggttcgattc    60
ccggtcaggg aa                                                        72

<210> SEQ ID NO 369
<211> LENGTH: 72
<212> TYPE: DNA
<213> ORGANISM: Homo sapiens

<400> SEQUENCE: 369
```

```
tccctggtgg tctagtggtt aggattcggc gctctcaccg ccgcggcccg ggttcgattc    60
ccggtcaggg aa                                                       72

<210> SEQ ID NO 370
<211> LENGTH: 72
<212> TYPE: DNA
<213> ORGANISM: Homo sapiens

<400> SEQUENCE: 370
tccctggtgg tctagtggtt aggattcggc gctctcaccg ccgcggcccg ggttcgattc    60
ccggtcaggg aa                                                       72

<210> SEQ ID NO 371
<211> LENGTH: 72
<212> TYPE: DNA
<213> ORGANISM: Homo sapiens

<400> SEQUENCE: 371
tccctggtgg tctagtggtt aggattcggc gctctcaccg ccgcggcccg ggttcgattc    60
ccggtcaggg aa                                                       72

<210> SEQ ID NO 372
<211> LENGTH: 72
<212> TYPE: DNA
<213> ORGANISM: Homo sapiens

<400> SEQUENCE: 372
tccctggtgg tctagtggtt aggattcggc gctctcaccg ccgcggcccg ggttcgattc    60
ccggtcaggg aa                                                       72

<210> SEQ ID NO 373
<211> LENGTH: 69
<212> TYPE: DNA
<213> ORGANISM: Homo sapiens

<400> SEQUENCE: 373
tccctggtag tctagtggct aaagtttggc gctttcaccg ccgggactgg ttgattccag    60
atcagggga                                                           69

<210> SEQ ID NO 374
<211> LENGTH: 69
<212> TYPE: DNA
<213> ORGANISM: Homo sapiens

<400> SEQUENCE: 374
gcctgtggtc tagtggttag aattcagtgt tttcagtgct ctagtccagg ttcaattcct    60
ggtcaggga                                                           69

<210> SEQ ID NO 375
<211> LENGTH: 69
<212> TYPE: DNA
<213> ORGANISM: Homo sapiens

<400> SEQUENCE: 375
ccctgtggtc tagtggttag gagttggtgc tttcgtcatg acagcccagg ttcaattcct    60
ggttagaga                                                           69

<210> SEQ ID NO 376
```

```
<211> LENGTH: 71
<212> TYPE: DNA
<213> ORGANISM: Homo sapiens

<400> SEQUENCE: 376
accctgtggt ctagtggcta agactttgtg ctttcattgc tgcatcctag gttcaattcc    60
cagtcaggga a                                                         71

<210> SEQ ID NO 377
<211> LENGTH: 73
<212> TYPE: DNA
<213> ORGANISM: Homo sapiens

<400> SEQUENCE: 377
tccctggtgg tctagtggct aggattcggc gctttcaccg cctgcagctc gagttcgatt    60
cctggtcagg gaa                                                       73

<210> SEQ ID NO 378
<211> LENGTH: 72
<212> TYPE: DNA
<213> ORGANISM: Homo sapiens

<400> SEQUENCE: 378
gcgttggtgg tgtagtggtg agcacagctg cctttcaagc agttaacgcg ggttcgattc    60
ccgggtaacg aa                                                        72

<210> SEQ ID NO 379
<211> LENGTH: 72
<212> TYPE: DNA
<213> ORGANISM: Homo sapiens

<400> SEQUENCE: 379
tccctggtgg tctagtggct aggattcggc gctttcaccg ccgcggcccg ggttcgattc    60
ccggtcaggg aa                                                        72

<210> SEQ ID NO 380
<211> LENGTH: 72
<212> TYPE: DNA
<213> ORGANISM: Homo sapiens

<400> SEQUENCE: 380
tccctggtgg tctagtggct aggattcggc gctttcaccg ccgcggcccg ggttcgattc    60
ccggtcaggg aa                                                        72

<210> SEQ ID NO 381
<211> LENGTH: 72
<212> TYPE: DNA
<213> ORGANISM: Homo sapiens

<400> SEQUENCE: 381
tccctggtgg tctagtggct aggattcggc gctttcaccg ccgcggcccg ggttcgattc    60
ccggccaggg aa                                                        72

<210> SEQ ID NO 382
<211> LENGTH: 72
<212> TYPE: DNA
<213> ORGANISM: Homo sapiens

<400> SEQUENCE: 382
tcccacatgg tctagcggtt aggattcctg gttttcaccc aggcggcccg ggttcgactc    60
```

```
ccggtgtggg aa                                                        72

<210> SEQ ID NO 383
<211> LENGTH: 72
<212> TYPE: DNA
<213> ORGANISM: Homo sapiens

<400> SEQUENCE: 383
tcccacatgg tctagcggtt aggattcctg gttttcaccc aggcggcccg ggttcgactc    60
ccggtgtggg aa                                                        72

<210> SEQ ID NO 384
<211> LENGTH: 72
<212> TYPE: DNA
<213> ORGANISM: Homo sapiens

<400> SEQUENCE: 384
tcccatatgg tctagcggtt aggattcctg gttttcaccc aggtggcccg ggttcgactc    60
ccggtatggg aa                                                        72

<210> SEQ ID NO 385
<211> LENGTH: 72
<212> TYPE: DNA
<213> ORGANISM: Homo sapiens

<400> SEQUENCE: 385
tcccatatgg tctagcggtt aggattcctg gttttcaccc aggtggcccg ggttcgactc    60
ccggtatggg aa                                                        72

<210> SEQ ID NO 386
<211> LENGTH: 71
<212> TYPE: DNA
<213> ORGANISM: Homo sapiens

<400> SEQUENCE: 386
gccttggtgg tgcagtggta gaattctcgc ctcccacgtg ggagacccgg gttcaattcc    60
cggccaatgc a                                                         71

<210> SEQ ID NO 387
<211> LENGTH: 71
<212> TYPE: DNA
<213> ORGANISM: Homo sapiens

<400> SEQUENCE: 387
gcgttggtgg tttagtggta gaattctcgc ctcccatgcg ggagacccgg gttcaattcc    60
cggccactgc a                                                         71

<210> SEQ ID NO 388
<211> LENGTH: 71
<212> TYPE: DNA
<213> ORGANISM: Homo sapiens

<400> SEQUENCE: 388
gcattggtgg ttcaatggta gaattctcgc ctcccacgca ggagacccag gttcgattcc    60
tggccaatgc a                                                         71

<210> SEQ ID NO 389
<211> LENGTH: 71
<212> TYPE: DNA
```

<213> ORGANISM: Homo sapiens

<400> SEQUENCE: 389
gcgccgctgg tgtagtggta tcatgcaaga ttcccattct tgcgacccgg gttcgattcc    60
cgggcggcgc a    71

<210> SEQ ID NO 390
<211> LENGTH: 71
<212> TYPE: DNA
<213> ORGANISM: Homo sapiens

<400> SEQUENCE: 390
gcgccgctgg tgtagtggta tcatgcaaga ttcccattct tgcgacccgg gttcgattcc    60
cgggcggcgc a    71

<210> SEQ ID NO 391
<211> LENGTH: 71
<212> TYPE: DNA
<213> ORGANISM: Homo sapiens

<400> SEQUENCE: 391
gcattggtgg ttcagtggta gaattctcgc ctcccacgcg ggagacccgg gttcaattcc    60
cggccaatgc a    71

<210> SEQ ID NO 392
<211> LENGTH: 71
<212> TYPE: DNA
<213> ORGANISM: Homo sapiens

<400> SEQUENCE: 392
gcattggtgg ttcagtggta gaattctcgc ctcccacgcg ggagacccgg gttcaattcc    60
cggccaatgc a    71

<210> SEQ ID NO 393
<211> LENGTH: 71
<212> TYPE: DNA
<213> ORGANISM: Homo sapiens

<400> SEQUENCE: 393
gcatgggtga ttcagtggta gaattttcac ctgccatgca ggaggtccag gttcatttcc    60
tggcctatgc a    71

<210> SEQ ID NO 394
<211> LENGTH: 71
<212> TYPE: DNA
<213> ORGANISM: Homo sapiens

<400> SEQUENCE: 394
gcattggtgg ttcagtggta gaattctcgc ctgccatgcg ggcggccggg cttcgattcc    60
tggccaatgc a    71

<210> SEQ ID NO 395
<211> LENGTH: 71
<212> TYPE: DNA
<213> ORGANISM: Homo sapiens

<400> SEQUENCE: 395
gcataggtgg ttcagtggta gaattcttgc ctgccacgca ggaggcccag gtttgattcc    60
tggcccatgc a    71

<210> SEQ ID NO 396
<211> LENGTH: 71
<212> TYPE: DNA
<213> ORGANISM: Homo sapiens

<400> SEQUENCE: 396
gcattggtgg ttcagtggta gaattctcgc ctgccacgcg ggaggcccgg gtttgattcc    60
cggccagtgc a    71

<210> SEQ ID NO 397
<211> LENGTH: 71
<212> TYPE: DNA
<213> ORGANISM: Homo sapiens

<400> SEQUENCE: 397
gcattggtgg ttcagtggta gaattctcgc ctgccacgcg ggaggcccgg gttcgattcc    60
cggccaatgc a    71

<210> SEQ ID NO 398
<211> LENGTH: 71
<212> TYPE: DNA
<213> ORGANISM: Homo sapiens

<400> SEQUENCE: 398
gcattggtgg ttcagtggta gaattctcgc ctgccacgcg ggaggcccgg gttcgattcc    60
cggccaatgc a    71

<210> SEQ ID NO 399
<211> LENGTH: 71
<212> TYPE: DNA
<213> ORGANISM: Homo sapiens

<400> SEQUENCE: 399
gcattggtgg ttcagtggta gaattctcgc ctgccacgcg ggaggcccgg gttcgattcc    60
cggccaatgc a    71

<210> SEQ ID NO 400
<211> LENGTH: 71
<212> TYPE: DNA
<213> ORGANISM: Homo sapiens

<400> SEQUENCE: 400
gcattggtgg ttcagtggta gaattctcgc ctgccacgcg ggaggcccgg gttcgattcc    60
cggccaatgc a    71

<210> SEQ ID NO 401
<211> LENGTH: 71
<212> TYPE: DNA
<213> ORGANISM: Homo sapiens

<400> SEQUENCE: 401
gcattggtgg ttcagtggta gaattctcgc ctgccacgcg ggaggcccgg gttcgattcc    60
cggccaatgc a    71

<210> SEQ ID NO 402
<211> LENGTH: 71
<212> TYPE: DNA
<213> ORGANISM: Homo sapiens

```
<400> SEQUENCE: 402
gcattggtgg ttcagtggta gaattctcgc ctgccacgcg ggaggcccgg gttcgattcc    60
cggccaatgc a                                                        71

<210> SEQ ID NO 403
<211> LENGTH: 71
<212> TYPE: DNA
<213> ORGANISM: Homo sapiens

<400> SEQUENCE: 403
gcatgggtgg ttcagtggta gaattctcgc ctgccacgcg ggaggcccgg gttcgattcc    60
cggcccatgc a                                                        71

<210> SEQ ID NO 404
<211> LENGTH: 71
<212> TYPE: DNA
<213> ORGANISM: Homo sapiens

<400> SEQUENCE: 404
gcatgggtgg ttcagtggta gaattctcgc ctgccacgcg ggaggcccgg gttcgattcc    60
cggcccatgc a                                                        71

<210> SEQ ID NO 405
<211> LENGTH: 71
<212> TYPE: DNA
<213> ORGANISM: Homo sapiens

<400> SEQUENCE: 405
gcatgggtgg ttcagtggta gaattctcgc ctgccacgcg ggaggcccgg gttcgattcc    60
cggcccatgc a                                                        71

<210> SEQ ID NO 406
<211> LENGTH: 71
<212> TYPE: DNA
<213> ORGANISM: Homo sapiens

<400> SEQUENCE: 406
gcatgggtgg ttcagtggta gaattctcgc ctgccacgcg ggaggcccgg gttcgattcc    60
cggcccatgc a                                                        71

<210> SEQ ID NO 407
<211> LENGTH: 71
<212> TYPE: DNA
<213> ORGANISM: Homo sapiens

<400> SEQUENCE: 407
gcatgggtgg ttcagtggta gaattctcgc ctgccacgcg ggaggcccgg gttcgattcc    60
cggcccatgc a                                                        71

<210> SEQ ID NO 408
<211> LENGTH: 72
<212> TYPE: DNA
<213> ORGANISM: Homo sapiens

<400> SEQUENCE: 408
gcgttggtgg tatagtggtg agcatagttg ccttccaagc agttgacccg ggctcgattc    60
ccgcccaacg ca                                                       72
```

```
<210> SEQ ID NO 409
<211> LENGTH: 72
<212> TYPE: DNA
<213> ORGANISM: Homo sapiens

<400> SEQUENCE: 409
gcgttggtgg tatagtggta agcatagctg ccttccaagc agttgacccg ggttcgattc    60
ccggccaacg ca                                                       72

<210> SEQ ID NO 410
<211> LENGTH: 72
<212> TYPE: DNA
<213> ORGANISM: Homo sapiens

<400> SEQUENCE: 410
gcgttggtgg tatagtggtg agcatagctg ccttccaagc agttgacccg ggttcgattc    60
ccggccaacg ca                                                       72

<210> SEQ ID NO 411
<211> LENGTH: 72
<212> TYPE: DNA
<213> ORGANISM: Homo sapiens

<400> SEQUENCE: 411
gcgttggtgg tatagtggtg agcatagctg ccttccaagc agttgacccg ggttcgattc    60
ccggccaacg ca                                                       72

<210> SEQ ID NO 412
<211> LENGTH: 72
<212> TYPE: DNA
<213> ORGANISM: Homo sapiens

<400> SEQUENCE: 412
gcgttggtgg tatagtggtg agcatagctg ccttccaagc agttgacccg ggttcgattc    60
ccggccaacg ca                                                       72

<210> SEQ ID NO 413
<211> LENGTH: 72
<212> TYPE: DNA
<213> ORGANISM: Homo sapiens

<400> SEQUENCE: 413
gcgttggtgg tatagtggtg agcatagctg ccttccaagc agttgacccg ggttcgattc    60
ccggccaacg ca                                                       72

<210> SEQ ID NO 414
<211> LENGTH: 72
<212> TYPE: DNA
<213> ORGANISM: Homo sapiens

<400> SEQUENCE: 414
gcgttggtgg tatagtggtg agcatagctg ccttccaagc agttgacccg ggttcgattc    60
ccggccaacg ca                                                       72

<210> SEQ ID NO 415
<211> LENGTH: 72
<212> TYPE: DNA
<213> ORGANISM: Homo sapiens

<400> SEQUENCE: 415
```

```
gcgttggtgg tatagtggtg agcatagctg ccttccaagc agttgacccg ggttcgattc    60
ccggccaacg ca                                                        72

<210> SEQ ID NO 416
<211> LENGTH: 72
<212> TYPE: DNA
<213> ORGANISM: Homo sapiens

<400> SEQUENCE: 416
gcgttggtgg tatagtggtt agcatagctg ccttccaagc agttgacccg ggttcgattc    60
ccggccaacg ca                                                        72

<210> SEQ ID NO 417
<211> LENGTH: 72
<212> TYPE: DNA
<213> ORGANISM: Homo sapiens

<400> SEQUENCE: 417
gcagtgactg tatagtggtt agcactctgt gttgtggcca cagcaaccat ggttcaaatc    60
tgagtcatga ca                                                        72

<210> SEQ ID NO 418
<211> LENGTH: 72
<212> TYPE: DNA
<213> ORGANISM: Homo sapiens

<400> SEQUENCE: 418
gccatgatcg tatagtggtt agtactctgc gctgtggccg cagcaacctc ggttcgaatc    60
cgagtcacgg ca                                                        72

<210> SEQ ID NO 419
<211> LENGTH: 72
<212> TYPE: DNA
<213> ORGANISM: Homo sapiens

<400> SEQUENCE: 419
gccgtgatcg tatagtggtt agtactctgc gttgtggccg cagcaacctc ggttcgaatc    60
cgagtcacgg ca                                                        72

<210> SEQ ID NO 420
<211> LENGTH: 72
<212> TYPE: DNA
<213> ORGANISM: Homo sapiens

<400> SEQUENCE: 420
gccgtgatcg tatagtggtt agtactctgc gttgtggccg cagcaacctc ggttcgaatc    60
cgagtcacgg ca                                                        72

<210> SEQ ID NO 421
<211> LENGTH: 72
<212> TYPE: DNA
<213> ORGANISM: Homo sapiens

<400> SEQUENCE: 421
gccgtgatcg tatagtggtt agtactctgc gttgtggccg cagcaacctc ggttcgaatc    60
cgagtcacgg ca                                                        72

<210> SEQ ID NO 422
<211> LENGTH: 72
```

```
<212> TYPE: DNA
<213> ORGANISM: Homo sapiens

<400> SEQUENCE: 422
gccgtgatcg tatagtggtt agtactctgc gttgtggccg cagcaacctc ggttcgaatc    60
cgagtcacgg ca                                                        72

<210> SEQ ID NO 423
<211> LENGTH: 72
<212> TYPE: DNA
<213> ORGANISM: Homo sapiens

<400> SEQUENCE: 423
gccgtgatcg tatagtggtt agtactctgc gttgtggccg cagcaacctc ggttcgaatc    60
cgagtcacgg ca                                                        72

<210> SEQ ID NO 424
<211> LENGTH: 72
<212> TYPE: DNA
<213> ORGANISM: Homo sapiens

<400> SEQUENCE: 424
gccgtgatcg tatagtggtt agtactctgc gttgtggccg cagcaacctc ggttcgaatc    60
cgagtcacgg ca                                                        72

<210> SEQ ID NO 425
<211> LENGTH: 72
<212> TYPE: DNA
<213> ORGANISM: Homo sapiens

<400> SEQUENCE: 425
gccgtgatcg tatagtggtt agtactctgc gttgtggccg cagcaacctc ggttcgaatc    60
cgagtcacgg ca                                                        72

<210> SEQ ID NO 426
<211> LENGTH: 72
<212> TYPE: DNA
<213> ORGANISM: Homo sapiens

<400> SEQUENCE: 426
gccgtgatcg tatagtggtt agtactctgc gttgtggccg cagcaacctc ggttcgaatc    60
cgagtcacgg ca                                                        72

<210> SEQ ID NO 427
<211> LENGTH: 72
<212> TYPE: DNA
<213> ORGANISM: Homo sapiens

<400> SEQUENCE: 427
gccgtgatcg tatagtggtt agtactctgc gttgtggccg cagcaacctc ggttcgaatc    60
cgagtcacgg ca                                                        72

<210> SEQ ID NO 428
<211> LENGTH: 74
<212> TYPE: DNA
<213> ORGANISM: Homo sapiens

<400> SEQUENCE: 428
ggctggttag ttcagttggt tagagcgtgg tgctaataac gccaaggtcg tgggttcgat    60
```
ccccatatcg gcca                                                              74

<210> SEQ ID NO 429
<211> LENGTH: 74
<212> TYPE: DNA
<213> ORGANISM: Homo sapiens

<400> SEQUENCE: 429
ggccggttag ctcagtcggc tagagcgtgg tgctaataac gccaaggtcg cggggttcgat    60 ccccgtacgg gcca                                                              74

<210> SEQ ID NO 430
<211> LENGTH: 74
<212> TYPE: DNA
<213> ORGANISM: Homo sapiens

<400> SEQUENCE: 430
ggccggttag ctcagttggt cagagcgtgg tgctaataac gccaaggtcg cggggttcgat    60 ccccgtacgg gcca                                                              74

<210> SEQ ID NO 431
<211> LENGTH: 74
<212> TYPE: DNA
<213> ORGANISM: Homo sapiens

<400> SEQUENCE: 431
ggccggttag ctcagttggt cagagcgtgg tgctaataac gccaaggtcg cggggttcgat    60 ccccgtacgg gcca                                                              74

<210> SEQ ID NO 432
<211> LENGTH: 74
<212> TYPE: DNA
<213> ORGANISM: Homo sapiens

<400> SEQUENCE: 432
ggccggttag ctcagttggt tagagcgtgg tgctaataac gctaaggtcg cggggttcgat    60 ccccgtactg gcca                                                              74

<210> SEQ ID NO 433
<211> LENGTH: 74
<212> TYPE: DNA
<213> ORGANISM: Homo sapiens

<400> SEQUENCE: 433
ggccggttag ctcagttggt tagagcgtgg tgctaataac gccaaggtcg cggggttcgat    60 ccccgtacgg gcca                                                              74

<210> SEQ ID NO 434
<211> LENGTH: 74
<212> TYPE: DNA
<213> ORGANISM: Homo sapiens

<400> SEQUENCE: 434
ggccggttag ctcagttggt tagagcgtgg tgctaataac gccaaggtcg cggggttcgat    60 ccccgtacgg gcca                                                              74

<210> SEQ ID NO 435
<211> LENGTH: 74
<212> TYPE: DNA
<213> ORGANISM: Homo sapiens

<400> SEQUENCE: 435
ggccggttag ctcagttggt tagagcgtgg tgctaataac gccaaggtcg cggggttcgat    60 ccccgtacgg gcca    74

<210> SEQ ID NO 436
<211> LENGTH: 74
<212> TYPE: DNA
<213> ORGANISM: Homo sapiens

<400> SEQUENCE: 436
ggccggttag ctcagttggt tagagcgtgg tgctaataac gccaaggtcg cggggttcgat    60 ccccgtacgg gcca    74

<210> SEQ ID NO 437
<211> LENGTH: 74
<212> TYPE: DNA
<213> ORGANISM: Homo sapiens

<400> SEQUENCE: 437
ggccggttag ctcagttggt tagagcgtgg tgctaataac gccaaggtcg cggggttcgat    60 ccccgtacgg gcca    74

<210> SEQ ID NO 438
<211> LENGTH: 74
<212> TYPE: DNA
<213> ORGANISM: Homo sapiens

<400> SEQUENCE: 438
ggccggttag ctcagttggt tagagcgtgg tgctaataac gccaaggtcg cggggttcgaa    60 ccccgtacgg gcca    74

<210> SEQ ID NO 439
<211> LENGTH: 74
<212> TYPE: DNA
<213> ORGANISM: Homo sapiens

<400> SEQUENCE: 439
ggctggttag ctcagttggt tagagcgtgg tgctaataac gccaaggtcg cggggttcgat    60 ccccgtactg gcca    74

<210> SEQ ID NO 440
<211> LENGTH: 74
<212> TYPE: DNA
<213> ORGANISM: Homo sapiens

<400> SEQUENCE: 440
ggccggttag ctcagttggt tagagcgtgg tgctaataac gccaaggtcg cggggttcgat    60 ccccgtactg gcca    74

<210> SEQ ID NO 441
<211> LENGTH: 74
<212> TYPE: DNA
<213> ORGANISM: Homo sapiens

<400> SEQUENCE: 441
ggccggttag ctcagttggt tagagcgtgg cgctaataac gccaaggtcg cggggttcgat    60 ccccgtacgg gcca    74

<210> SEQ ID NO 442
<211> LENGTH: 74
<212> TYPE: DNA
<213> ORGANISM: Homo sapiens

<400> SEQUENCE: 442
ggccggttag ctcagttggt aagagcgtgg tgctgataac accaaggtcg cgggctcgac    60
tcccgcaccg gcca                                                      74

<210> SEQ ID NO 443
<211> LENGTH: 74
<212> TYPE: DNA
<213> ORGANISM: Homo sapiens

<400> SEQUENCE: 443
ggccggttag ctcagttggt aagagcgtgg tgctgataac accaaggtcg cgggctcgac    60
tcccgcaccg gcca                                                      74

<210> SEQ ID NO 444
<211> LENGTH: 74
<212> TYPE: DNA
<213> ORGANISM: Homo sapiens

<400> SEQUENCE: 444
ggccggttag ctcagttggt aagagcgtgg tgctgataac accaaggtcg cgggctcgac    60
tcccgcaccg gcca                                                      74

<210> SEQ ID NO 445
<211> LENGTH: 74
<212> TYPE: DNA
<213> ORGANISM: Homo sapiens

<400> SEQUENCE: 445
ggccggttag ctcagttggt aagagcgtgg tgctgataac accaaggtcg cgggctcgac    60
tcccgcaccg gcca                                                      74

<210> SEQ ID NO 446
<211> LENGTH: 74
<212> TYPE: DNA
<213> ORGANISM: Homo sapiens

<400> SEQUENCE: 446
ggccggttag ctcagttggt aagagcgtgg tgctgataac accaaggtcg cgggctcgac    60
tcccgcaccg gcca                                                      74

<210> SEQ ID NO 447
<211> LENGTH: 74
<212> TYPE: DNA
<213> ORGANISM: Homo sapiens

<400> SEQUENCE: 447
ggccggttag ctcagttggt aagagcgtgg tgctgataac accaaggtcg cgggctcgac    60
tcccgcaccg gcca                                                      74

<210> SEQ ID NO 448
<211> LENGTH: 74
<212> TYPE: DNA
<213> ORGANISM: Homo sapiens

<400> SEQUENCE: 448

```
ggccggttag ctcagttggt aagagcgtgg tgctgataac accaaggtcg cgggctcgac    60
tcccgcaccg gcca                                                     74

<210> SEQ ID NO 449
<211> LENGTH: 74
<212> TYPE: DNA
<213> ORGANISM: Homo sapiens

<400> SEQUENCE: 449
ggccggttag ctcagttggt aagagcgtgg tgctgataac accaaggtcg cgggctcgac    60
tcccgcaccg gcca                                                     74

<210> SEQ ID NO 450
<211> LENGTH: 94
<212> TYPE: DNA
<213> ORGANISM: Homo sapiens

<400> SEQUENCE: 450
gctccagtgg cgcaatcggt tagcgcgcgg tacttatatg gcagtatgtg tgcgagtgat    60
gccgaggttg tgagttcgag cctcacctgg agca                               94

<210> SEQ ID NO 451
<211> LENGTH: 94
<212> TYPE: DNA
<213> ORGANISM: Homo sapiens

<400> SEQUENCE: 451
gctccagtgg cgcaatcggt tagcgcgcgg tacttataca acagtatatg tgcgggtgat    60
gccgaggttg tgagttcgag cctcacctgg agca                               94

<210> SEQ ID NO 452
<211> LENGTH: 94
<212> TYPE: DNA
<213> ORGANISM: Homo sapiens

<400> SEQUENCE: 452
gctccagtgg cgcaatcggt tagcgcgcgg tacttataag acagtgcacc tgtgagcaat    60
gccgaggttg tgagttcaag cctcacctgg agca                               94

<210> SEQ ID NO 453
<211> LENGTH: 93
<212> TYPE: DNA
<213> ORGANISM: Homo sapiens

<400> SEQUENCE: 453
gctccagtgg cgcaatcggt tagcgcgcgg tacttataca gcagtacatg cagagcaatg    60
ccgaggttgt gagttcgagc ctcacctgga gca                                93

<210> SEQ ID NO 454
<211> LENGTH: 93
<212> TYPE: DNA
<213> ORGANISM: Homo sapiens

<400> SEQUENCE: 454
gctccagtgg cgcaatcggt tagcgcgcgg tacttatatg acagtgcgag cggagcaatg    60
ccgaggttgt gagttcgatc ctcacctgga gca                                93

<210> SEQ ID NO 455
```

-continued

```
<211> LENGTH: 82
<212> TYPE: DNA
<213> ORGANISM: Homo sapiens

<400> SEQUENCE: 455
ggtagcatgg ctgagtggtc taagattctg aattaagtct ccagtctctt tgggggcgtg      60
gttttcaatc ccaccgctgc ta                                              82

<210> SEQ ID NO 456
<211> LENGTH: 82
<212> TYPE: DNA
<213> ORGANISM: Homo sapiens

<400> SEQUENCE: 456
ggtagggtgg ccgagcggtc taaggcactg tattaagact ccagtctctt cagaggcatg      60
ggtttgaatc ccactgctgc ca                                              82

<210> SEQ ID NO 457
<211> LENGTH: 73
<212> TYPE: DNA
<213> ORGANISM: Homo sapiens

<400> SEQUENCE: 457
gggccagtgg ctcaatggat aatgcgtctg actaagaatc agaagattcc agccttgact      60
cctggctggc tca                                                        73

<210> SEQ ID NO 458
<211> LENGTH: 82
<212> TYPE: DNA
<213> ORGANISM: Homo sapiens

<400> SEQUENCE: 458
ggtagcgtgg ccgagtggtc taagacgctg gattaaggct ccagtctctt cggggcgtg      60 ggtttgaatc ccaccgctgc ca                                              82

<210> SEQ ID NO 459
<211> LENGTH: 82
<212> TYPE: DNA
<213> ORGANISM: Homo sapiens

<400> SEQUENCE: 459
ggtagcgtgg ccgagcggtc taaggcgctg gattaaggct ccagtctctt cggggcgtg      60 ggttcaaatc ccaccgctgc ca                                              82

<210> SEQ ID NO 460
<211> LENGTH: 82
<212> TYPE: DNA
<213> ORGANISM: Homo sapiens

<400> SEQUENCE: 460
ggtagcgtgg ccgagcggtc taaggcgctg gattaaggct ccagtctctt cggggcgtg      60 ggttcgaatc ccaccgctgc ca                                              82

<210> SEQ ID NO 461
<211> LENGTH: 82
<212> TYPE: DNA
<213> ORGANISM: Homo sapiens

<400> SEQUENCE: 461
ggtagcgtgg ccgagcggtc taaggcgctg gattaaggct ccagtctctt cggggcgtg      60
```

```
ggttcgaatc ccaccgctgc ca                                              82

<210> SEQ ID NO 462
<211> LENGTH: 82
<212> TYPE: DNA
<213> ORGANISM: Homo sapiens

<400> SEQUENCE: 462
ggtagcgtgg ccgagcggtc taaggcgctg gattaaggct ccagtctctt cggggcgtg    60 ggttcgaatc ccaccgctgc ca                                              82

<210> SEQ ID NO 463
<211> LENGTH: 82
<212> TYPE: DNA
<213> ORGANISM: Homo sapiens

<400> SEQUENCE: 463
ggtagcgtgg ccgagcggtc taaggcgctg gattaaggct ccagtctctt cggggcgtg    60 ggttcgaatc ccaccgctgc ca                                              82

<210> SEQ ID NO 464
<211> LENGTH: 82
<212> TYPE: DNA
<213> ORGANISM: Homo sapiens

<400> SEQUENCE: 464
ggtagcgtgg ccgagcggtc taaggcgctg gattaaggct ccagtctctt cggaggcgtg    60
ggttcgaatc ccaccgctgc ca                                              82

<210> SEQ ID NO 465
<211> LENGTH: 82
<212> TYPE: DNA
<213> ORGANISM: Homo sapiens

<400> SEQUENCE: 465
ggtagcgtgg ccgagcggtc taaggcgctg gattaaggct ccagtctctt cggaggcgtg    60
ggttcgaatc ccaccgctgc ca                                              82

<210> SEQ ID NO 466
<211> LENGTH: 82
<212> TYPE: DNA
<213> ORGANISM: Homo sapiens

<400> SEQUENCE: 466
ggtagcgtgg ccgagcggtc taaggcgctg gattaaggct ccagtctctt cggaggcgtg    60
ggttcgaatc ccaccgctgc ca                                              82

<210> SEQ ID NO 467
<211> LENGTH: 84
<212> TYPE: DNA
<213> ORGANISM: Homo sapiens

<400> SEQUENCE: 467
gtcaggatgg ccgagcagtc ttaaggcgct gcgttcaaat cgcaccctcc gctggaggcg    60
tgggttcgaa tcccactttt gaca                                            84

<210> SEQ ID NO 468
<211> LENGTH: 74
<212> TYPE: DNA
```

<213> ORGANISM: Homo sapiens

<400> SEQUENCE: 468

```
gcctccttag tgcagtaggt agcgcatcag tctcaaaatc tgaatggtcc tgagttcaag    60
cctcagaggg ggca                                                      74
```

<210> SEQ ID NO 469
<211> LENGTH: 106
<212> TYPE: DNA
<213> ORGANISM: Homo sapiens

<400> SEQUENCE: 469

```
gtcaggatgg ccgagtggtc taaggcgcca gactcaaggt aagcaccttg cctgcgggct    60
ttctggtctc cggatggagg cgtgggttcg aatcccactt ctgaca                  106
```

<210> SEQ ID NO 470
<211> LENGTH: 107
<212> TYPE: DNA
<213> ORGANISM: Homo sapiens

<400> SEQUENCE: 470

```
gtcaggatgg ccgagtggtc taaggcgcca gactcaagtt gctacttccc aggtttgggg    60
cttctggtct ccgcatggag gcgtgggttc gaatcccact tctgaca                 107
```

<210> SEQ ID NO 471
<211> LENGTH: 108
<212> TYPE: DNA
<213> ORGANISM: Homo sapiens

<400> SEQUENCE: 471

```
gtcaggatgg ccgagtggtc taaggcgcca gactcaagct tactgcttcc tgtgttcggg    60
tcttctggtc tccgtatgga ggcgtgggtt cgaatcccac ttctgaca                108
```

<210> SEQ ID NO 472
<211> LENGTH: 106
<212> TYPE: DNA
<213> ORGANISM: Homo sapiens

<400> SEQUENCE: 472

```
gtcaggatgg ccgagtggtc taaggcgcca gactcaagct aagcttcctc cgcggtgggg    60
attctggtct ccaatggagg cgtgggttcg aatcccactt ctgaca                  106
```

<210> SEQ ID NO 473
<211> LENGTH: 105
<212> TYPE: DNA
<213> ORGANISM: Homo sapiens

<400> SEQUENCE: 473

```
gtcaggatgg ccgagtggtc taaggcgcca gactcaagct tggcttcctc gtgttgagga    60
ttctggtctc caatggaggc gtgggttcga atcccacttc tgaca                   105
```

<210> SEQ ID NO 474
<211> LENGTH: 78
<212> TYPE: DNA
<213> ORGANISM: Homo sapiens

<400> SEQUENCE: 474

```
ggcagtggag tttagtggtt aaggacctgc tcagacatca caggtaggta gatctgggtt    60
caaaccctag ccctggca                                                  78
```

<210> SEQ ID NO 475
<211> LENGTH: 83
<212> TYPE: DNA
<213> ORGANISM: Homo sapiens

<400> SEQUENCE: 475
gtcaggatgg ccgagcggtc taaggcgctg cgttcaggtc gcagtctccc ctggaggcgt    60
gggttcgaat cccacttctg aca                                            83

<210> SEQ ID NO 476
<211> LENGTH: 83
<212> TYPE: DNA
<213> ORGANISM: Homo sapiens

<400> SEQUENCE: 476
gtcaggatgg ccgagcggtc taaggcgctg cgttcaggtc gcagtctccc ctggaggcgt    60
gggttcgaat cccacttctg aca                                            83

<210> SEQ ID NO 477
<211> LENGTH: 83
<212> TYPE: DNA
<213> ORGANISM: Homo sapiens

<400> SEQUENCE: 477
gtcaggatgg ccgagcggtc taaggcgctg cgttcaggtc gcagtctccc ctggaggcgt    60
gggttcgaat cccactcctg aca                                            83

<210> SEQ ID NO 478
<211> LENGTH: 83
<212> TYPE: DNA
<213> ORGANISM: Homo sapiens

<400> SEQUENCE: 478
gtcaggatgg ccgagcggtc taaggcgctg cgttcaggtc gcagtctccc ctggaggcgt    60
gggttcgaat cccactcctg aca                                            83

<210> SEQ ID NO 479
<211> LENGTH: 83
<212> TYPE: DNA
<213> ORGANISM: Homo sapiens

<400> SEQUENCE: 479
gtcaggatgg ccgagcggtc taaggcgctg cgttcaggtc gcagtctccc ctggaggcgt    60
gggttcgaat cccactcctg aca                                            83

<210> SEQ ID NO 480
<211> LENGTH: 83
<212> TYPE: DNA
<213> ORGANISM: Homo sapiens

<400> SEQUENCE: 480
gtcaggatgg ccgagcggtc taaggcgctg cgttcaggtc gcagtctccc ctggaggcgt    60
gggttcgaat cccactcctg aca                                            83

<210> SEQ ID NO 481
<211> LENGTH: 83
<212> TYPE: DNA
<213> ORGANISM: Homo sapiens

```
<400> SEQUENCE: 481
gtcaggatgg ccgagcggtc taaggcgctg cgttcaggtc gcagtctccc ctggaggcgt    60
gggttcgaat cccactcctg aca                                            83

<210> SEQ ID NO 482
<211> LENGTH: 83
<212> TYPE: DNA
<213> ORGANISM: Homo sapiens

<400> SEQUENCE: 482
gtcaggatgg ccgagcggtc taaggcgctg cgttcaggtc gcagtctccc ctggaggcgt    60
gggttcgaat cccactcctg aca                                            83

<210> SEQ ID NO 483
<211> LENGTH: 83
<212> TYPE: DNA
<213> ORGANISM: Homo sapiens

<400> SEQUENCE: 483
gtcaggatgg ccgagcggtc taaggcgctg cgttcaggtc gcagtctccc ctggaggcgt    60
gggttcgaat cccactcctg aca                                            83

<210> SEQ ID NO 484
<211> LENGTH: 75
<212> TYPE: DNA
<213> ORGANISM: Homo sapiens

<400> SEQUENCE: 484
gttaagatgg cagagcccgg caattgcata agacttaaaa ctttataatc agaggttcaa    60
ctcctctcat taaca                                                     75

<210> SEQ ID NO 485
<211> LENGTH: 83
<212> TYPE: DNA
<213> ORGANISM: Homo sapiens

<400> SEQUENCE: 485
actcatttgg ctgagtggtt aaggcattgg acttaagatc caatggagta gtggctgtgt    60
gggtttaaac cccactactg gta                                            83

<210> SEQ ID NO 486
<211> LENGTH: 75
<212> TYPE: DNA
<213> ORGANISM: Homo sapiens

<400> SEQUENCE: 486
gttaagatgg cagagcctgg taattgcata aaacttaaaa ttttataatc agaggttcaa    60
ctcctcttct taaca                                                     75

<210> SEQ ID NO 487
<211> LENGTH: 83
<212> TYPE: DNA
<213> ORGANISM: Homo sapiens

<400> SEQUENCE: 487
accgggatgg ctgagtggtt aaggcgttgg acttaagatc caatggacag gtgtccgcgt    60
gggttcgagc cccactcccg gta                                            83
```

```
<210> SEQ ID NO 488
<211> LENGTH: 83
<212> TYPE: DNA
<213> ORGANISM: Homo sapiens

<400> SEQUENCE: 488
accagaatgg ccgagtggtt aaggcgttgg acttaagatc caatggattc atatccgcgt      60
gggttcgaac cccacttctg gta                                              83

<210> SEQ ID NO 489
<211> LENGTH: 83
<212> TYPE: DNA
<213> ORGANISM: Homo sapiens

<400> SEQUENCE: 489
accgggatgg ccgagtggtt aaggcgttgg acttaagatc caatgggctg gtgcccgcgt      60
gggttcgaac cccactctcg gta                                              83

<210> SEQ ID NO 490
<211> LENGTH: 83
<212> TYPE: DNA
<213> ORGANISM: Homo sapiens

<400> SEQUENCE: 490
accaggatgg ccgagtggtt aaggcgttgg acttaagatc caatggacat atgtccgcgt      60
gggttcgaac cccactcctg gta                                              83

<210> SEQ ID NO 491
<211> LENGTH: 82
<212> TYPE: DNA
<213> ORGANISM: Homo sapiens

<400> SEQUENCE: 491
ggtagcgtgg ccgagtggtc taaggcgctg gatttaggct ccagtcattt cgatggcgtg      60
ggttcgaatc ccaccgctgc ca                                               82

<210> SEQ ID NO 492
<211> LENGTH: 82
<212> TYPE: DNA
<213> ORGANISM: Homo sapiens

<400> SEQUENCE: 492
ggtagtgtgg ccgagcggtc taaggcgctg gatttaggct ccagtctctt cggggcgtg       60 ggttcgaatc ccaccactgc ca                                               82

<210> SEQ ID NO 493
<211> LENGTH: 82
<212> TYPE: DNA
<213> ORGANISM: Homo sapiens

<400> SEQUENCE: 493
ggtagcgtgg ccgagcggtc taaggcgctg gatttaggct ccagtctctt cggaggcgtg      60
ggttcgaatc ccaccgctgc ca                                               82

<210> SEQ ID NO 494
<211> LENGTH: 73
<212> TYPE: DNA
<213> ORGANISM: Homo sapiens

<400> SEQUENCE: 494
```

```
aaccgaatag cttagttgat gaagcgtgag actcttaatc tcagggtagt gggttcaagc    60
cccacattgg aca                                                       73

<210> SEQ ID NO 495
<211> LENGTH: 73
<212> TYPE: DNA
<213> ORGANISM: Homo sapiens

<400> SEQUENCE: 495
ctgcagctag ctcagtcggt agagcatgag actcttaatc tcagggtcat gggttcgtgc    60
cccatgttgg gtg                                                       73

<210> SEQ ID NO 496
<211> LENGTH: 73
<212> TYPE: DNA
<213> ORGANISM: Homo sapiens

<400> SEQUENCE: 496
gcccagctag ctcagtcggt agagcataag actcttaatc tcagggttgt ggattcgtgc    60
cccatgctgg gtg                                                       73

<210> SEQ ID NO 497
<211> LENGTH: 73
<212> TYPE: DNA
<213> ORGANISM: Homo sapiens

<400> SEQUENCE: 497
gcccgactac ctcagtcggt ggagcatggg actcttcatc ccagggttgt gggttcgagc    60
cccacattgg gca                                                       73

<210> SEQ ID NO 498
<211> LENGTH: 73
<212> TYPE: DNA
<213> ORGANISM: Homo sapiens

<400> SEQUENCE: 498
gcctggctag ctcagtcggc aaagcatgag actcttaatc tcagggtcgt gggctcgagc    60
tccatgttgg gcg                                                       73

<210> SEQ ID NO 499
<211> LENGTH: 73
<212> TYPE: DNA
<213> ORGANISM: Homo sapiens

<400> SEQUENCE: 499
gcccagctag ctcagtcggt agagcatgag actcttaatc tcagggtcat ggtttgagc     60 cccacgtttg gtg                                                       73

<210> SEQ ID NO 500
<211> LENGTH: 73
<212> TYPE: DNA
<213> ORGANISM: Homo sapiens

<400> SEQUENCE: 500
gacgagctag ctcagtcggt agagcatggg actcttaatc ccagggtcgt ggtttgagc     60 cccatgttgg gca                                                       73

<210> SEQ ID NO 501
<211> LENGTH: 73
```

<212> TYPE: DNA
<213> ORGANISM: Homo sapiens

<400> SEQUENCE: 501
gcccggctag ctcagtcgat agagcatgag actcttaatc tcagggtcgt gggttcgagc    60
cgcacgttgg gcg                                                       73

<210> SEQ ID NO 502
<211> LENGTH: 73
<212> TYPE: DNA
<213> ORGANISM: Homo sapiens

<400> SEQUENCE: 502
gcccggctag ctcagtcggt agagcatggg actcttaatc tcagggtcgt gggttcgagc    60
cccacgttgg gcg                                                       73

<210> SEQ ID NO 503
<211> LENGTH: 73
<212> TYPE: DNA
<213> ORGANISM: Homo sapiens

<400> SEQUENCE: 503
gcccggctag ctcagtcggt agagcatgag acccttaatc tcagggtcgt gggttcgagc    60
cccacgttgg gcg                                                       73

<210> SEQ ID NO 504
<211> LENGTH: 73
<212> TYPE: DNA
<213> ORGANISM: Homo sapiens

<400> SEQUENCE: 504
gcccggctag ctcagtcggt agagcatgag actcttaatc tcagggtcgt gggttcgagc    60
cccacgttgg gcg                                                       73

<210> SEQ ID NO 505
<211> LENGTH: 73
<212> TYPE: DNA
<213> ORGANISM: Homo sapiens

<400> SEQUENCE: 505
gcccggctag ctcagtcggt agagcatgag actcttaatc tcagggtcgt gggttcgagc    60
cccacgttgg gcg                                                       73

<210> SEQ ID NO 506
<211> LENGTH: 73
<212> TYPE: DNA
<213> ORGANISM: Homo sapiens

<400> SEQUENCE: 506
gcccggctag ctcagtcggt agagcatgag actcttaatc tcagggtcgt gggttcgagc    60
cccacgttgg gcg                                                       73

<210> SEQ ID NO 507
<211> LENGTH: 73
<212> TYPE: DNA
<213> ORGANISM: Homo sapiens

<400> SEQUENCE: 507
gcccggctag ctcagtcggt agagcatgag actcttaatc tcagggtcgt gggttcgagc    60

```
cccacgttgg gcg                                                          73
```

<210> SEQ ID NO 508
<211> LENGTH: 73
<212> TYPE: DNA
<213> ORGANISM: Homo sapiens

<400> SEQUENCE: 508

```
gcccggctag ctcagtcggt agagcatgag actcttaatc tcagggtcgt gggttcgagc       60
cccacgttgg gcg                                                          73
```

<210> SEQ ID NO 509
<211> LENGTH: 73
<212> TYPE: DNA
<213> ORGANISM: Homo sapiens

<400> SEQUENCE: 509

```
gcccggctag ctcagtcggt agagcatggg actcttaatc ccagggtcgt gggttcgagc       60
cccacgttgg gcg                                                          73
```

<210> SEQ ID NO 510
<211> LENGTH: 73
<212> TYPE: DNA
<213> ORGANISM: Homo sapiens

<400> SEQUENCE: 510

```
gcccggctag ctcagtcggt agagcatggg actcttaatc ccagggtcgt gggttcgagc       60
cccacgttgg gcg                                                          73
```

<210> SEQ ID NO 511
<211> LENGTH: 71
<212> TYPE: DNA
<213> ORGANISM: Homo sapiens

<400> SEQUENCE: 511

```
accctgtggt acaggggcta atatgctggg cctttaccac ttcagcccag gttcgattcc       60
tggtcaggga a                                                            71
```

<210> SEQ ID NO 512
<211> LENGTH: 73
<212> TYPE: DNA
<213> ORGANISM: Homo sapiens

<400> SEQUENCE: 512

```
acctgggtag cttagttggt agagcattgg acttttaatt tgagggccca ggtttcaagt       60
ccctgtttgg gtg                                                          73
```

<210> SEQ ID NO 513
<211> LENGTH: 73
<212> TYPE: DNA
<213> ORGANISM: Homo sapiens

<400> SEQUENCE: 513

```
acccagatag ctcagtcagt agagcatcag acttttaatc tgagggtcca aggttcatgt       60
ccctttttgg gtg                                                          73
```

<210> SEQ ID NO 514
<211> LENGTH: 73
<212> TYPE: DNA
<213> ORGANISM: Homo sapiens

<400> SEQUENCE: 514
acctgggtag ctcagtaggt agaacatcag acttttaatc tgagggtcta gggttcaagt    60
ccctgtccag gcg                                                       73

<210> SEQ ID NO 515
<211> LENGTH: 73
<212> TYPE: DNA
<213> ORGANISM: Homo sapiens

<400> SEQUENCE: 515
gcccggagag ctcagtgggt agagcatcag acttttaatc tgagggtcca gggttcaagt    60
cctcgttcgg gca                                                       73

<210> SEQ ID NO 516
<211> LENGTH: 77
<212> TYPE: DNA
<213> ORGANISM: Homo sapiens

<400> SEQUENCE: 516
gcccacgtag ctcaatggtc agagcgtgcg gcttttaacc gcaaggaagg ctgcgagttc    60
gaccctcgcc gtgggct                                                   77

<210> SEQ ID NO 517
<211> LENGTH: 73
<212> TYPE: DNA
<213> ORGANISM: Homo sapiens

<400> SEQUENCE: 517
gcctggatag ctcagttggt agaacatcag acttttaatc tgacggtgca gggttcaagt    60
ccctgttcag gcg                                                       73

<210> SEQ ID NO 518
<211> LENGTH: 73
<212> TYPE: DNA
<213> ORGANISM: Homo sapiens

<400> SEQUENCE: 518
gcctgggtag ctcagtcggt agagcatcag acttttaatc tgagggtcca gggttcaagt    60
ccctgtccag gcg                                                       73

<210> SEQ ID NO 519
<211> LENGTH: 73
<212> TYPE: DNA
<213> ORGANISM: Homo sapiens

<400> SEQUENCE: 519
gcccggatag ctcagtcggt agagcatcag acttttaatc tgagggtccg gggttcaagt    60
ccctgttcgg gcg                                                       73

<210> SEQ ID NO 520
<211> LENGTH: 73
<212> TYPE: DNA
<213> ORGANISM: Homo sapiens

<400> SEQUENCE: 520
gcctggatag ctcagtcggt agagcatcag acttttaatc tgagggtcca gggttcaagt    60
ccctgttcag gcg                                                       73

<210> SEQ ID NO 521
<211> LENGTH: 73
<212> TYPE: DNA
<213> ORGANISM: Homo sapiens

<400> SEQUENCE: 521
gcccggatag ctcagtcggt agagcatcag acttttaatc tgagggtcca gggttcaagt    60
ccctgttcgg gcg                                                      73

<210> SEQ ID NO 522
<211> LENGTH: 73
<212> TYPE: DNA
<213> ORGANISM: Homo sapiens

<400> SEQUENCE: 522
gcccggatag ctcagtcggt agagcatcag acttttaatc tgagggtcca gggttcaagt    60
ccctgttcgg gcg                                                      73

<210> SEQ ID NO 523
<211> LENGTH: 73
<212> TYPE: DNA
<213> ORGANISM: Homo sapiens

<400> SEQUENCE: 523
gcccggatag ctcagtcggt agagcatcag acttttaatc tgagggtcca gggttcaagt    60
ccctgttcgg gcg                                                      73

<210> SEQ ID NO 524
<211> LENGTH: 73
<212> TYPE: DNA
<213> ORGANISM: Homo sapiens

<400> SEQUENCE: 524
gcccggatag ctcagtcggt agagcatcag acttttaatc tgagggtcca gggttcaagt    60
ccctgttcgg gcg                                                      73

<210> SEQ ID NO 525
<211> LENGTH: 73
<212> TYPE: DNA
<213> ORGANISM: Homo sapiens

<400> SEQUENCE: 525
gcccggatag ctcagtcggt agagcatcag acttttaatc tgagggtcca gggttcaagt    60
ccctgttcgg gcg                                                      73

<210> SEQ ID NO 526
<211> LENGTH: 73
<212> TYPE: DNA
<213> ORGANISM: Homo sapiens

<400> SEQUENCE: 526
gcctggatag ctcagttggt agagcatcag acttttaatc tgagggtcca gggttcaagt    60
ccctgttcag gcg                                                      73

<210> SEQ ID NO 527
<211> LENGTH: 73
<212> TYPE: DNA
<213> ORGANISM: Homo sapiens

<400> SEQUENCE: 527

```
gcctggatag ctcagttggt agagcatcag acttttaatc tgagggtcca gggttcaagt    60
ccctgttcag gca                                                       73

<210> SEQ ID NO 528
<211> LENGTH: 75
<212> TYPE: DNA
<213> ORGANISM: Homo sapiens

<400> SEQUENCE: 528
agcagagtgg tgcagtggaa gcatacctat gggcccataa cccagaggtt gatggatgga    60
aaccatcctc tgcta                                                     75

<210> SEQ ID NO 529
<211> LENGTH: 72
<212> TYPE: DNA
<213> ORGANISM: Homo sapiens

<400> SEQUENCE: 529
agcagagtgg cgcagcggaa gcgtgctggg cccataaccc agaggtcgat ggatctaaac    60
catcctctgc ta                                                        72

<210> SEQ ID NO 530
<211> LENGTH: 73
<212> TYPE: DNA
<213> ORGANISM: Homo sapiens

<400> SEQUENCE: 530
gccctcttag tgcagctggc agcgcgtcag tttcataatc tgaaagtcct gagttcaagc    60
ctcagagagg gca                                                       73

<210> SEQ ID NO 531
<211> LENGTH: 72
<212> TYPE: DNA
<213> ORGANISM: Homo sapiens

<400> SEQUENCE: 531
agcagagtgg cgcagcggaa gcgtgctggg cccataaccc agaggtcgat ggatcgaaac    60
catcctctgc ta                                                        72

<210> SEQ ID NO 532
<211> LENGTH: 72
<212> TYPE: DNA
<213> ORGANISM: Homo sapiens

<400> SEQUENCE: 532
agcagagtgg cgcagcggaa gcgtgctggg cccataaccc agaggtcgat ggatcgaaac    60
catcctctgc ta                                                        72

<210> SEQ ID NO 533
<211> LENGTH: 72
<212> TYPE: DNA
<213> ORGANISM: Homo sapiens

<400> SEQUENCE: 533
agcagagtgg cgcagcggaa gcgtgctggg cccataaccc agaggtcgat ggatcgaaac    60
catcctctgc ta                                                        72

<210> SEQ ID NO 534
```

```
<211> LENGTH: 72
<212> TYPE: DNA
<213> ORGANISM: Homo sapiens

<400> SEQUENCE: 534
agcagagtgg cgcagcggaa gcgtgctggg cccataaccc agaggtcgat ggatcgaaac      60
catcctctgc ta                                                         72

<210> SEQ ID NO 535
<211> LENGTH: 72
<212> TYPE: DNA
<213> ORGANISM: Homo sapiens

<400> SEQUENCE: 535
agcagagtgg cgcagcggaa gcgtgctggg cccataaccc agaggtcgat ggatcgaaac      60
catcctctgc ta                                                         72

<210> SEQ ID NO 536
<211> LENGTH: 72
<212> TYPE: DNA
<213> ORGANISM: Homo sapiens

<400> SEQUENCE: 536
agcagagtgg cgcagcggaa gcgtgctggg cccataaccc agaggtcgat ggatcgaaac      60
catcctctgc ta                                                         72

<210> SEQ ID NO 537
<211> LENGTH: 72
<212> TYPE: DNA
<213> ORGANISM: Homo sapiens

<400> SEQUENCE: 537
agcagagtgg cgcagcggaa gcgtgctggg cccataaccc agaggtcgat ggatcgaaac      60
catcctctgc ta                                                         72

<210> SEQ ID NO 538
<211> LENGTH: 72
<212> TYPE: DNA
<213> ORGANISM: Homo sapiens

<400> SEQUENCE: 538
agcagagtgg cgcagcggaa gcgtgctggg cccataaccc agaggtcgat ggatcgaaac      60
catcctctgc ta                                                         72

<210> SEQ ID NO 539
<211> LENGTH: 73
<212> TYPE: DNA
<213> ORGANISM: Homo sapiens

<400> SEQUENCE: 539
gcctcgttag cgcagtaggc agcgcgtcag tctcataatc tgaaggtcgt gagttcgagc      60
ctcacacggg gca                                                        73

<210> SEQ ID NO 540
<211> LENGTH: 73
<212> TYPE: DNA
<213> ORGANISM: Homo sapiens

<400> SEQUENCE: 540
gccctcttag cgcagctggc agcgcgtcag tctcataatc tgaaggtcct gagttcaagc      60
```

```
ctcagagagg gca                                                          73

<210> SEQ ID NO 541
<211> LENGTH: 73
<212> TYPE: DNA
<213> ORGANISM: Homo sapiens

<400> SEQUENCE: 541
gccctcttag cgcagcgggc agcgcgtcag tctcataatc tgaaggtcct gagttcgagc      60
ctcagagagg gca                                                          73

<210> SEQ ID NO 542
<211> LENGTH: 73
<212> TYPE: DNA
<213> ORGANISM: Homo sapiens

<400> SEQUENCE: 542
gccctcttag cgcagcgggc agcgcgtcag tctcataatc tgaaggtcct gagttcgagc      60
ctcagagagg gca                                                          73

<210> SEQ ID NO 543
<211> LENGTH: 73
<212> TYPE: DNA
<213> ORGANISM: Homo sapiens

<400> SEQUENCE: 543
gccctcttag cgcagcgggc agcgcgtcag tctcataatc tgaaggtcct gagttcgagc      60
ctcagagagg gca                                                          73

<210> SEQ ID NO 544
<211> LENGTH: 73
<212> TYPE: DNA
<213> ORGANISM: Homo sapiens

<400> SEQUENCE: 544
gcctccttag cgcagtaggc agcgcgtcag tctcataatc tgaaggtcct gagttcgaac      60
ctcagagggg gca                                                          73

<210> SEQ ID NO 545
<211> LENGTH: 73
<212> TYPE: DNA
<213> ORGANISM: Homo sapiens

<400> SEQUENCE: 545
gcctccttag cgcagtaggc agcgcgtcag tctcataatc tgaaggtcct gagttcgaac      60
ctcagagggg gca                                                          73

<210> SEQ ID NO 546
<211> LENGTH: 73
<212> TYPE: DNA
<213> ORGANISM: Homo sapiens

<400> SEQUENCE: 546
gccctcttag cgcagtgggc agcgcgtcag tctcataatc tgaaggtcct gagttcgagc      60
ctcagagagg gca                                                          73

<210> SEQ ID NO 547
<211> LENGTH: 73
<212> TYPE: DNA
```

<213> ORGANISM: Homo sapiens

<400> SEQUENCE: 547
gcctcgttag cgcagtaggt agcgcgtcag tctcataatc tgaaggtcgt gagttcgatc    60
ctcacacggg gca    73

<210> SEQ ID NO 548
<211> LENGTH: 76
<212> TYPE: DNA
<213> ORGANISM: Homo sapiens

<400> SEQUENCE: 548
gccgaaatag ctcaattggg agagtgttag actgaagatc ttctgcaggt ctctggttca    60
attccgggtt tcgaca    76

<210> SEQ ID NO 549
<211> LENGTH: 74
<212> TYPE: DNA
<213> ORGANISM: Homo sapiens

<400> SEQUENCE: 549
gctgaaatag ctcagttggg agagcgttag actgaagatc ttaaagttcc ctggttcaac    60
cctgggtttc agcc    74

<210> SEQ ID NO 550
<211> LENGTH: 73
<212> TYPE: DNA
<213> ORGANISM: Homo sapiens

<400> SEQUENCE: 550
gccaaaattg ctcagttggg agagcgttag actgaagatc taaaggtccc tggttcgatc    60
ccgggtttca cca    73

<210> SEQ ID NO 551
<211> LENGTH: 74
<212> TYPE: DNA
<213> ORGANISM: Homo sapiens

<400> SEQUENCE: 551
gccgaaatag ctcagttggg agagcgttag accgaagatc ttaaaggtcc ctggttcaat    60
cccgggtttc ggca    74

<210> SEQ ID NO 552
<211> LENGTH: 73
<212> TYPE: DNA
<213> ORGANISM: Homo sapiens

<400> SEQUENCE: 552
gccgagatag ctcagttggg agagcgttag actgaagatc taaaggtccc tggttcaatc    60
ccgggtttcg gca    73

<210> SEQ ID NO 553
<211> LENGTH: 73
<212> TYPE: DNA
<213> ORGANISM: Homo sapiens

<400> SEQUENCE: 553
gccgaaatag ctcagttggg agagcgttag actgaagatc taaaggtccc tggttcaatc    60
ccgggtttcg gca    73

<210> SEQ ID NO 554
<211> LENGTH: 73
<212> TYPE: DNA
<213> ORGANISM: Homo sapiens

<400> SEQUENCE: 554
gccgaaatag ctcagttggg agagcgttag actgaagatc taaaggtccc tggttcgatc    60
ccgggtttcg gca                                                       73

<210> SEQ ID NO 555
<211> LENGTH: 73
<212> TYPE: DNA
<213> ORGANISM: Homo sapiens

<400> SEQUENCE: 555
gccgaaatag ctcagttggg agagcgttag actgaagatc taaaggtccc tggttcgatc    60
ccgggtttcg gca                                                       73

<210> SEQ ID NO 556
<211> LENGTH: 73
<212> TYPE: DNA
<213> ORGANISM: Homo sapiens

<400> SEQUENCE: 556
gccgaaatag ctcagttggg agagcgttag actgaagatc taaaggtccc tggttcgatc    60
ccgggtttcg gca                                                       73

<210> SEQ ID NO 557
<211> LENGTH: 73
<212> TYPE: DNA
<213> ORGANISM: Homo sapiens

<400> SEQUENCE: 557
gccgaaatag ctcagttggg agagcgttag actgaagatc taaaggtccc tggttcgatc    60
ccgggtttcg gca                                                       73

<210> SEQ ID NO 558
<211> LENGTH: 73
<212> TYPE: DNA
<213> ORGANISM: Homo sapiens

<400> SEQUENCE: 558
gccgaaatag ctcagttggg agagcgttag actgaagatc taaaggtccc tggttcgatc    60
ccgggtttcg gca                                                       73

<210> SEQ ID NO 559
<211> LENGTH: 73
<212> TYPE: DNA
<213> ORGANISM: Homo sapiens

<400> SEQUENCE: 559
gccgaaatag ctcagttggg agagcgttag actgaagatc taaaggtccc tggttcgatc    60
ccgggtttcg gca                                                       73

<210> SEQ ID NO 560
<211> LENGTH: 72
<212> TYPE: DNA
<213> ORGANISM: Homo sapiens

```
<400> SEQUENCE: 560
ggctcgttgg tctaggggta tgattctcgc ttagggtgcg agaggtcccg ggttcaaatc    60
ccggacgagc cc                                                        72

<210> SEQ ID NO 561
<211> LENGTH: 72
<212> TYPE: DNA
<213> ORGANISM: Homo sapiens

<400> SEQUENCE: 561
ggctcgttgg tctaggggta tgattctcgc ttagggtgcg agaggtcccg ggttcaaatc    60
ccggacgagc cc                                                        72

<210> SEQ ID NO 562
<211> LENGTH: 72
<212> TYPE: DNA
<213> ORGANISM: Homo sapiens

<400> SEQUENCE: 562
ggctcgttgg tctaggggta tgattctcgc ttagggtgcg agaggtcccg ggttcaaatc    60
ccggacgagc cc                                                        72

<210> SEQ ID NO 563
<211> LENGTH: 72
<212> TYPE: DNA
<213> ORGANISM: Homo sapiens

<400> SEQUENCE: 563
ggctcgttgg tctaggggta tgattctcgc ttagggtgcg agaggtcccg ggttcaaatc    60
ccggacgagc cc                                                        72

<210> SEQ ID NO 564
<211> LENGTH: 72
<212> TYPE: DNA
<213> ORGANISM: Homo sapiens

<400> SEQUENCE: 564
ggctcgttgg tctaggggta tgattctcgc ttagggtgcg agaggtcccg ggttcaaatc    60
ccggacgagc cc                                                        72

<210> SEQ ID NO 565
<211> LENGTH: 72
<212> TYPE: DNA
<213> ORGANISM: Homo sapiens

<400> SEQUENCE: 565
ggctcgttgg tctaggggta tgattctcgc ttagggtgcg agaggtcccg ggttcaaatc    60
ccggacgagc cc                                                        72

<210> SEQ ID NO 566
<211> LENGTH: 72
<212> TYPE: DNA
<213> ORGANISM: Homo sapiens

<400> SEQUENCE: 566
ggctcgttgg tctaggggta tgattctcgc ttagggtgcg agaggtcccg ggttcaaatc    60
ccggacgagc cc                                                        72
```

<210> SEQ ID NO 567
<211> LENGTH: 72
<212> TYPE: DNA
<213> ORGANISM: Homo sapiens

<400> SEQUENCE: 567
ggctcgttgg tctaggggta tgattctcgc ttagggtgcg agaggtcccg ggttcaaatc    60
ccggacgagc cc                                                        72

<210> SEQ ID NO 568
<211> LENGTH: 72
<212> TYPE: DNA
<213> ORGANISM: Homo sapiens

<400> SEQUENCE: 568
ggctcgttgg tctaggggta tgattctcgc ttaggatgcg agaggtcccg ggttcaaatc    60
ccggacgagc cc                                                        72

<210> SEQ ID NO 569
<211> LENGTH: 95
<212> TYPE: DNA
<213> ORGANISM: Homo sapiens

<400> SEQUENCE: 569
ggctcgttgg tctagggtg tggttctcgc ttagggacca cagggacaag cccgggagac     60
ccaagaggtc ccgggttcaa atcccggacg agccc                               95

<210> SEQ ID NO 570
<211> LENGTH: 72
<212> TYPE: DNA
<213> ORGANISM: Homo sapiens

<400> SEQUENCE: 570
ggctcgttgg tctaggggta tgattctcgc ttcgggtgtg agaggtcccg ggttcaaatc    60
ccggacgagc cc                                                        72

<210> SEQ ID NO 571
<211> LENGTH: 72
<212> TYPE: DNA
<213> ORGANISM: Homo sapiens

<400> SEQUENCE: 571
ggctcgttgg tctaggggta tgattctcgc ttcgggtgcg agaggtcccg ggttcaaatc    60
ccggacgagc cc                                                        72

<210> SEQ ID NO 572
<211> LENGTH: 72
<212> TYPE: DNA
<213> ORGANISM: Homo sapiens

<400> SEQUENCE: 572
ggctcgttgg tctaggggta tgattctcgc ttcgggtgcg agaggtcccg ggttcaaatc    60
ccggacgagc cc                                                        72

<210> SEQ ID NO 573
<211> LENGTH: 72
<212> TYPE: DNA
<213> ORGANISM: Homo sapiens

<400> SEQUENCE: 573

```
ggctcgttgg tctaggggta tgattctcgc ttcgggtgcg agaggtcccg ggttcaaatc    60
ccggacgagc cc                                                        72

<210> SEQ ID NO 574
<211> LENGTH: 72
<212> TYPE: DNA
<213> ORGANISM: Homo sapiens

<400> SEQUENCE: 574
ggctcgttgg tctaggggta tgattctcgc tttgggtgcg agaggtcccg ggttcaaatc    60
ccggacgagc cc                                                        72

<210> SEQ ID NO 575
<211> LENGTH: 72
<212> TYPE: DNA
<213> ORGANISM: Homo sapiens

<400> SEQUENCE: 575
ggctcgttgg tctaggggta tgattctcgc tttgggtgcg agaggtcccg ggttcaaatc    60
ccggacgagc cc                                                        72

<210> SEQ ID NO 576
<211> LENGTH: 72
<212> TYPE: DNA
<213> ORGANISM: Homo sapiens

<400> SEQUENCE: 576
ggctcgttgg tctaggggta tgattctcgc tttgggtgcg agaggtcccg ggttcaaatc    60
ccggacgagc cc                                                        72

<210> SEQ ID NO 577
<211> LENGTH: 72
<212> TYPE: DNA
<213> ORGANISM: Homo sapiens

<400> SEQUENCE: 577
ggctcgttgg tctaggggta tgattctcgc tttgggtgcg agaggtcccg ggttcaaatc    60
ccggacgagc cc                                                        72

<210> SEQ ID NO 578
<211> LENGTH: 72
<212> TYPE: DNA
<213> ORGANISM: Homo sapiens

<400> SEQUENCE: 578
ggctcgttgg tctaggggta tgattctcgc tttgggtgcg agaggtcccg ggttcaaatc    60
ccggacgagc cc                                                        72

<210> SEQ ID NO 579
<211> LENGTH: 72
<212> TYPE: DNA
<213> ORGANISM: Homo sapiens

<400> SEQUENCE: 579
ggctcgttgg tctaggggta tgattctcgg tttgggtccg agaggtcccg ggttcaaatc    60
ccggacgagc cc                                                        72

<210> SEQ ID NO 580
<211> LENGTH: 72
```

```
<212> TYPE: DNA
<213> ORGANISM: Homo sapiens

<400> SEQUENCE: 580
ggctcgttgg tctagtggta tgattctcgc tttgggtgcg agaggtcccg ggttcaaatc    60
ccggacgagc cc                                                       72

<210> SEQ ID NO 581
<211> LENGTH: 82
<212> TYPE: DNA
<213> ORGANISM: Homo sapiens

<400> SEQUENCE: 581
gatagcaagg ccgagcggtc taaggctccg gattaaggcg ccggtgtctt cggaggcatg    60
ggttcgaatt ccacctctgc ca                                            82

<210> SEQ ID NO 582
<211> LENGTH: 78
<212> TYPE: DNA
<213> ORGANISM: Homo sapiens

<400> SEQUENCE: 582
gaccaattag caagcacagt tggctagaac atggtgctaa taaggccacg gtcaggggtt    60
caattccctt atgggctg                                                 78

<210> SEQ ID NO 583
<211> LENGTH: 75
<212> TYPE: DNA
<213> ORGANISM: Homo sapiens

<400> SEQUENCE: 583
tggctgatga gctcagctgg tgggagcatg gtgttaatga ggctgaggtc gtgggttcaa    60
tccccaccgg gctat                                                    75

<210> SEQ ID NO 584
<211> LENGTH: 74
<212> TYPE: DNA
<213> ORGANISM: Homo sapiens

<400> SEQUENCE: 584
ggccggttaa cttaattggt tagagcgtgg tgctaataat gtcaaggttg cgggttggat    60
ccccgaacgg gcca                                                     74

<210> SEQ ID NO 585
<211> LENGTH: 176
<212> TYPE: DNA
<213> ORGANISM: Homo sapiens

<400> SEQUENCE: 585
ggctgtatag ctcagtggta gagcatttga ctacagaatc ctatactcag gggaaggaga    60
actgggggtt tctcagtggg tcaaaggact tgtagtggta aatcaaaagc aactctataa   120
gctatgtaac aaactttaaa gtcatatgta gctgggttca atcctgtttt ctgcca       176

<210> SEQ ID NO 586
<211> LENGTH: 74
<212> TYPE: DNA
<213> ORGANISM: Homo sapiens

<400> SEQUENCE: 586
```

```
ggccggttag ctcagttggt tagagcgtgc tgctactaat gccagggtcg aggtttcgat    60
ccccgtacgg gcct                                                      74

<210> SEQ ID NO 587
<211> LENGTH: 72
<212> TYPE: DNA
<213> ORGANISM: Homo sapiens

<400> SEQUENCE: 587
ggtaatgtag cctcgtggtt aggggctgca ttctagagct atgctgccca ggttcaaatt    60
ctggtgccac tc                                                        72

<210> SEQ ID NO 588
<211> LENGTH: 72
<212> TYPE: DNA
<213> ORGANISM: Homo sapiens

<400> SEQUENCE: 588
gggggtatag ctcagggaca gagcacgtgg ttagcatgcg tgaggtcctg cgttcaactt    60
ccagtatttc ca                                                        72

<210> SEQ ID NO 589
<211> LENGTH: 72
<212> TYPE: DNA
<213> ORGANISM: Homo sapiens

<400> SEQUENCE: 589
cgctctttgg tctaggggta tgatcttcgc ttagggtgcg agaggtgcct ggatcaactc    60
cttcacaagc cg                                                        72

<210> SEQ ID NO 590
<211> LENGTH: 71
<212> TYPE: DNA
<213> ORGANISM: Homo sapiens

<400> SEQUENCE: 590
ggctggttgg tctagggcta tgattctcac ttagggtgca agaggtcctg gttcaaatcc    60
cagaggagcc c                                                         71

<210> SEQ ID NO 591
<211> LENGTH: 72
<212> TYPE: DNA
<213> ORGANISM: Homo sapiens

<400> SEQUENCE: 591
ggctggttgg tctagggcta tgattctcac ttagggtgca aaaggtcctg ggttcaaatc    60
ccagaggagc cc                                                        72

<210> SEQ ID NO 592
<211> LENGTH: 68
<212> TYPE: DNA
<213> ORGANISM: Homo sapiens

<400> SEQUENCE: 592
catagggtag tggctaagaa cctaaactct aaatttagat gtcctgagtt caaatcccag    60
ctgtatgc                                                             68

<210> SEQ ID NO 593
<211> LENGTH: 73
```

```
<212> TYPE: DNA
<213> ORGANISM: Homo sapiens

<400> SEQUENCE: 593
gcttctgtaa tgtagtggtt atcacattcg cctcacacat gaaaggtcac cagtttgaga    60
ccgggccaaa aca                                                       73

<210> SEQ ID NO 594
<211> LENGTH: 73
<212> TYPE: DNA
<213> ORGANISM: Homo sapiens

<400> SEQUENCE: 594
gtttctgtag tatagtggtt atcatgtttg cctcacatgt gaaagaccct tggctcgaga    60
ctggagggaa aca                                                       73

<210> SEQ ID NO 595
<211> LENGTH: 73
<212> TYPE: DNA
<213> ORGANISM: Homo sapiens

<400> SEQUENCE: 595
gtttctgtgg tgtagtggtt attatgttcg cttcacatat gaaaggtctc tggttcgaga    60
ctgcgtggga aca                                                       73

<210> SEQ ID NO 596
<211> LENGTH: 73
<212> TYPE: DNA
<213> ORGANISM: Homo sapiens

<400> SEQUENCE: 596
gtttctgtgg tgtagtggtt attatgttcg cttcacatat gaaaggtctc tggttcgaga    60
ctgcgtggga aca                                                       73

<210> SEQ ID NO 597
<211> LENGTH: 72
<212> TYPE: DNA
<213> ORGANISM: Homo sapiens

<400> SEQUENCE: 597
tactcagtgg tctagtggtt aggattcagc gctcccaccg ccgcagcccg ggttcgattc    60
ccggtcatgg aa                                                        72

<210> SEQ ID NO 598
<211> LENGTH: 71
<212> TYPE: DNA
<213> ORGANISM: Homo sapiens

<400> SEQUENCE: 598
gcactggtgg ttcagtggta gaattctcgc ctcccacgcg ggagacccgg gtttaattcc    60
cggtcaagat a                                                         71

<210> SEQ ID NO 599
<211> LENGTH: 69
<212> TYPE: DNA
<213> ORGANISM: Homo sapiens

<400> SEQUENCE: 599
gcattcgtag ttcagcggca gaaatttcgt ctcctacgcg ggagactcgg gttcgacttc    60
```

```
ggccatgca                                                              69

<210> SEQ ID NO 600
<211> LENGTH: 71
<212> TYPE: DNA
<213> ORGANISM: Homo sapiens

<400> SEQUENCE: 600
ggatttgtgg tccagtggta gaattctcac cgcctgcata ggagaccctg gtttaattcc      60
tggccaatgc a                                                           71

<210> SEQ ID NO 601
<211> LENGTH: 71
<212> TYPE: DNA
<213> ORGANISM: Homo sapiens

<400> SEQUENCE: 601
ggattggtgg tccagtggta gaattctcac cgcctgcata ggagaccctg gtttaattcc      60
tggccaatgc a                                                           71

<210> SEQ ID NO 602
<211> LENGTH: 71
<212> TYPE: DNA
<213> ORGANISM: Homo sapiens

<400> SEQUENCE: 602
gcattggtag ttcagcggtg gcattctccc cacctacgcg ggagacctgg gttcaactcc      60
cggccaaagc a                                                           71

<210> SEQ ID NO 603
<211> LENGTH: 71
<212> TYPE: DNA
<213> ORGANISM: Homo sapiens

<400> SEQUENCE: 603
gcattggtag ttcagcggtg gcattctccc cacctacgcg ggagacctgg gttcaactcc      60
cggccaaagc a                                                           71

<210> SEQ ID NO 604
<211> LENGTH: 73
<212> TYPE: DNA
<213> ORGANISM: Homo sapiens

<400> SEQUENCE: 604
ggcgggataa tgtagtggtt aaaggcatgg gctctagagc cagacttcct gggttcaaat      60
ctcagacctg cta                                                         73

<210> SEQ ID NO 605
<211> LENGTH: 68
<212> TYPE: DNA
<213> ORGANISM: Homo sapiens

<400> SEQUENCE: 605
ggcagggtag ggtagaggtt aaaaccatgg attctagagc cagatgggtt caaatcccgg      60
ctctgccg                                                               68

<210> SEQ ID NO 606
<211> LENGTH: 72
<212> TYPE: DNA
```

<400> SEQUENCE: 606
tccctggtgt tccggtggtt aggatttggc attctcactg ttgtggtgcg gattcaatcc    60
tggcttaggg ta    72

<210> SEQ ID NO 607
<211> LENGTH: 73
<212> TYPE: DNA
<213> ORGANISM: Homo sapiens

<400> SEQUENCE: 607
ccgtggatag cccagcggct atgggagccg ggctctcact ctgacgtcct gggttcaagt    60
cccagtgtgc aca    73

<210> SEQ ID NO 608
<211> LENGTH: 73
<212> TYPE: DNA
<213> ORGANISM: Homo sapiens

<400> SEQUENCE: 608 ccc ctggcgg tctagtggtt aggattcggc gctctcatcc accgcggcct gggttcgact    60
cgtggtcaga gtg    73

<210> SEQ ID NO 609
<211> LENGTH: 75
<212> TYPE: DNA
<213> ORGANISM: Homo sapiens

<400> SEQUENCE: 609
ctctggtggt ttagtggcta ggattcacct ctctcactgc tgcagcccag ggttccattc    60
cctgggagtc agatg    75

<210> SEQ ID NO 610
<211> LENGTH: 72
<212> TYPE: DNA
<213> ORGANISM: Homo sapiens

<400> SEQUENCE: 610 cccc ttgtag tctagtggtt agaattctgc ggtctcacag ccgcggcccg ggttcgattc    60
ccattccggg aa    72

<210> SEQ ID NO 611
<211> LENGTH: 72
<212> TYPE: DNA
<213> ORGANISM: Homo sapiens

<400> SEQUENCE: 611
ttattattat acctgtggtt aggattcggc gctctcaccg ccacgacccg ggttcaattc    60
ccggtcaggg aa    72

<210> SEQ ID NO 612
<211> LENGTH: 72
<212> TYPE: DNA
<213> ORGANISM: Homo sapiens

<400> SEQUENCE: 612
cccctggtag tctagtggtt aggctttgcc gctctcagtg ccgctgcctg ggttggattc    60
ccagtcatgt ga    72

```
<210> SEQ ID NO 613
<211> LENGTH: 72
<212> TYPE: DNA
<213> ORGANISM: Homo sapiens

<400> SEQUENCE: 613
tccctgcttg tctagtggtt agaattcagc actctcactg ccacagccca ggttcaattc    60
cctgtcagag aa                                                        72

<210> SEQ ID NO 614
<211> LENGTH: 73
<212> TYPE: DNA
<213> ORGANISM: Homo sapiens

<400> SEQUENCE: 614
ttccccttgg tctagtggtt aggattcaac actctcaccg ccgcagcccg ggtttgattc    60
ccaggcaggg aag                                                       73

<210> SEQ ID NO 615
<211> LENGTH: 72
<212> TYPE: DNA
<213> ORGANISM: Homo sapiens

<400> SEQUENCE: 615
cccctggtgg tctagtgctt aggatttggc actctcgcca ccgcagcctg cgttcaattc    60
ccggtcaggg aa                                                        72

<210> SEQ ID NO 616
<211> LENGTH: 72
<212> TYPE: DNA
<213> ORGANISM: Homo sapiens

<400> SEQUENCE: 616
tccctggtgg tctaatggtt aggagtcggc actctcaccg ccgcggctgg ggtttgattc    60
ccagtcatgt aa                                                        72

<210> SEQ ID NO 617
<211> LENGTH: 76
<212> TYPE: DNA
<213> ORGANISM: Homo sapiens

<400> SEQUENCE: 617
gtgagactgc acagcccagt ggtgcagggc atggctctga cacctggcgg cctgggttca    60
aatcccagct tctaca                                                    76

<210> SEQ ID NO 618
<211> LENGTH: 72
<212> TYPE: DNA
<213> ORGANISM: Homo sapiens

<400> SEQUENCE: 618
ggttccatga tgtaatggtg agcgctttgg actctgagta cggtgatcag cgttcaagtc    60
tcagtgggac ct                                                        72

<210> SEQ ID NO 619
<211> LENGTH: 72
<212> TYPE: DNA
<213> ORGANISM: Homo sapiens

<400> SEQUENCE: 619
```

```
ggtagtgtag tctactggtt aaacgcttgg gctctgacat taacgtcctg ggttcaaatc    60
ccagctttgt ca                                                        72

<210> SEQ ID NO 620
<211> LENGTH: 75
<212> TYPE: DNA
<213> ORGANISM: Homo sapiens

<400> SEQUENCE: 620
ctaggacgtg gtgtaatagg tagcacagag aattctggat tctcaggggt aggttcaatt    60
cctatagaac ctagg                                                     75

<210> SEQ ID NO 621
<211> LENGTH: 72
<212> TYPE: DNA
<213> ORGANISM: Homo sapiens

<400> SEQUENCE: 621
ggttccatgg tgtaatggtg agggctttgg actctgacta cagtgatcag agttcaagtc    60
tcagtgggac ct                                                        72

<210> SEQ ID NO 622
<211> LENGTH: 72
<212> TYPE: DNA
<213> ORGANISM: Homo sapiens

<400> SEQUENCE: 622
ggttccatgg gttaatggtg agcaccctgg actctgaatc aagcgatccg agttcaaatc    60
tcggtggtac ct                                                        72

<210> SEQ ID NO 623
<211> LENGTH: 74
<212> TYPE: DNA
<213> ORGANISM: Homo sapiens

<400> SEQUENCE: 623
gcctggctac ctcagttggt agagcatggg actcttaatc ccagagtcag tgggttcaag    60
cctcacattg agtg                                                      74

<210> SEQ ID NO 624
<211> LENGTH: 73
<212> TYPE: DNA
<213> ORGANISM: Homo sapiens

<400> SEQUENCE: 624
gcccagctag ctcagccggt agagcacaag actcttaatc tcagggtcgt gggtttgagc    60
cctgtgttga gca                                                       73

<210> SEQ ID NO 625
<211> LENGTH: 73
<212> TYPE: DNA
<213> ORGANISM: Homo sapiens

<400> SEQUENCE: 625
gtctagctag atcagttggt agagcataag actcttaatc tcagggtcat gggtttgagc    60
cctacgttgg gcg                                                       73

<210> SEQ ID NO 626
```

```
<211> LENGTH: 73
<212> TYPE: DNA
<213> ORGANISM: Homo sapiens

<400> SEQUENCE: 626
accagcatgt ctcagtcggt atagtgtgag actcttaatc tcagggtcgt gggttcaagc    60
cccacattgg gcg                                                        73

<210> SEQ ID NO 627
<211> LENGTH: 73
<212> TYPE: DNA
<213> ORGANISM: Homo sapiens

<400> SEQUENCE: 627
gccaaaatag ctcagctggg agagtattag gttgaagata caaagttcct tggctcaatc    60
cagagtttgg ggg                                                        73

<210> SEQ ID NO 628
<211> LENGTH: 73
<212> TYPE: DNA
<213> ORGANISM: Homo sapiens

<400> SEQUENCE: 628
gctgagatag ctcggttggg agggcatcag cctgaagatc taaaggagac tggttcaatt    60
ctgggttttg gca                                                        73

<210> SEQ ID NO 629
<211> LENGTH: 72
<212> TYPE: DNA
<213> ORGANISM: Homo sapiens

<400> SEQUENCE: 629
tgcatggttg tctagtggct aggattcggt gctgaaagcg tcacggcccg ggttcgattc    60
ccggtcaggg aa                                                         72

<210> SEQ ID NO 630
<211> LENGTH: 72
<212> TYPE: DNA
<213> ORGANISM: Homo sapiens

<400> SEQUENCE: 630
tgcatggttg tctagtggct aggattcggt gctgaaagag ccacggcccg ggttcgattc    60
ccggtcaggg aa                                                         72

<210> SEQ ID NO 631
<211> LENGTH: 73
<212> TYPE: DNA
<213> ORGANISM: Homo sapiens

<400> SEQUENCE: 631
gccaaaatag ctcagctggg agagcattag actgaagatc taaaggtctc tggtttgatc    60
ctgggtttca gaa                                                        73

<210> SEQ ID NO 632
<211> LENGTH: 73
<212> TYPE: DNA
<213> ORGANISM: Homo sapiens

<400> SEQUENCE: 632
gggggtatat ctcaggggggc agagcatttg actgcagatc aagaggtccc cggttgaaat    60
```
ccgggtgctg gat                                                          73

<210> SEQ ID NO 633
<211> LENGTH: 73
<212> TYPE: DNA
<213> ORGANISM: Homo sapiens

<400> SEQUENCE: 633
ggcagtgtgg catagtggtt agaaatgtgc gctctggggc tgctgatccc aggctcaaac       60
cctggcgctg tca                                                          73

<210> SEQ ID NO 634
<211> LENGTH: 73
<212> TYPE: DNA
<213> ORGANISM: Homo sapiens

<400> SEQUENCE: 634
gtcagtgttg cacaacggtt aagtgaagag gctgtaaacc cagactggat gggttcaatt       60
cccatctctg ccg                                                          73

<210> SEQ ID NO 635
<211> LENGTH: 76
<212> TYPE: DNA
<213> ORGANISM: Homo sapiens

<400> SEQUENCE: 635
tcaattatag ctcagtggta gagcatttaa ctgtagatca agaggtccct ggatcaactc       60
tgggtgcccc ctttaa                                                       76

<210> SEQ ID NO 636
<211> LENGTH: 72
<212> TYPE: DNA
<213> ORGANISM: Homo sapiens

<400> SEQUENCE: 636
tccttgttac tatagtggtg agtatctctg cctgtcatgc gtgagagagg gggtcgattc       60
cccgacgggg ag                                                           72

<210> SEQ ID NO 637
<211> LENGTH: 74
<212> TYPE: DNA
<213> ORGANISM: Homo sapiens

<400> SEQUENCE: 637
gtctctgtgg cacaatcggt tagcttgttc ggctgttaat ctagaggttg gtggttagag       60
cccactgagg gatg                                                         74

<210> SEQ ID NO 638
<211> LENGTH: 74
<212> TYPE: DNA
<213> ORGANISM: Homo sapiens

<400> SEQUENCE: 638
gtctctgtgg cacaatcggt tagagcgttc ggctgttaat ctaaaggttg gtggctagaa       60
cccactgagg gacg                                                         74

<210> SEQ ID NO 639
<211> LENGTH: 74
<212> TYPE: DNA

-continued

<213> ORGANISM: Homo sapiens

<400> SEQUENCE: 639
gtctctgtgg cacaatcggt tagcgcgttc ggctgttaat ctagaggttg gtggttagag    60
cccactgagg gatg                                                      74

<210> SEQ ID NO 640
<211> LENGTH: 75
<212> TYPE: DNA
<213> ORGANISM: Homo sapiens

<400> SEQUENCE: 640
gttaagatgg catagcccag caattgcata aaacttaaga cttttataatt agaagttcaa   60 cacctcttct taaca                                                     75

<210> SEQ ID NO 641
<211> LENGTH: 75
<212> TYPE: DNA
<213> ORGANISM: Homo sapiens

<400> SEQUENCE: 641
gttaagatgg cagagcccag cgattgcata aaacttaaca ctttataatc agaggttcaa    60
ctcctcttct taaca                                                     75

<210> SEQ ID NO 642
<211> LENGTH: 75
<212> TYPE: DNA
<213> ORGANISM: Homo sapiens

<400> SEQUENCE: 642
gttaagatgg cagagcccag caattgcata aaacttaaaa ctttacaatc agaggttcaa    60
ctcctcttct taaca                                                     75

<210> SEQ ID NO 643
<211> LENGTH: 75
<212> TYPE: DNA
<213> ORGANISM: Homo sapiens

<400> SEQUENCE: 643
gttaagatgg cagagcccag caattgcata aatcttaaaa ctttataatc agaggttcga    60
ctcctcttct taaca                                                     75

<210> SEQ ID NO 644
<211> LENGTH: 75
<212> TYPE: DNA
<213> ORGANISM: Homo sapiens

<400> SEQUENCE: 644
gttaagacgg cagagcccgg caattgcgta aaatttacaa ctttatgggc agaggttcaa    60
ttcctcttct taaca                                                     75

<210> SEQ ID NO 645
<211> LENGTH: 82
<212> TYPE: DNA
<213> ORGANISM: Homo sapiens

<400> SEQUENCE: 645
ggtagtgtgg ttgaatggtc taaggcactg aatttaggct ccagtctctt tggggacgtg    60
ggtttaaatc ccactgctgc aa                                             82

<210> SEQ ID NO 646
<211> LENGTH: 72
<212> TYPE: DNA
<213> ORGANISM: Homo sapiens

<400> SEQUENCE: 646
gtgttgatgg tatagtggtg agcatagctg ccttccaagc aattgacccg acttcaattc    60
ccagccaacg ca    72

<210> SEQ ID NO 647
<211> LENGTH: 72
<212> TYPE: DNA
<213> ORGANISM: Homo sapiens

<400> SEQUENCE: 647
gtgttgatgg tatagtggtg agcatagctg ccttccaagc aattgacccg acttcgattc    60
ccagccaatg ca    72

<210> SEQ ID NO 648
<211> LENGTH: 69
<212> TYPE: DNA
<213> ORGANISM: Homo sapiens

<400> SEQUENCE: 648
gaaaaagtca tagggttat gaggctggct tgaaaccagc cttaggaggt tcaattcctt    60
cctttttg    69

<210> SEQ ID NO 649
<211> LENGTH: 70
<212> TYPE: DNA
<213> ORGANISM: Homo sapiens

<400> SEQUENCE: 649
gagaaggtca tagaggttat gggattggct tgaaaccagt ctctgggggg ttcgattccc    60
tccttttca    70

<210> SEQ ID NO 650
<211> LENGTH: 70
<212> TYPE: DNA
<213> ORGANISM: Homo sapiens

<400> SEQUENCE: 650
gggggagtgg tgtggttacg aatgtggcct ctgcaagcag acagcctggg ttcaattccc    60
agcttggcca    70

<210> SEQ ID NO 651
<211> LENGTH: 72
<212> TYPE: DNA
<213> ORGANISM: Homo sapiens

<400> SEQUENCE: 651
gtggatgtag tttagtggta gaacgcgcgc tttgcatgta tgaggtcccg gtttcgatcc    60
ctggcgtttc ca    72

<210> SEQ ID NO 652
<211> LENGTH: 77
<212> TYPE: DNA
<213> ORGANISM: Homo sapiens

<400> SEQUENCE: 652
gccaggagag ctcagtggtg atgggatgag atctggactc acacctctag gcctgggttc    60
aaatcccagg tctagcg    77

<210> SEQ ID NO 653
<211> LENGTH: 72
<212> TYPE: DNA
<213> ORGANISM: Homo sapiens

<400> SEQUENCE: 653
taggacttgg tgtaataggt agcacgaaga gatttggatt ctcagggggta ggttcaattc    60 ctatagttct gg    72

<210> SEQ ID NO 654
<211> LENGTH: 71
<212> TYPE: DNA
<213> ORGANISM: Homo sapiens

<400> SEQUENCE: 654
ggcctgttgg tctagaggta tgattctcgc tttgggtgcg agaggccccg gtgcgagtcc    60
cagaggagcc c    71

<210> SEQ ID NO 655
<211> LENGTH: 72
<212> TYPE: DNA
<213> ORGANISM: Homo sapiens

<400> SEQUENCE: 655
ggcagcctgg cttagtggaa agggaatagg ctttagagcc agactgcctg ggtttgaatc    60
ccagccccgc ca    72

<210> SEQ ID NO 656
<211> LENGTH: 69
<212> TYPE: DNA
<213> ORGANISM: Homo sapiens

<400> SEQUENCE: 656
tccctggtct agtggttagg atttattatt ttcatggctg tggcctgagt tcaatttcca    60
atcagggaa    69

<210> SEQ ID NO 657
<211> LENGTH: 72
<212> TYPE: DNA
<213> ORGANISM: Homo sapiens

<400> SEQUENCE: 657
tccctggtgg tctggtggct agaatttagc gctttcaccg ccgcagctcg ggttggatta    60
ccagtcaggg aa    72

<210> SEQ ID NO 658
<211> LENGTH: 73
<212> TYPE: DNA
<213> ORGANISM: Homo sapiens

<400> SEQUENCE: 658
tccgtggtgg tctagtggct aggattcggc gctttcaccg cctgcagctc gagttcgatt    60
cctggtcagg gaa    73

```
<210> SEQ ID NO 659
<211> LENGTH: 71
<212> TYPE: DNA
<213> ORGANISM: Homo sapiens

<400> SEQUENCE: 659
gcaatggtgg ttcagtggta gaattctcgc ctttcacaca ggagacccgg gttcaattcc      60
tgacccatgt a                                                          71

<210> SEQ ID NO 660
<211> LENGTH: 72
<212> TYPE: DNA
<213> ORGANISM: Homo sapiens

<400> SEQUENCE: 660
tgtctggtgg tcaagtggct aggatttggc gctttcactg ccgcggcccg cgttcgattc      60
ccggtcaggg aa                                                         72

<210> SEQ ID NO 661
<211> LENGTH: 72
<212> TYPE: DNA
<213> ORGANISM: Homo sapiens

<400> SEQUENCE: 661
tccttggtgg tctagtggct aggattcggt gctttcacct gtgcggcccg ggttcaattc      60
ccgatgaagg aa                                                         72

<210> SEQ ID NO 662
<211> LENGTH: 72
<212> TYPE: DNA
<213> ORGANISM: Homo sapiens

<400> SEQUENCE: 662
taggacgtgg tgtgataggt agcacagaga attttggatt ctcagggta ggttaaattc       60 ctatagtact ag                                                         72

<210> SEQ ID NO 663
<211> LENGTH: 72
<212> TYPE: DNA
<213> ORGANISM: Homo sapiens

<400> SEQUENCE: 663
taggacgtgg tgtgataggt agcatgggga attttggatt ctcagggtg ggttcaattc       60 ctatagttct ag                                                         72

<210> SEQ ID NO 664
<211> LENGTH: 74
<212> TYPE: DNA
<213> ORGANISM: Homo sapiens

<400> SEQUENCE: 664
ggcaatgtag cattgtggct aagtgcacag gctttggaaa ctggcaggcc tgggttcaaa      60
tcccagctta ttca                                                       74

<210> SEQ ID NO 665
<211> LENGTH: 72
<212> TYPE: DNA
<213> ORGANISM: Homo sapiens

<400> SEQUENCE: 665
```

```
taggatgtgg tgtaataggt ggcatggaga attttggatt atcaggggta ggttcaattc     60
ctatagttct ag                                                          72

<210> SEQ ID NO 666
<211> LENGTH: 72
<212> TYPE: DNA
<213> ORGANISM: Homo sapiens

<400> SEQUENCE: 666
tagtacatag tgtaataggt agcacagata attttggatt ctcaggggta ggttcaattc     60
ttatagttct ag                                                          72

<210> SEQ ID NO 667
<211> LENGTH: 73
<212> TYPE: DNA
<213> ORGANISM: Homo sapiens

<400> SEQUENCE: 667
agcagtgtag cctagtggct aggtcctctg actttgaaac cacgtggtct gggtttaagt     60
ctcagctgtg cta                                                         73

<210> SEQ ID NO 668
<211> LENGTH: 72
<212> TYPE: DNA
<213> ORGANISM: Homo sapiens

<400> SEQUENCE: 668
taggatgtgg tgtgacaggt agcatggaga attttggatt ctcagggtta ggttcaattc     60
ctatagttct ag                                                          72

<210> SEQ ID NO 669
<211> LENGTH: 73
<212> TYPE: DNA
<213> ORGANISM: Homo sapiens

<400> SEQUENCE: 669
agctgtatat tatagtggaa taaatgtgga ctttgaagtt agatacacct gggttcaaat     60
cccagtgctg tca                                                         73

<210> SEQ ID NO 670
<211> LENGTH: 72
<212> TYPE: DNA
<213> ORGANISM: Homo sapiens

<400> SEQUENCE: 670
taggacgtgg tgtgataggt agcacggaga attttggatt ctcagggatg ggttcaattc     60
ctgtagttct ag                                                          72

<210> SEQ ID NO 671
<211> LENGTH: 75
<212> TYPE: DNA
<213> ORGANISM: Homo sapiens

<400> SEQUENCE: 671
tttaggacgt ggtgtaatag gtagcacaga gaattttgga ttctcaggtg caggttcaat     60
tcctatattc tagag                                                       75

<210> SEQ ID NO 672
<211> LENGTH: 72
```

```
<212> TYPE: DNA
<213> ORGANISM: Homo sapiens

<400> SEQUENCE: 672
taggacgtgg tgtgataggt agcatggaga attttggatt ctcagggatg ggttcaattc    60
ctatagtcct ag                                                       72

<210> SEQ ID NO 673
<211> LENGTH: 75
<212> TYPE: DNA
<213> ORGANISM: Homo sapiens

<400> SEQUENCE: 673
tctaggatgt ggtgtgatag gtagcatgga gaattttgga ttctcagggg taggttcaat    60
tcctatattc tagaa                                                    75

<210> SEQ ID NO 674
<211> LENGTH: 72
<212> TYPE: DNA
<213> ORGANISM: Homo sapiens

<400> SEQUENCE: 674
taggatgtgg tgtattaggt agcacagaga attttggatt ctcaggggta ggttcgattc    60
ctataattct ac                                                       72

<210> SEQ ID NO 675
<211> LENGTH: 72
<212> TYPE: DNA
<213> ORGANISM: Homo sapiens

<400> SEQUENCE: 675
taggacgtgg tgtagtaggt agcatggaga atgttgaatt ctcagggta ggttcaattc    60 ctatagttct ag                                                       72

<210> SEQ ID NO 676
<211> LENGTH: 72
<212> TYPE: DNA
<213> ORGANISM: Homo sapiens

<400> SEQUENCE: 676
taggacatgg tgtgataggt agcatggaga attttggatt ctcagggta ggttcaattc    60 ctacagttct ag                                                       72

<210> SEQ ID NO 677
<211> LENGTH: 73
<212> TYPE: DNA
<213> ORGANISM: Homo sapiens

<400> SEQUENCE: 677
ggctgtgtac ctcagtgggc aagggtatgg actttgaagc cagactattt gggttcaaat    60
cccagcttgg cct                                                      73

<210> SEQ ID NO 678
<211> LENGTH: 70
<212> TYPE: DNA
<213> ORGANISM: Homo sapiens

<400> SEQUENCE: 678
tcctatagcc cagtgattag gattctttgc ttttactacc atgacctggg ttcaataccc    60
```
agtcagggaa                                                             70

<210> SEQ ID NO 679
<211> LENGTH: 73
<212> TYPE: DNA
<213> ORGANISM: Homo sapiens

<400> SEQUENCE: 679
gttggggtaa ctcagttggt agagtagcag acttttcatc tgagggtcca gggtttaagt      60
ccatgtccag gca                                                         73

<210> SEQ ID NO 680
<211> LENGTH: 73
<212> TYPE: DNA
<213> ORGANISM: Homo sapiens

<400> SEQUENCE: 680
acccagatag ctcagttgat agagcatcag acttttaatc tgagggtcca gggttcatgt      60
ccctgttcct taa                                                         73

<210> SEQ ID NO 681
<211> LENGTH: 74
<212> TYPE: DNA
<213> ORGANISM: Homo sapiens

<400> SEQUENCE: 681
gcctgggtag ctcagtcggt agagctatca gactttttagc ctgaggattc agggttcaat     60
cccttgctgg ggcg                                                        74

<210> SEQ ID NO 682
<211> LENGTH: 73
<212> TYPE: DNA
<213> ORGANISM: Homo sapiens

<400> SEQUENCE: 682
gccaggatag ttcaggtggt agagcatcag acttttaacc tgagggttca gggttcaagt      60
ctctgtttgg gcg                                                         73

<210> SEQ ID NO 683
<211> LENGTH: 74
<212> TYPE: DNA
<213> ORGANISM: Homo sapiens

<400> SEQUENCE: 683
gaccgtgtgg ccttaatgga taaggtgtct gacttcagat cagaagattg agggtttgag      60 tcccttttgtg gtca                                                       74

<210> SEQ ID NO 684
<211> LENGTH: 86
<212> TYPE: DNA
<213> ORGANISM: Homo sapiens

<400> SEQUENCE: 684
gctcggatga tcctcagtgg tctggggtgc aggcttcaaa cctgtagctg tctagtgaca      60
gagtggttca attccacctt tgtagg                                           86

<210> SEQ ID NO 685
<211> LENGTH: 86
<212> TYPE: DNA
<213> ORGANISM: Homo sapiens

<400> SEQUENCE: 685
gcccggatga tcctcagtgg tctggggtgc aggcttcaaa cctgtagctg tctagcgaca    60
gagtggttca attccacctt tcgggc    86

<210> SEQ ID NO 686
<211> LENGTH: 82
<212> TYPE: DNA
<213> ORGANISM: Homo sapiens

<400> SEQUENCE: 686
tgagttgtag ctgagtggtt aaggcaacga gctagaaatt cgttggtttc tctctgtgca    60
ggtttgaatc ctgctaatta tg    82

<210> SEQ ID NO 687
<211> LENGTH: 72
<212> TYPE: DNA
<213> ORGANISM: Homo sapiens

<400> SEQUENCE: 687
gggtgtatgg ctcaggggta gagaatttga ctagagatca agaggtccct ggttcaaatc    60
caggtgcccc ct    72

<210> SEQ ID NO 688
<211> LENGTH: 82
<212> TYPE: DNA
<213> ORGANISM: Homo sapiens

<400> SEQUENCE: 688
gtagtcgtgg ccgagtggtt aaggtgatgg actagaaacc cattggggtc tccccgcgca    60
ggttcgaatc ctgccgacta cg    82

<210> SEQ ID NO 689
<211> LENGTH: 82
<212> TYPE: DNA
<213> ORGANISM: Homo sapiens

<400> SEQUENCE: 689
gtagtcgtgg ccgagtggtt aaggcgatgg actagaaatc cattggggtt tccccacgca    60
ggttcgaatc ctgccgacta cg    82

<210> SEQ ID NO 690
<211> LENGTH: 82
<212> TYPE: DNA
<213> ORGANISM: Homo sapiens

<400> SEQUENCE: 690
gtagtcgtgg ccgagtggtt aaggcgatgg actagaaatc cattggggtc tccccgcgca    60
ggttcgaatc ctgccgacta cg    82

<210> SEQ ID NO 691
<211> LENGTH: 82
<212> TYPE: DNA
<213> ORGANISM: Homo sapiens

<400> SEQUENCE: 691
gtagtcgtgg ccgagtggtt aaggcgatgg actagaaatc cattggggtc tccccgcgca    60
ggttcgaatc ctgccgacta cg    82

<210> SEQ ID NO 692
<211> LENGTH: 82
<212> TYPE: DNA
<213> ORGANISM: Homo sapiens

<400> SEQUENCE: 692
gtagtcgtgg ccgagtggtt aaggcgatgg actagaaatc cattggggtc tccccgcgca    60
ggttcgaatc ctgccgacta cg                                              82

<210> SEQ ID NO 693
<211> LENGTH: 82
<212> TYPE: DNA
<213> ORGANISM: Homo sapiens

<400> SEQUENCE: 693
gtagtcgtgg ccgagtggtt aaggcgatgg actagaaatc cattggggtc tccccgcgca    60
ggttcgaatc ctgccgacta cg                                              82

<210> SEQ ID NO 694
<211> LENGTH: 82
<212> TYPE: DNA
<213> ORGANISM: Homo sapiens

<400> SEQUENCE: 694
gtagtcgtgg ccgagtggtt aaggcgatgg actagaaatc cattggggtc tccccgcgca    60
ggttcgaatc ctgccgacta cg                                              82

<210> SEQ ID NO 695
<211> LENGTH: 82
<212> TYPE: DNA
<213> ORGANISM: Homo sapiens

<400> SEQUENCE: 695
gtagtcgtgg ccgagtggtt aaggcgatgg actagaaatc cattggggtc tccccgcgca    60
ggttcgaatc ctgccgacta cg                                              82

<210> SEQ ID NO 696
<211> LENGTH: 82
<212> TYPE: DNA
<213> ORGANISM: Homo sapiens

<400> SEQUENCE: 696
gtagtcgtgg ccgagtggtt aaggcgatgg actagaaatc cattggggtt tccccgcgca    60
ggttcgaatc ctgccgacta cg                                              82

<210> SEQ ID NO 697
<211> LENGTH: 82
<212> TYPE: DNA
<213> ORGANISM: Homo sapiens

<400> SEQUENCE: 697
gtcacggtgg ccgagtggtt aaggcgttgg actcgaaatc caatggggtt tccccgcaca    60
ggttcgaatc ctgttcgtga cg                                              82

<210> SEQ ID NO 698
<211> LENGTH: 82
<212> TYPE: DNA
<213> ORGANISM: Homo sapiens

<400> SEQUENCE: 698
gctgtgatgg ccgagtggtt aaggtgttgg actcgaaatc caatgggggt tccccgcgca    60
ggttcaaatc ctgctcacag cg                                            82

<210> SEQ ID NO 699
<211> LENGTH: 82
<212> TYPE: DNA
<213> ORGANISM: Homo sapiens

<400> SEQUENCE: 699
gctgtgatgg ccgagtggtt aaggcgttgg actcgaaatc caatggggtc tccccgcgca    60
ggttcaaatc ctgctcacag cg                                            82

<210> SEQ ID NO 700
<211> LENGTH: 82
<212> TYPE: DNA
<213> ORGANISM: Homo sapiens

<400> SEQUENCE: 700
gctgtgatgg ccgagtggtt aaggcgttgg actcgaaatc caatggggtc tccccgcgca    60
ggttcgaatc ctgctcacag cg                                            82

<210> SEQ ID NO 701
<211> LENGTH: 84
<212> TYPE: DNA
<213> ORGANISM: Homo sapiens

<400> SEQUENCE: 701
ggagaggcct ggccgagtgg ttaaggcgat ggactgctaa tccattgtgc tctgcacgcg    60
tgggttcgaa tcccatcctc gtcg                                          84

<210> SEQ ID NO 702
<211> LENGTH: 82
<212> TYPE: DNA
<213> ORGANISM: Homo sapiens

<400> SEQUENCE: 702
gacgaggtgg ccgagtggtt aaggcgatgg actgctaatc cattgtgctc tgcacacgtg    60
ggttcgaatc ccatcctcgt cg                                            82

<210> SEQ ID NO 703
<211> LENGTH: 82
<212> TYPE: DNA
<213> ORGANISM: Homo sapiens

<400> SEQUENCE: 703
gacgaggtgg ccgagtggtt aaggcgatgg actgctaatc cattgtgctc tgcacgcgtg    60
ggttcgaatc ccatcctcgt cg                                            82

<210> SEQ ID NO 704
<211> LENGTH: 82
<212> TYPE: DNA
<213> ORGANISM: Homo sapiens

<400> SEQUENCE: 704
gacgaggtgg ccgagtggtt aaggcgatgg actgctaatc cattgtgctc tgcacgcgtg    60
ggttcgaatc ccatcctcgt cg                                            82

<210> SEQ ID NO 705

```
<211> LENGTH: 82
<212> TYPE: DNA
<213> ORGANISM: Homo sapiens

<400> SEQUENCE: 705
gacgaggtgg ccgagtggtt aaggcgatgg actgctaatc cattgtgctc tgcacgcgtg     60
ggttcgaatc ccatcctcgt cg                                              82

<210> SEQ ID NO 706
<211> LENGTH: 82
<212> TYPE: DNA
<213> ORGANISM: Homo sapiens

<400> SEQUENCE: 706
gacgaggtgg ccgagtggtt aaggcgatgg actgctaatc cattgtgctt tgcacgcgtg     60
ggttcgaatc ccatcctcgt cg                                              82

<210> SEQ ID NO 707
<211> LENGTH: 82
<212> TYPE: DNA
<213> ORGANISM: Homo sapiens

<400> SEQUENCE: 707
gacgaggtgg ccgagtggtt aaggcgatgg actgctaatc cattgtgctc tgcacgcgtg     60
ggttcgaatc ccaccttcgt cg                                              82

<210> SEQ ID NO 708
<211> LENGTH: 82
<212> TYPE: DNA
<213> ORGANISM: Homo sapiens

<400> SEQUENCE: 708
gacgaggtgg ccgagtggtt aaggcgatgg actgctaatc cattgtgctc tgcacgcgtg     60
ggttcgaatc ccaccctcgt cg                                              82

<210> SEQ ID NO 709
<211> LENGTH: 70
<212> TYPE: DNA
<213> ORGANISM: Homo sapiens

<400> SEQUENCE: 709
gagaaggtca cagaggttat gggattggct tgaaaccagt ctgtgggggg ttcgattccc     60
tccttttca                                                             70

<210> SEQ ID NO 710
<211> LENGTH: 82
<212> TYPE: DNA
<213> ORGANISM: Homo sapiens

<400> SEQUENCE: 710
gtagtcgtgg ccgagtggtt aaggcgatgg acttgaaatc cattgggtt tccccgcgca      60 ggttcgaatc ctgtcggcta cg                                              82

<210> SEQ ID NO 711
<211> LENGTH: 82
<212> TYPE: DNA
<213> ORGANISM: Homo sapiens

<400> SEQUENCE: 711
gtagtcgtgg ccgagtggtt aaggcgatgg acttgaaatc cattggggtc tccccgcgca     60
```

```
ggttcgaatc ctgccgacta cg                                           82

<210> SEQ ID NO 712
<211> LENGTH: 82
<212> TYPE: DNA
<213> ORGANISM: Homo sapiens

<400> SEQUENCE: 712
gtagtcgtgg ccgagtggtt aaggcgatgg acttgaaatc cattggggtt tccccgcgca   60
ggttcgaatc ctgccgacta cg                                           82

<210> SEQ ID NO 713
<211> LENGTH: 82
<212> TYPE: DNA
<213> ORGANISM: Homo sapiens

<400> SEQUENCE: 713
gcagcgatgg ccgagtggtt aaggcgttgg acttgaaatc caatggggtc tccccgcgca   60
ggttcgaacc ctgctcgctg cg                                           82

<210> SEQ ID NO 714
<211> LENGTH: 74
<212> TYPE: DNA
<213> ORGANISM: Homo sapiens

<400> SEQUENCE: 714
ggcagtgacg cctactggtt tagagcacag attctagatc gagacattcc tgggttcaaa   60
tcccagcact gttg                                                    74

<210> SEQ ID NO 715
<211> LENGTH: 71
<212> TYPE: DNA
<213> ORGANISM: Homo sapiens

<400> SEQUENCE: 715
ggcagtgaca tgtaatggtt atgagggtgg actttaacca cactgcctag gttcaaatcc   60
tgactctgtc a                                                       71

<210> SEQ ID NO 716
<211> LENGTH: 71
<212> TYPE: DNA
<213> ORGANISM: Homo sapiens

<400> SEQUENCE: 716
gcccggatag ttcagttggt agagcatcag acttaatcag agggtccagg gttcaagtcc   60
ctgtttgggt g                                                       71

<210> SEQ ID NO 717
<211> LENGTH: 74
<212> TYPE: DNA
<213> ORGANISM: Homo sapiens

<400> SEQUENCE: 717
agcaccatgg cttagctggt taaagcacct gtctagtaaa caggagatcc tgagtttcaa   60
ttccaatggt gcct                                                    74

<210> SEQ ID NO 718
<211> LENGTH: 74
<212> TYPE: DNA
```

<213> ORGANISM: Homo sapiens

<400> SEQUENCE: 718
ggccctgtgg cttagctggt caaagcgcct gtctagtaaa caggagatcc tgggttcgaa    60
tcccagcggg gcct    74

<210> SEQ ID NO 719
<211> LENGTH: 74
<212> TYPE: DNA
<213> ORGANISM: Homo sapiens

<400> SEQUENCE: 719
ggcttcgtgg cttagctggt taaagcgcct gtctagtaaa caggagatcc tgggttcgaa    60
tcccagcgag gcct    74

<210> SEQ ID NO 720
<211> LENGTH: 74
<212> TYPE: DNA
<213> ORGANISM: Homo sapiens

<400> SEQUENCE: 720
ggcgccgtgg cttagctggt taaagcgcct gtctagtaaa caggagatcc tgggttcgaa    60
tcccagcggt gcct    74

<210> SEQ ID NO 721
<211> LENGTH: 74
<212> TYPE: DNA
<213> ORGANISM: Homo sapiens

<400> SEQUENCE: 721
ggctccgtag cttagttggt taaagcgcct gtctagtaaa caggagatcc tgggttcgac    60
tcccagcggg gcct    74

<210> SEQ ID NO 722
<211> LENGTH: 74
<212> TYPE: DNA
<213> ORGANISM: Homo sapiens

<400> SEQUENCE: 722
ggctccgtgg cttagctggt taaagcgcct gtctagtaaa caggagatcc tgggttcgaa    60
tcccagcggg gcct    74

<210> SEQ ID NO 723
<211> LENGTH: 74
<212> TYPE: DNA
<213> ORGANISM: Homo sapiens

<400> SEQUENCE: 723
ggctccgtgg cttagctggt taaagcgcct gtctagtaaa caggagatcc tgggttcgaa    60
tcccagcggg gcct    74

<210> SEQ ID NO 724
<211> LENGTH: 74
<212> TYPE: DNA
<213> ORGANISM: Homo sapiens

<400> SEQUENCE: 724
ggcgccgtgg cttagttggt taaagcgcct gtctagtaaa caggagatcc tgggttcgaa    60
tcccagcggt gcct    74

<210> SEQ ID NO 725
<211> LENGTH: 74
<212> TYPE: DNA
<213> ORGANISM: Homo sapiens

<400> SEQUENCE: 725
ggcgccgtgg cttagttggt taaagcgcct gtctagtaaa caggagatcc tgggttcgaa    60
tcccagcggt gcct                                                      74

<210> SEQ ID NO 726
<211> LENGTH: 74
<212> TYPE: DNA
<213> ORGANISM: Homo sapiens

<400> SEQUENCE: 726
ggcgccgtgg cttagttggt taaagcgcct gtctagtaaa caggagatcc tgggttcgaa    60
tcccagcggt gcct                                                      74

<210> SEQ ID NO 727
<211> LENGTH: 72
<212> TYPE: DNA
<213> ORGANISM: Homo sapiens

<400> SEQUENCE: 727
ggcagagtgg tgcagcggaa gcgtgctggg cccgtaaccc agaggtcaat ggatcgaagc    60
catccttggc ta                                                        72

<210> SEQ ID NO 728
<211> LENGTH: 74
<212> TYPE: DNA
<213> ORGANISM: Homo sapiens

<400> SEQUENCE: 728
ggccctgtag ctcagcggtt ggagcgctgg tctcgtaaac ctaggggtcg tgagttcaaa    60
tctcaccagg gcct                                                      74

<210> SEQ ID NO 729
<211> LENGTH: 72
<212> TYPE: DNA
<213> ORGANISM: Homo sapiens

<400> SEQUENCE: 729
ggcgcggtgg ccaagtggta aggcgtcggt ctcgtaaacc gaagatcgcg ggttcgaacc    60
ccgtccgtgc ct                                                        72

<210> SEQ ID NO 730
<211> LENGTH: 74
<212> TYPE: DNA
<213> ORGANISM: Homo sapiens

<400> SEQUENCE: 730
ggctctgtgg cttagttggc taaagcgcct gtctcgtaaa caggagatcc tgggttcgaa    60
tcccagcggg gcct                                                      74

<210> SEQ ID NO 731
<211> LENGTH: 72
<212> TYPE: DNA
<213> ORGANISM: Homo sapiens

<400> SEQUENCE: 731
ggcgcggtgg ccaagtggta aggcgtcggt ctcgtaaacc gaagatcacg ggttcgaacc    60
ccgtccgtgc ct    72

<210> SEQ ID NO 732
<211> LENGTH: 74
<212> TYPE: DNA
<213> ORGANISM: Homo sapiens

<400> SEQUENCE: 732
ggctctatgg cttagttggt taaagcgcct gtctcgtaaa caggagatcc tgggttcgac    60
tcccagtggg gcct    74

<210> SEQ ID NO 733
<211> LENGTH: 72
<212> TYPE: DNA
<213> ORGANISM: Homo sapiens

<400> SEQUENCE: 733
ggctccatag ctcaggggtt agagcactgg tcttgtaaac cagggtcgcg agttcaaatc    60
tcgctggggc ct    72

<210> SEQ ID NO 734
<211> LENGTH: 73
<212> TYPE: DNA
<213> ORGANISM: Homo sapiens

<400> SEQUENCE: 734
ggccctatag ctcaggggtt agagcactgg tcttgtaaac caggggtcgc gagttcaaat    60
ctcgctgggg cct    73

<210> SEQ ID NO 735
<211> LENGTH: 73
<212> TYPE: DNA
<213> ORGANISM: Homo sapiens

<400> SEQUENCE: 735
ggctccatag ctcaggggtt agagcactgg tcttgtaaac caggggtcgc gagttcaaat    60
ctcgctgggg cct    73

<210> SEQ ID NO 736
<211> LENGTH: 73
<212> TYPE: DNA
<213> ORGANISM: Homo sapiens

<400> SEQUENCE: 736
ggctccatag ctcaggggtt agagcgctgg tcttgtaaac caggggtcgc gagttcaatt    60
ctcgctgggg cct    73

<210> SEQ ID NO 737
<211> LENGTH: 73
<212> TYPE: DNA
<213> ORGANISM: Homo sapiens

<400> SEQUENCE: 737
ggctccatag ctcagtggtt agagcactgg tcttgtaaac caggggtcgc gagttcgatc    60
ctcgctgggg cct    73

```
<210> SEQ ID NO 738
<211> LENGTH: 74
<212> TYPE: DNA
<213> ORGANISM: Homo sapiens

<400> SEQUENCE: 738
ggctctatgg cttagttggt taaagcgcct gtcttgtaaa caggagatcc tgggttcgaa    60
tcccagtaga gcct                                                      74

<210> SEQ ID NO 739
<211> LENGTH: 74
<212> TYPE: DNA
<213> ORGANISM: Homo sapiens

<400> SEQUENCE: 739
ggaaggatgg ggccaagctg gaaagcctgt gggctccaca gtcatgtgcc tgggttcaat    60
tcccagttct gcat                                                      74

<210> SEQ ID NO 740
<211> LENGTH: 72
<212> TYPE: DNA
<213> ORGANISM: Homo sapiens

<400> SEQUENCE: 740
gacctcgtgg cgcaacggca gcgcgtctga ctccagatca gaaggttgcg tgttcaaatc    60
acgtcggggt ca                                                        72

<210> SEQ ID NO 741
<211> LENGTH: 72
<212> TYPE: DNA
<213> ORGANISM: Homo sapiens

<400> SEQUENCE: 741
gacctcgtgg cgcaacggta gcgcgtctga ctccagatca gaaggctgcg tgttcgaatc    60
acgtcggggt ca                                                        72

<210> SEQ ID NO 742
<211> LENGTH: 72
<212> TYPE: DNA
<213> ORGANISM: Homo sapiens

<400> SEQUENCE: 742
gacctcgtgg cgcaacggta gcgcgtctga ctccagatca gaaggttgcg tgttcaaatc    60
acgtcggggt ca                                                        72

<210> SEQ ID NO 743
<211> LENGTH: 72
<212> TYPE: DNA
<213> ORGANISM: Homo sapiens

<400> SEQUENCE: 743
gacctcgtgg cgcaacggta gcgcgtctga ctccagatca gaaggttgcg tgttcaaatc    60
acgtcggggt ca                                                        72

<210> SEQ ID NO 744
<211> LENGTH: 72
<212> TYPE: DNA
<213> ORGANISM: Homo sapiens

<400> SEQUENCE: 744
```

```
gacctcgtgg cgcaacggta gcgcgtctga ctccagatca gaaggttgcg tgttcaaatc    60
acgtcggggt ca                                                       72

<210> SEQ ID NO 745
<211> LENGTH: 72
<212> TYPE: DNA
<213> ORGANISM: Homo sapiens

<400> SEQUENCE: 745
gacctcgtgg cgcaatggta gcgcgtctga ctccagatca gaaggttgcg tgttcaagtc    60
acgtcggggt ca                                                       72

<210> SEQ ID NO 746
<211> LENGTH: 72
<212> TYPE: DNA
<213> ORGANISM: Homo sapiens

<400> SEQUENCE: 746
ggcctcgtgg cgcaacggta gcgcgtctga ctccagatca gaaggttgcg tgttcaaatc    60
acgtcggggt ca                                                       72

<210> SEQ ID NO 747
<211> LENGTH: 99
<212> TYPE: DNA
<213> ORGANISM: Homo sapiens

<400> SEQUENCE: 747
ggcagaggag ggtgcagttg gcagcctgtc caagtccagc acggttggag cacaggattt    60
agaatgggat ggtcctgggt tcaaacccca gctgcgccc                           99

<210> SEQ ID NO 748
<211> LENGTH: 93
<212> TYPE: DNA
<213> ORGANISM: Homo sapiens

<400> SEQUENCE: 748
ccttcaatag ttcagctggt agagcagagg actatagcta cttcctcagt aggagacgtc    60
cttaggttgc tggttcgatt ccagcttgaa gga                                 93

<210> SEQ ID NO 749
<211> LENGTH: 73
<212> TYPE: DNA
<213> ORGANISM: Homo sapiens

<400> SEQUENCE: 749
gggggtatag ctcagggcta gagcttttg actgtagagc aagaggtccc tggttcaaat    60
ccaggttctc cct                                                      73

<210> SEQ ID NO 750
<211> LENGTH: 94
<212> TYPE: DNA
<213> ORGANISM: Homo sapiens

<400> SEQUENCE: 750
ccttcgatag ctcagctggt agagcggagg actgtagcct gtagaaacat ttgtggacat    60
ccttaggtcg ctggttcgat tccggctcga agga                               94

<210> SEQ ID NO 751
<211> LENGTH: 94
```

```
<212> TYPE: DNA
<213> ORGANISM: Homo sapiens

<400> SEQUENCE: 751
ccttcgatag ctcagctggt agagcggagg actgtagatt gtatagacat ttgcggacat      60
ccttaggtcg ctggttcgat tccagctcga agga                                  94

<210> SEQ ID NO 752
<211> LENGTH: 94
<212> TYPE: DNA
<213> ORGANISM: Homo sapiens

<400> SEQUENCE: 752
ccttcgatag ctcagctggt agagcggagg actgtagact gcggaaacgt ttgtggacat      60
ccttaggtcg ctggttcaat tccggctcga agga                                  94

<210> SEQ ID NO 753
<211> LENGTH: 94
<212> TYPE: DNA
<213> ORGANISM: Homo sapiens

<400> SEQUENCE: 753
ccttcgatag ctcagctggt agagcggagg actgtagatt gtacagacat ttgcggacat      60
ccttaggtcg ctggttcgat tccggctcga agga                                  94

<210> SEQ ID NO 754
<211> LENGTH: 89
<212> TYPE: DNA
<213> ORGANISM: Homo sapiens

<400> SEQUENCE: 754
ccttcgatag ctcagctggt agagcggagg actgtagtac ttaatgtgtg gtcatcctta      60
ggtcgctggt tcgattccgg ctcgaagga                                        89

<210> SEQ ID NO 755
<211> LENGTH: 91
<212> TYPE: DNA
<213> ORGANISM: Homo sapiens

<400> SEQUENCE: 755
ccttcgatag ctcagttggt agagcggagg actgtagttg gctgtgtcct tagacatcct      60
taggtcgctg gttcgaatcc ggctcgaagg a                                     91

<210> SEQ ID NO 756
<211> LENGTH: 90
<212> TYPE: DNA
<213> ORGANISM: Homo sapiens

<400> SEQUENCE: 756
ctttcgatag ctcagttggt agagcggagg actgtaggtt cattaaacta aggcatcctt      60
aggtcgctgg ttcgaatccg gctcgaagga                                       90

<210> SEQ ID NO 757
<211> LENGTH: 89
<212> TYPE: DNA
<213> ORGANISM: Homo sapiens

<400> SEQUENCE: 757
ccttcgatag ctcagttggt agagcggagg actgtaggct cattaagcaa ggtatcctta      60
```

```
ggtcgctggt tcgaatccgg ctcggagga                                              89

<210> SEQ ID NO 758
<211> LENGTH: 89
<212> TYPE: DNA
<213> ORGANISM: Homo sapiens

<400> SEQUENCE: 758
ccttcgatag ctcagctggt agagcggagg actgtagggg tttgaatgtg gtcatcctta           60
ggtcgctggt tcgaatccgg ctcggagga                                             89

<210> SEQ ID NO 759
<211> LENGTH: 89
<212> TYPE: DNA
<213> ORGANISM: Homo sapiens

<400> SEQUENCE: 759
ccttcgatag ctcagttggt agagcggagg actgtagtgg atagggcgtg gcaatcctta           60
ggtcgctggt tcgattccgg ctcgaagga                                             89

<210> SEQ ID NO 760
<211> LENGTH: 88
<212> TYPE: DNA
<213> ORGANISM: Homo sapiens

<400> SEQUENCE: 760
tcttcaatag ctcagctggt agagcggagg actgtaggtg cacgcccgtg gccattctta           60
ggtgctggtt tgattccgac ttggagag                                              88

<210> SEQ ID NO 761
<211> LENGTH: 93
<212> TYPE: DNA
<213> ORGANISM: Homo sapiens

<400> SEQUENCE: 761
ccttcgatag ctcagctggt agagcggagg actgtagcta cttcctcagc aggagacatc           60
cttaggtcgc tggttcgatt ccggctcgaa gga                                        93

<210> SEQ ID NO 762
<211> LENGTH: 89
<212> TYPE: DNA
<213> ORGANISM: Homo sapiens

<400> SEQUENCE: 762
ccttcgatag ctcagctggt agagcggagg actgtaggcg cgcgcccgtg gccatcctta           60
ggtcgctggt tcgattccgg ctcgaagga                                             89

<210> SEQ ID NO 763
<211> LENGTH: 73
<212> TYPE: DNA
<213> ORGANISM: Homo sapiens

<400> SEQUENCE: 763
gtttccatag tgtactggtt atcacattca cctaacacgc gaaaggtcct tggtttgaaa           60
ccaggcagaa aca                                                              73

<210> SEQ ID NO 764
<211> LENGTH: 72
<212> TYPE: DNA
<213> ORGANISM: Homo sapiens
```

```
<400> SEQUENCE: 764
gggggtgtag ctcagtggta gagcgtatgc ttaacattca tgaggctctg ggttcgatcc     60
ccagcacttc ca                                                        72

<210> SEQ ID NO 765
<211> LENGTH: 73
<212> TYPE: DNA
<213> ORGANISM: Homo sapiens

<400> SEQUENCE: 765
gtttccgtag tgtagtggtt atcacgtttg cctaacacgc gaaaggtccc cggttcgaaa     60
ccgggcagaa aca                                                       73

<210> SEQ ID NO 766
<211> LENGTH: 73
<212> TYPE: DNA
<213> ORGANISM: Homo sapiens

<400> SEQUENCE: 766
gtttccgtag tgtagtggtt atcacgttcg cctaacacgc gaaaggtccg cggttcgaaa     60
ccgggcggaa aca                                                       73

<210> SEQ ID NO 767
<211> LENGTH: 73
<212> TYPE: DNA
<213> ORGANISM: Homo sapiens

<400> SEQUENCE: 767
gtttccgtag tgtagtggtt atcacgttcg cctaacacgc gaaaggtccc tggatcaaaa     60
ccaggcggaa aca                                                       73

<210> SEQ ID NO 768
<211> LENGTH: 73
<212> TYPE: DNA
<213> ORGANISM: Homo sapiens

<400> SEQUENCE: 768
gtttccgtag tgtagtggtc atcacgttcg cctaacacgc gaaaggtccc cggttcgaaa     60
ccgggcggaa aca                                                       73

<210> SEQ ID NO 769
<211> LENGTH: 73
<212> TYPE: DNA
<213> ORGANISM: Homo sapiens

<400> SEQUENCE: 769
gtttccgtag tgtagtggtt atcacgttcg cctaacacgc gaaaggtccc cggttcgaaa     60
ccgggcggaa aca                                                       73

<210> SEQ ID NO 770
<211> LENGTH: 73
<212> TYPE: DNA
<213> ORGANISM: Homo sapiens

<400> SEQUENCE: 770
gtttccgtag tgtagtggtt atcacgttcg cctaacacgc gaaaggtccc cggttcgaaa     60
ccgggcggaa aca                                                       73
```

```
<210> SEQ ID NO 771
<211> LENGTH: 73
<212> TYPE: DNA
<213> ORGANISM: Homo sapiens

<400> SEQUENCE: 771
gtttccgtag tgtagtggtt atcacgttcg cctaacacgc gaaaggtccc cggttcgaaa      60
ccgggcggaa aca                                                         73

<210> SEQ ID NO 772
<211> LENGTH: 73
<212> TYPE: DNA
<213> ORGANISM: Homo sapiens

<400> SEQUENCE: 772
gtttccgtag tgtagtggtt atcacgttcg cctaacacgc gaaaggtccc cggttcgaaa      60
ccgggcggaa aca                                                         73

<210> SEQ ID NO 773
<211> LENGTH: 73
<212> TYPE: DNA
<213> ORGANISM: Homo sapiens

<400> SEQUENCE: 773
gtttccgtag tgtagtggtt atcacgttcg cctaacacgc gaaaggtccc cggttcgaaa      60
ccgggcggaa aca                                                         73

<210> SEQ ID NO 774
<211> LENGTH: 74
<212> TYPE: DNA
<213> ORGANISM: Homo sapiens

<400> SEQUENCE: 774
ttttctgtag tgtagttgtt aacacgttcg cctcacacgc ttaaagttct ctggttggat      60
accagatgga aatg                                                        74

<210> SEQ ID NO 775
<211> LENGTH: 73
<212> TYPE: DNA
<213> ORGANISM: Homo sapiens

<400> SEQUENCE: 775
gtttctgtgg tgtagtggtt atcatgttcg cctcacacga gaaaagtccc tgattcgaga      60
ctgggtggga acg                                                         73

<210> SEQ ID NO 776
<211> LENGTH: 73
<212> TYPE: DNA
<213> ORGANISM: Homo sapiens

<400> SEQUENCE: 776
gtttctgtag tatggtggtt atcacgttag tctcacacgt gaaaggtccc tggttcgaaa      60
ccaggtggaa aca                                                         73

<210> SEQ ID NO 777
<211> LENGTH: 71
<212> TYPE: DNA
<213> ORGANISM: Homo sapiens

<400> SEQUENCE: 777
```

```
gcactggtgg ttcagtggta gaattctcgc ctcacacgcg ggacacccgg gttcaattcc    60
cggtcaaggc a                                                          71

<210> SEQ ID NO 778
<211> LENGTH: 73
<212> TYPE: DNA
<213> ORGANISM: Homo sapiens

<400> SEQUENCE: 778
gtttccgtag tgtagtggtt attatgttcg cctcacacgc gaaaagtccc cggttcgaaa    60
tcaggcggga aca                                                        73

<210> SEQ ID NO 779
<211> LENGTH: 73
<212> TYPE: DNA
<213> ORGANISM: Homo sapiens

<400> SEQUENCE: 779
gtttccgtag tggagtggtt atcacgttcg cctcacacgc gaaaggtccc cggtttgaaa    60
ccaggcggaa aca                                                        73

<210> SEQ ID NO 780
<211> LENGTH: 74
<212> TYPE: DNA
<213> ORGANISM: Homo sapiens

<400> SEQUENCE: 780
gtttccgtag tgtagtggtt atcacgttcg cctcacacgc gtaaaggtcc ccggttcgaa    60
accgggcgga aaca                                                       74

<210> SEQ ID NO 781
<211> LENGTH: 73
<212> TYPE: DNA
<213> ORGANISM: Homo sapiens

<400> SEQUENCE: 781
gtttccgtag tgtagtggtt atcacgttcg cctcacacgc gaaaggtccc cggttcgaaa    60
ctgggcggaa aca                                                        73

<210> SEQ ID NO 782
<211> LENGTH: 73
<212> TYPE: DNA
<213> ORGANISM: Homo sapiens

<400> SEQUENCE: 782
gtttccgtag tgtagcggtt atcacattcg cctcacacgc gaaaggtccc cggttcgatc    60
ccgggcggaa aca                                                        73

<210> SEQ ID NO 783
<211> LENGTH: 73
<212> TYPE: DNA
<213> ORGANISM: Homo sapiens

<400> SEQUENCE: 783
gcttctgtag tgtagtggtt atcacgttcg cctcacacgc gaaaggtccc cggttcgaaa    60
ccgggcagaa gca                                                        73

<210> SEQ ID NO 784
```

```
<211> LENGTH: 73
<212> TYPE: DNA
<213> ORGANISM: Homo sapiens

<400> SEQUENCE: 784
gtttccgtag tgtagtggtt atcacgttcg cctcacacgc gaaaggtccc cggttcgaaa       60
ccgggcggaa aca                                                         73

<210> SEQ ID NO 785
<211> LENGTH: 73
<212> TYPE: DNA
<213> ORGANISM: Homo sapiens

<400> SEQUENCE: 785
gtttccgtag tgtagtggtt atcacgttcg cctcacacgc gaaaggtccc cggttcgaaa       60
ccgggcggaa aca                                                         73

<210> SEQ ID NO 786
<211> LENGTH: 73
<212> TYPE: DNA
<213> ORGANISM: Homo sapiens

<400> SEQUENCE: 786
gtttccgtag tgtagtggtt atcacgttcg cctcacacgc gaaaggtccc cggttcgaaa       60
ccgggcggaa aca                                                         73

<210> SEQ ID NO 787
<211> LENGTH: 73
<212> TYPE: DNA
<213> ORGANISM: Homo sapiens

<400> SEQUENCE: 787
gtttccgtag tgtagtggtt atcacgttcg cctcacacgc gaaaggtccc cggttcgaaa       60
ccgggcggaa aca                                                         73

<210> SEQ ID NO 788
<211> LENGTH: 73
<212> TYPE: DNA
<213> ORGANISM: Homo sapiens

<400> SEQUENCE: 788
gtttccgtag tgtagtggtt atcacgttcg cctcacacgc gaaaggtccc cggttcgaaa       60
ccgggcggaa aca                                                         73

<210> SEQ ID NO 789
<211> LENGTH: 73
<212> TYPE: DNA
<213> ORGANISM: Homo sapiens

<400> SEQUENCE: 789
gtttccgtag tgtagtggtt atcacgttcg cctcacacgc gaaaggtccc cggttcgaaa       60
ccgggcggaa aca                                                         73

<210> SEQ ID NO 790
<211> LENGTH: 73
<212> TYPE: DNA
<213> ORGANISM: Homo sapiens

<400> SEQUENCE: 790
gtttccgtgg tgtagtggtt atcacattcg ccttacacgc gaaaggtcct cgggtcgaaa       60
```

```
ccgagcggaa aca                                                          73

<210> SEQ ID NO 791
<211> LENGTH: 73
<212> TYPE: DNA
<213> ORGANISM: Homo sapiens

<400> SEQUENCE: 791
ggttccatag tgtagtggtt atcacatctg ctttacacgc agaaggtcct gggttcaagc       60
cccagtggaa cca                                                          73

<210> SEQ ID NO 792
<211> LENGTH: 73
<212> TYPE: DNA
<213> ORGANISM: Homo sapiens

<400> SEQUENCE: 792
ggttccatag tgtagcggtt atcacgtctg ctttacacgc agaaggtcct gggttcgagc       60
cccagtggaa cca                                                          73

<210> SEQ ID NO 793
<211> LENGTH: 73
<212> TYPE: DNA
<213> ORGANISM: Homo sapiens

<400> SEQUENCE: 793
ggttccatag tgtagtggtt atcacgtctg ctttacacgc agaaggtcct gggttcgagc       60
cccagtggaa cca                                                          73

<210> SEQ ID NO 794
<211> LENGTH: 73
<212> TYPE: DNA
<213> ORGANISM: Homo sapiens

<400> SEQUENCE: 794
ggttccatag tgtagtggtt atcacgtctg ctttacacgc agaaggtcct gggttcgagc       60
cccagtggaa cca                                                          73

<210> SEQ ID NO 795
<211> LENGTH: 72
<212> TYPE: DNA
<213> ORGANISM: Homo sapiens

<400> SEQUENCE: 795
taggatatgg tttaataggt agcatggaga attttggagt ctcagggata ggttcaattc       60
ctatagttcc ag                                                           72

<210> SEQ ID NO 796
<211> LENGTH: 72
<212> TYPE: DNA
<213> ORGANISM: Homo sapiens

<400> SEQUENCE: 796
ggtcccatgg tgtaatggtt agcactctgg actttgaatc cagcaatccg agttcgaatc       60
tcggtgggac ct                                                           72
```

NEUROPROTECTIVE MOLECULES AND METHODS OF TREATING NEUROLOGICAL DISORDERS AND INDUCING STRESS GRANULES

CLAIM OF PRIORITY

This application is a 35 U.S.C. §371 national phase application of International Application No. PCT/US2011/043400, filed Jul. 8, 2011, which claims the benefit of U.S. Provisional Application Ser. No. 61/362,526, filed Jul. 8, 2010, the entire contents of each of which are incorporated by reference herein.

STATEMENT AS TO FEDERALLY-SPONSORED RESEARCH

This invention was made with government support under federal research grant AI0658568 awarded by the National Institutes of Health. The government has certain rights in the invention.

TECHNICAL FIELD

This invention relates to neuroprotective molecules and methods of treating neurological diseases associated with neuron death, inducing stress granule formation in a cell, inhibiting translation in a cell, and decreasing stress-induced cell death.

BACKGROUND

Amyotrophic lateral sclerosis (ALS) is a progressive neurodegenerative disease distinguished by a specific loss of motor neurons in the brain, brain stem, and spinal cord. Initial symptoms of loss of motor neuron activity, including distal muscle weakness and wasting, increased muscle tone with hyperreflexia, and diaphragmatic and/or bulbar weakness are first noticed at an average age of 55. Death occurs from respiratory failure at an average of 4 years after disease onset. The only recognized treatment for ALS is riluzole which extends survival by only about 3 months with no improvement in motor muscular function.

Although ALS is a rare disease (~1-2 persons per 100,000 population), an understanding of its pathogenesis is likely to impact other neurological diseases that share some pathological features (e.g., frontotemporal lobal degeneration, Alzheimer's disease, Huntington's disease, spinal motor atrophy and fragile X mental retardation). Approximately 10% of ALS cases are familial and the rest are sporadic. Mutations in the Cu,Zn superoxide dismutase 1 gene (ALS1; SOD1) have been identified in ~20% of familial and in ~3% of sporadic ALS patients, making SOD1 mutations the most common cause of this disease. The RNA-binding proteins TDP-43 and FUS/TLS are the next most commonly mutated genes, each of which is responsible for ~4% of familial cases. A number of dominantly-inherited genes associated with atypical ALS phenotypes are each responsible for 1-3% of ALS cases (e.g., ALS with dementia/parkinsonism: microtubule-associated protein tau (MAPT); progressive lower motor neuron disease: dynactin subunit 1 (DCTN1); ALS8: vesicle-associated membrane protein-associated protein B/C (VAPB); juvenile onset autosomal dominant ALS: senataxin (SETX)).

ALS genes involved in RNA metabolism include TDP-43 and FUS/TLS: two RNA-binding proteins implicated in transcription, splicing, and translation. Both of these proteins are components of stress granules: cytoplasmic foci that are characterized as signaling centers assembled from proteins and untranslated mRNAs in cells exposed to adverse conditions. ALS-linked genes associated with RNA/stress response pathways include: mutant SOD1 which inactivates a retrograde transport pathway that causes proteins to accumulate in the endoplasmic reticulum and trigger the unfolded protein response (UPR), a pro-survival program; vesicle-associated membrane protein (VAPB), an endoplasmic reticulum protein that interacts with ATF6, a UPR-activated transcription factor; senataxin, a DNA/RNA helicase associated with tRNA metabolism and the oxidative stress response; and angiogenin (ANG), a stress-activated ribonuclease that promotes motor neuron survival and extends the survival of SOD1$^{G93A}$ mice in a murine model of ALS. These genes indicate an association between mutations in proteins involved in stress granule formation and ALS, a neurological disorder associated with neuron death.

SUMMARY

Provided herein are neuroprotective molecules that contain a sequence of 25-35 contiguous nucleotides that is at least 80% identical to a contiguous sequence between nucleotide 1 and nucleotide 50 of a mature human tRNA that are useful for inducing or increasing stress granule formation in a cell, decreasing protein translation in a cell, reducing stress-induced cell death, and treating a neurological disorder associated with neuron death in a subject. The invention is based on the discovery that these neuroprotective molecules are taken up by motor neurons in the absence of transfection agents, induce stress granule formation in motor neurons, and confer protection against stress-induced motor neuron death.

Provided herein are neuroprotective molecules containing a sequence of 25-35 contiguous nucleotides that is at least 80% identical to a contiguous sequence between nucleotide 1 and nucleotide 50 of a mature human RNA, and at least four (e.g., at least five or six) contiguous guanosine-containing nucleotides, where the sequence of 25-35 contiguous nucleotides contains a D-loop stem structure, the at least four contiguous guanosine-containing nucleotides are located at the 5' end of the neuroprotective molecule, and the neuroprotective molecule contains at least one (e.g., at least two, three, or four) deoxyribonucleotide. In some embodiments, the sequence of 25-35 contiguous nucleotides is at least 80% identical to a contiguous sequence between nucleotide 1 and nucleotide 50 of a mature human tRNA having a sequence selected from the group consisting of: SEQ ID NOS: 4, 5, 8-11, 13-17, 32, 37, and 40-173.

Also provided are neuroprotective molecules containing a sequence of 25-35 contiguous nucleotides that is at least 80% identical to a contiguous sequence between nucleotide 1 and nucleotide 50 of a mature human tRNA selected from the group of: tRNA$^{Arg}$, tRNA$^{Asp}$, tRNA$^{Glu}$, tRNA$^{Gln}$, tRNA$^{Gly}$, tRNA$^{His}$, tRN$^{Ile}$, tRNA$^{Leu}$, tRNA$^{Lys}$, tRNA$^{Met}$, tRNA$^{Pro}$, tRNA$^{SeC}$, tRNA$^{Ser}$, tRNA$^{Sup}$, tRNA$^{Thr}$, tRNA$^{Trp}$, tRNA$^{Tyr}$, tRNA$^{Val}$, tRNA$^{Asn}$, and tRNA$^{Phe}$; and at least four (e.g., at least five or six) contiguous guanosine-containing nucleotides, where the sequence of 25-35 contiguous nucleotides contains a D-loop stem structure and the at least four contiguous guanosine-containing nucleotides are located at the 5' end of the neuroprotective molecule. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 5, 8, 9, 11, 14-17, 32, 37, 56, 57, and 63-173. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 11 and 107-116.

In some embodiments, the neuroprotective molecule further comprises a 5'-monophosphate. In some embodiments, the neuroprotective molecule contains at least one modified nucleotide (e.g, a nucleotide containing a modified base and/or a modified sugar). In some embodiments, the neuroprotective molecule contains at least one modification in the phosphate backbone. In some embodiments, the neuroprotective molecule contains a 5' and/or a 3' protective group. In some embodiments, the neuroprotective molecule has a total length of between 39 to 60 nucleotides (e.g., 39 to 50 nucleotides or 50 to 60 nucleotides).

Also provided are pharmaceutical compositions that contain at least one neuroprotective molecule described herein (e.g., any of the neuroprotective molecules described herein).

Also provided are methods of inducing or increasing stress granule formation in a cell that include administering to a cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to induce or increase stress granule formation in the cell.

Also provided are methods of decreasing protein translation in a cell that include administering to a cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to decrease protein translation in the cell.

Also provided are methods of decreasing stress-induced cell death that include administering to the cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to decrease stress-induced cell death.

In some embodiments, the cell is in vitro. In some embodiments, the cell is in vivo. In some embodiments, the cell is a neuron (e.g., a motor neuron).

Also provided are methods of treating a neurological disorder associated with neuron death (necrosis and/or apoptosis, or stress-induced cell death) in a subject that include administering a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to treat the neurological disorder associated with neuron death in the subject.

In some embodiments, the neurological disorder associated with neuron death is selected from the group of: amyotrophic lateral sclerosis, Alzheimer's disease, Parkinson's disease, Huntington's disease, muscular dystrophy, multiple sclerosis, and stroke. In some embodiments, the neuroprotective molecule or the isolated C-myc oligonucleotide is administered intravenously, intraarterially, intracranially, ocularly, intraperitoneally, subcutaneously, or intramuscularly. In some embodiments, the subject is administered at least one additional therapeutic agent.

Also provided are methods of identifying a candidate translation inhibitor nucleic acid that include (a) attaching to the 5' end of a nucleic acid sequence of between 20-50 nucleotides at least four (e.g., at least five or six) guanosine-containing nucleotides, and (b) determining the level of protein translation in the presence of the molecule produced in (a), where a decrease in the level of protein translation in the presence of the molecule produced in (a) relative to the level of protein translation in the absence of the molecule produced in (a) identifies the molecule produced in (a) as a candidate translation inhibitory nucleic acid.

In some embodiments, the nucleic acid sequence of between 20-50 nucleotides contains at least 50% (e.g., at least 55%, 60%, 65%, or 70%) guanosine-containing/cytosine-containing nucleotides. In some embodiments, the nucleic acid sequence of between 20-50 nucleotides is at least 80% identical to a contiguous sequence in a mature human tRNA sequence. In some embodiments, the level of protein translation is determined in a cell. In some embodiments, the cell is a fibroblast or a motor neuron. In some embodiments, the cell is human. In some embodiments, the level of protein translation is determined in a cell lysate (e.g., a rabbit reticulocyte lysate).

By the phrase "mature human tRNA" is meant a human transfer RNA molecule in which the intron sequences have been removed.

By the phrase "D-loop stem structure" is meant a secondary loop structure present in mature human tRNAs that is formed by approximately nucleotides 5 to 28 of a mature human tRNA or a significantly similar stem-loop structure. Several exemplary three-dimensional structures of mature human tRNAs have been described and modeled by those skilled in the art.

By the phrase "deoxyribonucleotide" is meant a nucleotide that contains a 2'-deoxyribose. This term also includes nucleotides that contain modifications at other positions within the deoxyribose sugar or in the attached base.

By the phrase "guanosine-containing nucleotide" is meant a nucleotide that contains a guanosine or a modified guanosine. In some embodiments, the guanosine-containing nucleotide has the ability to form a G-quadruplex.

By the phrase "cytosine-containing nucleotide" is meant a nucleotide that contains a cytosine or a modified cytosine.

By the term "G-quadraplex" is meant a square structural arrangement of four guanines that is stabilized by Hoogsteen hydrogen bonds. A G-quadraplex can also be stabilized by the presence of a monovalent cation (e.g., potassium) in the center of the tetrad. A G-quadraplex can be formed by a DNA, a RNA, an LNA, or a PNA molecule (or any combination thereof). In some embodiments, the G-quadraplex is formed by four guanines that are present in the same molecule (e.g., any of the neuroprotective molecules or C-myc oligonucleotides described herein).

By the term "modified nucleotide" is meant a nucleotide that has a modification in its sugar and/or in its base. Non-limiting examples of modified nucleotides are described herein. Additional examples of modified nucleotides are known in the art.

By the phrase "5' or 3' protective group" is meant a moiety that is attached to the 5'- or the 3'-end of an oligonucleotide that prevents nuclease degradation or decreases (e.g., significantly decreases) the rate of nuclease degradation of the oligonucleotide. In some embodiments, the neuroprotective molecules or the C-myc oligonucleotides described herein contain a 5' and/or 3' protective group. Non-limiting examples of 5' and 3' protective groups are described herein. Additional examples of 5' and 3' protective groups are known in the art.

By the term "stress granule formation" is meant the formation or detection of at least one stress granule in a cell. Stress granule formation in a cell can be detected, for example, by microscopy (e.g., immunofluorescence microscopy) or the detection of phosphorylated eIF2α. Additional methods for detecting stress granule formation in a cell are described herein and are known in the art.

By the term "stress granule" is meant an aggregate of proteins and mRNAs that form in a cell under stress conditions. The poly(A)-mRNAs in a stress granule are present in stalled pre-initiation complexes. A stress granule can contain one or more (e.g., two, three, four, or five) of the following proteins/complexes, including but not limited to: 40S ribosomal subunits, eIF4E, eIF4G, eIF4A, eIF4B, poly (A) binding protein (Pabp), eIF3, and eIF2. Additional examples of proteins that can be found in stress granules are described herein. Additional examples of proteins that can be found in stress granules are known in the art (see, for example, Buchan et al., Mol. Cell 36:932, 2009).

By the term "protein translation" is meant the synthesis of a polypeptide from a messenger ribonucleic acid (RNA) molecule (e.g., a capped or uncapped mRNA molecule). The mRNA molecule typically contains a polyA 3'-tail. Protein translation can be performed in a cell or in a cellular lysate. Methods for detecting protein translation or the rate of protein translation are described herein. Additional methods for detecting protein translation or the rate of protein translation are known in the art.

By the term "neurological disorder associated with neuron death" is meant a neurological disease that is characterized by neuron death (e.g., motor neuron death) or has an etiology that involves neuron death (e.g., motor neuron death). Neuron death (apoptosis or necrosis) in these disorders can occur by a variety of different means (e.g., oxidative stress, excitotoxicity, and neuroinflammation). Methods for detecting neuron death in vivo or in vitro are described herein and are known in the art. Non-limiting examples of neurological disorders associated with neuron death are described herein. Additional examples of neurological disorders associated with neuron death are known in the art. In general, the methods do not require that cell death be detected in a subject prior to treatment, if the subject has a disorder known in the art to be associated with neuron death.

By the term "treating" is meant decreasing the number of symptoms or decreasing (e.g., a significant or detectable decrease) the severity, frequency, or duration of one or more symptoms of a disease in a subject. The term "treating" can also include decreasing (e.g., a significant or detectable decrease) the rate of neuron death in a subject having a neurological disorder associated with neuron death (e.g., compared to the rate of neuron death in the same subject prior to treatment or compared to the rate of neuron death in a control subject having the same disease but not receiving treatment or receiving a different treatment). A decrease in neuron death or the rate of neuron death in a subject can be assessed in a subject by a decrease in the rate of the development of one or more symptoms of a neurological disease associated with neuron death or a decrease in the worsening or exacerbation of one of more symptoms of a neurological disease associated with neuron death in a subject.

By the term "stress-induced cell death" is meant cell death that is triggered by or occurs in response to a cellular stress condition (e.g., oxidative stress, neuroexicitotoxicity, and neuroinflammation). Methods for detecting stress-induced cell death are described herein. Additional methods of detecting stress-induced cell death are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 23 shows the nucleotide sequences of the G-rich oligodeoxynucleotides used in some experiments described herein. The 5'-terminal guanines are indicated in bold.

DETAILED DESCRIPTION

Figure 1:
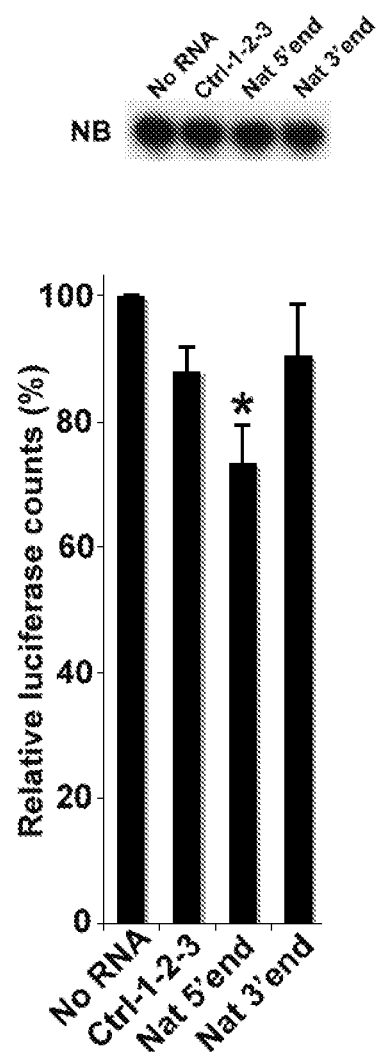
FIG. 1 is a graph showing the relative amount of luciferase expression in rabbit reticulocyte lysate (RRL) containing uncapped luciferase mRNA following treatment with a control RNA mix (Ctrl 1-2-3), natural 5'-tiRNAs (Nat 5' end), or natural 3'-tiRNAs (Nat 3' end) compared to luciferase expression in untreated lysates (bottom), and a Northern blot showing the levels of luciferase mRNA in these experiments (top). The means and standard deviations shown are from three independent experiments (*p=0.01-0.02, Student's t-test, n=3).

Neuroprotective molecules that are capable of inhibiting protein translation, inducing or increasing stress granule formation in a cell (e.g., a motor neuron), and decreasing stress-induced cell death (e.g., motor neuron death) have been discovered. These neuroprotective molecules are based, in part, on sequences present within mature human tRNAs. Some of these neuroprotective molecules have been shown to be taken up by motor neurons in the absence of transfection agents. The structural features of the neuroprotective molecules are described below, as well as their use in methods of inhibiting protein translation in a cell, inducing or increasing stress granule formation in a cell, reducing stress-induced cell death, and treating a neurological disorder associated with neuron death. Also provided herein are methods of identifying a candidate translation inhibitory nucleic acid.

Compositions

Provided herein are neuroprotective molecules containing a sequence of 25-35 contiguous nucleotides (e.g., 25-30 nucleotides or 30-35 nucleotides) that is at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or 100% identical) to a contiguous sequence between nucleotide 1 to nucleotide 50 (e.g., between nucleotide 1 to nucleotide 30) of a mature human tRNA (e.g., any of the mature human tRNA sequences described herein or known in the art), and at least four (e.g., five, six, seven, or eight) guanosine-containing nucleotides, where the sequence of 25-35 contiguous nucleotides contains a D-loop stem structure, the at least four contiguous guanosine-containing nucleotides are located at the 5'-end of the neuroprotective molecule, and the neuroprotective molecule contains at least one (e.g., two, three, four, five, six, seven, eight, nine, or ten) deoxyribonucleotide. In some embodiments, the sequence of 25-35 contiguous nucleotides is at least 80% identical to a contiguous sequence of between nucleotide 1 and nucleotide 50 of a mature human tRNA having a sequence selected from: SEQ ID NOS: 4, 5, 8-11, 13-17, 32, 37, and 40-173.

Also provided are neuroprotective molecules containing a sequence of 25-35 contiguous nucleotides (e.g., 25-30 nucleotides or 30-35 nucleotides) that is at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or 100% identical) to a contiguous sequence between nucleotide 1 and nucleotide 50 (e.g., between nucleotide 1 to nucleotide 30) of a mature human tRNA selected from the group of: tRNA$^{Arg}$, tRNA$^{Asp}$, tRNA$^{Glu}$, tRNA$^{Gln}$, tRNA$^{Gly}$, tRNA$^{His}$, tRN$^{Ile}$, tRNA$^{Leu}$, tRNA$^{Lys}$, tRNA$^{Met}$, tRNA$^{Pro}$, tRNA$^{SeC}$, tRNA$^{Ser}$, tRNA$^{Sup}$, tRNA$^{Thr}$, tRNA$^{Trp}$, tRNA$^{Tyr}$, tRNA$^{Val}$, tRNA$^{Asn}$, and tRNA$^{Phe}$; (e.g., any of the sequences described herein or known in the art), and at least four (e.g., five, six, seven, or eight) contiguous guanosine-containing nucleotides, where the sequence of 25-35 contiguous nucleotides contains a D-loop stem structure and the at least four contiguous guanosine-containing nucleotides are located at the 5' end of the neuroprotective molecule. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 5, 8, 9, 11, 14-17, 32, 37, 56, 57, and 63-173. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 11 and 107-116.

The comparison of sequences and determination of percent identity between two sequences can be accomplished using a mathematical algorithm. The percent identity between two amino acid sequences is determined using the Needleman and Wunsch J. Mol. Biol. 48:444-453, 1970) algorithm, which has been incorporated into the GAP program in the GCG software package (available the at http://www.gcg.com), using either a Blossum 62 matrix or a PAM250 matrix, and a gap weight of 16 and a length weight of 1. The percent identity between two nucleotide sequences is determined using the GAP program in the GCG software package (available the Accelrys Inc. website), using a NWS-gapdna.CMP matrix and a gap weight of 40 and a length weight of 1. The calculation of percent identity as described herein, recognizes a uracil-containing nucleotide (deoxyuracil and ribouracil) as being the same as a "T" (deoxythymine or ribothymine).

In some embodiments, the neuroprotective molecules can contain a sequence of 25, 26, 27, 28, 29, 30, 31, 32, 33, 34, or 35 contiguous nucleotides that is at least 80% identical to a contiguous sequence present between nucleotide 1 and nucleotide 50 of a mature human tRNA. In some embodiments, the contiguous sequence between nucleotide 1 and nucleotide 50 of a mature human tRNA starts at nucleotide number 1, 2, 3, 4, 5, 6, or 7 of the mature human tRNA sequence.

Non-limiting examples of mature human tRNAs are listed below. Any of the human tRNA molecules described herein or known in the art can be used to design the neuroprotective molecules described herein.

Non-limiting exemplary Ala tRNA sequences are listed below.

```
Ala tRNA
                                    (SEQ ID NO: 40)
gggggguguag cucaguggua gagcgcgug uu (SEQ ID NO: 41)
gggggguguag cucaguggua gagcgcgugc u (SEQ ID NO: 42)
ggggggugua gcucaguggu agagcgcgug cu (SEQ ID NO: 43)
gggggguguag cucaguggua gagcgcgugc (SEQ ID NO: 44)
ggggggugua gcucaguggu agagcgcgug c (SEQ ID NO: 45)
gggggunuag cucaguggua gagcgcgugc uu
(n is a, c, g, or u;

(SEQ ID NO: 46)
gggggguguag cucaguggua gagcgcgug (SEQ ID NO: 47)
guguagcuca gugguagagc gcgugcuucg c SEQ ID NO: 48)
ggggunuagc ucaguggua gagcgcgugcu u
(n is a, c, g, or u;

SEQ ID NO: 49)
gggggunua gcucaguggu agagcgcgug cu
(n is a, c, g, or u;

(SEQ ID NO: 50)
ggggguguagc ucagugguag agagcgugcu u (SEQ ID NO: 51)
gggggunuag cucaguggua gagcgcgugc (SEQ ID NO: 52)
gggggguguag cucaguggua gagagcgugc u (SEQ ID NO: 53)
ggggauguag cucaguggua gagcgcaugc u (SEQ ID NO: 54)
gggggauuag cucaaauggu agagcgcucg (SEQ ID NO: 55)
ggggaunuag cucaguggua gagcgcaugc u
```

A non-limiting exemplary Arg tRNA sequence is ggcucuguug cgcaauggau agcgcau (SEQ ID NO: 56) and a non-limiting exemplary Asp tRNA sequence is uccucauuag uauaguggug aguauccc (SEQ ID NO: 57).

Non-limiting exemplary Cys tRNA sequences are listed below.

```
Cys tRNA
                                    (SEQ ID NO: 58)
gggggguauag cucaguggua gagcauuuga (SEQ ID NO: 59)
gggggguauag cucaguggua gagcauuug (SEQ ID NO: 60)
gggggguauag cucaguggua gagcauuu (SEQ ID NO: 61)
gggggguuuag cucagugggu agagcau (SEQ ID NO: 62)
ggggguguaa cucaguggua gagcauuuga
```

A non-limiting exemplary Gln tRNA sequence is gguuccaugg uguaauggu agcacucug (SEQ ID NO: 63).

Non-limiting exemplary Gly tRNA sequences are listed below.

```
Gly tRNA
                                    (SEQ ID NO: 64)
uuggugguuc agugguagaa uucucgccug cc (SEQ ID NO: 65)
uuggugguuc agugguagaa uucucgccug c (SEQ ID NO: 66)
uuggugguuc agugguagaa uucucgccug (SEQ ID NO: 67)
uggugguuca gugguagaau ucucgccug (SEQ ID NO: 68)
auuggugguu cagugguaga auucucgccu g (SEQ ID NO: 69)
uuggugguuc agugguagaa uucucgccu (SEQ ID NO: 70)
ggcauuggug guucagugu agaauucucg c (SEQ ID NO: 71)
auuggugguu cagugguaga auucucgcc (SEQ ID NO: 72)
agcauuggug guucagugu agaauucucg c (SEQ ID NO: 73)
cauuggugu ucagugguag aauucucgc (SEQ ID NO: 74)
gggaggcccg gguucguuuc ccggccaaug ca (SEQ ID NO: 75)
gcauugggg uucaguggua gaauucucac (SEQ ID NO: 76)
cgggaggccc ggguucgguu cccggccaau gc (SEQ ID NO: 77)
uuggugguuc agugguagaa uucucgc (SEQ ID NO: 78)
gacauuggug guucagugu agaauucu (SEQ ID NO: 79)
ugguucagug guagaauucu cgccucc (SEQ ID NO: 80)
gcauugguau aguguauca ugcaaga (SEQ ID NO: 81)
agcguuggug guauaguggu gagcauagcu gc
```

Non-limiting examples of His tRNA sequences are listed below.

```
His tRNA
                                    (SEQ ID NO: 82)
ggccgugauc guauaguggu uaguacucug (SEQ ID NO: 83)
ucgccgugau cguauagugg uuaguacucu g (SEQ ID NO: 84)
ggccgugauc guauaguggu uaguacuc (SEQ ID NO: 85)
aggccgugau cguauagugg uuaguacuc (SEQ ID NO: 86)
ggccgugauc guauaguggu uaguacu
```

-continued

```
                                  (SEQ ID NO: 87)
ggccgugauc guauaguggu uaguac
```

Non-limiting examples of Ile tRNA sequences are listed below.

```
Ile tRNA
                                  (SEQ ID NO: 88)
ggccgguuag cucaguuggu uagagc (SEQ ID NO: 89)
ggccgguuag cucaguuggu cagagc (SEQ ID NO: 90)
ggccgguuag cucaguuggu aagagcuugg u (SEQ ID NO: 91)
ggggcggccg guuagcucag uugguaagag c (SEQ ID NO: 92)
ggccgguuag cucaguuggu aagugc
```

Non-limiting examples of Leu tRNA sequences are listed below.

```
Leu tRNA
                                  (SEQ ID NO: 93)
gguagugugg ccgagcgguc uuaggc (SEQ ID NO: 94)
guagucgugg ccgagugguu aaggcuaugg a (SEQ ID NO: 95)
gacgaggugg ccgagugguu aaggcuaugg au (SEQ ID NO: 96)
gacgaggugg ccgagugguu aaggcuaugg ac (SEQ ID NO: 97)
gacgaggugg ccgagugguu aaggcuaugg a (SEQ ID NO: 98)
gacgaggugg ccgagugguu aaggcuaugg (SEQ ID NO: 99)
gacgaggugg ccgagugguu aaggcaaugg a (SEQ ID NO: 100)
gacgaggugg ccgagugguu aaggcaaugg (SEQ ID NO: 101)
uguagucgug gccgaguggu uaaggc
```

Non-limiting examples of Lys tRNA sequences are listed below.

```
Lys tRNA
                                  (SEQ ID NO: 102)
gccuggauag cucaguuggu agagcaucag a (SEQ ID NO: 103)
gccuggauag cucaguuggu agagcauca (SEQ ID NO: 104)
gccugguag cucagucggu agagcaucag ac (SEQ ID NO: 105)
gccugguag cucaguuggu agagcaucag a (SEQ ID NO: 106)
gccugguag cucagucggu agagcaucag
```

Non-limiting examples of Met tRNA sequences are listed below.

```
Met tRNA
                                  (SEQ ID NO: 107)
gcagaguggc gcagcggaag cgugcugggc cc (SEQ ID NO: 108)
ggcagagugg cgcagcggaa gcgugcuggg cc (SEQ ID NO: 109)
gcagaguggc gcagcggaag cgugcugg (SEQ ID NO: 110)
ugcagagugg cgcagcggaa gcgugcugg (SEQ ID NO: 111)
gcaguggcgc agcggaagcg ugcugggcc (SEQ ID NO: 112)
gcagaguggc gcagcggaag cgugcug (SEQ ID NO: 113)
cgcagagucg cgcagcggaa gcgugcuggg cc (SEQ ID NO: 114)
cagagucgcg cagcggaagc gugcugggcc c (SEQ ID NO: 115)
agaguugcgc agcggaagcg ugcugggccc a (SEQ ID NO: 116)
gagauagcag aguggcgcag cggaagc
```

Non-limiting examples of Pro tRNA sequences are ggcucguugg ucuaggggua ugauucucgg (SEQ ID NO: 117) and aggcucguug gucuaguggu augauucucg (SEQ ID NO: 118).

A non-limiting example of a SeC (selenocysteine) tRNA sequence is gcccggauga uccucagugg ucuggggugc (SEQ ID NO: 119).

Non-limiting examples of Ser tRNA sequences are listed below.

```
Ser tRXA
                                  (SEQ ID NO: 120)
uguagucgug gccgaguggu uaaggc (SEQ ID NO: 121)
gacgaggugg ccgagugguu aaggcuaugg ac (SEQ ID NO: 122)
gacgaggugg ccgagugguu aaggcuaugg au (SEQ ID NO: 123)
gacgaggugg ccgagugguu aaggcuaugg a (SEQ ID NO: 124)
gacgaggugg ccgagugguu aaggcaaugg a (SEQ ID NO: 125)
gacgaggugg ccgagugguu aaggcuaugg (SEQ ID NO: 126)
gacgaggugg ccgagugguu aaggcaaugg
```

Non-limiting examples of Sup (suppressor) tRNA sequences are gccuggauag cucaguuggu agagcaucaga (SEQ ID NO: 127) and gccuggauag cucaguuggu agagcauca (SEQ ID NO: 128).

Non-limiting examples of Thr tRNA sequences are listed below.

```
Thr tRNA
                                  (SEQ ID NO: 129)
ggcagagugg cgcagcggaa gcgugcuggg cc
```

```
                                    (SEQ ID NO: 130)
gcagaguggc gcagcggaag cgugcugggc cc (SEQ ID NO: 131)
gcagaguggc gcagcggaag cgugcugg (SEQ ID NO: 132)
cggaagcgug cugggcccau aacccaga (SEQ ID NO: 133)
ugcagagugg cgcagcggau gcgugcugg (SEQ ID NO: 134)
gcaguggcgc agcggaagcg ugcugggcc (SEQ ID NO: 135)
gcagaguggc gcagcggaag cgugcug (SEQ ID NO: 136)
cgcagagucg cgcagcggaa gcgugcuggg cc (SEQ ID NO: 137)
cagagucgcg cagcggaagc gugcugggcc c (SEQ ID NO: 138)
agaguugcgc agcggaagcg ugcugggccc a
```

Non-limiting examples of Tyr tRNA sequences include gccuggauag cucaguuggu agagcaucaga (SEQ ID NO: 139) and gccuggauag cucaguuggu agagcauca (SEQ ID NO: 140).

Non-limiting examples of Val tRNA sequences are listed below.

```
Val tRNA
                                    (SEQ ID NO: 141)
uuccguagug uagugguuau cacguucgcc uc (SEQ ID NO: 142)
uuccguagug uagugguuau cacguucgcc (SEQ ID NO: 143)
uccguagugu agugguuauc acguucgccu ga (SEQ ID NO: 144)
uccguagugu agugguuauc acguucgccu g (SEQ ID NO: 145)
uccguagugu agugguuauc acguucgccu ca (SEQ ID NO: 146)
uccguagugu agugguuauc acguucgccu (SEQ ID NO: 147)
guuuccguag uguagugguc aucacguucg cc (SEQ ID NO: 148)
ccguagugua gugguuauca cguucgcc (SEQ ID NO: 149)
guuuccguag uguagugguc aucacguucg (SEQ ID NO: 150)
cguaguguag ugguuaucac guucgcc (SEQ ID NO: 151)
uccguagugu agugguuauc acuuucgccu (SEQ ID NO: 152)
uccguagugu acugguuauc acguucgccu g (SEQ ID NO: 153)
cguaguguag uggucaucac guucgccu (SEQ ID NO: 154)
gggguguag cucaguggua gagcgcgugc uu (SEQ ID NO: 155)
gggguguag cucaguggua gagcgcgugc u (SEQ ID NO: 156)
gggguguag cucaguggua gagcgcgugc (SEQ ID NO: 157)
gggguguag cucaguggua gagcgcgug (SEQ ID NO: 158)
ggggguguag cucaguggu agagcgcgug cu (SEQ ID NO: 159)
uugguggguc aguggguagaa uucucgccug cc (SEQ ID NO: 160)
uugguggguc aguggguagaa uucucgccug c (SEQ ID NO: 161)
uugguggguc aguggguagaa uucucgccug (SEQ ID NO: 162)
uugguggguc aguggguagaa uucucgccu (SEQ ID NO: 163)
uggugguuca guggguagaau ucucgccug (SEQ ID NO: 164)
auugguggguu cagugguaga auucucgccu g (SEQ ID NO: 165)
auugguggguu cagugguaga auucucgcc (SEQ ID NO: 166)
ggcauuggug guucaguggu agaauucucg c (SEQ ID NO: 167)
uugguggguc aguggguagaa uucucgc (SEQ ID NO: 168)
ugguucagug guagaauucu cgccucc (SEQ ID NO: 169)
cauugguggu ucaguggguag aauucucgc (SEQ ID NO: 170)
agcauuggug guucaguggu agaauucucg c (SEQ ID NO: 171)
gcauuggugg uucaguggua gaauucucac
```

A non-limiting example of a Asn tRNA sequence is gtctctgtgg cgcaatcggt tagcgcgttc ggctgttaac (SEQ ID NO: 172). A non-limiting example of a Phe tRNA sequence is gccgaaatag ctcagttggg agagcgttag actgaagatc (SEQ ID NO: 173). Additional non-limiting examples of human mature tRNA sequences that can be used to generate any of the neuroprotective molecules described herein are listed in the Sequence Appendix and are described in U.S. Patent Application Publication No. 20110046209 (herein incorporated by reference). Additional examples of human mature tRNA sequences that can be used to generate any of the neuroprotective molecules described herein are known in the art (see, NCBI website, the UCSC genomic tRNA database website (address: gtrnadb.ucsc.edu), and the Unversitat Leipzig tRNAdb website (address:trandb.bioinf.uni-leipzig.edu).

The sequence of 25-35 contiguous nucleotides that is at least 80% identical to a contiguous sequence present between nucleotide 1 and nucleotide 50 of a mature human tRNA incorporated in the neuroprotective molecules described herein should be sufficient to allow the formation of a D-stem loop structure in the neuroprotective molecules. The D-stem loop structure of mature human tRNAs is typically comprised of a region extending from about nucleotide 6 to about nucleotide 27. The formation of a D-loop stem structure within the neuroprotective molecules described herein can be assessed by its gel migration (e.g., in the presence or absence of denaturing agents) or by circular dichroism. Additional methods for the detection of the D-loop stem structure within a nucleic acid are known in the art.

In some embodiments, the guanosine-containing nucleotide can contain a ribose. In some embodiments, the guanosine-containing nucleotide can contain a deoxyribose. In some embodiments, the guanosine-containing nucleotide can contain a modified sugar (e.g., any of the modified sugars described herein). In some embodiments, the guanosine-containing nucleotide can contain modified guanosine (e.g., 7-methyl guanosine or 6-thioguanosine). In preferred embodiments, the at least four contiguous guanosine-containing nucleotides form a G-quadraplex (e.g., a G-quadraplex with guanosines within the neuroprotective molecule).

The neuroprotective molecules described herein can contain one or more (e.g., two, three, four, of five) modified nucleotides. The modified nucleotides can contain a modified base or a modified sugar. Non-limiting examples of modified bases include: xanthine, diaminopurine, 8-oxo-$N^6$-methyladenine, 7-deazaxanthine, 7-deazaguanine, $N^4$, $N^4$-ethanocytosin, $N^6$, $N^6$-ethano-2,6-diaminopurine, 5-methylcytosine, 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, and inosine. Additional non-limiting examples of modified bases include those nucleobases described in U.S. Pat. Nos. 5,432,272 and 3,687,808 (herein incorporated by reference), Freier et al., *Nucleic Acid Res.* 25:4429-4443, 1997; Sanghvi, Antisense Research and Application, Chapter 15, Ed. S. T. Crooke and B. Lebleu, CRC Press, 1993; Englisch, et al., *Angewandte Chemie* 30:613-722, 1991, Kroschwitz, Concise Encyclopedia of Polymer Science and Engineering, John Wiley & Sons, pp. 858-859, 1990; and Cook, *Anti-Cancer Drug Design* 6:585-607, 1991. Additional non-limiting examples of modified bases include universal bases (e.g., 3-nitropyrole and 5-nitroindole). Other modified bases include pyrene and pyridyloxazole derivatives, pyrenyl, pyrenylmethylglycerol derivatives, and the like. Other preferred universal bases include pyrrole, diazole, or triazole derivatives, including those universal bases known in the art.

In some embodiments, the modified nucleotide can contain a modification in its sugar moiety. A non-limiting examples of modified nucleotides that contains a modified sugar are locked nucleic acids (LNAs). LNA monomers are described in WO 99/14226 and U.S. Patent Application Publications Nos. 20110076675, 20100286044, 20100279895, 20100267018, 20100261175, 20100035968, 20090286753, 20090023594, 20080096191, 20030092905, 20020128381, and 20020115080 (herein incorporated by reference). Additional non-limiting examples of LNAs are disclosed in U.S. Pat. No. 6,043,060, U.S. Pat. No. 6,268,490, WO 01/07455, WO 01/00641, WO 98/39352, WO 00/56746, WO 00/56748, and WO 00/66604 (herein incorporated by reference), as well as in Morita et al., *Bioorg. Med. Chem. Lett.* 12(1):73-76, 2002; Hakansson et al., *Bioorg. Med. Chem. Lett.* 11(7):935-938, 2001; Koshkin et al., *J. Org. Chem.* 66(25):8504-8512, 2001; Kvaerno et al., *J. Org. Chem.* 66(16):5498-5503, 2001; Hakansson et al., *J. Org. Chem.* 65(17):5161-5166, 2000; Kvaerno et al., *J. Org. Chem.* 65(17):5167-5176, 2000; Pfundheller et al., *Nucleosides Nucleotides* 18(9):2017-2030, 1999; and Kumar et al., *Bioorg. Med. Chem. Lett.* 8(16):2219-2222, 1998. In some embodiments, the modified nucleotide is an oxy-LNA monomer, such as those described in WO 03/020739.

The neuroprotective molecules described herein can also contain a modification in the phosphodiester backbone. For example, at least one linkage between any two contiguous (adjoining) nucleotides in the neuroprotective molecule can be connected by a moiety containing 2 to 4 groups/atoms selected from the group of: —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$S—R)—O—, —O—PO(BH$_3$)—O—, —O—PO(NHR$^N$)—O—, —O—P(O)$_2$—$NR^H$—, —$NR^H$—P(O)$_2$—O—, —O—P(O,NR$^H$)$_2$—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—, —O—P(O,S)—O—, —O—P(S)$_2$—O—, —$NR^H$—P(O)$_2$—O—, —O—P(O,$NR^H$)—O—, —O—PO(R")—O—, —O—PO(CH$_3$)—O—, and —O—PO(NHR$^N$)—O—, where $R^H$ is selected form hydrogen and $C_{1-4}$-alkyl, and R" is selected from $C_{1-6}$-alkyl and phenyl. Further illustrative examples are given in Mesmaeker et. al., *Curr. Opin. Struct. Biol.* 5:343-355, 1995; and Freier et al., *Nucleic Acids Research* 25:4429-43, 1997. The left-hand side of the internucleoside linkage is bound to the 5-membered ring as substituent P* at the 3'-position, whereas the right-hand side is bound to the 5'-position of a preceding monomer.

In some embodiments, any of the neuroprotective molecules described herein can be modified at either the 3' and/or 5' end by any type of modification known in the art. For example, either or both ends may be capped with a protecting group, attached to a flexible linking group, attached to a reactive group to aid in attachment to the substrate surface. Non-limiting examples of 3' and/or 5' blocking groups include: 2-amino-2-oxyethyl, 2-aminobenzoyl, 4-aminobenzoyl, acetyl, acetyloxy, (acetylamino)m- ethyl, 3-(9-acridinyl), tricyclo[3.3.1.1(3,7)]dec-1-yloxy, 2-aminoethyl, propenyl, (9-anthracenylmethoxy)carbonyl, (1,1-dmimethylpropoxy)carbonyl, (1,1-dimethylpropoxy)carbonyl, [1-methyl-1-[4-(phenylazo)phenyl]ethoxy]carbonyl, bromoacetyl, (benzoylamino)methyl, (2-bromoethoxy)carbonyl, (diphenylmethoxy)carbonyl, 1-methyl-3-oxo-3-phenyl-1-propenyl, (3-bromo-2-nitrophenyl)thio, (1,1-dimethylethoxy)carbonyl, [[(1,1-dimethylethoxy)carbonyl]amino]ethyl, 2-(phenylmethoxy)phenoxy, (1=[1,1'-biphenyl]-4-yl-1-methylethoxy)carbonyl, bromo, (4-bromophenyl)sulfonyl, 1H-benzotriazol-1-yl, [(phenylmethyl)thio]carbonyl, [(phenylmethyl)thio]methyl, 2-methylpropyl, 1,1-dimethylethyl, benzoyl, diphenylmethyl, phenylmethyl, carboxyacetyl, aminocarbonyl, chlorodifluoroacetyl, trifluoromethyl, cyclohexylcarbonyl, cycloheptyl, cyclohexyl, cyclohexylacetyl, chloro, carboxymethyl, cyclopentylcarbonyl, cyclopentyl, cyclopropylmethyl, ethoxycarbonyl, ethyl, fluoro, formyl, 1-oxohexyl, iodo, methyl, 2-methoxy-2-oxoethyl, nitro, azido, phenyl, 2-carboxybenzoyl, 4-pyridinylmethyl, 2-piperidinyl, propyl, 1-methylethyl, sulfo, and ethenyl. Additional examples of 5' and 3' blocking groups are known in the art. In some embodiments, the 5' and/or 3' blocking groups prevent nuclease degradation of the neuroprotective molecule.

The neuroprotective molecules described herein can be synthesized using any methods known in the art for synthesizing nucleic acids (see, e.g., Usman et al., *J. Am. Chem. Soc.* 109:7845, 1987; Scaringe et al., *Nucleic Acid Res.* 18:5433, 1990; Wincott et al., *Methods Mol. Biol.* 74:59, 1997; and Milligan, *Nucleic Acid Res.* 21:8783, 1987). These typically make use of common nucleic acid protecting and coupling groups. Synthesis can be performed on commercial equipment designed for this purpose, e.g., a 394 Applied Biosystems, Inc synthesizer, using protocols supplied by the manufacturer. Additional methods for synthesizing the neuroprotective molecules described herein are known in the art. Alternatively, neuroprotective molecules of the invention can be specially ordered from commercial vendors that synthesize oligonucleotides.

Any of the neuroprotective molecules described herein can be tested for activity (e.g., ability to inhibit or decrease protein translation, the ability to induce or increase stress granule formation in a cell, the ability to translocate into a cell in the absence of cell transfection reagents, the ability to treat a neurological disorder associated with neuron death, or the ability to confer upon cells (e.g., neurons) resistance to stress-induced cell death). Methods for detecting or assessing protein translation (e.g., the amount of translation over a specific period of time or rate of protein translation), methods for detecting or assessing the formation of at least one stress granule in a cell, methods of detecting or assessing the cellular uptake, methods of determining treatment of a neurological disorder associated with neuron death in a subject, and methods of determining whether a neuroprotective molecule confers protection against stress-induced cell death are described herein. Additional methods for assessing these activities are known in the art.

Pharmaceutical Compositions

Also provided herein are pharmaceutical compositions that contain at least one (e.g., one, two, three, or four) of the neuroprotective molecules (e.g., any of the neuroprotective molecules described herein) or C-myc oligonucleotides described herein. Two or more (e.g., two, three, or four) of any of the neuroprotective molecules or C-myc oligonucleotides described herein can be present in a pharmaceutical composition in any combination. The pharmaceutical compositions may be formulated in any manner known in the art.

Pharmaceutical compositions are formulated to be compatible with their intended route of administration (e.g., intravenous, intracranial, ocular, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents such as benzyl alcohol or methyl parabens, chlorobutanol, phenol, ascorbic acid, thimerosal, and the like, antioxidants such as ascorbic acid or sodium bisulfite, chelating agents such as ethylenediaminetetraacetic acid, buffers such as acetates, citrates, or phosphates, and isotonic agents such as sugars (e.g., dextrose), polyalcohols (e.g., manitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the neuroprotective molecule or C-myc oligonucleotide can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the neuroprotective molecules or C-myc oligonucleotides described herein can be formulated for parenteral (e.g., intravenous, intraarterial, intramuscular, intradermal, subcutaneous, or intraperitoneal), intracranial, or ocular administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) neuroprotective molecules or C-myc oligonucleotides (e.g., any of the neuroprotective molecules or C-myc oligonucleotides described herein) will be an amount that treats a neurological disorder associated with neuron death (e.g., amyotrophic lateral sclerosis) in a subject (e.g., a human), decreases the severity, frequency, and/or duration of one or more symptoms of a neurological disorder associated with neuron death (e.g., amyotrophic lateral sclerosis) in a subject (e.g., a human), decreases the rate of neuron death (apoptosis and/or necrosis) in a subject (e.g., a human) having a neurological disorder associated with neuron death, induces or increases stress granule formation in a neuron (e.g., a motor neuron) in a subject having a neurological disorder associated with neuron death (e.g., amyotrophic lateral sclerosis), and/or decreases or inhibits protein translation in a neuron (e.g, a motor neuron) in a subject (e.g., a human) having a neurological disorder associated with neuron death (e.g., as compared to a control subject having the same disease but not receiving treatment or a different treatment, or the same subject prior to treatment). The effectiveness and dosing of any of the neuroprotective molecules or C-myc oligonucleotides described herein can be determined by a health care professional using methods known in the art, as well as by the observation of one or more symptoms of a neurological disorder associated with neuron death in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the neuroprotective molecules or C-myc oligonucleotides described herein per kilogram of the subject's weight (e.g., about 100 ng/kg to about 500 mg/kg; 500 ng/kg to about 1 mg/kg; 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg). While these doses cover a broad range, one of ordinary skill in the art will understand that therapeutic agents, including the neuroprotective molecules and the C-myc oligonucleotides, vary in their potency, and effective amounts can be determined by methods known in the art. Typically, relatively low doses are administered at first, and the attending health care professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the neuroprotective molecule or C-myc oligonucleotide in vivo.

The pharmaceutical compositions can be included in a container, pack, or dispenser together with instructions for administration.

Methods of Inducing/Increasing Stress Granule Formation in a Cell

Provided herein are methods of inducing or increasing stress granule formation in a cell that include administering to a cell a neuroprotective molecule (e.g., any of the neuroprotective molecules described herein) or an isolated C-myc oligonucleotide containing the sequence of GGGAGGGTGG GGAGGGTGGGG (SEQ ID NO: 174) (e.g., any of the C-myc oligonucleotides described herein), wherein the neuroprotective molecule or isolated C-myc oligonucleotide is administered in an amount sufficient to induce or increase (e.g., a significant or detectable increase) stress granule formation in the cell. In some embodiments, the increase in stress granule formation is the formation of at least one stress granule in a cell that does not contain stress granules prior to treatment.

Stress granules are formed in the cytosol and nucleus of mammalian cells (e.g., neurons) in response to stress stimuli (e.g., oxidative stress). Stress granules contain both proteins and messenger RNAs (e.g., polyA mRNAs) that are stalled in translation pre-initiation complexes. Stress granules range between 100 nm to 200 nm in size and are not surrounded by a cellular membrane. A variety of proteins have been identified as being present within stress granules and the presence of stress granules can be identified by the localization of one or more (e.g., two, three, or four) of the following proteins/complexes in distinct foci within a cell (e.g., within the cytoplasm or nucleus of a cell): 40S ribosomal subunit, Ago2, AKAP350, APOBEC3G, Ataxin-2/Pbp1, BRF1, Calreticulin, Caprin1, CCAR1, Ccr4, CIRP, CPEB, CUG-BP1, Dcp1/Dcp1a, Dcp2; DDX1, DDX3/Ded1, DIC1/DHC1, DIS1, Eap1, Ebs1, Edc1-2, Edc3, eIF2, eIF2B, eIF3, eIF4A, eIF4E, eIF4E-T, eIF4G, eRF1, eRF3, FAK, FAST, FBP/KSRP, FMRP, FXR1P, FXR2P, G3BP, Gbp2, Ge-1/Hed1s, Grb7, GW182, hMex3A, hMex3B, hnRNP A1, hnRNP A3, hnRNP K, hnRNP Q, Hrp1, Htt, Hsp27, HuD, HuR, IP5K, Importin-8, KHC/KLC, Lin28, LINE1 ORF1p, Lsm1, MBNL1, MEX67, MLN51, Musahi, Nrp1, NXF7, p97/NAT1, PABP/Pab1, Pan2/3, Pat1, PCBP2, Plakophilin 1/3, PMR1, Pop2/Caf1, Prohibitin 2, PRTB, Pum1, Pum2, RACK1, RBM42, Rap55/Sed6, RCK/Dhh1, RHAU, Roquin, Rpm2, RSK2, Sam68, SERBP1, SGNP, Smaug 1, Staufen, SMN, TDP-43, TDRD3, TIA-1/Pub1, TIA-R/Ngr1, TNRC6B, TRAF2, TTP, Upf1, Upf2, Upf3, Vts1, Xrn1, YB-1, Ygr250c, and ZBP1. Typically, the presence of stress granules in a cell are detected using microscopy (e.g., immunofluorescence microscopy) using one or more antibodies that recognize the localization one or more of the following proteins in discrete foci in the cell: 40S ribosomal subunit, eIF4E, eIF4G, eIF4A, eIF4B, poly(A) binding protein (Pabp), eIF3, and eIF2. The presence of a stress granule can also be detected by assessment of the level of phosphorylated eIF2α present in the cell (e.g., an increased level of phospho-eIF2α indicates the presence of stress granules in the cell). Additional methods for detecting the formation or presence of stress granules in the cell are known in the art.

The formation of stress granule formation in a cell can be compared to the same cell prior to treatment or can be compared to at least one second cell or a population of cells not receiving treatment or receiving a different treatment. In some embodiments, the cell is treated with the at least one neuroprotective molecule or the C-myc oligonucleotide for at least 2 hours (e.g., at least 6 hours, 12 hours, 16 hours, 20 hours, or 24 hours) before the formation of stress granules is determined in the cell.

An increase in stress granule formation in a cell (e.g., a motor neuron) can be indirectly observed in a subject having a neurological disorder associated with neuron death (e.g., stress-induced motor neuron death) by a decrease (e.g., a detectable decrease) in the rate of the development of at least one symptom of a neurological disorder associated with neuron death or a decrease in the rate of the worsening or exacerbation of at least one symptom (e.g., an increase in the intensity, duration, or frequency of at least one symptom over time) of a neurological disorder associated with neuron death in a subject.

In some embodiments, a C-myc oligonucleotide containing the sequence of SEQ ID NO: 174 is administered to the cell. The C-myc oligonucleotides that can be used in these methods can include at least one modified nucleotide (e.g., any of the modified oligonucleotides described herein). In addition, the C-myc oligonucleotides can contain at least one modification in the phosphate backbone (the phosphodiester linkage between two adjoining nucleotides) (e.g., any of linkages described herein). The C-myc oligonucleotides described herein can also include a 5' and/or a 3' blocking group (e.g., a 5' and/or 3' blocking group that decreases or inhibits nuclease degradation) (e.g., any of the 5' and/or 3' blocking groups described herein or known in the art). In some embodiments, the C-myc oligonucleotides have a total length of between 21 to 50 nucleotides (e.g., 21-30 nucleotides, 30-40 nucleotides, or 40-50 nucleotides).

In various embodiments of these methods, the cell can be a neuron (e.g., a motor neuron), a fibroblast, an epithelial cell, an endothelial cell, or a muscle cell. In any of the methods described herein, the cell is a human cell. In some embodiments of these methods, the cell is in vitro (in tissue culture). In some embodiments of these methods, the cell is in vivo (in a human). In some embodiments, the cell is ex vivo (e.g., a primary human neuron or a primary rat neuron).

The neuroprotective molecule or C-myc oligonucleotide can be administered to the cell by a laboratory worker (a research scientist), a health care professional (e.g., a physician, a physician's assistant, or a nurse), or a subject (e.g., self-administration). In instances where the neuroprotective molecule or C-myc oligonucleotide are administered to a to a cell in vivo (in a subject), the dosing and administration of the neuroprotective molecule or C-myc oligonucleotide can be performed as described below.

Methods of Decreasing Protein Translation in a Cell

The data in the Examples show that the neuroprotective molecules and the C-myc oligonucleotides described herein inhibit protein translation of mRNA (capped and uncapped mRNAs) by displacing eIF4G/eIF4A from uncapped RNAs and by displacing eIF4F from the $m^7G$ cap of mRNAs. Accordingly, provided herein are methods of decreasing protein translation in a cell that include administering to a cell a neuroprotective molecule (e.g., any of the neuroprotective molecules described herein) or an isolated C-myc oligonucleotide (e.g., any of the C-myc oligonucleotides described herein), where the neuroprotective molecule or the isolated C-myc oligonucleotide is administered in an amount sufficient to decrease (e.g., a significant or detectable decrease) protein translation in the cell.

In some embodiments, the decrease in protein translation is detected by the amount of protein translation (new proteins translated) over a specific period of time (e.g., at least 1 hour, 2 hours, 4 hours, or 6 hours). In some embodiments, the decrease is protein translation is a decrease in the rate of protein translation in the cell (e.g., as measured by radio-isotope labeling ($^{35}S$) of newly translated proteins or by detection of the biological activity of a newly expressed protein). The decrease in protein translation in a cell can be compared to a control cell or population of cells not receiving the treatment or receiving a different treatment. Additional methods for detecting protein translation are described herein and are known in the art.

An decrease in protein translation in a cell (e.g., a motor neuron) can be indirectly observed in a subject having a neurological disorder associated with neuron death (e.g., stress-induced motor neuron death) by a decrease (e.g., a detectable decrease) in the rate of the development of at least one symptom of a neurological disorder associated with neuron death or a decrease in the rate of the worsening or exacerbation of at least one symptom (e.g., an increase in the intensity, duration, or frequency of at least one symptom over time) of a neurological disorder associated with neuron death in a subject.

In various embodiments of these methods, the cell can be a neuron (e.g., a motor neuron), a fibroblast, an epithelial cell, an endothelial cell, or a muscle cell. In any of the methods described herein, the cell is a human cell. In some embodiments of these methods, the cell is in vitro (in tissue culture). In some embodiments of these methods, the cell is in vivo (in a human). In some embodiments the cell is ex vivo (e.g., a primary human neuron or a primary rat neuron).

The neuroprotective molecule or C-myc oligonucleotide can be administered to the cell by a laboratory worker (a research scientist), a health care professional (e.g., a physician, a physician's assistant, or a nurse), or a subject (e.g., self-administration). In instances where the neuroprotective molecule or C-myc oligonucleotide are administered to a cell in vivo (administered to a subject), the dosing and administration of the neuroprotective molecule or C-myc oligonucleotide can be performed as described below.

Methods of Treating Neurological Disorders Associated with Neuron Death

Also provided herein are methods of treating neurological disorders associated with neuron death (apoptosis and/or necrosis, or stress-induced neuron death). These methods include administering a neuroprotective molecule (e.g., any of the neuroprotective molecules described herein) or an isolated C-myc oligonucleotide (e.g., any of the C-myc oligonucleotides described herein), where the neuroprotective molecule or C-myc oligonucleotide are administered in an amount sufficient to treat the neurological disorder associated with neuron death in the subject.

Neurological disorders associated with neuron death are a group of diseases that are characterized by neuron death (e.g., motor neuron death or stress-induced motor neuron death) and/or have an etiology that involves neuron death (e.g., motor neuron death or stress-induced motor neuron death). Non-limiting examples of neurological disorders associated with neuron death include amyotrophic lateral sclerosis, Alzheimer's disease, Parkinson's disease, Huntington's disease, muscular dystrophy, multiple sclerosis, and stroke. Neuronal death in this group of disorders can be induced by a variety of stress stimuli, including, for example, oxidative stress, excitotoxicity, and neuroinflammation. The data in the Examples herein show that induction of stress granules (e.g., by administration of any of the neuroprotective molecules or C-myc oligonucleotides described herein) mediates an increase in resistance to stress-induced neuronal death. Thus, by virtue of their ability to induce an increase in stress granule formation in neurons (e.g., motor neurons) in a subject, administration of the neuroprotective molecules and the C-myc oligonucleotides described herein can treat a neurological disorder associated with neuron death in a subject. Some of the neuroprotective molecules and C-myc oligonucleotides described herein have the further advantage that they are taken up by neurons (e.g., motor neurons) without the addition of a transfection agent.

Non-limiting symptoms of neurological disorders associated with neuron death include: hyperflexia, weak muscles, twitching, speech problems, breathing problems, swallowing difficulties, loss of memory, confusion, disorientation, difficulty writing, depression, anxiety, social withdrawal, mood swings, aggressiveness, changes in sleeping habits, tremors, bradykinesia, rigid muscles, impaired balance, involuntary facial movements, numbness or weakness in limbs, partial or complete loss of vision, fatigue, dizziness, paralysis on one side of body or face, and headache. A neurological disorder associated with neuronal death can be diagnosed by a health care professional by detecting or observing one or more (e.g., two, three, or four) symptoms (any of the above listed symptoms) in a subject.

In some embodiments, the administering results in a decrease in the number of symptoms of a neurological disorder associated with neuron death (e.g., as compared to the number of symptoms in a subject prior to treatment or to a subject having the same neurological disorder and not receiving treatment or receiving a different treatment). In some embodiments, the administering results in a decrease (e.g., a detectable or observable decrease) in the severity, frequency, or duration of one or more symptoms of a neurological disorder associated with neuron death (e.g., those symptoms listed herein) (e.g., as compared to a subject having the same neurological disorder and not receiving treatment or receiving a different treatment).

In some embodiments, the administering results in a decrease (e.g., a detectable or observable decrease) in the rate of the development of one or more new symptoms of a neurological disorder associated with neuron death in a subject having a neurological disorder associated with neuron death (e.g., as compared to the rate of the development of one or more new symptoms of a neurological disorder associated with neuron death in a subject having the same neurological disorder and not receiving treatment or receiving a different treatment). In some embodiments, the administering results in a decrease (e.g., a detectable or observable decrease) in the rate of worsening or exacerbation of one or more symptoms of a neurological disorder associated with neuron death (e.g., an increase in the severity, frequency, or duration of one or more symptoms of a neurological disorder associated with neuron death over time) (e.g., any of those symptoms described herein) (e.g., as compared to a subject having the same neurological disorder and not receiving treatment or receiving a different treatment).

In some embodiments, the administering results in an increase in stress granule formation in a neuron (e.g., a motor neuron) in a subject that has a neurological disorder associated with neuron death (e.g., as compared to a subject having the same neurological disorder and not receiving treatment or receiving a different treatment). In some embodiments, the administering results in a decrease or inhibition in protein translation in a cell (e.g., a motor neuron) in a subject that has a neurological disorder associated with neuron death (e.g., as compared to a subject having the same neurological disorder and not receiving treatment or receiving a different treatment). In some embodiments, the administering results in a decrease in neuron death or a decrease in the rate of neuron death (e.g., stress-induced motor neuron death) over a period of time (e.g., at least one month, at least one year, or at least five years) (e.g., as compared to a subject having the same neurological disorder and not receiving treatment or receiving a different treatment). A decrease in protein translation in a neuron (e.g., a motor neuron), an increase in stress granule in a neuron (e.g., a motor neuron), or a decrease in the amount or rate of neuron death over time can be indirectly observed by a physician by a decrease (e.g., a detectable or observable decrease) in the rate of the development of at least one new symptom of a neurological disorder associated with neuron death in a subject (e.g., a decrease in further development of at least one additional symptom of the disorder) or a decrease in the rate of exacerbation of at least one symptom (e.g., a decreased rate of increasing frequency, severity, and/or duration of at least one symptom of the neurological disorder associated with neuron death) (e.g., as compared to a subject having the same neurological disorder and not receiving treatment or receiving a different treatment).

Any of the neuroprotective molecules or C-myc oligonucleotides described herein can be used in these methods. In preferred embodiments, the neuroprotective molecule or C-myc oligonucleotide is taken up by a neuron in the subject in the absence of a transfection agent. In some embodiments, the neuroprotective molecule or the C-myc oligonucleotide contains a modified nucleotide (e.g., any of the modified bases and/or sugars described herein). In some embodiments, the neuroprotective molecule or the C-myc oligonucleotide contains at least one modification in its phosphate (phosphodiester) backbone (e.g., any of the moieties described herein that can be used to link two adjoining nucleotides).

The neuroprotective molecule or C-myc oligonucleotide can be administered by a health care professional (e.g., a physician, a physician's assistant, a nurse, or a laboratory or clinic worker), the subject (i.e., self-administration), or a friend or family member of the subject. The administering can be performed in a clinical setting (e.g., at a clinic or a hospital), in an assisted living facility, or at a pharmacy.

The neuroprotective molecule or C-myc oligonucleotide can be administered to a subject that has been diagnosed as having a neurological disorder associated with neuron death. In some non-limiting embodiments, the subject is a man or a woman, an adult, or an adolescent. The subject can have experienced one or more symptoms of the neurological disorder associated with neuron death for at least one year, two years, three years, four years, or five years. The subject can also be diagnosed as having a later or severe form (an advanced stage) of the neurological disorder associated with neuron death.

In some embodiments of any of the methods described herein, the subject is administered at least one (e.g., at least 1, 2, 3, 4, 5, 6, 7, 8, 9, 10, 15, 20, 25, or 30) dose of a composition containing at least one (e.g., one, two, three, or four) of any of the neuroprotective molecules, C-myc oligonucleotides, or pharmaceutical compositions described herein. In any of the methods described herein, the neuroprotective molecule, C-myc oligonucleotide, or pharmaceutical composition (e.g., any of the neuroprotective molecules, C-myc oligonucleotides, or pharmaceutical compositions described herein) can be administered intravenously, intraarterially, subcutaneously, intraperitoneally, intracranially, ocularly, or intramuscularly to the subject. In some embodiments, the neuroprotective molecule, C-myc oligonucleotide, or pharmaceutical composition is administered intracranially, ocularly, or to the spinal fluid.

In some embodiments, the subject is administered the neuroprotective molecule, C-myc oligonucleotide, or pharmaceutical composition (e.g., any of the neuroprotective molecules, C-myc oligonucleotides, or pharmaceutical compositions described herein) and at least one additional therapeutic agent. The at least one additional therapeutic agent can be selected from the group consisting of: mexiletine, phenyloin, baclofen, dantrolene, carbamazepine, corticosteroids, β-interferons, glatiramer, fingolimod, natalizumab, mitoxantrone, aspirin, tissue plasminogen activator, anticholinergics (e.g., benzotropine and trihexyphenidyl), glutamate (NMDA) blocking drugs (e.g., amantadine), riluzole, cholesterase inhibitors (e.g., donepezil, galactamine, and rivastigmine), memantine, levodopa, carbidopa, dopamine agonists (e.g., pramipexole, ropinicole, and apomorphine), monoamine oxidase B inhibitors (e.g., selegiline and vasagiline), catechol O-methyl transferase inhibitors (e.g., tolcapone and entracapone), tetrabenazine, and anti-psychotic drugs (e.g., haloperidol and clozapine). In some embodiments, at least one additional therapeutic agent and at least one neuroprotective molecule or C-myc oligonucleotide (e.g., any of the neuroprotective molecules or C-myc oligonucleotides described herein) are administered in the same composition (e.g., the same pharmaceutical composition). In some embodiments, the at least one additional therapeutic agent and the neuroprotective molecule or C-myc oligonucleotide are administered to the subject using different routes of administration (e.g., at least one additional therapeutic agent delivered by oral administration and the neuroprotective molecule or C-myc oligonucleotide delivered by intravenous administration).

In any of the methods described herein, the neuroprotective molecule, C-myc oligonucleotide, or pharmaceutical composition (e.g., any of the neuroprotective molecules, C-myc oligonucleotides, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different neuroprotective molecules and/or C-myc oligonucleotides are administered in the same composition (e.g., a liquid composition). In some embodiments, the neuroprotective molecule or C-myc oligonucleotide and at least one additional therapeutic agent are administered in the same composition (e.g., a liquid composition). In some embodiments, the neuroprotective molecule or C-myc oligonucleotide and the at least one additional therapeutic agent are administered in two different compositions (e.g., a liquid composition containing the neuroprotective molecule or C-myc oligonucleotide and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to administering the neuroprotective molecule, C-myc oligonucleotide, or pharmaceutical composition (e.g., any of the neuroprotective molecules, C-myc oligonucleotides, or pharmaceutical compositions described herein). In some embodiments, the one or more additional therapeutic agents can be administered to the subject after administering the neuroprotective molecule, C-myc oligonucleotide, or pharmaceutical composition (e.g., any of the neuroprotective molecules, C-myc oligonucleotides, or pharmaceutical compositions described herein). In some embodiments, the one or more additional therapeutic agents and the neuroprotective molecule, C-myc oligonucleotide, or pharmaceutical composition (e.g., any of the neuroprotective molecules, C-myc oligonucleotides, or pharmaceutical compositions described herein) are administered to the subject such that there is an overlap in the bioactive period of the one or more additional therapeutic agents and the neuroprotective molecule or C-myc oligonucleotide (e.g., any of the neuroprotective molecules or C-myc oligonucleotides described herein) in the subject.

In some embodiments, the subject can be administered the neuroprotective molecule, C-myc oligonucleotide, or pharmaceutical composition (e.g., any of the neuroprotective molecules, C-myc oligonucleotides, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, or 10 years). A skilled medical professional may determine the length of the treatment period using any of the methods described herein for diagnosing or following the effectiveness of treatment (e.g., using the methods above and those known in the art). As described herein, a skilled medical professional can also change the identity and number (e.g., increase or decrease) of neuroprotective molecules or C-myc oligonucleotides (and/or one or more additional therapeutic agents) administered to the subject and can also adjust (e.g., increase or decrease) the dosage or frequency of administration of the neuroprotective molecule or C-myc oligonucleotide (and/or one or more additional therapeutic agents) to the subject based on an assessment of the effectiveness of the treatment (e.g., using any of the methods described herein and known in the art). A skilled medical professional can further determine when to discontinue treatment (e.g., for example, when the subject's symptoms are significantly decreased).

Methods of Identifying a Candidate Translation Inhibitory Nucleic Acid

Also provided herein are methods of identifying a candidate translation inhibitory nucleic acid. These methods include (a) attaching to the 5' end of a nucleic acid sequence of between 20-50 nucleotides (e.g., 20-30 nucleotides, 30-40 nucleotides, or 40-50 nucleotides) at least four (e.g., at least five, six, or seven) guanosine-containing nucleotides, and (b) determining the level of protein translation in the presence of the molecule produced in (a). A decrease (e.g., a significant or detectable decrease) in the level of protein translation in the presence of the molecule produced in (a) relative to the level of protein synthesis in the absence of the molecule produced in (a) identifies the molecule produced in (a) as a candidate translation inhibitory nucleic acid.

In some embodiments, the nucleic acid sequence of between 20-50 nucleotides contains at least 50% (e.g., at least 55%, 60%, 65%, or 70%) guanosine-containing/cytosine-containing nucleotides. In some embodiments, the sequence of between 20-50 nucleotides is at least 80% identical to a contiguous sequence between nucleotide 1 and nucleotide 50 of a mature human tRNA sequence (e.g., any of the tRNA sequences described or referenced herein, or any mature human tRNA sequence known in the art). The nucleic acid sequence of between 20-50 nucleotides can contain at least one modified nucleotide (e.g., can contain any of the base modifications or sugar modifications described herein). The nucleic acid sequence of between 20-50 nucleotides can also contain at least one modification in the phosphate (phosphodiester) backbone (e.g., any of the linking moieties between two adjoining nucleotides described herein). The molecule produced in (a) can also contain a 5' and/or 3' protective group (e.g., a protective group that decreases nuclease degradation of the molecule produced in (a)) (e.g., any of the 5' or 3' protective groups described herein or known in the art).

In some embodiments of these methods, the level of protein translation is determined in a cell (e.g., a fibroblast, a neuron (e.g., a motor neuron), an endothelial cell, an epithelial cell, or a muscle cell) (e.g., a cell in vitro). In some embodiments, the level of protein translation is determined in a cell lysate (e.g., a reticulocyte lysate). In some embodiments of all of the above methods, the cell is a human cell.

The level of protein synthesis in these methods can be the total amount of protein translation that occurs over a specific period of time (e.g., at least 2 hours, 6 hours, 12 hours, 16 hours, 20 hours, or 24 hours) or the rate of protein synthesis. Methods for measuring or detecting protein translation are described herein. Additional methods for measuring or detecting protein synthesis are known in the art.

Candidate translation inhibitory nucleic acids identified in these methods can be further modified by the incorporation of modified nucleotides (e.g., modified bases and/or sugars), by introducing a modification in the phosphate (phosphodiester) backbone (e.g., introduction of one of the linking moieties described herein), and/or by adding a 5' and/or 3' blocking group to the molecule produced in (a), and further tested to determine the molecule's ability to decrease protein translation.

EXAMPLE

The invention is further described in the following examples, which do not limit the scope of the invention described in the claims.

Example 1. Endogenous 5'-tiRNAs Inhibit Translation

Experiments were performed in order to determine whether natural 5'- and 3'-tRNA fragments (tiRNAs) purified from angiogenin-treated U2OS cells would inhibit translation of uncapped luciferase transcripts in rabbit reticulocyte lysate (RRL). The following methods were used to perform these experiments.

Tissue Culture and Cell Treatment

U2OS cells were maintained at 37° C. in a $CO_2$ incubator in Minimal Essential Medium (DMEM) supplemented with 10% fetal bovine serum (FBS) (Sigma) and 1% of penicillin/streptomycin (Sigma). The cells were treated with angiogenin (0.5 μg/mL) as described in Kedersha et al., *Methods Enzymol.* 448:521-552, 2008.

Isolation of tiRNAs

Extraction of tiRNAs from angiogenin-treated U2OS cells was done as previously described (Yamasaki et al., *J. Cell Biol.* 185:35-42, 2009).

In Vitro Translation of mRNA Reporters in Rabbit Reticulocyte Lysates (RRLs)

The Flexi Rabbit Reticulocyte Lysate (RRL) System (Promega) was used for the in vitro analysis of mRNA translation according to the manufacture's recommendations with some modifications. In all cases, translation reactions (10 μl final volume) contained 70% of reticulocyte lysates or mixtures of RRL supplemented with 20% of microccocal nuclease-treated U2OS extract (RRL+20% U2OS lysate) and 8 units of RNasin Ribonuclease Inhibitor (Promega). Fifty ng of uncapped Firefly RNA (Promega) were used per translation reaction. One hundred picomoles of control RNAs or tiRNAs were added to translation reactions, mixed, and incubated for 30 minutes at 30° C. The reactions were stopped at 4° C. and the activity of Firefly luciferase was measured using ⅕ of the translation reactions with the Luciferase Assay System (Promega) according to the manufacture's recommendations (2 second measurement delay followed by 10 second measurement read).

Northern Blot Analysis

RNA was separated on either a 10% or 15% TBE-UREA Gel (Invitrogen) and transferred to Supercharge nylon transfer membranes (Nytran SPC; 0.45 μm pore size; Whatman). The RNA on the membranes was UV cross-linked using a FB-UVXL-1000 cross-linker (Fisher Scientific). The membranes were then pre-hybridized in hybridization solution (5×SSC, 20 mM $Na_2HPO_4$ pH 7.4, 7% SDS, 1×Denhardt's) at 47° C. for 30 minutes and then hybridized with the $^{32}P$ 5'-end labeled oligonucleotide probe (ME8: 5'CTTTATGTTTTGGCGTCTTCCATCTCGAGGC3'; SEQ ID NO: 175) overnight at 47° C. The membranes were washed twice for 15 minutes at 47° C. with 3×SSC/5% SDS and once with 1×SSC/1% SDS for 15 minutes at room temperature. After washing, RNA signals were detected by autoradiography on X-Omat film (Kodak) after overnight exposure at −80° C.

Results

Uncapped Firefly luciferase mRNA (Promega) was translated in RRL in the presence of a control RNA mix (Ctrl 1-2-3; derived from Piwi-interacting RNAs (piRNAs) or random sequences), natural 5'-tiRNAs (Nat 5' end), or natural 3'-tiRNAs (Nat 3' end) using the methods described above. Luciferase expression was compared to the level of expression in the absence of RNA (No RNA=100%). The data from these experiments show that natural 5'-tiRNAs (but not 3'-tiRNAs) gel-purified from angiogenin-treated U2OS cells significantly inhibit translation of uncapped luciferase transcripts in RRLs (FIG. 1, bottom). Northern blotting analysis confirmed that the luciferase transcripts were not degraded during the experiment (FIG. 1, top).

Example 2. Selected Synthetic 5'-tiRNAs are Potent Inhibitors of Translation

Since natural tiRNA preparations are contaminated with ribosomal and mRNA fragments, experiments were performed to compare the activity of synthetic 5'-end phosphorylated 5'-tiRNAs (5'-tiRNAs) and unphosphorylated 3'-tiRNAs (3'-tiRNAs) (Emara et al., *J. Biol. Chem.* 285:10959-10968, 2010) in the above-described in vitro RRL translation assay. The synthetic tiRNAs used in this study were synthesized by Integrated DNA Technology and were at least 95% homogenous. The synthetic sequences used in these experiments were:

```
                                           (SEQ ID NO: 1)
Ctrl1:
5'-UGA AGG GUU UUU UGU GUC UCU AUU UCC UUC-3'
(piR006650);

(SEQ ID NO: 2)
Ctrl2:
5'-phospho-UGU GAG UCA CGU GAG GGC AGA AUC

UGC UC-3'
(piR58620);

(SEQ ID NO: 3)
Ctrl3:
5'-phospho-GCA UUC ACU UGG AUA GUA AAU CCA

AGC UGA A-3'
(random);

(SEQ ID NO: 4)
5'Ala:
5'-Phospho-GGG GGU GUA GCU CAG UGG UAG AGC

GCG UGC-3';

(SEQ ID NO: 5)
5'-Val:
5'-phospho-GUU UCC GUA GUG UAG UGG UUA UCA

CGU UCG CC-3';

(SEQ ID NO: 6)
5'-Gly-GCC:
5'-Phospho-GCA UGG GUG GUU CAG UGG UAG AAU

UCU CGC-3';

(SEQ ID NO: 7)
5'-GlyCCC:
5'-phospho-GCG CCG CUG GUG UAG UGG UAU CAU

GCA AGA U-3';
```

-continued

5'-Pro: (SEQ ID NO: 8)
5'-Phospho-GGC UCG UUG GUC UAG GGG UAU GAU UCU CGG -3';

5'-Gln: (SEQ ID NO: 9)
5'-Phospho- GGU UCC AUG GUG UAA UGG UUA GCA CUC UG -3';

5'-Cys: (SEQ ID NO: 10)
5'-Phospho-GGG GGU AUA GCU CAG UGG UAG AGC AUU UGA-3';

5'-Met: (SEQ ID NO: 11)
5'-Phospho-GCC UCG UUA GCG CAG UAG GUA GCG CGU CAG U -3';

5'-Met-I: (SEQ ID NO: 12)
5'-Phospho-AGC AGA GUG GCG CAG CGG AAG CGU GCU GG -3';

3'-Ala: (SEQ ID NO: 13)
5'-CUU AGC AUG CAC GAG GCC CCG GGU UCA AUC CCC GGC ACC UCCA-3';

3'-Arg: (SEQ ID NO: 14)
5'- GGA UCA GAA GAU UGA GGG UUC GGG UCC CUU CGU GGU CG-3';

3'-Gly: (SEQ ID NO: 15)
5'- CCA CGC GGG AGG CCC GGG UUC GAU UCC CGG CCA AUG CA-3';

3'-Gln: (SEQ ID NO: 16)
5'-GAC UCU GAA UCC AGC GAU CCG AGU UCA AAU CUC GGU GGA ACC U -3';
and 3'-Pro: (SEQ ID NO: 17)
5'-UUA GGA UGC GAG AGG UCC CGG GUU CAA AUC CCG GAC GAG CCC -3'.

The levels of luciferase mRNA were also determined in these experiments using Northern blot using the methods described above.

Figure 2:
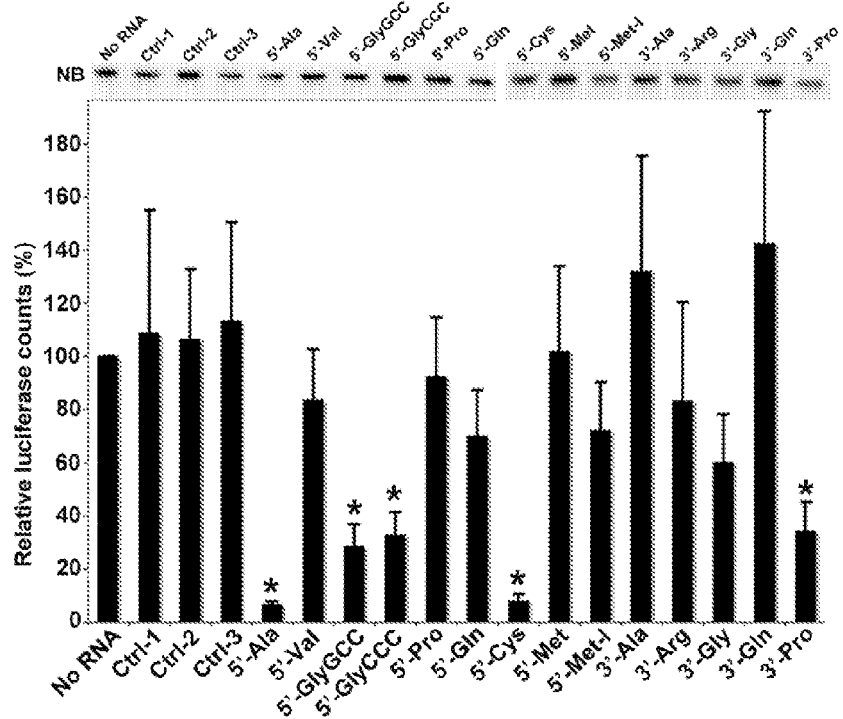
FIG. 2 is a graph showing the relative amount of luciferase expression in RRL containing uncapped luciferase mRNA (50 ng/10 µL) following treatment with synthetic 5'-tiRNAs or 3'-tiRNAs (100 picomoles/10 µL) compared to luciferase expression in untreated lysates (*p<0.05, Student's t-test, n=4) (bottom), and a Northern blot showing the levels of luciferase mRNA in these experiments (top).
Figure 3:
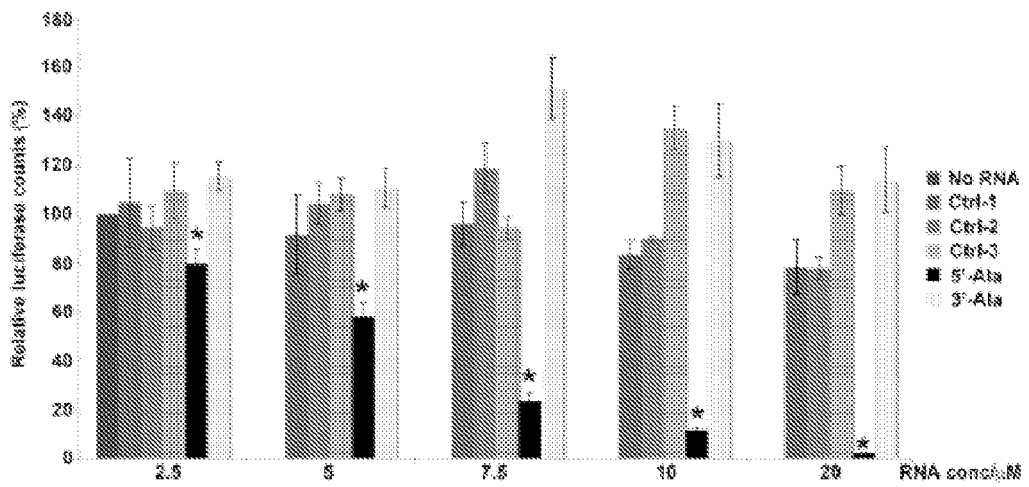
FIG. 3 is a graph showing the dose-dependent inhibition of uncapped luciferase mRNA translation in RRL following treatment with control RNAs (ctrl-1, ctrl-2, and ctrl-3), synthetic 5'-tiRNA$^{Ala}$(5'-Ala), or synthetic 3'-tiRNA$^{Ala}$ (3'-Ala). Translation of the reporter in the absence of any RNA (No RNA) was assigned a relative value of 100%. The error bars reflect the standard deviations of the mean (*p<0.05, relative to no RNA and all three control RNAs (ctrl-1, ctrl-2, and ctrl-3), Student's t-test, n=3).

The data from these experiments show that although several tiRNAs significantly inhibit translation, 5'-tiRNA$^{Ala}$ and 5'-tiRNA$^{Cys}$ are particularly potent translational inhibitors (FIG. 2, bottom). Northern blotting analysis confirmed that luciferase transcripts were not degraded under these conditions (FIG. 2, top). Data from a dose response experiment comparing 5'- and 3'-tiRNA$^{Ala}$ shows that 5'-tiRNA$^{Ala}$ represses translation at low micromolar concentrations (FIG. 3). Since the abundance of tiRNAs in angiogenin- or ansenite-treated cells is ~10-fold less than that of tRNA (intracellular tRNA concentration is estimated to be ~10-200 µM depending on cell type), similar inhibitory concentrations of tiRNAs are likely found in stressed cells. These calculations indicate that the ratio of tiRNAs to mRNAs in stressed cells is ~8, which is consistent with their ability to repress translation in vivo.

Additional experiments were performed to determine whether 5'-tiRNA$^{Ala}$ and 3'-tiRNA$^{Ala}$ inhibit the translation of capped luciferase transcripts. These experiments were performed using the RRL translation assay described above with 10 nm of capped Firefly mRNA. To prepare capped Firefly luciferase mRNA, 2 mg of commercial uncapped Firefly luciferase mRNA (Promega) was capped by Vaccinia Virus Capping enzyme using ScriptCap m$^7$G Capping System (EPICENTRE Biotechnologies) according to the manufacture's recommendations. Capped mRNA was purified by standard ethanol precipitation and quantified by spectrophotometry (Beckman DU 640 instrument).

Figure 4:
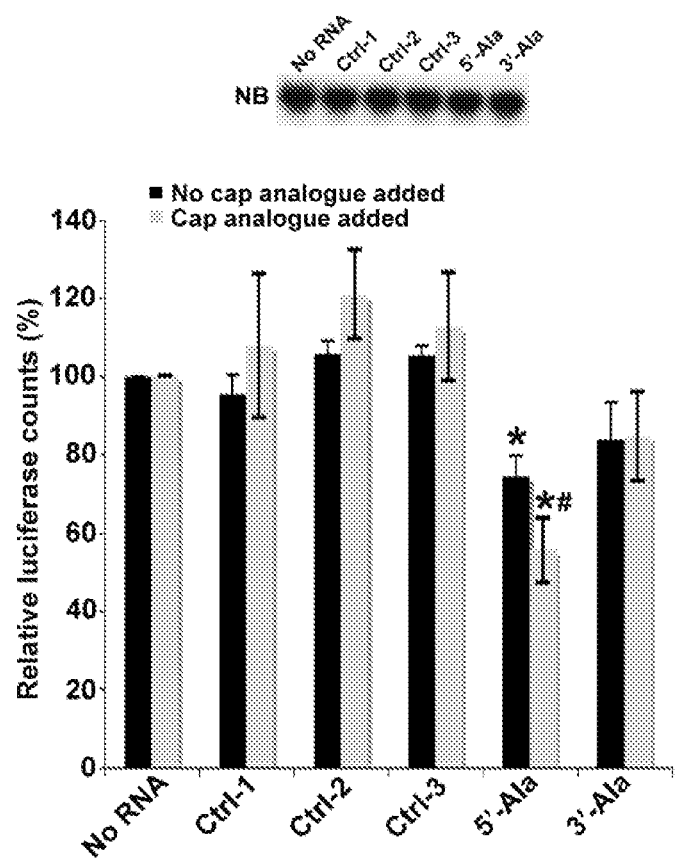
FIG. 4 is a graph showing the relative amount of luciferase expression in RRL containing capped luciferase mRNA (10 ng/10 µL) in the presence or absence of the indicated synthetic RNAs (100 picomoles/10 µL) in the absence (dark bars) or presence (light bars) of cap analogue (m$^7$GpppG, 0.1 mM) (*p<0.05, comparing 5'-tiRNA$^{Ala}$ in the presence or absence of the cap analogue, Student's t-test, n=3) (bottom), and a Northern blot showing the levels of luciferase mRNA in these experiments (top).

The data from these experiments show that 5'-tiRNA$^{Ala}$ (but not 3'-tiRNA$^{Ala}$) also significantly inhibits the translation of capped luciferase transcripts (FIG. 4, bottom), and that the addition of a cap analogue that inhibits cap-dependent translation significantly increases the relative translational repression. The cap analogue reduces the basal level of capped mRNA translation by ~2.5-fold. Northern blotting analysis (performed as described above) confirmed that luciferase transcripts are not degraded under these conditions (FIG. 4, top). Since translation of uncapped mRNAs or capped mRNAs in the presence of cap analogue depends on eIF4G binding to the 5'-terminus of mRNA (De Gregorio et al., RNA 4:828-836, 1998), these data suggest that 5'-tiRNA$^{Ala}$ interferes with some functions of eIF4G (e.g., binding to mRNA and/or to eIF4E).

Example 3. Encephalomyocarditis Virus Internal Ribosomal Entry Site (EMCV IRES)-Mediated Translation Additional experiments were performed in order to determine the role of eIF4G in tiRNA-mediated translational repression. In these experiments, the translation of capped or uncapped bicistronic reporter transcripts encoding an upstream Firefly luciferase and a downstream EMCV IRES-driven *Renilla* luciferase in the absence or presence of tiRNAs was quantitated. These experiments were performed using the methods generally described above with the modifications described below.

RNA transcripts for use in the RRL assay were prepared by first linearizing the bicistronic reporter plasmid (pF/R) (Bochkov et al., *BioTechniques* 41:283-284, 286, 288, 2006) by digestion with HpaI (New England Biolabs), separating the cut plasmids on 1% agarose gel, and then purifying the plasmids from the gel with QIAquick Gel Extraction Kit (Qiagen). Riboprobe T7 in vitro transcription System (Promega) was used to synthesize pF/R RNA using T7 RNA Polymerase according to the manufacturer's recommendations. Subsequently, in vitro transcribed RNA was purified using Trizol (Invitrogen) extraction followed by isopropanol precipitation. Purified RNA was analyzed for purity on a formaldehyde gel and quantified by spectrophotometry (Beckman DU 640). One hundred nanograms of pF/R bicistronic mRNA were used per translation reaction and the activities of Firefly and *Renilla* luciferase were measured using ⅕ of translation reactions with the Dual-Luciferase Reporter Assay System (Promega).

Figure 5:
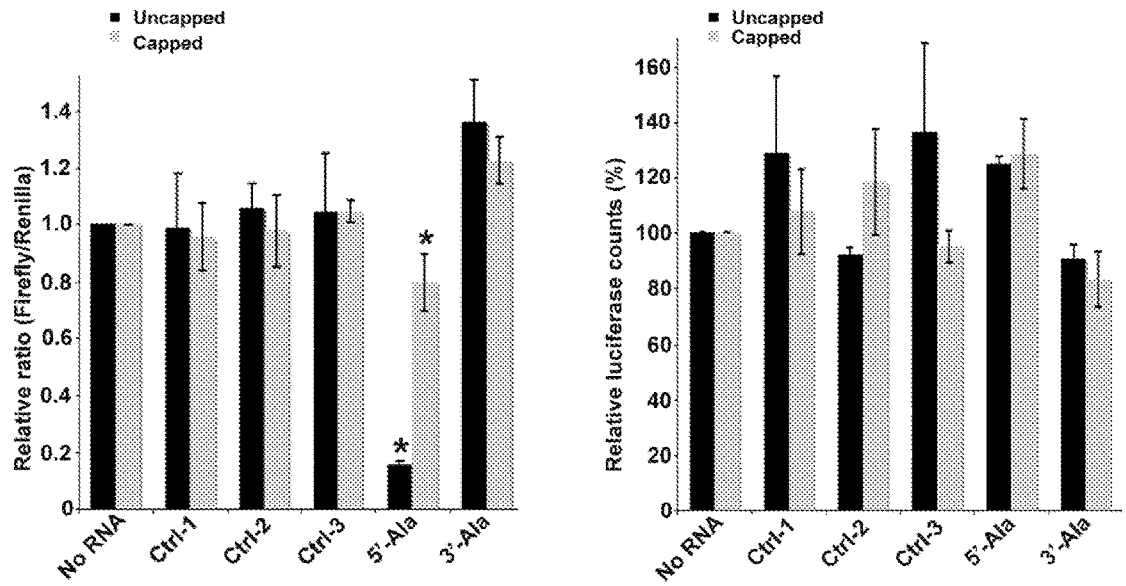
FIG. 5 is a graph showing the relative ratio of Firefly to Renilla luciferase counts produced in a RRL assay using uncapped (dark bars) or capped (light bars) pF/R bicistronic transcripts in the presence of 5'-tiRNA$^{Ala}$ (*p<0.05, compared to no RNA and three control RNAs (ctrl-1, -2, and -3), Student's t-test, n=3-4) (right panel), and a graph showing the luciferase counts from EMCV IRES-driven translation of the Renilla ORF relative to the no RNA control (100%) in the RRL using uncapped (dark bars) or capped (light bars) pF/R bicistronic transcripts in the presence of 5'-tiRNA$^{Ala}$ (left panel).
Figure 6:
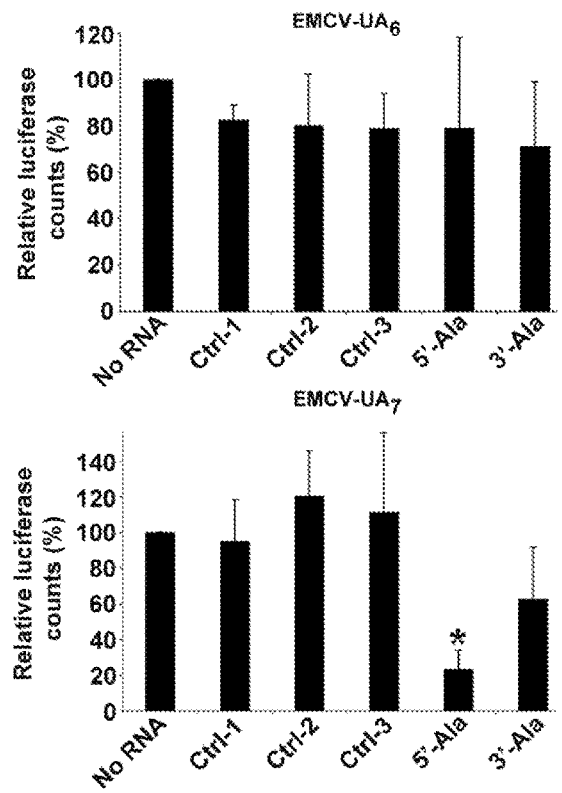
FIG. 6 is two graphs showing the luciferase expression in RRL assays using monocistronic transcripts encoding *Renilla* luciferase under the control of different EMCV IRES variants (WT EMCV-UA$_6$ (upper graph) and EMVC-UA$_7$ (lower graph)) in the presence of control RNAs (ctrl-1, -2, and -3), 5'-tiRNA$^{Ala}$, or 3'-tiRNA$^{Ala}$ (*p<0.05 compared to no RNA and three control RNAs (ctrl-1, -2, and -3), Student's t-test, n=3).
Figure 7:
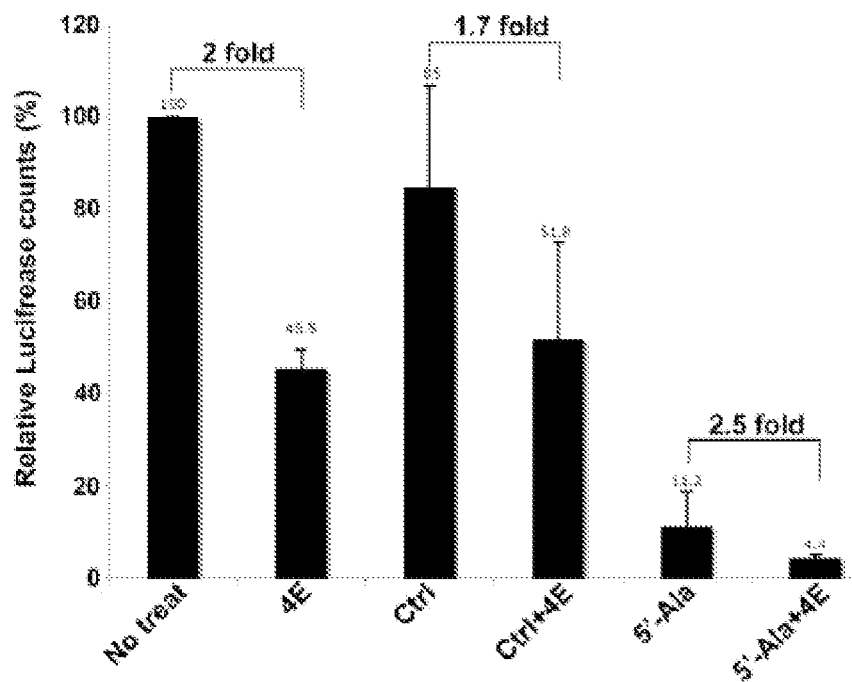
FIG. 7 is a graph showing the luciferase expression in RRL assays using uncapped Firefly luciferase RNA in the presence of control RNA or synthetic 5'-tiRNA$^{Ala}$ (5'-Ala) supplemented with a two-molar excess of recombinant eIF4E protein (+4E). Translation of the reporter in the absence of any RNA (no RNA) is assigned a relative value of 100%. The error bars reflect standard deviations of the mean.

The data from these experiments show that 5'- (but not 3'-tiRNA$^{Ala}$) significantly reduces the Firefly/*Renilla* luciferase ratio (FIG. 5, left panel) without affecting the translation of *Renilla* luciferase (FIG. 5, right panel). This result indicates that 5'-tiRNA$^{Ala}$ does not prevent the recruitment of eIF4G to the EMCV IRES. As this result was not consistent with the ability of tiRNAs to preferentially inhibit the eIF4G-dependent translation of uncapped RNA, additional experiments were performed using an EMCV IRES variant that has reduced affinity for eIF4G and less efficient translation initiation (Bockhov et al., supra; Kaminski et al., *EMBO J.* 13:1673-1681, 1998).

Figure 8:
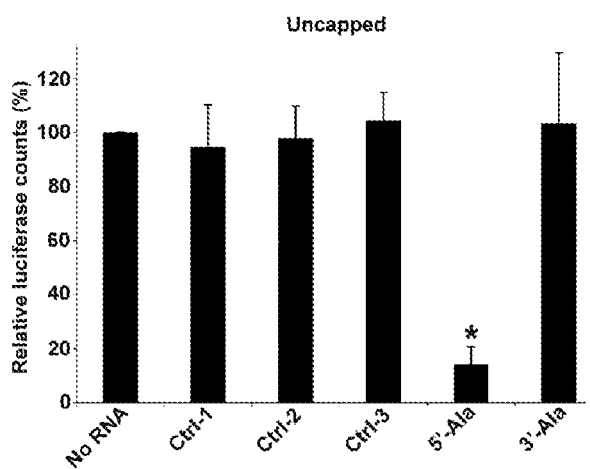
FIG. 8 is a graph showing luciferase expression in translation assays using uncapped polyA-biotinylated *Renilla* luciferase transcript in RRL supplemented with U2OS extract in the presence of the indicated control RNAs or tiRNAs (*p<0.05, compared to no RNA and three control RNAs (ctrl-1, -2, and -3), Student's t-test, n=3) (top), and an immunoblot of the streptavidin pull-down of uncapped polyA-biotinylated transcripts (bottom). In vitro translation was performed in the presence of control RNA (Ctrl), 5'-tiRNA$^{Ala}$, or cap analogue (Cap, m$^7$GpppG, 0.1 mM). Streptavidin beads were used to pull down reporter RNA-protein complexes. The bound proteins were identified by Western blotting using the indicated antibodies.
Figure 8:
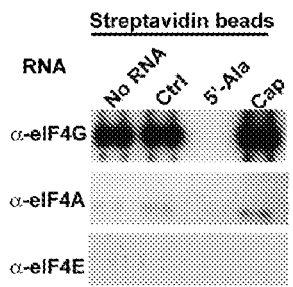

The recruitment of eIF4G to the EMCV IRES is critically dependent upon binding to the J-K domain which includes a $UA_6$ bifurcation loop located upstream from the AUG translation start site. A variant bifurcation loop ($UA_7$) reduces the binding of eIF4G to reduce translation efficiency and infectivity of encephalomyocarditis virus. Additional experiments were performed to compare the ability of control RNAs and tiRNAs to inhibit the translation of luciferase from monocistronic luciferase constructs expressing the wild type ($UA_6$) or mutant ($UA_7$) EMCV IRES. The experiments were performed using the methods generally described above with the modifications described below.

The pcDNA3-EMCV-R-luc (EMCV-UA6) plasmid used in these experiments was prepared by amplifying a fragment of the pF/R plasmid encoding EMCV IRES by PCR and subcloning the fragment into pcDNA3 vector using BamHI and XhoI sites. The ORF of *Renilla* luciferase was amplified by PCR and inserted into pcDNA3-EMCV construct using XhaI and XbaI sites.

RNA transcripts for use in the RRL assay were prepared by first linearizing the plasmids pcDNA3-EMCV-R-luc (EMCV-$UA_6$), pRL-5boxB, and pEMCV-RL-5boxB by digestion with XbaI (New England Biolabs), and separating and purifying the linearized plasmids as described above. Riboprobe T7 in vitro transcription System (Promega) was used to synthesize corresponding RNA and the RNA was purified as described above. Luciferase expression was also measured as described above.

The resulting data show that 5'-tiRNA$^{Ala}$ does not inhibit translation from the wild type ($UA_6$) IRES (FIG. 6, upper panel), but potently inhibits translation from the mutant ($UA_7$) IRES (FIG. 6, lower panel). These data suggest that 5'-tiRNA$^{Ala}$-mediated translational repression is a function of the strength of the eIF4G-RNA interaction. Recombinant eIF4E inhibits the translation of uncapped mRNAs by ~50%. This is presumably due to the fact that eIF4E:eIF4G complexes do not efficiently bind to the 5'-end of uncapped mRNA. The ability of tiRNAs to inhibit EMCV-IRES ($UA_7$) makes it unlikely that eIF4E is the primary target for translational repression. To further support this conclusion, additional experiments were performed to determine whether recombinant eIF4E competitively inhibits tiRNA$^{Ala}$-induced translational repression in RRL. These experiments were performed as described above.

The resulting data show that eIF4E does not competitively inhibit tiRNA$^{Ala}$-induced translational repression (FIG. 7). In fact, the combination of tiRNA$^{Ala}$ and recombinant eIF4E results in 2.5-fold more inhibition than tiRNA$^{Ala}$ alone: a result suggesting that these two factors act independently to inhibit translation.

Example 4. 5'-tiRNAs Displace eIF4G

Additional experiments were performed to determine whether 5'-tiRNAs displace eIF4G from RNA. In these experiments, biotin-tagged capped or uncapped luciferase transcripts were added to heterologous (80% RRL+20% U2OS) lysates containing control RNA or tiRNAs in the above described in vitro translation assays. After streptavidin pull down, the reporter RNA-bound proteins were quantitated by immunoblotting. These experiments were performed as described above with the additions or modifications described below.

Poly-A biotinylated mRNAs used for streptavidin pull-down assays were prepared by polyadenylating capped or uncapped pRL-5boxB RNAs using Poly(A) Polymerase Tailing Kit (EPICENTRE Biotechnologies) according to the manufacturer's recommendation, but in the presence of 10 nM biotin-ATP (PerkinElmer).

Streptavidin agarose beads (Invitrogen) (40 μL per sample) were washed twice with RNAse-free Biotin Binding Buffer (10 mM Tris-HCl, pH 7.2, 100 mM NaCl, 1 mM EDTA, 0.1% NP-40). Five hundred pmoles of biotinylated RNAs were added to streptavidin beads and incubated for 1 hour at room temperature with rotation in 0.75 mL of Biotin Binding Buffer. After incubation, immobilized biotinylated RNA-streptavidin complexes were washed twice with RNAse-free Wash Buffer II (15 mM Tris HCl, pH 7.2, 750 mM NaCl, 1 mM EDTA, 0.1% NP-40) and once with ice-cold RNAse-free Wash Buffer I (15 mM Tris HCl, pH 7.2, 150 mM NaCl, 1 mM EDTA, 0.1% NP-40) at room temperature to remove unbound RNA. Pre-cleared U2OS lysates (200 μl of lysate per reaction, corresponding to 20% of lysate (in Lysis Buffer: 50 mM Tris-HCl, pH 7.2, 100 mM NaCl, 1 mM EDTA, 0.5% NP-40, with protease inhibitor cocktail "Complete," Roche) prepared from one 15-cm dish of 80% confluent U2OS cells) were added to the biotinylated RNA-streptavidin bead complexes, incubated for 2 hours at 4° C. with rotation, and washed 3 times with Wash Buffers (15 mM Tris HCl, pH 7.2, 1 mM EDTA, 0.1% NP-40) containing different NaCl concentrations (0.1 M, 0.3 M or 0.5 M). Proteins were eluted using 60 μl of 1×SDS PAGE Loading Buffer.

For pull-down of biotinylated polyA mRNAs, 200 ng of capped or uncapped pRL-5boxB mRNAs were used for in vitro translation in rabbit reticulocyte lysate supplemented with 20% U2OS extract under the conditions described above. This heterologous in vitro translation system (RRL with cell extract) is capable of translating mRNAs with similar to Flexi Rabbit Reticulocyte Lysate System efficiency, but allows for the detection of eIF4G (human) by Western Blotting (the antibodies used do not detect eIF4G of rabbit origin). One hundred picomoles of control RNAs or tiRNAs were added to translation reactions. After completion of translation, streptavidin agarose beads (Invitrogen) (40 μL per sample) were added to reactions and incubated at 4° C. for 30 minutes. Streptavidin beads were precipitated by centrifugation (1000 rpm, 5 minutes), the supernatants were removed, and the beads were washed once with ice-cold Wash buffer (15 mM Tris HCl, pH 7.2, 150 mM NaCl, 1 mM EDTA, 0.1% NP-40). The resulting mRNA-protein complexes were eluted from the beads using 60 μl of 1×SDS PAGE Loading Buffer.

For Western blotting, proteins were separated on a 4-20% gradient SDS-PAGE (Invitrogen) and transferred to nitrocellulose filter membranes (0.45 μm pore size; Invitrogen). The membranes were blocked with 5% normal horse serum (NHS) in 1×TBS at room temperature for 1 hour and incubated with protein-specific antibodies in TBS containing 5% NHS overnight at 4° C. The membranes were washed three times with 1×TBS containing 0.1% Tween-20 and incubated with secondary antibodies conjugated with horseradish peroxidase (GE Healthcare). After washing, the specific proteins were detected using the Super Signal chemiluminescent detection system (Pierce) and autoradiography on X-Omat film (Kodak).

The data from these experiments show that uncapped RNA is bound to eIF4G, but not eIF4E (FIG. 8, lower panel): these results are consistent with the ability of eIF4G to bind to the 5'-end of uncapped transcripts. 5'-tiRNA$^{Ala}$, but not control RNAs or the cap analogue, quantitatively displaces eIF4G from these uncapped transcripts (FIG. 8, lower panel). In contrast, biotin-tagged capped mRNA is bound to eIF4G and eIF4E (FIG. 9, lower panel). 5'-tiRNA$^{Ala}$ only partially displaces eIF4G (~75% displacement) suggesting that stabilization of eIF4G conferred by cap-bound eIF4E may inhibit tiRNA-induced displacement (FIG. 9). 5'-tiR-NAs also modestly displace eIF4E suggesting that its effect on eIF4G may reduce the affinity of eIF4E:cap interactions.

Example 5. 5'-tiRNAs Displace eIF4F from the m$^7$G Cap

Additional experiments were performed in order to determine whether 5'-tiRNAs affect eIF4F:cap interactions. For these experiments, eIF4E complexes were assembled (e.g., eIF4F (eIF4E:eIF4G) and eIF4E:4E-BP1) on m$^7$GTP-Sepharose from U2OS cell lysates. The Sepharose-bound complexes were incubated with 3'-end biotinylated control or tiRNAs before analyzing retained components of the eIF4E-containing complexes using Western blotting. The methods used to perform these experiments are described in detail below.

7-Methyl GTP Sepharose Chromatography

A 7-methyl-GTP-Sepharose 4B (m$^7$GTP-Sepharose, GE Healthcare) suspension was washed twice with ice-cold RNAse-free Buffer A (15 mM Tris HCl, pH 7.0, 100 mM NaCl, 1 mM EDTA) to remove sodium azide. U2OS cells were grown until 70-80% confluence in 15-cm dishes under standard conditions, and then collected by scraping with Lysis Buffer (50 mM Tris-HCl, pH 7.2, 100 mM NaCl, 1 mM EDTA, 0.5% NP-40) supplemented with protease inhibitors (Protease Inhibitor Cocktail "Complete," Roche) into Eppendorf tubes followed by tumbling at 4° C. for 15 minutes. Cell debris and nuclei were removed by centrifugation (20 minutes, 13200 rpm, 4° C.), the cytoplasmic fraction (supernatant) was applied to pre-washed m$^7$GTP-Sepharose, and incubated for 1 hour at 4° C. Typically, 10-20 μl of m$^7$GTP-Sepharose suspension was used per sample of synthetic RNA (50 or 100 pmoles). After incubation, the m$^7$GTP-Sepharose was washed three times with Lysis Buffer and m$^7$GTP-bound protein complexes were divided into equal parts. Synthetic RNAs (50 or 100 pmoles, final concentrations 20-40 nM) were added to the complexes and incubated for 1 hour at 4° C. Unbound proteins were removed by washing once with Lysis Buffer and the proteins bound to m$^7$GTP-Sepharose were eluted with 60 μl of 1×SDS PAGE Loading Buffer. Eluted proteins were analyzed by Western Blotting using protein-specific antibodies.

Goat polyclonal anti-eIF3b, goat polyclonal anti-eIF4A, rabbit polyclonal anti-eIF4G, mouse monoclonal anti-eIF4E were purchased from Santa Cruz Biotechnology. Rabbit polyclonal anti-eIF4EBP1 was purchased from Cell Signaling. Anti-mouse, anti-goat, and anti-rabbit secondary antibodies conjugated with horseradish peroxidase (HRP) were purchased from GE Healthcare.

Figure 9:
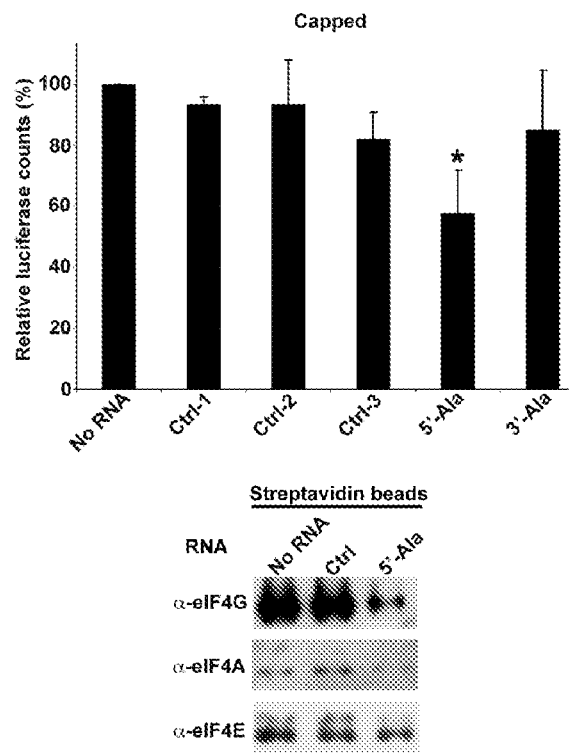
FIG. 9 is a graph showing luciferase expression in translation assays using capped polyA-biotinylated *Renilla* luciferase transcript in RRL supplemented with U2OS extract in the presence of the indicated control RNAs or tiRNAs (*p<0.05, compared to no RNA and three control RNAs (ctrl-1, -2, and -3), Student's t-test, n=3), and an immunoblot of the streptavidin pull-down of capped polyA-biotinylated transcripts (bottom). In vitro translation was performed in the presence of control RNA (Ctrl), 5'-tiRNA$^{Ala}$, or without any RNA (No RNA). Streptavidin beads were used to pull down reporter RNA-protein complexes. The bound proteins were identified by Western blotting using the indicated antibodies.
Figure 10:
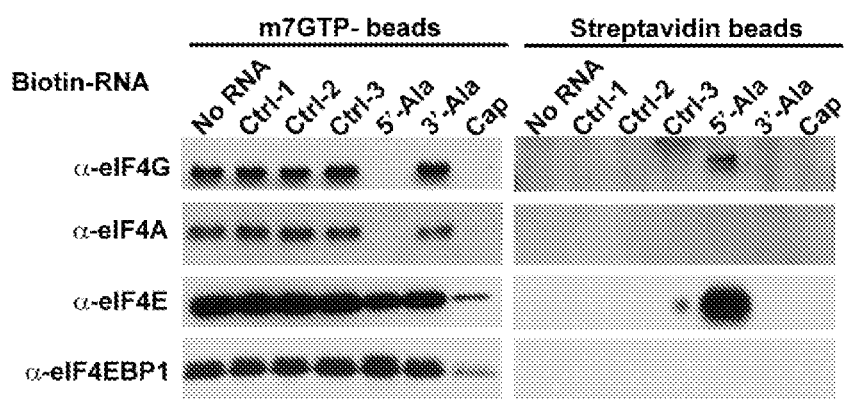
FIG. 10 is two Western blots showing the displaced components following incubation of eIF4E complexes (assembled on m$^7$GTP-Sepharose using U2OS lysates) with various components. The right blot shows the displaced components following incubation of the complexes with the indicated 3'-end biotinylated RNAs or cap analogue (Cap, m$^7$GpppG, 0.1 mM). Streptavidin beads were used to pull down displaced RNA-bound proteins and were identified by Western blotting (left blot).
Figure 11:
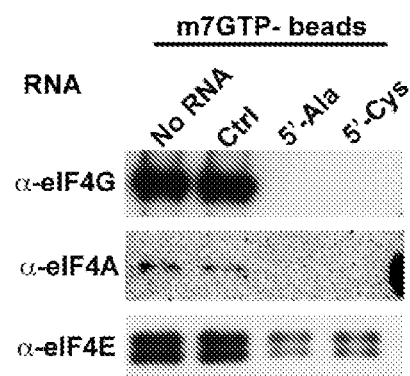
FIG. 11 is an immunoblot showing the displaced components following incubation of eIF4E complexes (assembled on m$^7$GTP-Sepharose using RRL supplemented U2OS extract) with no RNA, control RNA (ctrl), 5'-tiRNA$^{Ala}$, or 5'-tiRNA$^{Cys}$. The integrity of the eIF4F complex was monitored by Western blotting using anti-eIF4E, anti-eIF4G, and anti-eIF4A antibodies.

The resulting data show that although control RNAs did not displace initiation factors from m$^7$GTP-Sepharose, 5'-tiRNA$^{Ala}$ (but not 3'-tiRNA$^{Ala}$) completely displaces eIF4G and eIF4A, and partially displaces (~50%) eIF4E from the beads (FIG. 10, left panel). In contrast, 4E-BP1 is not displaced from the beads, suggesting that the retained eIF4E is complexed with 4E-BP1. Cap analogue displaces both eIF4F and eIF4E:4E-BP1 from m$^7$GTP-Sepharose (FIG. 10, left panel; cap). The supernatants containing displaced initiation factors were collected and streptavidin beads were used to capture biotin-RNA oligonucleotides and their associated proteins. Western blot analysis reveals that biotin-5'-tiRNA$^{Ala}$ is in a stable complex with eIF4G and eIF4E (FIG. 10, right panel). These data suggest that 5'-tiRNA$^{Ala}$ binds, directly or indirectly, to an eIF4E:eIF4G complex and causes its disassociation from m$^7$GTP-Sepharose in U2OS lysate much more efficiently than it displaces eIF4G from capped mRNA in RRL (FIG. 9). Similar results were obtained using heterologous lysate (80% RRL+20% U2OS extract, FIG. 11), suggesting that this difference is not conferred by the nature of the lysate.

Example 6. Structure/Function Analyses of tiRNAs tRNA$^{Ala}$ and tRNA$^{Cys}$ are the only human tRNAs with terminal oligo-guanine (TOG) motifs (4-5 guanine residues) at their 5' ends (up-to-date alignments for *H. sapiens* tRNAs can be found at the Lowe Lab website at the address: lowelab.ucsc.edu/GtRNAdb/Hsapi19/Hsapi19-align.html) (see, secondary structure of tRNA$^{Ala}$, FIG. 12). This structural feature in tRNA$^{Ala}$ and tRNA$^{Cys}$ is extremely well-conserved among all vertebrates, insects, and worms (>95% of all tRNA$^{Ala}$ and tRNA$^{Cys}$ genes), well conserved in plants (>95% of all tRNA$^{Ala}$ genes), and less conserved in fungi and protozoa (<50% of all tRNA$^{Ala}$ genes). In contrast, 5'-TOG motifs are extremely rare in all other tRNAs.

Additional experiments were performed to determine whether these 5'-TOG motifs are required for translation repression. In these experiments, the ability of truncation and substitution mutants to inhibit translation was determined using the RRL translation assays described herein using Firefly luciferase mRNAs. The specific tiRNAs and control oligonucleotides used in these experiments were synthesized and purified by Integrated DNA Technology (at least 95% homogenous), and are listed below.

```
                                               (SEQ ID NO: 1)
Ctrl1:
5'-UGA AGG GUU UUU UGU GUC UCU AUU UCC UUC-3'
(piR006650)

(SEQ ID NO: 2)
Ctrl2:
5'-phospho-UGU GAG UCA CGU GAG GGC AGA AUC
UGC UC-3'
(piR58620)

(SEQ ID NO: 3)
Ctrl3:
5'-phospho-GCA UUC ACU UGG AUA GUA AAU CCA
AGC UGA A-3'
(random)

(SEQ ID NO: 4)
5'Ala:
5'-phospho-GGG GGU GUA GCU CAG UGG UAG AGC
GCG UGC-3'

(SEQ ID NO: 18)
U4G:
5'-phospho-UGG GGU GUA GCU CAG UGG UAG AGC
GCG UGC-3'
```

```
                                            (SEQ ID NO: 19)
4G:
5'-phospho-GG GGU GUA GCU CAG UGG UAG AGC

GCG UGC-3'

(SEQ ID NO: 20)
UU3G:
5'-phospho-UUG GGU GUA GCU CAG UGG UAG AGC

GCG UGC-3'

(SEQ ID NO: 21)
3G:
5'-phospho-G GGU GUA GCU CAG UGG UAG AGC

GCG UGC-3'

(SEQ ID NO: 22)
GG-UU:
5'-phospho-GGG GGU GUA GCU CAG UUU UAG AGC

GCG UGC-3'

(SEQ ID NO: 23)
27mer:
5'-phospho-GGG GGU GUA GCU CAG UGG UAG AGC

GCG-3'

(SEQ ID NO: 24)
24mer:
5'-phospho-GGG GGU GUA GCU CAG UGG UAG

AGC-3'

(SEQ ID NO: 25)
21mer:
5'-phospho-GGG GGU GUA GCU CAG UGG UAG-3'
```

Figure 12:
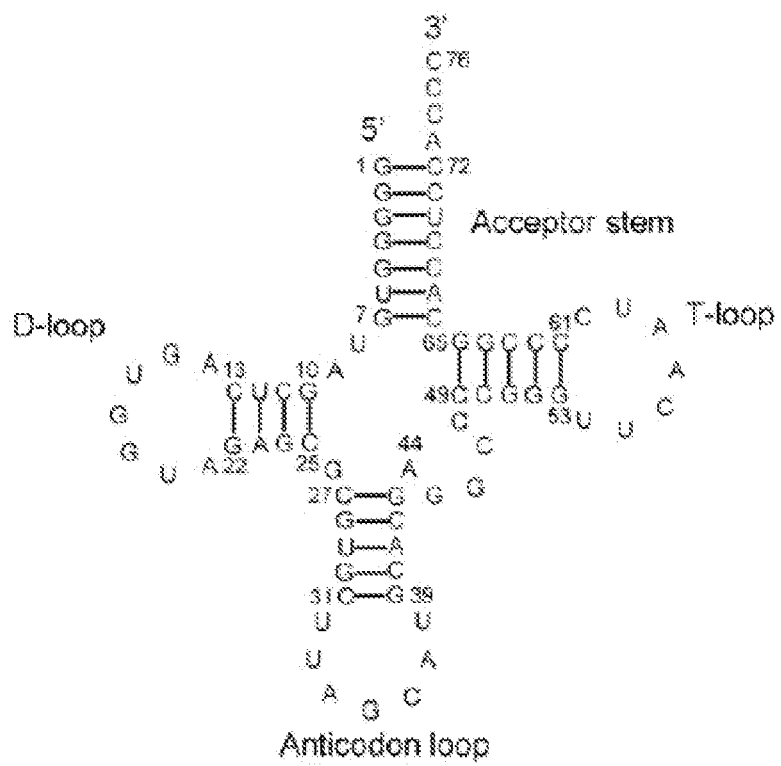
FIG. 12 is the secondary structure of 5'-tiRNA$^{Ala}$.
Figure 13:
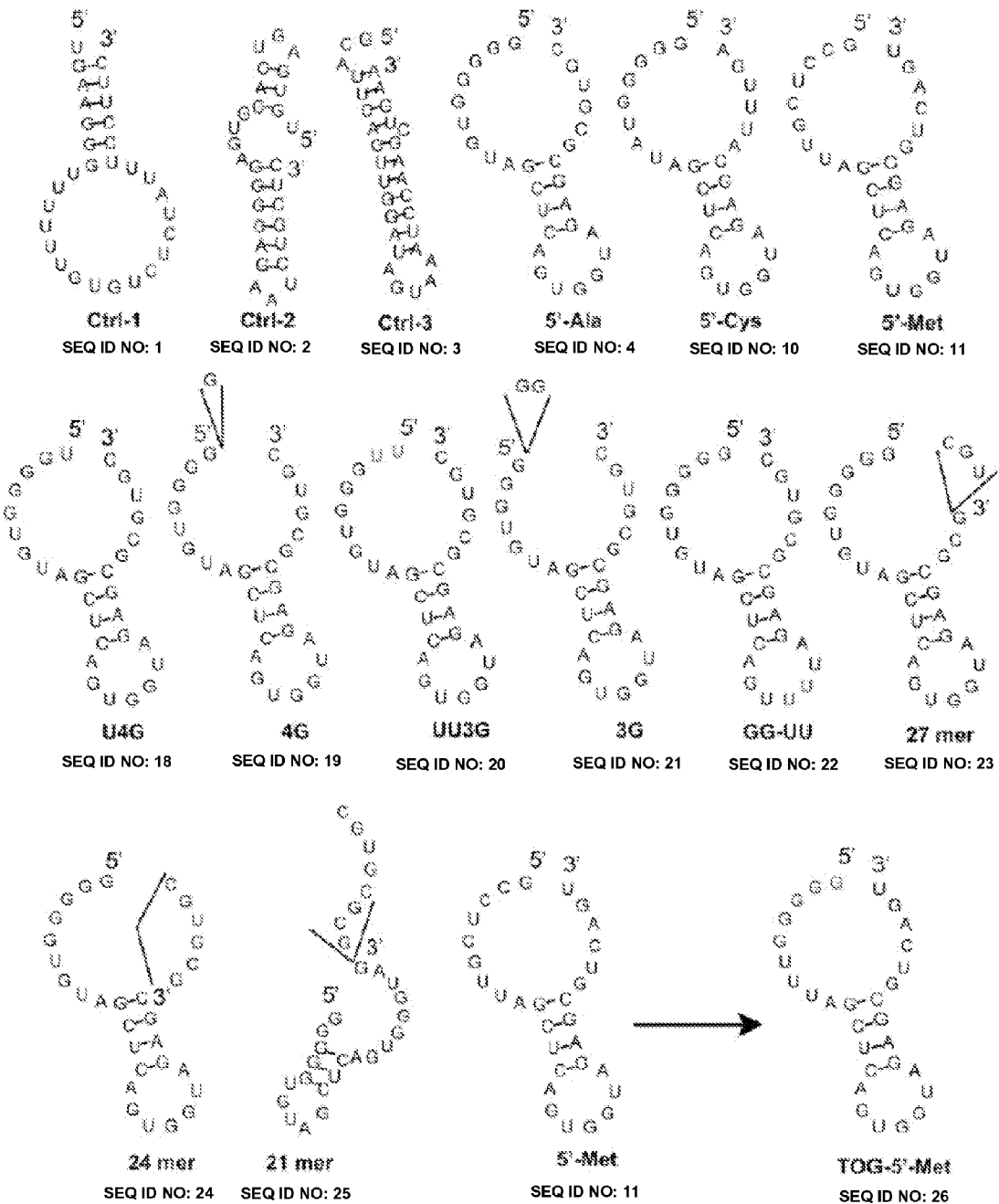
FIG. 13 is the predicted secondary structures of the control RNAs and 5'-tiRNA$^{Ala}$, 5'-tiRNA$^{Cys}$, 5'-tiRNA$^{Met}$, the mutants of 5'-tiRNA$^{Ala}$, and the modified 5'-tiRNA$^{Met}$.
Figure 14:
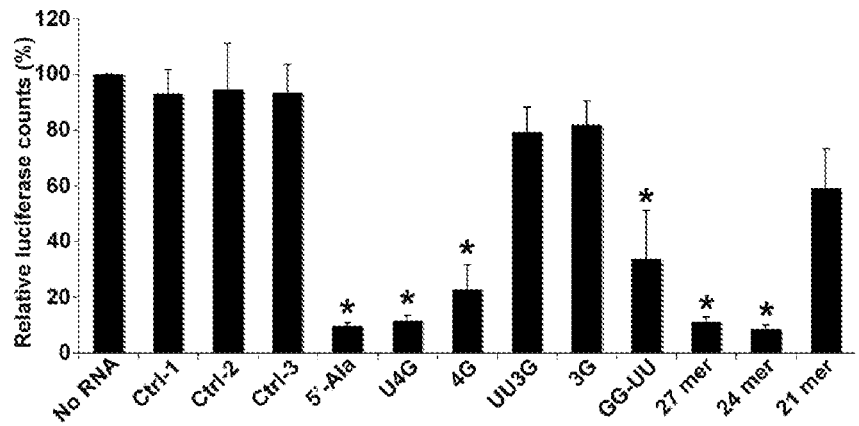
FIG. 14 is a graph of the relative luciferase expression in RRL in the presence of synthetic control RNAs (ctrl-1, -2, and -3), 5'-tiRNA$^{Ala}$, or the indicated mutants relative to the luciferase expression that is observed in the absence of any RNA (No RNA=100%) (*p<0.05, Student's t-test, n=4).

To determine whether the 5'-TOG structural feature is required for translational repression the ability of truncation and substitution mutants of tiRNAs (FIG. 13) to inhibit the translation of reporter mRNA in RRL was determined. These data show that while 5'-tiRNA$^{Ala}$ mutants with a singly truncated (4G) or G to U substituted (U4G) guanine residue retain their activity, mutants with doubly truncated (3G) or GG to UU substituted (UU3G) guanine residues are completely inactive (FIG. 14). Thus, at least four guanines at or near to the 5'-end of tiRNAs are absolutely required for translational repression. In contrast, substitution of two invariant guanine residues within the D-loop region (GG to UU) does not prevent translational repression. RNAfold predicts that 5'-tiRNAs are composed of a single stranded 5'-TOG motif followed by a stem-loop structure resembling the D-loop of tRNA, followed by a single stranded 3' region (FIGS. 12 and 13). Truncations from the 3' end of 5'-tiRNA$^{Ala}$ retain their activity until the region of the tRNA D-loop is encroached upon (i.e., 21-mer; see, FIG. 14) suggesting that the structure formed by the D-loop region may contribute to translational repression.

Additional experiments were performed to determine whether the ability of the 5'-tiRNA$^{Ala}$ mutants to inhibit mRNA translation closely correlates with their ability to displace eIF4F from m$^7$GTP-Sepharose, or their ability to induce stress granule assembly (when transfected into U2OS cells). The m$^7$GTP-Sepharose experiments were performed as described above using the 5'-tiRNA$^{Ala}$ mutants described herein. The transfection of U2OS cells and the methods for determining stress granule assembly are described below.

Cell Transfections

Cells were transfected with the RNA oligonucleotides using Lipofectamine 2000 (Invitrogen). Before transfection, RNA-complexes were pre-incubated in serum-free medium (Opti-MEM medium, Invitrogen) for 20 minutes at room temperature. U2OS cells (1×10$^5$/well) were plated in 24-well plates for 24 hours, and then transfected with 750 nM synthetic tiRNAs using 2.5 µl Lipofectamine 2000.

Immunofluorescence Microscopy and Quantification of Stress Granules

Cells (1×10$^5$) were seeded onto coverslips (Fisher Scientific) and were transfected with synthetic tiRNAs using Lipofectamine 2000 24-hours later (Invitrogen). After 7 hours, the cells were fixed in 4% para-formaldehyde for 15 minutes and permeabilized using 100% chilled methanol for 10 minutes. The cells were rinsed several times with PBS and incubated overnight with blocking buffer (5% normal horse serum in PBS containing 0.02% sodium azide) at 4° C. An appropriate primary antibody diluted in blocking buffer (1:200 for anti-eIF3b, anti-eIF4G, and anti-G3BP antibody) was then added to the cells and incubated for 1 hour at room temperature or overnight at 4° C. (Kedersha et al., *Methods Enzymol.* 448:521-522, 2007). The cells were washed three times with PBS and incubated with the appropriate secondary antibodies (Jackson Immunoresearch, ML grade) diluted 1:200 in blocking buffer containing 0.5 µg/ml Hoechst 33258 dye (Molecular probes) for 1 hour at room temperature. After washing with PBS, the cover slips were mounted in polyvinyl mounting medium, and the cells were viewed and photographed with an Eclipse E800 (Nikon) microscope equipped with a digital camera (CCD-SPOT RT; Diagnostic Instrument) using 60× oil immersion objective lens. The images were merged and analyzed using Adobe Photoshop (v. 10).

Quantification of Stress Granules

U2OS cells (1×10$^5$) were seeded onto coverslips (Fisher Scientific) and were transfected 24 hours later with the indicated RNA oligonucleotides (final concentration of 750 nM) using Lipofectamine 2000. After 7 hours, the cells were subjected to immunofluorescence microscopy as described above. The coverslips were coded and all quantifications were done blindly and repeated at least twice. The percentage of cells with stress granules was quantified by counting 200-350 cells/experiment.

Figure 15:
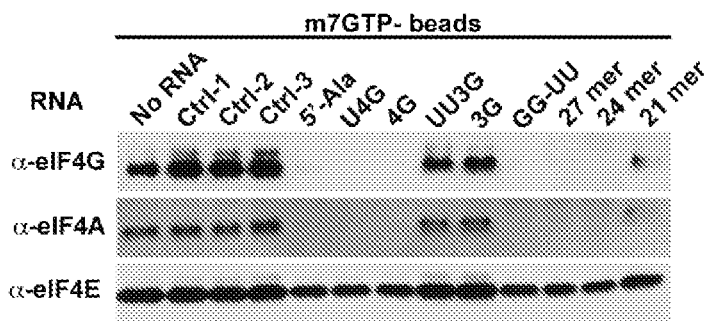
FIG. 15 is a Western blot showing the displacement of eIF4F complexes from m$^7$GTP-Sepharose in U2OS lysates following the addition of the indicated RNAs to the beads.
Figure 16:
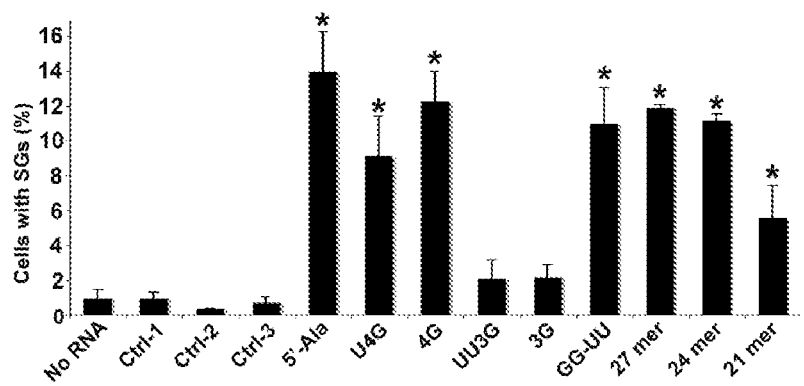
FIG. 16 is a graph showing the percentage of cells with stress granules following transfection with the control and synthetic RNAs shown (200 cells/experiment; *p<0.05, compared to a control without any RNA, Student's t-test, n=3).

The resulting data show that the ability of 5'-tiRNA$^{Ala}$ and its mutants to inhibit mRNA translation closely correlates with their ability to displace eIF4F from m$^7$GTP-Sepharose (FIG. 15). In addition, the ability of 5'-tiRNA$^{Ala}$ and its mutants to inhibit mRNA translation closely correlates with their ability to induce the assembly of stress granules when transfected into U2OS cells (FIG. 16).

Figure 17:
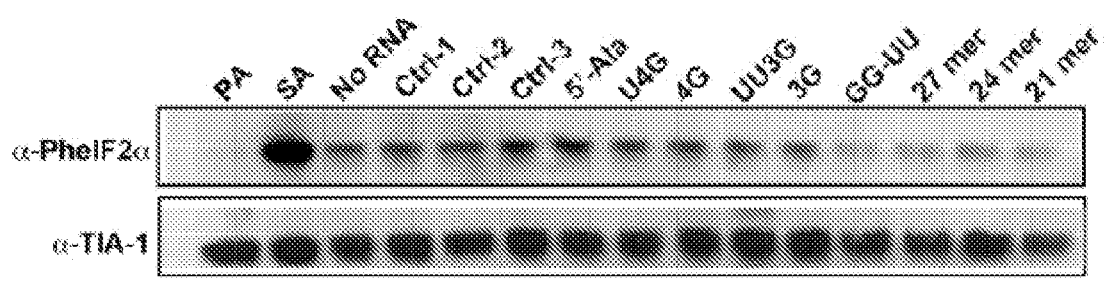
FIG. 17 is a Western blot showing the level of phospho-eIF2α in U2OS cells treated with pateamine A (PA; 15 nM) or sodium arsenite (SA; 70 μM), or transfected with no RNA, control RNA (ctrl-1, -2, or -3), 5'-tiRNA$^{Ala}$, and its mutants. Phospho-eIF2α was detected with polyclonal antibodies specific for eIF2α phosphorylated at S52 (Assay Designs) (upper panels). Detection of TIA-1 (lower panels) was used as a loading control.

Additional immunoblotting experiments were performed to determine whether transfection with these oligonucleotides induced the phosphorylation of eIF2a, a classical trigger of stress granule assembly. These data show that transfection of wild type or mutant 5'-tiRNA$^{Ala}$ does not induce phosphorylation of eIF2α (FIG. 17). The data show that 5'-tiRNA$^{Ala}$ inhibits translation in live cells (in which most of the target transcripts are presumably capped). The close correlation between translational repression in RRL, displacement of eIF4F from m$^7$GTP-Sepharose, and stress granule assembly suggests that eIF4F is a target for tiRNA-induced translational repression.

Example 7. Addition of 5'-TOG Activates 5'-tiRNA$^{Met}$

Figure 18:
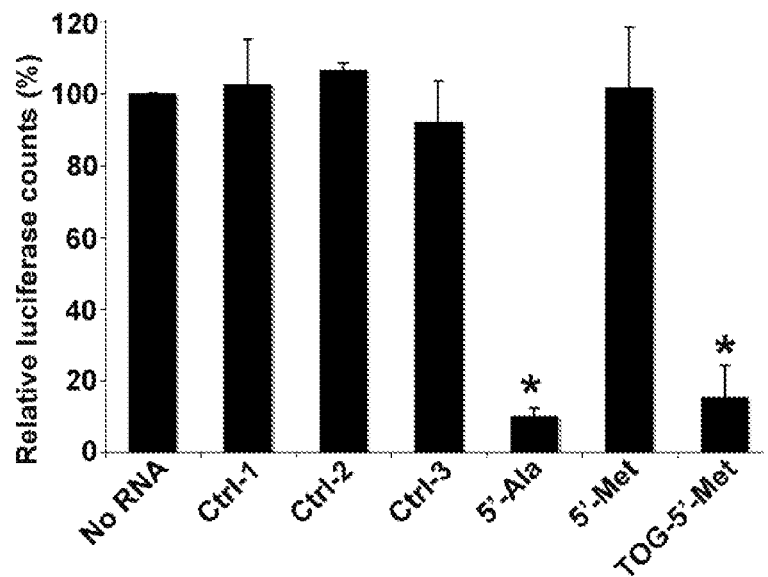
FIG. 18 is a graph of the relative luciferase expression in RRL in the presence of synthetic control RNAs (ctrl-1, -2, and -3) or the indicated 5'-tiRNAs relative to the luciferase expression that is produced in the absence of any RNA (No RNA=100%) (*p<0.05, Student's t-test, n=3).
Figure 19:
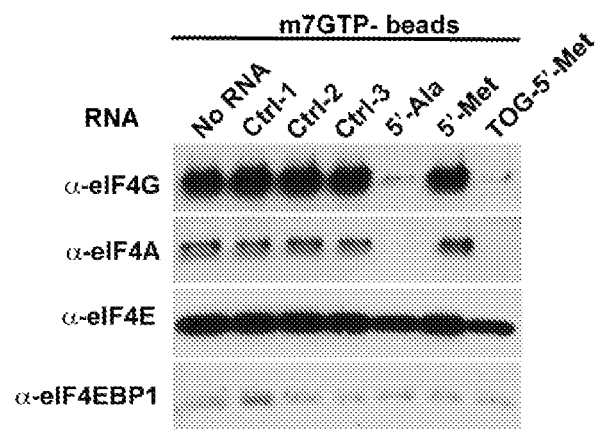
FIG. 19 is a Western blot showing the displacement of eIF4F complexes from m$^7$GTP-Sepharose in U2OS lysates following addition of the indicated RNAs to the beads. The Western blot was developed to detect eIF4F complexes and eIF4E-BP1.
Figure 20:
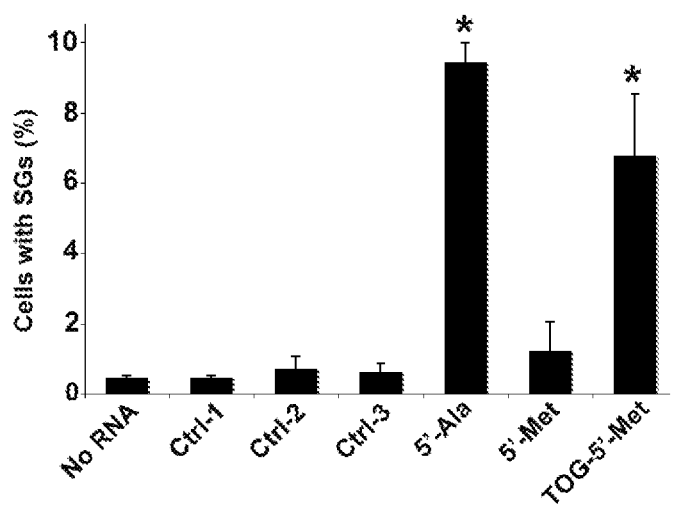
FIG. 20 is a graph showing the percentage of cells with stress granules following transfection with the indicated RNAs (200 cells/experiment; *p<0.05, Student's t-test, n=3).

Additional experiments were performed to confirm the importance of the 5'-TOG motif for tiRNA activity. In these experiments, the first 5 nucleotides of non-TOG-containing 5'-tiRNA$^{Met}$ was substituted with 5 guanine residues (FIG. 13) (5'-phospho-GGG GGU UUA GCG CAG UAG GUA GCG CGU CAG U-3; SEQ ID NO: 26). This substituted 5'-tiRNA$^{Met}$ was used in RRL translation assays, the eIF4F displacement assays using m$^7$GTP-Sepharose assays, and stress granule formation assays (cellular assays) performed as described above. The resulting data show that although endogenous 5'-tiRNA$^{Met}$ does not inhibit translation in RRL (FIG. 18), displace eIF4F from m$^7$GTP-Sepharose (FIG. 19), or induce the assembly of stress granules (FIG. 20), the addition of a 5'-TOG motif to 5'-tiRNA$^{Met}$ is sufficient to confer these activities on this tRNA fragment (FIGS. 18-20).

Example 8. Identification of tiRNA-Interacting

Pull-down of RNA-protein complexes using biotinylated control RNA or 5'-tiRNA$^{Ala}$ immobilized on streptavidin beads was used to purify proteins that interact with these RNAs. RNA-bound proteins were identified by mass spectrometry. Independent pull-down experiments were performed to confirm the ability of several of these proteins to interact with tiRNA$^{Ala}$. These experiments were performed using biotinylated control or 5'-tiRNA$^{Ala}$ using streptavidin beads as described above. The individual 3'-biotinylated oligonucleotides used in these assays were synthesized by and purchased from Integrated DNA Technology (listed below). Silver staining and mass spectrometry identification of tiRNA-binding proteins was performed as described below.

```
Biotinylated Oligonucleotides
                                      (SEQ ID NO: 27)
Ctrl1-bio:
5'-UGA AGG GUU UUU UGU GUC UCU AUU UCC UUC- 3'-biotin (SEQ ID NO: 28)
Ctrl2-bio:
5'-phospho-UGU GAG UCA CGU GAG GGC AGA AUC UGC UC-3'-biotin (SEQ ID NO: 29)
Ctrl3-bio:
5'-Phospho-GCA UUC ACU UGG AUA GUA AAU CCA AGC UGA A-3'-biotin (SEQ ID NO: 30)
5'-Ala-bio:
5'-phospho-GGG GGU GUA GCU CAG UGG UAG AGC GCG UGC-3'-biotin (SEQ ID NO: 31)
3'-Ala-bio:
5'-CUU AGC AUG CAC GAG GCC CCG GGU UCA AUC CCC GGC ACC UCCA-3'-biotin
```

Silver Staining of SDS PAGE Gels

To detect proteins recovered from affinity purification with biotinylated RNAs, eluted protein samples were run on gradient 4-20% SDS PAGE gels (Invitrogen) and fixed with Protein Fixation Buffer (30% ethanol:10% acetic acid) for 30 minutes. SilverSNAP Stain Kit II (Pierce) was used according to the manufacture's recommendation to detect proteins.

Mass Spectrometry Identification of tiRNA-Binding Proteins

For mass spectrometry, protein solutions from affinity purification using 3'-end biotinylated RNAs were precipitated with trichloroacetic acid (TCA). Briefly, eluted protein samples were adjusted to 20% final volume of TCA using 100% TCA (in water) solution. The resulting mixture was placed on ice for 20 minutes followed by centrifugation (20 minutes, 13200 rpm, 4° C.). Protein pellet was washed once with 1 ml of cold (−20° C.) acetone (HPLC grade, Sigma), followed by centrifugation (20 minutes, 13200 rpm, 4° C.). The supernatant was carefully removed and the pellet was air-dried for 10 minutes at room temperature. The identification of tiRNA-binding proteins was done by Taplin Mass Spectrometry Facility according to standard protocols (Harvard Medical School).

Figure 21:
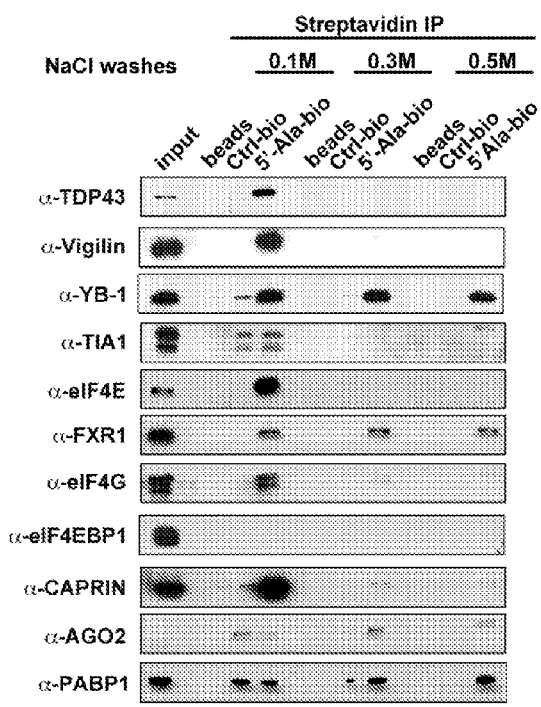
FIG. 21 is an immunoblot showing proteins bound to biotinylated control RNA and 5'-tiRNA$^{Ala}$ that were purified using streptavidin beads, subjected to the indicated salt washes (0.1 M, 0.3 M, or 0.5 M NaCl), and eluted.

The resulting data confirmed that several proteins involved in the regulation of RNA metabolism, including TDP-43 (TARDBP), Vigilin (HDLBP), YB-1 (YBX1), eIF4E, FXR1, eIF4G, CAPRIN1 (CAPRIN), Argonaute-2 (EIF2C2), and PABP1 (PABPC1) bind to 5'-tiRNA$^{Ala}$ more strongly than control RNA (FIG. 21). Some of these interactions (e.g., YB-1, FXR-1, and PABP1) are maintained under high salt wash conditions.

Figure 22:
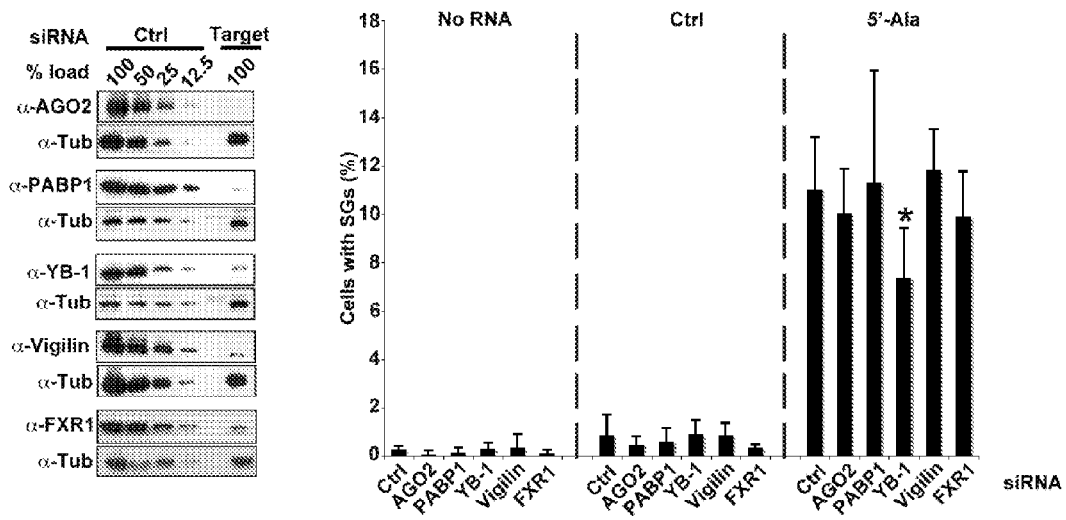
FIG. 22 is an immunoblot showing the expression of specific binding proteins following transfection with a control (Ctrl) or the different siRNAs shown (Target) (left panel) (tubulin was used as a specificity and loading control), and a graph showing the percentage of cells having stress granules following treatment with the indicated siRNAs, followed by mock transfection or transfection with control RNA (Ctrl) or 5'-tiRNA$^{Ala}$ (200 cells/experiment; AGO2 siRNA, n=7; PABP1 siRNA, n=3; YB-1 siRNA, n=9; Vigilin siRNA, n=3; FXR1 siRNA, n=3) (*p<0.0001 when comparing the percentage of cells with stress granules in control and YB-1 siRNA treated cells; no other treatment reached statistical significance).

Example 9. tiRNA-Binding Proteins are Required for 5'-tiRNA$^{Ala}$-Induced Stress Granule Assembly Additional experiments were performed to determine whether the identified 5'-tiRNA$^{Ala}$ binding proteins are required for translational repression. In these experiments, AGO2, PABP1, YB-1, Vigilin, and FXR1 were knocked down using siRNA prior to quantifying tiRNA-induced stress granule assembly in U2OS cells (assays performed as described above). These data show that, of the tested binding proteins, YB-1 was the only 5'-tiRNA$^{Ala}$ binding protein required for the assembly of stress granules (FIG. 22). YB-1 is a protein that inhibits translation of both uncapped and capped mRNAs by displacing eIF4G from the eIF4F complex and by displacing eIF4E from the m$^7$G cap.

Example 10. Synthetic DNA Equivalents of 5'-tiRNA$^{Ala}$ and Anti-Proliferative DNAs Inhibit Translation and Induce Stress Granule Formation Experiments were performed to test the ability of synthetic DNA equivalents of 5'-tiRNA$^{Ala}$ and anti-proliferative G-rich oligodeoxynucleotides (shown in FIG. 23) to inhibit translation of luciferase transcripts in RRL assays, induce stress granule formation in cells, and displace eIF4G, eIF4A, and eIF4E from m$^7$GTP-Sepharose in vitro (performed generally as described above).

Figure 24:
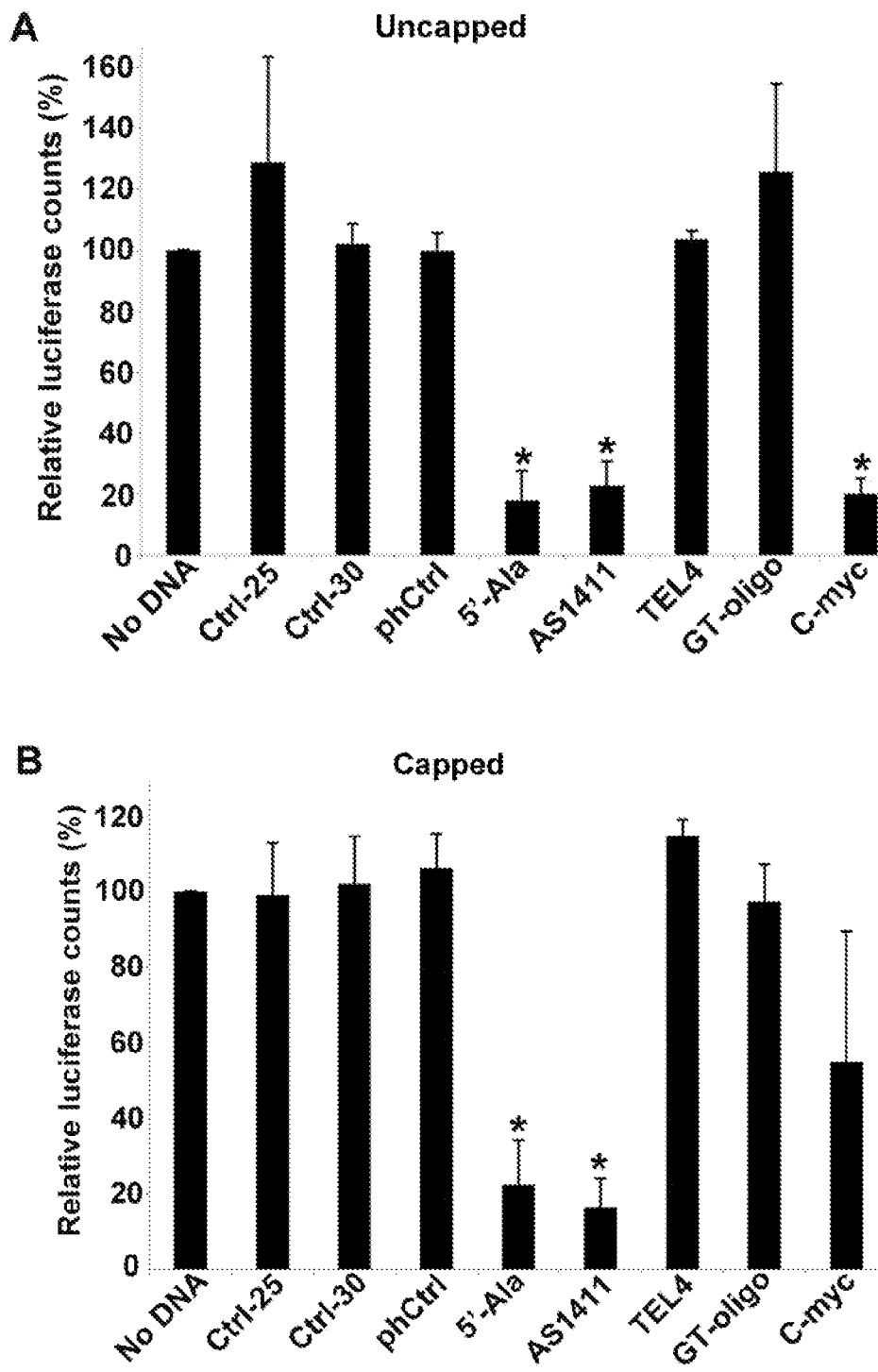
FIG. 24 is two graphs showing the relative luciferase count from translation assays performed using uncapped (A) or capped (B) Firefly luciferase mRNA and RRL lysate in the presence of control G-rich oligonucleotides (Ctrl 25, Ctrl 30, and phCtrl) or the indicated G-rich oligodeoxynucleotides. The percentage luciferase expression shown is relative to the luciferase expression observed in the absence of any DNA oligonucleotide (No DNA=100%). The means and standard deviations from at least three independent experiments are shown (*p<0.05).

The resulting data show that 5'-tiDNA$^{Ala}$, AS1411, and c-myc oligodeoxynucleotides are potent inhibitors of translation in the RRL assay (none of these compounds alters the amount of luciferase RNA as assessed by Northern blotting analysis performed as described above) (FIG. 24). In contrast, neither TEL4, nor GT-oligo inhibit translation in this assay. Thus, some G-rich oligodeoxynucleotides inhibit translation, whereas others do not.

Figure 25:
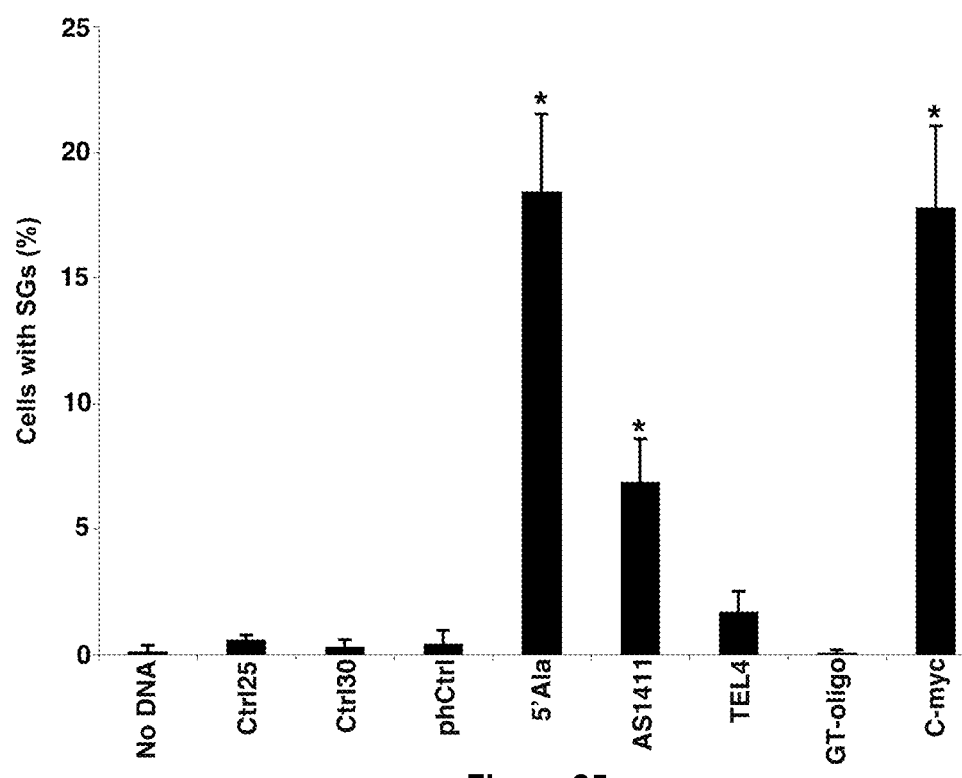
FIG. 25 shows the percentage of U2OS cells having stress granules following transfection with the indicated control or G-rich oligodeoxynucleotides (0.75 μM) using Lipofectamine. After 24 hours, the cells were processed for immunofluorescence microscopy using antibodies reactive with the stress granule components eIF3, G3BP, and TIA-1. The percentage of cells with stress granules is depicted as the mean±standard error (n=3) (*p<0.05, compared with control oligodeoxynucleotides).
Figure 26:
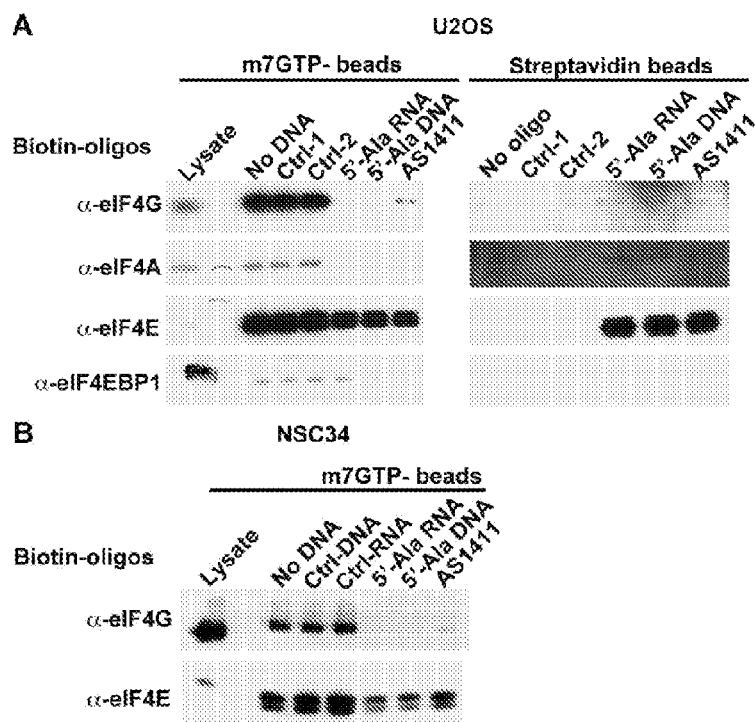
FIG. 26 shows two immunoblots showing the displacement of eIF4F from eIF4F:m$^7$GTP-Sepharose complexes formed in U2OS (A) or NSC34 (B) lysates upon co-incubation with the indicated 3'-biotinylated control or G-rich oligodeoxynucleotides. Synthetic 5'-tiRNA$^{Ala}$ served as a positive control for displacement of eIF4F complex from m$^7$GTP beads (A; left panel). Streptavidin beads were used to pull down displaced DNA-bound proteins that were identified by immunoblotting (A; right panel).

The data also show that the ability of the 5'-tiRNAs to inhibit translation correlates with their ability to trigger stress granule assembly in cells (following cellular transfection with these molecules) (FIG. 25). In U2OS cells, 5'-tiDNA$^{Ala}$, AS1411, and c-myc oligodeoxynucleotides induce stress granule assembly, whereas TEL4 and GT-oligo did not (FIG. 25). Similar results were observed in NSC34 cells, indicating that selected G-rich oligodeoxynucleotides can promote stress granule assembly in motor neurons. The molecular mechanism(s) by which these oligodeoxynucleotides mediate translation inhibition was further investigated by determining their ability to displace eIF4F from $m^7$-GTP Sepharose. The data from these experiments show that, in lysates from both U2OS (FIG. 26A) and NSC34 cells (FIG. 26B), 5'-tiRNA$^{Ala}$, 5'-tiDNA$^{Ala}$, and AS1411 displace eIF4G, eIF4A, and eIF4E from $m^7G$ in vitro. These data suggest that these oligodeoxynucleotides mimic angiogenin-induced tiRNAs in their ability to trigger a stress response program.

Example 11. Cellular Uptake of Synthetic 5' G-Rich Oligodeoxynucleotides

Figure 27:
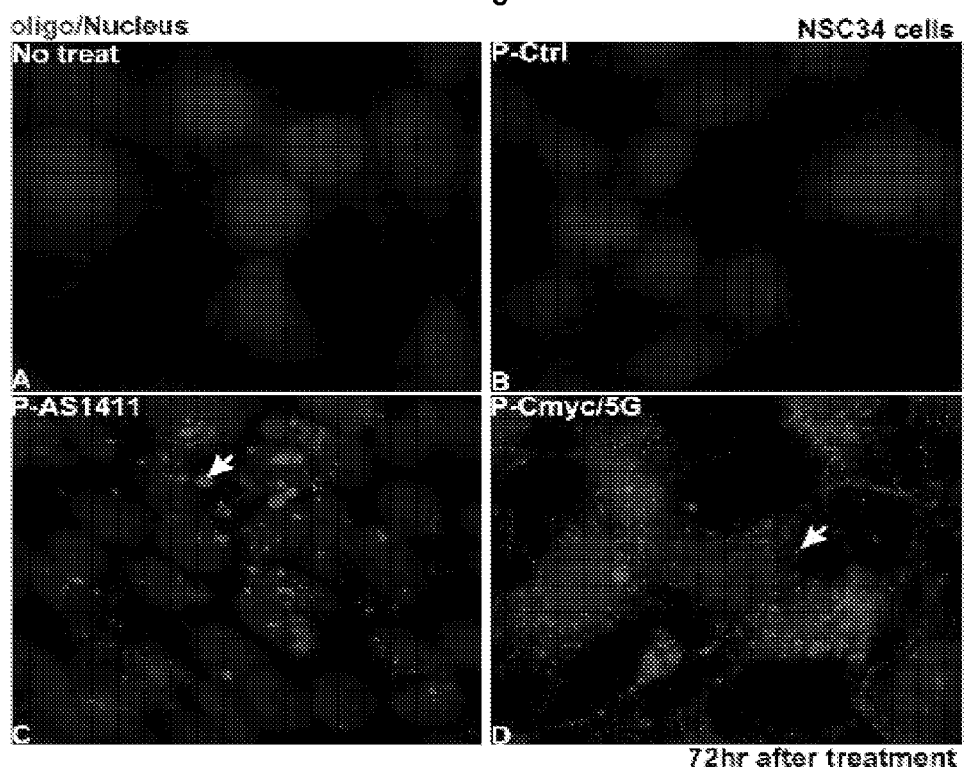
FIG. 27 is a set of four photomicrographs of NSC34 cells treated with no DNA (A; upper left panel) or 1.5 μM of biotin-labeled control DNA (p-ctrl) (B; upper right panel), AS1411 (p-PS1411) (C; lower left panel), or C-myc oligodeoxynucleotide (D; lower right panel), and then stained with Cy3-streptavidin 72 hours after oligodeoxynucleotide treatment. White arrows indicate the presence of the biotin-labeled oligodeoxynucleotides in the cell.

Additional experiments were performed in order to determine whether the 5' G-rich oligodeoxynucleotides would be taken up by motor neurons in the absence of transfection agents. In these experiments NSC34 cells were treated with biotin-labeled C-myc, biotin-labeled AS1411, or biotin-labeled C-rich control oligodeoxynucleotides and cellular uptake was detected using Cy3-streptavidin. The resulting data show that AS1411 and c-myc, but not control oligodeoxynucleotides were found in cytoplasmic puncta within NSC34 cells: a result that is consistent with endosomal uptake (FIG. 27). In addition, some cells showed diffuse fluorescence consistent with cytoplasmic localization. Similar results were obtained with 5'-tiDNA$^{Ala}$. These results indicate the ability of these G-rich oligodeoxynucleotides to spontaneously enter motor neurons and gain access to the cytoplasm.

Example 12. Functional Effect of G-Rich Oligodeoxynucleotides

Figure 28:
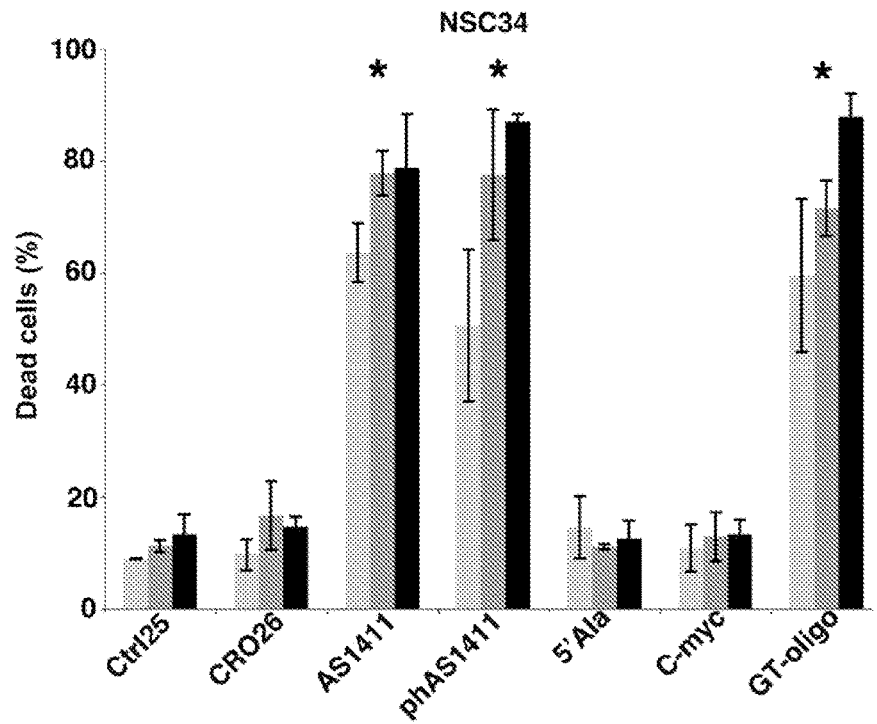
FIG. 28 is a graph showing the percent dead NSC34 cells (percent Trypan Blue-positive NSC34 cells) following treatment with the indicated G-rich deoxyoligonucleotides for 72 hours. The means and standard deviations are from four independent experiments (*p<0.05 compared to controls). The increased shading of the bars indicates an increased concentration of the G-rich deoxyoligonucleotide.

Additional experiments were performed to test the effect of the G-rich oligodeoxynucleotides on motor neurons. A first set of dose response experiments were performed in order to determine whether the tested G-rich oligodeoxynucleotides were toxic to motor neurons in vitro. These data show that the AS1411 and oligo-GT oligodeoxynucleotides markedly increased NSC34 cell death at the end of a 72-hour incubation (FIG. 28). In contrast, the control piDNA (ctrl 25, AAAAAACTCG AGATGGCGCACGCTG; SEQ ID NO: 38), C-rich control (CRO26, CCTCCTCCTCCTTCTCCTCCTCCTCC; SEQ ID NO: 39), 5'-tiDNA$^{Ala}$, and c-myc oligodeoxynucleotides do not reduce the numbers of viable NSC34 cells.

Figure 29:
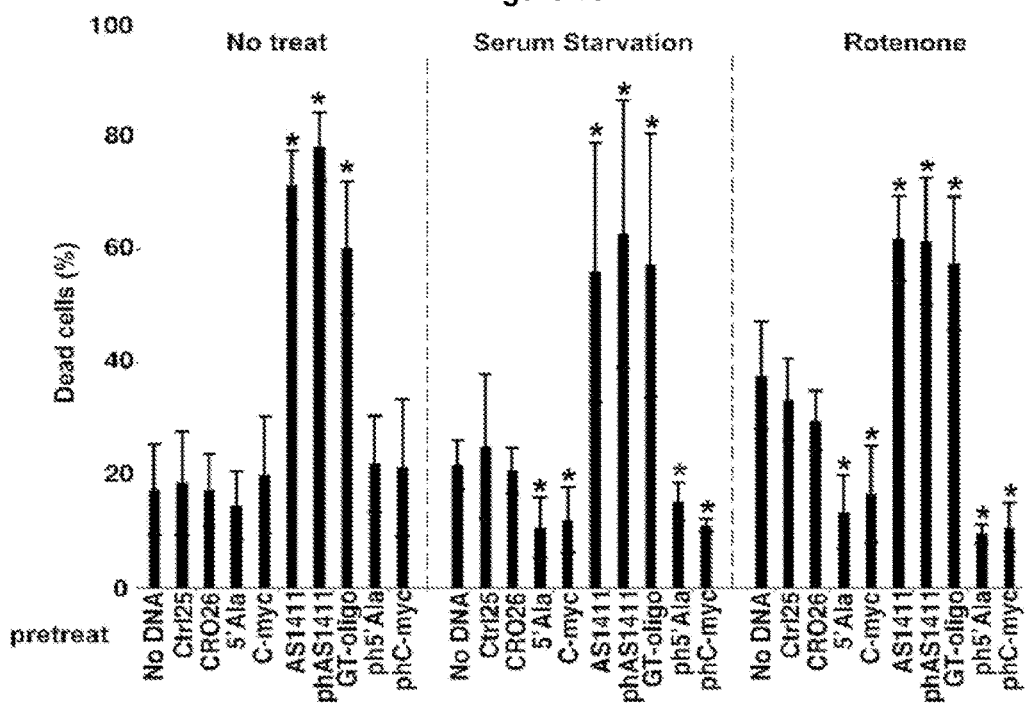
FIG. 29 is a graph showing the percent dead NSC34 cells following pretreatment for 72 hours with the indicated G-rich oligodeoxynucleotides and subsequent exposure to serum starvation or rotenone treatment (10 μM) for 24 hours. No treatment (No treat) served as a control. The percentage of dead cells was determined by Trypan Blue staining. The means and standard deviations are from four independent experiments (*p<0.05 compared to controls).

A second set of experiments was performed to determine whether the tested G-rich oligodeoxynucleotides are neuroprotective. In these experiments NSC34 cells were cultured in the presence of the individual oligodeoxynucleotides, then subjected to nutrient (serum starvation) or mitochondrial (rotenone) stress for 24 hours. NSC34 cells treated with either 5'-tiDNA$^{Ala}$ or c-myc oligodeoxynucleotides, but not AS1411 or oligo-GT oligodeoxynucleotides were significantly protected from the adverse effects of stress (cell death; FIG. 29). These data suggest that there are three different functional classes of G-rich oligodeoxynucleotides: Class I oligodeoxynucleotides (e.g., oligo-GT) that reduce NSC34 cell survival; Class II oligodeoxynucleotides (e.g., 5'-tiDNA$^{Ala}$ and c-myc) that promote NSC34 cell survival by activating a stress response program; and Class III oligodeoxynucleotides (e.g., AS1411) that reduce NSC34 survival, but also activate a stress response program. The modest therapeutic effects of AS1411 may be a consequence of this cytoprotective stress response program. These data identify 5'-tiDNA$^{Ala}$ and c-myc oligodeoxynucleotides as promising compounds for the development of therapeutic agent for treating a neurological disorder (e.g., a neurological disorder that involves motor neuron death, such as amyotrophic lateral sclerosis).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE APPENDIX

Additional tRNA sequences that can be used to generate any of the neuroprotective molecules described herein are listed below.

```
                                                    (SEQ ID NO: 176)
Homo_sapiens_chr6.trna95-AlaAGC (58249908-58249836)
Ala (AGC) 73 bp Sc: 42.26
GGGGAATTAGCTCAAGCGGTAGAGCGCTCCCTTAGCATGCGAGAGGTAGCGGGATCGACG

CCCCCATTCTCTA (SEQ ID NO: 177)
Homo_sapiens_chr6.trna25-AlaAGC (26859897-26859969)
Ala (AGC) 73 bp Sc: 46.89
GGGGGATTAGCTCAAGCGGTAGGGTGCCTGCTTAGCATGCAAGAGGTAGCAGGATCGACG

CCTGCATTCTCCA (SEQ ID NO: 178)
Homo_sapiens_chr1.trna87-AlaAGC (148284076-148284006)
Ala (AGC) 71 bp Sc: 48.21
GGGGGTGTAGATCAGTGGTAGGGCGCACGCTTAGCATGCATGAGGCCCTGGGTCAATCCC

CAGCACCTCCA (SEQ ID NO: 179)
Homo_sapiens_chr6.trna94-AlaAGC (58250620-58250548)
Ala (AGC) 73 bp Sc: 54.62
```

```
                                             -continued
GGGGGATTAGCTCAAGCGGTAGAGCGCCTGCTTAGCATGCAAGAGGTAGCAGGATCGATG

CCTGCATTCTCCA (SEQ ID NO: 180)
Homo_sapiens_chr6.trna160-AlaAGC (26881822-26881750)
Ala (AGC) 73 bp Sc: 54.69
GGGGAATTGGCTCAAGCGGTAGAGCGCTTGCTTAGCATGCAAGAGGTAGCAGGATCGACG

CCTGCACTCTCCA (SEQ ID NO: 181)
Homo_sapiens_chr6.trna23-AlaAGC (26836235-26836307)
Ala (AGC) 73 bp Sc: 54.69
GGGGAATTGGCTCAAGCGGTAGAGCGCTTGCTTAGCATGCAAGAGGTAGCAGGATCGACG

CCTGCACTCTCCA (SEQ ID NO: 182)
Homo_sapiens_chr6.trna90-AlaAGC (58295475-58295403)
Ala (AGC) 73 bp Sc: 54.84
GGGGAATTAGCGCAAGTGGTAGAGTGCTTGCTTAGCATGCAAGAGGTAGTGGGATCGATG

CCCACATTCTCCA (SEQ ID NO: 183)
Homo_sapiens_chr6.trna89-AlaAGC (58304654-58304582)
Ala (AGC) 73 bp Sc: 57.89
GGGGAATTAGCCCAAGTGGTAGAGCGCTTGCTTAGCATGCAAGAGGTAGTGGGATCGATG

CCCACATTCTCCA (SEQ ID NO: 184)
Homo_sapiens_chr14.trna9-AlaAGC (88515195-88515267)
Ala (AGC) 73 bp Sc: 59.85
GGGGAATTAGCTCAAGTGGTAGAGCGCTCGCTTAGCATGCGAGAGGTAGTGGGATCGATG

CCCGCATTCTCCA (SEQ ID NO: 185)
Homo_sapiens_chr6.trna18-AlaAGC (26781569-26781641)
Ala (AGC) 73 bp Sc: 60.72
GGGGAATTAGCTCAAGTGGTAGAGCGCTTGCTTAGCATGCAAGAGGTAGTGGGATCAATG

CCCACATTCTCCA (SEQ ID NO: 186)
Homo_sapiens_chr6.trna22-AlaAGC (26813585-26813657)
Ala (AGC) 73 bp Sc: 61.81
GGGGAATTAGCTCAAGCGGTAGAGCGCTTGCTTAGCATGCAAGAGGTAGTGGGATCGATG

CCCACATTCTCCA (SEQ ID NO: 187)
Homo_sapiens_chr6.trna93-AlaAGC (58272659-58272587)
Ala (AGC) 73 bp Sc: 61.81
GGGGAATTAGCTCAAGCGGTAGAGCGCTTGCTTAGCATGCAAGAGGTAGTGGGATCGATG

CCCACATTCTCCA (SEQ ID NO: 188)
Homo_sapiens_chr6.trna159-AlaAGC (26904057-26903985)
Ala (AGC) 73 bp Sc: 62.45
GGGGAATTAGCTCAAGTGGTAGAGCGCTTGCTTAGCATGCAAGAGGTAGTGGGATCGATG

CCCACATTCTCCA (SEQ ID NO: 189)
Homo_sapiens_chr6.trna19-AlaAGC (26790694-26790766)
Ala (AGC) 73 bp Sc: 62.45
GGGGAATTAGCTCAAGTGGTAGAGCGCTTGCTTAGCATGCAAGAGGTAGTGGGATCGATG

CCCACATTCTCCA (SEQ ID NO: 190)
Homo_sapiens_chr6.trna91-AlaAGC (58290710-58290638)
Ala (AGC) 73 bp Sc: 62.45
GGGGAATTAGCTCAAGTGGTAGAGCGCTTGCTTAGCATGCAAGAGGTAGTGGGATCGATG

CCCACATTCTCCA
```

-continued (SEQ ID NO: 191)
*Homo_sapiens*_chr6.trna166-AlaAGC (26680143-26680071)
Ala (AGC) 73 bp Sc: 63.06
GGGGAATTAGCTCAAATGGTAGAGCGCTCGCTTAGCATGCGAGAGGTAGCGGGATCGATG

CCCGCATTCTCCA (SEQ ID NO: 192)
*Homo_sapiens*_chr6.trna20-AlaAGC (26795464-26795536)
Ala (AGC) 73 bp Sc: 63.16
GGGGAATTAGCTCAAGTGGTAGAGCGCTTGCTTAGCACGCAAGAGGTAGTGGGATCGATG

CCCACATTCTCCA (SEQ ID NO: 193)
*Homo_sapiens*_chr6.trna161-AlaAGC (26879341-26879269)
Ala (AGC) 73 bp Sc: 63.36
GGGGAATTAGCTCAGGCGGTAGAGCGCTCGCTTAGCATGCGAGAGGTAGCGGGATCGACG

CCCGCATTCTCCA (SEQ ID NO: 194)
*Homo_sapiens*_chr6.trna24-AlaAGC (26838716-26838788)
Ala (AGC) 73 bp Sc: 63.36
GGGGAATTAGCTCAGGCGGTAGAGCGCTCGCTTAGCATGCGAGAGGTAGCGGGATCGACG

CCCGCATTCTCCA (SEQ ID NO: 195)
*Homo_sapiens*_chr2.trna3-AlaAGC (27127586-27127658)
Ala (AGC) 73 bp Sc: 63.68
GGGGGATTAGCTCAAATGGTAGAGCGCTCGCTTAGCATGCGAGAGGTAGCGGGATCGATG

CCCGCATCCTCCA (SEQ ID NO: 196)
*Homo_sapiens*_chr8.trna6-AlaAGC (67188978-67189050)
Ala (AGC) 73 bp Sc: 63.68
GGGGGATTAGCTCAAATGGTAGAGCGCTCGCTTAGCATGCGAGAGGTAGCGGGATCGATG

CCCGCATCCTCCA (SEQ ID NO: 197)
*Homo_sapiens*_chr6.trna68-AlaAGC (28795460-28795531)
Ala (AGC) 72 bp Sc: 70.19
GGGGGTGTAGCTCAGTGGTAGAGCGCGTGCTTAGCATGCACGAGGCCCCGGGTTCAATCC

CTGGCACCTCCA (SEQ ID NO: 198)
*Homo_sapiens*_chr6.trna105-AlaAGC (28887899-28887828)
Ala (AGC) 72 bp Sc: 71.23
GGGGGTATAGCTCAGCGGTAGAGCGCGTGCTTAGCATGCACGAGGTCCTGGGTTCAATCC

CCAATACCTCCA (SEQ ID NO: 199)
*Homo_sapiens*_chr6.trna67-AlaAGC (28786345-28786416)
Ala (AGC) 72 bp Sc: 75.68
GGGGGTGTAGCTCAGTGGTAGAGCGCGTGCTTAGCATGCACGAGGCCCTGGGTTCAATCC

CCAGCACCTCCA (SEQ ID NO: 200)
*Homo_sapiens*_chr6.trna120-AlaAGC (28734064-28733993)
Ala (AGC) 72 bp Sc: 75.78
GGGGATGTAGCTCAGTGGTAGAGCGCATGCTTAGCATGCATGAGGTCCCGGGTTCGATCC

CCAGCATCTCCA (SEQ ID NO: 201)
*Homo_sapiens*_chr6.trna65-AlaAGC (28682912-28682983)
Ala (AGC) 72 bp Sc: 76.69
GGGGGTGTAGCTCAGTGGTAGAGCGCGTGCTTAGCATGTACGAGGTCCCGGGTTCAATCC

CCGGCACCTCCA (SEQ ID NO: 202)
*Homo_sapiens*_chr6.trna101-AlaAGC (28939512-28939441)
Ala (AGC) 72 bp Sc: 77.18

```
-continued
GGGGGTGTAGCTCAGTGGTAGAGCGCGTGCTTAGCATGCACGAGGCCCCGGGTTCAATCC

CCGGCACCTCCA (SEQ ID NO: 203)
Homo_sapiens_chr6.trna102-AlaAGC (28914271-28914200)
Ala (AGC) 72 bp Sc: 77.18
GGGGGTGTAGCTCAGTGGTAGAGCGCGTGCTTAGCATGCACGAGGCCCCGGGTTCAATCC

CCGGCACCTCCA (SEQ ID NO: 204)
Homo_sapiens_chr6.trna108-AlaAGC (28871791-28871720)
Ala (AGC) 72 bp Sc: 81.12
GGGGGTATAGCTCAGTGGTAGAGCGCGTGCTTAGCATGCACGAGGTCCTGGGTTCGATCC

CCAGTACCTCCA (SEQ ID NO: 205)
Homo_sapiens_chr6.trna117-AlaCGC (28771759-28771688)
Ala (CGC) 72 bp Sc: 56.63
GGGGGTGTAGATCAGTGGTAGAGCGCATGCTTCGCATGTACGAGGTCCCTGGTTCAATCC

CTGGTACCTCCA (SEQ ID NO: 206)
Homo_sapiens_chr6.trna70-AlaCGC (28805071-28805142)
Ala (CGC) 72 bp Sc: 70.09
GGGGGTGTAGCTCAGTGGTAGAGCGCGTGCTTCGCATGTACGAGGCCCCGGGTTCGACCC

CCGGCTCCTCCA (SEQ ID NO: 207)
Homo_sapiens_chr2.trna13-AlaCGC (156965527-156965598)
Ala (CGC) 72 bp Sc: 73.12
GGGGATGTAGCTCAGTGGTAGAGCGCGCGCTTCGCATGTGTGAGGTCCCGGGTTCAATCC

CCGGCATCTCCA (SEQ ID NO: 208)
Homo_sapiens_chr6.trna119-AlaCGC (28749663-28749592)
Ala (CGC) 72 bp Sc: 74.81
GGGGATGTAGCTCAGTGGTAGAGCGCATGCTTCGCATGTATGAGGCCCCGGGTTCGATCC

CCGGCATCTCCA (SEQ ID NO: 209)
Homo_sapiens_chr6.trna10-AlaCGC (26661710-26661781)
Ala (CGC) 72 bp Sc: 78.91
GGGGATGTAGCTCAGTGGTAGAGCGCATGCTTCGCATGTATGAGGTCCCGGGTTCGATCC

CCGGCATCTCCA (SEQ ID NO: 210)
Homo_sapiens_chr11.trna18-AlaTGC (50190526-50190455)
Ala (TGC) 72 bp Sc: 51.06
GGGGGTGTAGCTCAGTGGTAGAGCGGATGCTTTGCATGTATGAGACTTTGGGTTGGATCC

CCAGCACCTCCA (SEQ ID NO: 211)
Homo_sapiens_chr6.trna107-AlaTGC (28878626-28878556)
Ala (TGC) 71 bp Sc: 59.75
GGGGGTGTAGCTCAGTGGTAGAGCGCATGCTTTGCATGTATGAGGCCTCGGTTCGATCCC

CGACACCTCCA (SEQ ID NO: 212)
Homo_sapiens_chr6.trna113-AlaTGC (28834191-28834120)
Ala (TGC) 72 bp Sc: 67.60
GGGGGTGTAGCTCAGTGGTAGAGCACATGCTTTGCATGTGTGAGGCCCCGGGTTCGATCC

CCGGCACCTCCA (SEQ ID NO: 213)
Homo_sapiens_chr6.trna104-AlaTGC (28893062-28892991)
Ala (TGC) 72 bp Sc: 70.95
GGGGGTGTAGCTCAGTGGTAGAGCGCATGCTTTGCATGTATGAGGCCTCGGGTTCGATCC

CCGACACCTCCA
```

(SEQ ID NO: 214)
*Homo_sapiens*_chr12.trna8-AlaTGC (123990465-123990536)
Ala (TGC) 72 bp Sc: 73.41
GGGGATGTAGCTCAGTGGTAGAGCGCATGCTTTGCACGTATGAGGCCCCGGGTTCAATCC

CCGGCATCTCCA (SEQ ID NO: 215)
*Homo_sapiens*_chr12.trna13-AlaTGC (123972325-123972254)
Ala (TGC) 72 bp Sc: 74.45
GGGGATGTAGCTCAGTGGTAGAGCGCATGCTTTGCATGTATGAGGCCCCGGGTTCGATCC

CCGGCATCTCCA (SEQ ID NO: 216)
*Homo_sapiens*_chr5.trna8-AlaTGC (180566474-180566545)
Ala (TGC) 72 bp Sc: 74.45
GGGGATGTAGCTCAGTGGTAGAGCGCATGCTTTGCATGTATGAGGCCCCGGGTTCGATCC

CCGGCATCTCCA (SEQ ID NO: 217)
*Homo_sapiens*_chr6.trna66-AlaTGC (28719201-28719272)
Ala (TGC) 72 bp Sc: 78.55
GGGGATGTAGCTCAGTGGTAGAGCGCATGCTTTGCATGTATGAGGTCCCGGGTTCGATCC

CCGGCATCTCCA (SEQ ID NO: 218)
*Homo_sapiens*_chr6.trna110-AlaTGC (28865597-28865526)
Ala (TGC) 72 bp Sc: 79.16
GGGGGTGTAGCTCAGTGGTAGAGCGCATGCTTTGCATGTATGAGGTCCCGGGTTCGATCC

CCGGCACCTCCA (SEQ ID NO: 219)
*Homo_sapiens*_chr3.trna11-ArgACG (45705567-45705495)
Arg (ACG) 73 bp Sc: 68.07
GGGCCAGTGGCGCAATGGATAACGCGTCTGACTACGGATCAGAAGATTCTAGGTTCGACT

CCTGGCTGGCTCG (SEQ ID NO: 220)
*Homo_sapiens*_chr6.trna138-ArgACG (27746395-27746323)
Arg (ACG) 73 bp Sc: 68.07
GGGCCAGTGGCGCAATGGATAACGCGTCTGACTACGGATCAGAAGATTCTAGGTTCGACT

CCTGGCTGGCTCG (SEQ ID NO: 221)
*Homo_sapiens*_chr6.trna156-ArgACG (27289674-27289602)
Arg (ACG) 73 bp Sc: 68.07
GGGCCAGTGGCGCAATGGATAACGCGTCTGACTACGGATCAGAAGATTCTAGGTTCGACT

CCTGGCTGGCTCG (SEQ ID NO: 222)
*Homo_sapiens*_chr6.trna36-ArgACG (27290931-27291003)
Arg (ACG) 73 bp Sc: 68.07
GGGCCAGTGGCGCAATGGATAACGCGTCTGACTACGGATCAGAAGATTCTAGGTTCGACT

CCTGGCTGGCTCG (SEQ ID NO: 223)
*Homo_sapiens*_chr14.trna7-ArgACG (22468750-22468822)
Arg (ACG) 73 bp Sc: 72.37
GGGCCAGTGGCGCAATGGATAACGCGTCTGACTACGGATCAGAAGATTCCAGGTTCGACT

CCTGGCTGGCTCG (SEQ ID NO: 224)
*Homo_sapiens*_chr6.trna6-ArgACG (26436347-26436419)
Arg (ACG) 73 bp Sc: 72.37
GGGCCAGTGGCGCAATGGATAACGCGTCTGACTACGGATCAGAAGATTCCAGGTTCGACT

CCTGGCTGGCTCG (SEQ ID NO: 225)
*Homo_sapiens*_chr6.trna8-ArgACG (26645705-26645777)
Arg (ACG) 73 bp Sc: 72.37

```
GGGCCAGTGGCGCAATGGATAACGCGTCTGACTACGGATCAGAAGATTCCAGGTTCGACT

CCTGGCTGGCTCG (SEQ ID NO: 226)
Homo_sapiens_chr17.trna23-ArgCCG (63446547-63446475)
Arg (CCG) 73 bp Sc: 65.49
GACCCAGTGGCCTAATGGATAAGGCATCAGCCTCCGGAGCTGGGGATTGTGGGTTCGAGT

CCCATCTGGGTCG (SEQ ID NO: 227)
Homo_sapiens_chr17_random.trna1-ArgCCG (1739927-1739999)
Arg (CCG) 73 bp Sc: 65.49
GACCCAGTGGCCTAATGGATAAGGCATCAGCCTCCGGAGCTGGGGATTGTG

GGTTCGAGTCCCATCTGGGTCG (SEQ ID NO: 228)
Homo_sapiens_chr16.trna1-ArgCCG (3140676-3140748)
Arg (CCG) 73 bp Sc: 69.88
GGCCGCGTGGCCTAATGGATAAGGCGTCTGATTCCGGATCAGAAGATTGAGGGTTCGAGT

CCCTTCGTGGTCG (SEQ ID NO: 229)
Homo_sapiens_chr6.trna114-ArgCCG (28818780-28818708)
Arg (CCG) 73 bp Sc: 69.88
GGCCGCGTGGCCTAATGGATAAGGCGTCTGATTCCGGATCAGAAGATTGAGGGTTCGAGT

CCCTTCGTGGTCG (SEQ ID NO: 230)
Homo_sapiens_chr6.trna73-ArgCCG (28957144-28957216)
Arg (CCG) 73 bp Sc: 69.88
GGCCGCGTGGCCTAATGGATAAGGCGTCTGATTCCGGATCAGAAGATTGAGGGTTCGAGT

CCCTTCGTGGTCG (SEQ ID NO: 231)
Homo_sapiens_chr16.trna12-ArgCCT (3183919-3183991)
Arg (CCT) 73 bp Sc: 59.77
GCCCCAGTGGCCTGATGGATAAGGTACTGGCCTCCTAAGCCAGGGATTGTGGGTTCGAGT

TCCACCTGGGGTA (SEQ ID NO: 232)
Homo_sapiens_chr7.trna3-ArgCCT (138675986-138676058)
Arg (CCT) 73 bp Sc: 67.28
GCCCCAGTGGCCTAATGGATAAGGCATTGGCCTCCTAAGCCAGGGATTGTGGGTTCGAGT

CCCATCTGGGGTG (SEQ ID NO: 233)
Homo_sapiens_chr16.trna2-ArgCCT (3142902-3142974)
Arg (CCT) 73 bp Sc: 71.53
GCCCCGGTGGCCTAATGGATAAGGCATTGGCCTCCTAAGCCAGGGATTGTGGGTTCGAGT

CCCACCCGGGGTA (SEQ ID NO: 234)
Homo_sapiens_chr17.trna21-ArgCCT (70542193-70542121)
Arg (CCT) 73 bp Sc: 73.41
GCCCCAGTGGCCTAATGGATAAGGCACTGGCCTCCTAAGCCAGGGATTGTGGGTTCGAGT

CCCACCTGGGGTG (SEQ ID NO: 235)
Homo_sapiens_chr17.trna18-ArgCCT (70541596-70541668)
Arg (CCT) 73 bp Sc: 73.88
GCCCCAGTGGCCTAATGGATAAGGCACTGGCCTCCTAAGCCAGGGATTGTGGGTTCGAGT

CCCACCTGGGGTA (SEQ ID NO: 236)
Homo_sapiens_chr9.trna2-ArgTCG (112000624-112000696)
Arg (TCG) 73 bp Sc: 56.18
GGCCGTGTGGCCTAATGGATAAGGCGTCTGACTTCGGATCAAAAGATTGCAGGTTTGAGT

TCTGCCACGGTCG
```

-continued (SEQ ID NO: 237)
*Homo_sapiens*_chr6.trna124-ArgTCG (28618942-28618870)
Arg (TCG) 73 bp Sc: 69.08
GACCACGTGGCCTAATGGATAAGGCGTCTGACTTCGGATCAGAAGATTGAGGGTTCGAAT

CCCTTCGTGGTTG (SEQ ID NO: 238)
*Homo_sapiens*_chr6.trna3-ArgTCG (26407884-26407956)
Arg (TCG) 73 bp Sc: 69.55
GACCACGTGGCCTAATGGATAAGGCGTCTGACTTCGGATCAGAAGATTGAGGGTTCGAAT

CCCTTCGTGGTTA (SEQ ID NO: 239)
*Homo_sapiens*_chr17.trna19-ArgTCG (70542803-70542875)
Arg (TCG) 73 bp Sc: 70.52
GACCGCGTGGCCTAATGGATAAGGCGTCTGACTTCGGATCAGAAGATTGAGGGTTCGAGT

CCCTTCGTGGTCG (SEQ ID NO: 240)
*Homo_sapiens*_chr6.trna4-ArgTCG (26431025-26431097)
Arg (TCG) 73 bp Sc: 72.33
GACCACGTGGCCTAATGGATAAGGCGTCTGACTTCGGATCAGAAGATTGAGGGTTCGAAT

CCCTCCGTGGTTA (SEQ ID NO: 241)
*Homo_sapiens*_chr15.trna4-ArgTCG (87679308-87679380)
Arg (TCG) 73 bp Sc: 76.93
GGCCGCGTGGCCTAATGGATAAGGCGTCTGACTTCGGATCAGAAGATTGCAGGTTCGAGT

CCTGCCGCGGTCG (SEQ ID NO: 242)
*Homo_sapiens*_chr1.trna86-ArgTCT (157378098-157378025)
Arg (TCT) 74 bp Sc: 76.29
GTCTCTGTGGCGCAATGGACGAGCGCGCTGGACTTCTAATCCAGAGGTTCCGGGTTCGAG

TCCCGGCAGAGATG (SEQ ID NO: 243)
*Homo_sapiens*_chr9.trna4-ArgTCT (130142266-130142176)
Arg (TCT) 91 bp Sc: 67.17
GGCTCTGTGGCGCAATGGATAGCGCATTGGACTTCTAGCTGAGCCTAGTGTGGTCATTCA

AAGGTTGTGGGTTCGAGTCCCACCAGAGTCG (SEQ ID NO: 244)
*Homo_sapiens*_chr6.trna52-ArgTCT (27637942-27638028)
Arg (TCT) 87 bp Sc: 65.24
GGCTCTGTGGCGCAATGGATAGCGCATTGGACTTCTAGCCTAAATCAAGAGATTCAAAGG

TTGCGGGTTCGAGTCCCTCCAGAGTCG (SEQ ID NO: 245)
*Homo_sapiens*_chr11.trna3-ArgTCT (59075343-59075428)
Arg (TCT) 86 bp Sc: 71.13
GGCTCTGTGGCGCAATGGATAGCGCATTGGACTTCTAGATAGTTAGAGAAATTCAAAGGT

TGTGGGTTCGAGTCCCACCAGAGTCG (SEQ ID NO: 246)
*Homo_sapiens*_chr17.trna4-ArgTCT (7964968-7965055)
Arg (TCT) 88 bp Sc: 71.27
GGCTCTGTGGCGCAATGGATAGCGCATTGGACTTCTAGTGACGAATAGAGCAATTCAAAG

GTTGTGGGTTCGAATCCCACCAGAGTCG (SEQ ID NO: 247)
*Homo_sapiens*_chr1.trna9-ArgTCT (94085717-94085801)
Arg (TCT) 85 bp Sc: 71.18
GGCTCCGTGGCGCAATGGATAGCGCATTGGACTTCTAGAGGCTGAAGGCATTCAAAGGTT

CCGGGTTCGAGTCCCGGCGGAGTCG (SEQ ID NO: 248)
*Homo_sapiens*_chr1.trna20-AsnATT (146185653-146185726)
Asn (ATT) 74 bp Sc: 52.07

```
GTCTCTGTGGCGCAATCGGTCAGAGCGTTCGGCTATTAACCGAACGGTGAGTAGTTCAAG

ACCACCCAGGGACG
```

(SEQ ID NO: 249)
*Homo_sapiens*_chr1.trna13-AsnGTT (144097086-144097161)
Asn (GTT) 76 bp Sc: 44.21
```
GTCTCTGTGGCGCCATCGGTTAGTGCCTTCGGCTGTTTGAACCGAAAGGCTGGTGGTTCA

AGCCCACCCAGAGATG
```

(SEQ ID NO: 250)
*Homo_sapiens*_chr1.trna93-AsnGTT (147936754-147936681)
Asn (GTT) 74 bp Sc: 46.92
```
ATCTCCGTGGAGCAATTGGTTAGCGCGTTCGGCCGTTAACCGGAAAGTTGGTGGTTCGAG

CCTACCCAGGGACG
```

(SEQ ID NO: 251)
*Homo_sapiens*_chr1.trna134-AsnGTT (16731553-16731480)
Asn (GTT) 74 bp Sc: 48.81
```
GTCTCTGTGGTGCAATCGGTTAGCGCGTTCGGCTGTTAACCATAAGGTTGGTGGTTACAG

ACCACCCAGGGACG
```

(SEQ ID NO: 252)
*Homo_sapiens*_chr1.trna50-AsnGTT (159858089-159858162)
Asn (GTT) 74 bp Sc: 49.69
```
GTTTCTGTAGCGCGATCGGTTAGCGCCTTCGGCTGTTAAACGAAAGGTTGGTGGTTCGTT

CCCACCCCGGGACA
```

(SEQ ID NO: 253)
*Homo_sapiens*_chr1.trna10-AsnGTT (142481551-142481624)
Asn (GTT) 74 bp Sc: 49.96
```
GTCTCTGTGGCGCAATCGGTTAGCGCGTTTGACTGTTAACTGAAAGGTTGGTGGTGCAAG

CCCATCCAGGGATG
```

(SEQ ID NO: 254)
*Homo_sapiens*_chr1.trna122-AsnGTT (143200273-143200200)
Asn (GTT) 74 bp Sc: 49.96
```
GTCTCTGTGGCGCAATCGGTTAGCGCGTTTGACTGTTAACTGAAAGGTTGGTGGTGCAAG

CCCATCCAGGGATG
```

(SEQ ID NO: 255)
*Homo_sapiens*_chr1.trna123-AsnGTT (143020044-143019971)
Asn (GTT) 74 bp Sc: 49.96
```
GTCTCTGTGGCGCAATCGGTTAGCGCGTTTGACTGTTAACTGAAAGGTTGGTGGTGCAAG

CCCATCCAGGGATG
```

(SEQ ID NO: 256)
*Homo_sapiens*_chr1.trna24-AsnGTT (146344161-146344234)
Asn (GTT) 74 bp Sc: 49.96
```
GTCTCTGTGGCGCAATCGGTTAGCGCGTTTGACTGTTAACTGAAAGGTTGGTGGTGCAAG

CCCATCCAGGGATG
```

(SEQ ID NO: 257)
*Homo_sapiens*_chr1.trna30-AsnGTT (147875233-147875306)
Asn (GTT) 74 bp Sc: 49.96
```
GTCTCTGTGGCGCAATCGGTTAGCGCGTTTGACTGTTAACTGAAAGGTTGGTGGTGCAAG

CCCATCCAGGGATG
```

(SEQ ID NO: 258)
*Homo_sapiens*_chr1.trna101-AsnGTT (147551200-147551127)
Asn (GTT) 74 bp Sc: 51.19
```
ATCTCCGTGGAGCAATTGGTTAGCGCGTTCGGCTGTTAACCGGAAAGTTGGTGGTTCGAG

CCTACCCAGGGACG
```

(SEQ ID NO: 259)
*Homo_sapiens*_chr1.trna12-AsnGTT (143193197-143193270)
Asn (GTT) 74 bp Sc: 53.66
```
GTCTCTGTGGTGCAATCGGTTAGCGCGTTCCGCTGTTAACCGAAAGCTTGGTGGTTTGAG

CCCACCCAGGGATG
```

(SEQ ID NO: 260)
*Homo_sapiens*_chr1.trna6-AsnGTT (17074545-17074618)
Asn (GTT) 74 bp Sc: 56.35
GTCTCTGTGGTGCAATCGGTTAGCGCGTTCGGCTGTTAACCATAAGGTTGGTGGTTAGAG

ACCACCCAGGGACG (SEQ ID NO: 261)
*Homo_sapiens*_chr1.trna97-AsnGTT (147592969-147592896)
Asn (GTT) 74 bp Sc: 59.90
GTCTCTGTGGCGCAATCGGCTAGCGCGTTTGGCTGTTAACTAAAAGTTGGTGGTTCGAA

CACACCCAGAGGCG (SEQ ID NO: 262)
*Homo_sapiens*_chr1.trna11-AsnGTT (143012968-143013041)
Asn (GTT) 74 bp Sc: 60.57
GTCTCTGTGGTGCAATCGGTTAGCGCGTTCCGCTGTTAACCGAAAGCTTGGTGGTTCGAG

CCCACCCAGGGATG (SEQ ID NO: 263)
*Homo_sapiens*_chr1.trna95-AsnGTT (147882314-147882241)
Asn (GTT) 74 bp Sc: 60.57
GTCTCTGTGGTGCAATCGGTTAGCGCGTTCCGCTGTTAACCGAAAGCTTGGTGGTTCGAG

CCCACCCAGGGATG (SEQ ID NO: 264)
*Homo_sapiens*_chr1_random.trna2-AsnGTT (906435-906508)
Asn (GTT) 74 bp Sc: 66.79
GTCTCTGTGGCGCAATCGGCTAGCGCGTTTGGCTGTTAACTAAAAGGTTGGCGGTTCGAA

CCCACCCAGAGGCG (SEQ ID NO: 265)
*Homo_sapiens*_chr1.trna113-AsnGTT (145987464-145987391)
Asn (GTT) 74 bp Sc: 70.44
GTCTCTGTGGCGCAATCGGTTAGCGCGTTCGGCTGTTAACTGAAAGGTTAGTGGTTCGAG

CCCACCCGGGGACG (SEQ ID NO: 266)
*Homo_sapiens*_chr1.trna115-AsnGTT (144690464-144690391)
Asn (GTT) 74 bp Sc: 70.44
GTCTCTGTGGCGCAATCGGTTAGCGCGTTCGGCTGTTAACTGAAAGGTTAGTGGTTCGAG

CCCACCCGGGGACG (SEQ ID NO: 267)
*Homo_sapiens*_chr1.trna89-AsnGTT (147978495-147978422)
Asn (GTT) 74 bp Sc: 71.43
GTCTCTGTGGCGCAATCGGCTAGCGCGTTTGGCTGTTAACTAAAAGGTTGGTGGTTCGAA

CCCACCCAGAGGCG (SEQ ID NO: 268)
*Homo_sapiens*_chr1.trna25-AsnGTT (146467429-146467502)
Asn (GTT) 74 bp Sc: 72.61
GTCTCTGTGGCGTAGTCGGTTAGCGCGTTCGGCTGTTAACCGAAAAGTTGGTGGTTCGAG

CCCACCCAGGAACG (SEQ ID NO: 269)
*Homo_sapiens*_chr1.trna103-AsnGTT (147497267-147497194)
Asn (GTT) 74 bp Sc: 77.16
GTCTCTGTGGCGCAATGGGTTAGCGCGTTCGGCTGTTAACCGAAAGGTTGGTGGTTCGAG

CCCATCCAGGGACG (SEQ ID NO: 270)
*Homo_sapiens*_chr1.trna135-AsnGTT (16719740-16719667)
Asn (GTT) 74 bp Sc: 77.65
GTCTCTGTGGCGCAATCGGTTAGCGCGTTCGGCTGTTAACTGAAAGGTTGGTGGTTCGAG

CCCACCCAGGGACG (SEQ ID NO: 271)
*Homo_sapiens*_chr1.trna7-AsnGTT (17088759-17088832)
Asn (GTT) 74 bp Sc: 80.35
GTCTCTGTGGCGCAATCGGTTAGCGCGTTCGGCTGTTAACCGAAAGATTGGTGGTTCGAG

CCCACCCAGGGACG (SEQ ID NO: 272)
*Homo_sapiens*_chr1.trna107-AsnGTT (147027053-147026980)
Asn (GTT) 74 bp Sc: 80.52
GTCTCTGTGGCGCAATCGGTTAGCGCATTCGGCTGTTAACCGAAAGGTTGGTGGTTCGAG

CCCACCCAGGGACG (SEQ ID NO: 273)
*Homo_sapiens*_chr1.trna108-AsnGTT (146865011-146864938)
Asn (GTT) 74 bp Sc: 80.52
GTCTCTGTGGCGCAATCGGTTAGCGCATTCGGCTGTTAACCGAAAGGTTGGTGGTTCGAG

CCCACCCAGGGACG (SEQ ID NO: 274)
*Homo_sapiens*_chr1.trna26-AsnGTT (146614739-146614812)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 275)
*Homo_sapiens*_chr1.trna83-AsnGTT (159664564-159664491)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 276)
*Homo_sapiens*_chr10.trna4-AsnGTT (22558517-22558444)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 277)
*Homo_sapiens*_chr13.trna7-AsnGTT (30146174-30146101)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 278)
*Homo_sapiens*_chr17.trna31-AsnGTT (34161633-34161560)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 279)
*Homo_sapiens*_chr19.trna1-AsnGTT (1334562-1334635)
Asn (GTT) 74 bp Sc: 82.24
GTCTCTGTGGCGCAATCGGTTAGCGCGTTCGGCTGTTAACCGAAAGGTTGGTGGTTCGAG

CCCACCCAGGGACG (SEQ ID NO: 280)
*Homo_sapiens*_chr1.trna47-AsnGTT (159776655-159776728)
Asn (GTT) 74 bp Sc: 83.66
GTCTCTGTGGCGCAATCGGTTAGCGCGTTCGGCTGTTAACCGAAAGGTTGGTGGTTCGAT

CCCACCCAGGGACG (SEQ ID NO: 281)
*Homo_sapiens*_chr1.trna48-AspGTC (159841212-159841283)
Asp (GTC) 72 bp Sc: 30.22
TCCTTGTTACTATAGTGGTAAGTATCTCTGCCTGTCATGCATGAGAGAGGGGGTCGATTC

CCTGACGGGGAG (SEQ ID NO: 282)
*Homo_sapiens*_chr12.trna7-AspGTC (121426877-121426947)
Asp (GTC) 71 bp Sc: 32.33

```
TCCTTGTTAGTATAGTGGTGAGTGTTTCTGCCTGTCATGTGGAGACTGGAGTTTGAGTCC

CCAACAGGGAG (SEQ ID NO: 283)
Homo_sapiens_chr1.trna46-AspGTC (159768539-159768610)
Asp (GTC) 72 bp Sc: 34.08
TACTCGTTAGTATAGTGGTGCGTATCCCCGTCTGTCACGCGGGAGAGCGGGGTTCGCTCT

CCCGACGGGGAG (SEQ ID NO: 284)
Homo_sapiens_chr3.trna3-AspGTC (185848859-185848789)
Asp (GTC) 71 bp Sc: 43.84
TTCTTGTTAATATAGTGGTGAGTATTCCCACCTGTCATGCGGGAGACGGGGTTCAATTCC

CTGATGGGGAG (SEQ ID NO: 285)
Homo_sapiens_chr5.trna22-AspGTC (141754243-141754172)
Asp (GTC) 72 bp Sc: 54.87
TCCTCATCAGTATAGTGGTGAGTATCCCCGCCTGTCACGCGGGAGACTGGGGTTCGATTC

CCTGAGGAGGAG (SEQ ID NO: 286)
Homo_sapiens_chr9.trna6-AspGTC (76707881-76707810)
Asp (GTC) 72 bp Sc: 54.95
TCCTCGTTAGTATGGTGGTGAGTATCCCTGCCTGTCACGCGGGAGACCGGGGTTCGATTC

CCCAACGGGGAG (SEQ ID NO: 287)
Homo_sapiens_chr6.trna144-AspGTC (27659286-27659215)
Asp (GTC) 72 bp Sc: 64.62
TCCTCGTTAGTATAGTGGTGAGTGTCCCCGTCTGTCACGCGGGAGACCGGGGTTCGATTC

CCCGACGGGGAG (SEQ ID NO: 288)
Homo_sapiens_chr1.trna69-AspGTC (159706900-159706829)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 289)
Homo_sapiens_chr1.trna72-AspGTC (159699519-159699448)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 290)
Homo_sapiens_chr1.trna75-AspGTC (159692109-159692038)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 291)
Homo_sapiens_chr1.trna78-AspGTC (159684728-159684657)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 292)
Homo_sapiens_chr1.trna81-AspGTC (159677310-159677239)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 293)
Homo_sapiens_chr12.trna10-AspGTC (123990217-123990146)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG
```

-continued (SEQ ID NO: 294)
*Homo_sapiens*_chr12.trna12-AspGTC (123977915-123977844)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 295)
*Homo_sapiens*_chr12.trna4-AspGTC (94953930-94954001)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 296)
*Homo_sapiens*_chr17.trna38-AspGTC (8066352-8066281)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 297)
*Homo_sapiens*_chr6.trna45-AspGTC (27555432-27555503)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 298)
*Homo_sapiens*_chr6.trna48-AspGTC (27579502-27579573)
Asp (GTC) 72 bp Sc: 72.92
TCCTCGTTAGTATAGTGGTGAGTATCCCCGCCTGTCACGCGGGAGACCGGGGTTCGATTC

CCCGACGGGGAG (SEQ ID NO: 299)
*Homo_sapiens*_chr12.trna5-AspGTC (97421412-97421483)
Asp (GTC) 72 bp Sc: 74.76
TCCTCGTTAGTATAGTGGTTAGTATCCCCGCCTGTCACGCGGGAGACCGGGGTTCAATTC

CCCGACGGGGAG (SEQ ID NO: 300)
*Homo_sapiens*_chr17.trna30-CysGCA (34243572-34243501)
Cys (GCA) 72 bp Sc: 51.58
GGGGGTAGGGCTCAGGGATAGAGCATTTGACTGCAGATCAAGAGGTCCCCGGTTCGAATC

TAGGTGCCCCCT (SEQ ID NO: 301)
*Homo_sapiens*_chr7.trna19-CysGCA (148923309-148923238)
Cys (GCA) 72 bp Sc: 57.52
GGGGGTATAGCTCACAGGTAGAGCATTTGACTGCAGATCAAGAGGTCCCCGGTTCAAATC

CGGTTACTCCCT (SEQ ID NO: 302)
*Homo_sapiens*_chr7.trna8-CysGCA (148884735-148884806)
Cys (GCA) 72 bp Sc: 59.93
GGGCGTATAGCTCAGGGGTAGAGCATTTGACTGCAGATCAAGAGGTCCCCAGTTCAAATC

TGGGTGCCCACT (SEQ ID NO: 303)
*Homo_sapiens*_chr7.trna14-CysGCA (148992848-148992919)
Cys (GCA) 72 bp Sc: 60.15
GGGGGTATAGCTCACAGGTAGAGCATTTGACTGCAGATCAAGAGGTCCCCGGTTCAAATC

TGGGTGCCCCCT (SEQ ID NO: 304)
*Homo_sapiens*_chr7.trna11-CysGCA (148925979-148926050)
Cys (GCA) 72 bp Sc: 65.84
GGGCGTATAGCTCAGGGGTAGAGCATTTGACTGCAGATCAAGAGGTCCCCAGTTCAAATC

TGGGTGCCCCCT (SEQ ID NO: 305)
*Homo_sapiens*_chr7.trna18-CysGCA (148941160-148941089)
Cys (GCA) 72 bp Sc: 67.69
GGGGGTATAGCTCAGGGGTAGAGCATTTGACTGCAAATCAAGAGGTCCCTGATTCAAATC

CAGGTGCCCCCT (SEQ ID NO: 306)
*Homo_sapiens*_chr7.trna23-CysGCA (148703854-148703783)
Cys (GCA) 72 bp Sc: 68.91
GGGGGTATAGTTCAGGGGTAGAGCATTTGACTGCAGATCAAGAGGTCCCTGGTTCAAATC

CAGGTGCCCCCT (SEQ ID NO: 307)
*Homo_sapiens*_chr7.trna16-CysGCA (149019276-149019205)
Cys (GCA) 72 bp Sc: 69.30
GGGGATATAGCTCAGGGGTAGAGCATTTGACTGCAGATCAAGAGGTCCCCGGTTCAAATC

CGGGTGCCCCCC (SEQ ID NO: 308)
*Homo_sapiens*_chr7.trna7-CysGCA (148874564-148874635)
Cys (GCA) 72 bp Sc: 69.62
GGGGGTATAGCTCAGGGGTAGAGCACTTGACTGCAGATCAAGAAGTCCTTGGTTCAAATC

CAGGTGCCCCCT (SEQ ID NO: 309)
*Homo_sapiens*_chr7.trna10-CysGCA (148912749-148912820)
Cys (GCA) 72 bp Sc: 69.82
GGGGGTATAGCTCAGGGGTAGAGCATTTGACTGCAGATCAAGAGGTCTCTGGTTCAAATC

CAGGTGCCCCCT (SEQ ID NO: 310)
*Homo_sapiens*_chr17.trna29-CysGCA (34271534-34271463)
Cys (GCA) 72 bp Sc: 70.63
GGGGGTATAGCTCAGGGGTAGAGCATTTGACTGCAGATCAAGAAGTCCCCGGTTCAAATC

CGGGTGCCCCCT (SEQ ID NO: 311)
*Homo_sapiens*_chr7.trna25-CysGCA (148683770-148683699)
Cys (GCA) 72 bp Sc: 71.19
GGGGGTATAGCTCAGGGGTAGAGCATTTGACTGCAGATCAAGAGGTCCCCAGTTCAAATC

TGGGTGCCCCCT (SEQ ID NO: 312)
*Homo_sapiens*_chr7.trna17-CysGCA (148975050-148974979)
Cys (GCA) 72 bp Sc: 71.81
GGGGGTATAGCTTAGGGGTAGAGCATTTGACTGCAGATCAAAAGGTCCCTGGTTCAAATC

CAGGTGCCCCTT (SEQ ID NO: 313)
*Homo_sapiens*_chr7.trna21-CysGCA (148743233-148743162)
Cys (GCA) 72 bp Sc: 73.76
GGGGGTATAGCTTAGCGGTAGAGCATTTGACTGCAGATCAAGAGGTCCCCGGTTCAAATC

CGGGTGCCCCCT (SEQ ID NO: 314)
*Homo_sapiens*_chr7.trna22-CysGCA (148705605-148705534)
Cys (GCA) 72 bp Sc: 73.86
GGGGGTATAGCTCAGGGGTAGAGCATTTGACTGCAGATCAAGAGGTCCCTGGTTCAAATC

CAGGTGCCCCCC (SEQ ID NO: 315)
*Homo_sapiens*_chr3.trna6-CysGCA (133433403-133433332)
Cys (GCA) 72 bp Sc: 74.20
GGGGGTATAGCTCAGGGGTAGAGCATTTGACTGCAGATCAAGAGGTCCCTGGTTCAAATC

CAGGTGCCCCCT (SEQ ID NO: 316)
*Homo_sapiens*_chr7.trna13-CysGCA (148963711-148963782)
Cys (GCA) 72 bp Sc: 74.20

```
GGGGGTATAGCTCAGGGGTAGAGCATTTGACTGCAGATCAAGAGGTCCCTGGTTCAAATC

CAGGTGCCCCCT (SEQ ID NO: 317)
Homo_sapiens_chr7.trna15-CysGCA (149035693-149035764)
Cys (GCA) 72 bp Sc: 74.20
GGGGGTATAGCTCAGGGGTAGAGCATTTGACTGCAGATCAAGAGGTCCCTGGTTCAAATC

CAGGTGCCCCCT (SEQ ID NO: 318)
Homo_sapiens_chr7.trna6-CysGCA (148659153-148659224)
Cys (GCA) 72 bp Sc: 74.20
GGGGGTATAGCTCAGGGGTAGAGCATTTGACTGCAGATCAAGAGGTCCCTGGTTCAAATC

CAGGTGCCCCCT (SEQ ID NO: 319)
Homo_sapiens_chr14.trna8-CysGCA (72499432-72499503)
Cys (GCA) 72 bp Sc: 74.26
GGGGGTATAGCTCAGGGGTAGAGCATTTGACTGCAGATCAAGAGGTCCCCGGTTCAAATC

CGGGTGCCCCCT (SEQ ID NO: 320)
Homo_sapiens_chr1.trna126-CysGCA (93754494-93754422)
Cys (GCA) 73 bp Sc: 74.38
GGGGGTATAGCTCAGGTGGTAGAGCATTTGACTGCAGATCAAGAGGTCCCCGGTTCAAAT

CCGGGTGCCCCCT (SEQ ID NO: 321)
Homo_sapiens_chr3.trna7-CysGCA (133430705-133430634)
Cys (GCA) 72 bp Sc: 74.42
GGGGGTGTAGCTCAGTGGTAGAGCATTTGACTGCAGATCAAGAGGTCCCTGGTTCAAATC

CAGGTGCCCCCT (SEQ ID NO: 322)
Homo_sapiens_chr15.trna3-CysGCA (77824052-77824124)
Cys (GCA) 73 bp Sc: 74.95
GGGGGTATAGCTCAGTGGGTAGAGCATTTGACTGCAGATCAAGAGGTCCCCGGTTCAAAT

CCGGGTGCCCCCT (SEQ ID NO: 323)
Homo_sapiens_chr17.trna28-CysGCA (34279142-34279071)
Cys (GCA) 72 bp Sc: 77.18
GGGGGTATAGCTCAGTGGTAGAGCATTTGACTGCAGATCAAGAGGTCCCTGGTTCAAATC

CGGGTGCCCCCT (SEQ ID NO: 324)
Homo_sapiens_chr7.trna20-CysGCA (148917168-148917097)
Cys (GCA) 72 bp Sc: 77.55
GGGGGTATAGCTCAGGGGTAGAGCACTTGACTGCAGATCAAGAGGTCCCTGGTTCAAATC

CAGGTGCCCCCT (SEQ ID NO: 325)
Homo_sapiens_chr17.trna15-CysGCA (34277424-34277495)
Cys (GCA) 72 bp Sc: 77.71
GGGGGTATAGCTCAGTGGTAGAGCATTTGACTGCAGATCAAGAGGTCCCCGGTTCAAATC

CGGGTGCCCCCT (SEQ ID NO: 326)
Homo_sapiens_chr17.trna26-CysGCA (34564341-34564270)
Cys (GCA) 72 bp Sc: 77.71
GGGGGTATAGCTCAGTGGTAGAGCATTTGACTGCAGATCAAGAGGTCCCCGGTTCAAATC

CGGGTGCCCCCT (SEQ ID NO: 327)
Homo_sapiens_chr17.trna27-CysGCA (34563584-34563513)
Cys (GCA) 72 bp Sc: 77.71
GGGGGTATAGCTCAGTGGTAGAGCATTTGACTGCAGATCAAGAGGTCCCCGGTTCAAATC

CGGGTGCCCCCT
```

```
                                                        (SEQ ID NO: 328)
Homo_sapiens_chr4.trna3-CysGCA (124649526-124649455)
Cys (GCA) 72 bp Sc: 77.71
GGGGGTATAGCTCAGTGGTAGAGCATTTGACTGCAGATCAAGAGGTCCCCGGTTCAAATC

CGGGTGCCCCCT (SEQ ID NO: 329)
Homo_sapiens_chr7.trna5-CysGCA (148638214-148638285)
Cys (GCA) 72 bp Sc: 79.54
GGGGGCATAGCTCAGTGGTAGAGCATTTGACTGCAGATCAAGAGGTCCCTGGTTCAAATC

CAGGTGCCCCCT (SEQ ID NO: 330)
Homo_sapiens_chr16.trna21-GlnCTG (70282391-70282464)
Gln (CTG) 74 bp Sc: 20.83
GGCAGTATGGTAGAGTGGTTAAGATCATGAACTCTGAAGTCAGAGATACTTGAATTTGAA

TGCTGGTTCTGTCA (SEQ ID NO: 331)
Homo_sapiens_chr20.trna1-GlnCTG (17803142-17803219)
Gln (CTG) 78 bp Sc: 21.25
GGCAGTGTAGCCCAGAGGTTCAAGGGCATTCGCTCTGGTATCAGAAGGGTCTGGGTTCAA

ATCCCTTGTGCACTGCTT (SEQ ID NO: 332)
Homo_sapiens_chr9.trna5-GlnCTG (125695415-125695343)
Gln (CTG) 73 bp Sc: 22.97
GAGCTGTAGCATAGTGATTAGGGACATGGACTCTGGAGCCAAATCTGCCTGGGTTCTAGT

CCCAGCTGTCTCA (SEQ ID NO: 333)
Homo_sapiens_chr12.trna3-GlnCTG (73137449-73137521)
Gln (CTG) 73 bp Sc: 34.73
GGTTCCATGGTGTAATGGTAAGCACCCTGGACTCTGAATCCAGCAACCAGAGTTCCAGTC

TCAGCGTGGACCT (SEQ ID NO: 334)
Homo_sapiens_chr1.trna114-GlnCTG (144943455-144943384)
Gln (CTG) 72 bp Sc: 40.01
GGTTCCATGGTGTAATGGTGACCACTTTGGACTCTGAATACAGTGATCAGAGTTCAAGTC

TCACTGGAACCT (SEQ ID NO: 335)
Homo_sapiens_chr1.trna120-GlnCTG (144090748-144090677)
Gln (CTG) 72 bp Sc: 44.40
GGTTCCATGGTGTAATGGTGAGCACTTTGGACTCTGAATACAGTGATCAGAGTTCAAGTC

TCACTGGGACCT (SEQ ID NO: 336)
Homo_sapiens_chr1.trna121-GlnCTG (143550864-143550793)
Gln (CTG) 72 bp Sc: 44.40
GGTTCCATGGTGTAATGGTGAGCACTTTGGACTCTGAATACAGTGATCAGAGTTCAAGTC

TCACTGGGACCT (SEQ ID NO: 337)
Homo_sapiens_chr1_random.trna1-GlnCTG (553277-553348)
Gln (CTG) 72 bp Sc: 44.40
GGTTCCATGGTGTAATGGTGAGCACTTTGGACTCTGAATACAGTGATCAGAGTTCAAGTC

TCACTGGGACCT (SEQ ID NO: 338)
Homo_sapiens_chr1.trna22-GlnCTG (146267561-146267632)
Gln (CTG) 72 bp Sc: 56.30
GGTTCCATGGTGTAATGGTAAGCACTCTGGACTCTGAATCCAGCCATCTGAGTTCGAGTC

TCTGTGGAACCT
```

(SEQ ID NO: 339)
*Homo_sapiens*_chr6.trna131-GlnCTG (27867185-27867114)
Gln (CTG) 72 bp Sc: 66.25
GGCCCCATGGTGTAATGGTCAGCACTCTGGACTCTGAATCCAGCGATCCGAGTTCAAATC

TCGGTGGGACCC (SEQ ID NO: 340)
*Homo_sapiens*_chr6.trna42-GlnCTG (27371191-27371262)
Gln (CTG) 72 bp Sc: 68.41
GGTTCCATGGTGTAATGGTTAGCACTCTGGACTCTGAATCCGGTAATCCGAGTTCAAATC

TCGGTGGAACCT (SEQ ID NO: 341)
*Homo_sapiens*_chr1.trna112-GlnCTG (146204077-146204006)
Gln (CTG) 72 bp Sc: 68.84
GGTTCCATGGTGTAATGGTAAGCACTCTGGACTCTGAATCCAGCGATCCGAGTTCGAGTC

TCGGTGGAACCT (SEQ ID NO: 342)
*Homo_sapiens*_chr1.trna28-GlnCTG (147452749-147452820)
Gln (CTG) 72 bp Sc: 68.84
GGTTCCATGGTGTAATGGTAAGCACTCTGGACTCTGAATCCAGCGATCCGAGTTCGAGTC

TCGGTGGAACCT (SEQ ID NO: 343)
*Homo_sapiens*_chr1.trna15-GlnCTG (144674661-144674732)
Gln (CTG) 72 bp Sc: 70.16
GGTTCCATGGTGTAATGGTGAGCACTCTGGACTCTGAATCCAGCGATCCGAGTTCGAGTC

TCGGTGGAACCT (SEQ ID NO: 344)
*Homo_sapiens*_chr1.trna19-GlnCTG (145971662-145971733)
Gln (CTG) 72 bp Sc: 70.16
GGTTCCATGGTGTAATGGTGAGCACTCTGGACTCTGAATCCAGCGATCCGAGTTCGAGTC

TCGGTGGAACCT (SEQ ID NO: 345)
*Homo_sapiens*_chr6.trna146-GlnCTG (27623581-27623510)
Gln (CTG) 72 bp Sc: 72.00
GGTTCCATGGTGTAATGGTTAGCACTCTGGACTCTGAATCCAGCGATCCGAGTTCAAGTC

TCGGTGGAACCT (SEQ ID NO: 346)
*Homo_sapiens*_chr15.trna7-GlnCTG (63948525-63948454)
Gln (CTG) 72 bp Sc: 73.65
GGTTCCATGGTGTAATGGTTAGCACTCTGGACTCTGAATCCAGCGATCCGAGTTCAAATC

TCGGTGGAACCT (SEQ ID NO: 347)
*Homo_sapiens*_chr17.trna3-GlnCTG (7963795-7963866)
Gln (CTG) 72 bp Sc: 73.65
GGTTCCATGGTGTAATGGTTAGCACTCTGGACTCTGAATCCAGCGATCCGAGTTCAAATC

TCGGTGGAACCT (SEQ ID NO: 348)
*Homo_sapiens*_chr6.trna1-GlnCTG (18944381-18944452)
Gln (CTG) 72 bp Sc: 73.65
GGTTCCATGGTGTAATGGTTAGCACTCTGGACTCTGAATCCAGCGATCCGAGTTCAAATC

TCGGTGGAACCT (SEQ ID NO: 349)
*Homo_sapiens*_chr6.trna49-GlnCTG (27595287-27595358)
Gln (CTG) 72 bp Sc: 73.65
GGTTCCATGGTGTAATGGTTAGCACTCTGGACTCTGAATCCAGCGATCCGAGTTCAAATC

TCGGTGGAACCT (SEQ ID NO: 350)
*Homo_sapiens*_chr6.trna99-GlnCTG (29017428-29017357)
Gln (CTG) 72 bp Sc: 73.65

```
                                                     (SEQ ID NO: 351)
Homo_sapiens_chr6.trna79-GlnTTG (37395973-37396045)
Gln (TTG) 73 bp Sc: 21.80
GTGCAGAGTAGTACAGTGGTTAAACCATGGTCTTTGGAGCCAGACTGCCTGGGGTCGGAT

CCCAGCTCTCACA (SEQ ID NO: 352)
Homo_sapiens_chr16.trna14-GlnTTG (3359814-3359885)
Gln (TTG) 72 bp Sc: 30.33
TAGGACTTGGTGTAATGGGTAGCACAGAGAATTTTGGATTCTCAGGGGTGGGTTCAATTC

CTTTCGTCCTAG (SEQ ID NO: 353)
Homo_sapiens_chr4.trna4-GlnTTG (40603572-40603500)
Gln (TTG) 73 bp Sc: 31.57
GACCATGTGGCCTAAGGGAAAAGACATCTCACTTTGGGTCAGAAGATTGAGGGTTCAAGT

CCTTTCATGGTCA (SEQ ID NO: 354)
Homo_sapiens_chr2.trna23-GlnTTG (117499050-117498979)
Gln (TTG) 72 bp Sc: 33.55
TAGGACATGGTGTAATAGGTAGAATGGAGAATTTTGAATTCTCAGGGGTAGGTTCAATTC

CTATAGTTCTAG (SEQ ID NO: 355)
Homo_sapiens_chr6.trna84-GlnTTG (145545552-145545623)
Gln (TTG) 72 bp Sc: 59.31
GGTCCCATGGTGTAATGGTTAGCACTCTGGGCTTTGAATCCAGCAATCCGAGTTCGAATC

TTGGTGGGACCT (SEQ ID NO: 356)
Homo_sapiens_chr6.trna130-GlnTTG (27871690-27871619)
Gln (TTG) 72 bp Sc: 68.31
GGCCCCATGGTGTAATGGTTAGCACTCTGGACTTTGAATCCAGCGATCCGAGTTCAAATC

TCGGTGGGACCT (SEQ ID NO: 357)
Homo_sapiens_chr6.trna173-GlnTTG (26420025-26419954)
Gln (TTG) 72 bp Sc: 68.31
GGCCCCATGGTGTAATGGTTAGCACTCTGGACTTTGAATCCAGCGATCCGAGTTCAAATC

TCGGTGGGACCT (SEQ ID NO: 358)
Homo_sapiens_chr6.trna174-GlnTTG (26419474-26419403)
Gln (TTG) 72 bp Sc: 68.31
GGCCCCATGGTGTAATGGTTAGCACTCTGGACTTTGAATCCAGCGATCCGAGTTCAAATC

TCGGTGGGACCT (SEQ ID NO: 359)
Homo_sapiens_chr17.trna16-GlnTTG (44624889-44624960)
Gln (TTG) 72 bp Sc: 73.77
GGTCCCATGGTGTAATGGTTAGCACTCTGGACTTTGAATCCAGCGATCCGAGTTCAAATC

TCGGTGGGACCT (SEQ ID NO: 360)
Homo_sapiens_chr1.trna29-GluCTC (147600896-147600964)
Glu (CTC) 69 bp Sc: 21.64
TCCCTGGTAGTCTAGTGGCTAAAGTTTGGCGCTCTCACCGCCGGGACTGGTTGATTCCAG

ATCAGGGGA (SEQ ID NO: 361)
Homo_sapiens_chr3.trna8-GluCTC (126895938-126895867)
Glu (CTC) 72 bp Sc: 29.87
CCCCTGGTGGTCTATCGGTTAGGATTCAGACCTCTCACCACTGCTACCCATGCTCGATTC

CTGGTCAGGGAA
```

-continued (SEQ ID NO: 362)
*Homo_sapiens*_chr18.trna1-GluCTC (41553749-41553820)
Glu (CTC) 72 bp Sc: 32.13
CCCCGGGTGGTGTAGTGGATGGGATTTGGCGCTCTCACCACCATGGCCCGGATTTGATTC

CCGGTCAGGGAA (SEQ ID NO: 363)
*Homo_sapiens*_chr8.trna3-GluCTC (59667352-59667422)
Glu (CTC) 71 bp Sc: 33.87
TCCTTGATGTCTAGTGGTTAGGATTTGGTGCTCTCACTGCAGCAGCCTGGGTTCATTTCT

CAGTCAGGGAA (SEQ ID NO: 364)
*Homo_sapiens*_chr13.trna4-GluCTC (40928132-40928061)
Glu (CTC) 72 bp Sc: 41.44
CCCCTGGTGGTCTAGTGCTTAGGATTCGGTGCTCTCACCGCTGCTGCCTGCGTTCGATTC

CCGGTCAGGGAA (SEQ ID NO: 365)
*Homo_sapiens*_chr1.trna59-GluCTC (247135070-247135141)
Glu (CTC) 72 bp Sc: 71.50
TCCCTGGTGGTCTAGTGGTTAGGATTCGGCGCTCTCACCGCCGCGGCCCGGGTTCGATTC

CCGGTCAGGAAA (SEQ ID NO: 366)
*Homo_sapiens*_chr1.trna116-GluCTC (144110661-144110590)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 367)
*Homo_sapiens*_chr1.trna71-GluCTC (159705884-159705813)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 368)
*Homo_sapiens*_chr1.trna74-GluCTC (159698504-159698433)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 369)
*Homo_sapiens*_chr1.trna77-GluCTC (159691093-159691022)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 370)
*Homo_sapiens*_chr1.trna80-GluCTC (159683713-159683642)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 371)
*Homo_sapiens*_chr6.trna77-GluCTC (29057955-29058026)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 372)
*Homo_sapiens*_chr6.trna87-GluCTC (126143157-126143086)
Glu (CTC) 72 bp Sc: 76.61
TCCCTGGTGGTCTAGTGGTTAGGATTCGGCGCTCTCACCGCCGCGGCCCGGGTTCGATTC

CCGGTCAGGGAA (SEQ ID NO: 373)
*Homo_sapiens*_chr1.trna31-GluTTC (147986426-147986494)
Glu (TTC) 69 bp Sc: 21.27
TCCCTGGTAGTCTAGTGGCTAAAGTTTGGCGCTTTCACCGCCGGGACTGGTTGATTCCAG

ATCAGGGGA (SEQ ID NO: 374)
*Homo_sapiens*_chr2.trna6-GluTTC (74977554-74977622)
Glu (TTC) 69 bp Sc: 23.54
GCCTGTGGTCTAGTGGTTAGAATTCAGTGTTTTCAGTGCTCTAGTCCAGGTTCAATTCCT

GGTCAGGGA (SEQ ID NO: 375)
*Homo_sapiens*_chr1.trna64-GluTTC (170424230-170424162)
Glu (TTC) 69 bp Sc: 26.19
CCCTGTGGTCTAGTGGTTAGGAGTTGGTGCTTTCGTCATGACAGCCCAGGTTCAATTCCT

GGTTAGAGA (SEQ ID NO: 376)
*Homo_sapiens*_chr14.trna14-GluTTC (31306637-31306567)
Glu (TTC) 71 bp Sc: 28.80
ACCCTGTGGTCTAGTGGCTAAGACTTTGTGCTTTCATTGCTGCATCCTAGGTTCAATTCC

CAGTCAGGGAA (SEQ ID NO: 377)
*Homo_sapiens*_chr1.trna94-GluTTC (147931051-147930979)
Glu (TTC) 73 bp Sc: 40.45
TCCCTGGTGGTCTAGTGGCTAGGATTCGGCGCTTTCACCGCCTGCAGCTCGAGTTCGATT

CCTGGTCAGGGAA (SEQ ID NO: 378)
*Homo_sapiens*_chr1.trna49-GluTTC (159849132-159849203)
Glu (TTC) 72 bp Sc: 54.07
GCGTTGGTGGTGTAGTGGTGAGCACAGCTGCCTTTCAAGCAGTTAACGCGGGTTCGATTC

CCGGGTAACGAA (SEQ ID NO: 379)
*Homo_sapiens*_chr1.trna133-GluTTC (16734432-16734361)
Glu (TTC) 72 bp Sc: 72.33
TCCCTGGTGGTCTAGTGGCTAGGATTCGGCGCTTTCACCGCCGCGGCCCGGGTTCGATTC

CCGGTCAGGGAA (SEQ ID NO: 380)
*Homo_sapiens*_chr1.trna84-GluTTC (159658578-159658507)
Glu (TTC) 72 bp Sc: 72.33
TCCCTGGTGGTCTAGTGGCTAGGATTCGGCGCTTTCACCGCCGCGGCCCGGGTTCGATTC

CCGGTCAGGGAA (SEQ ID NO: 381)
*Homo_sapiens*_chr1.trna5-GluTTC (17071665-17071736)
Glu (TTC) 72 bp Sc: 75.96
TCCCTGGTGGTCTAGTGGCTAGGATTCGGCGCTTTCACCGCCGCGGCCCGGGTTCGATTC

CCGGCCAGGGAA (SEQ ID NO: 382)
*Homo_sapiens*_chr13.trna3-GluTTC (44390133-44390062)
Glu (TTC) 72 bp Sc: 76.26
TCCCACATGGTCTAGCGGTTAGGATTCCTGGTTTTCACCCAGGCGGCCCGGGTTCGACTC

CCGGTGTGGGAA (SEQ ID NO: 383)
*Homo_sapiens*_chr15.trna11-GluTTC (23878545-23878474)
Glu (TTC) 72 bp Sc: 76.26
TCCCACATGGTCTAGCGGTTAGGATTCCTGGTTTTCACCCAGGCGGCCCGGGTTCGACTC

CCGGTGTGGGAA (SEQ ID NO: 384)
*Homo_sapiens*_chr13.trna5-GluTTC (40532945-40532874)
Glu (TTC) 72 bp Sc: 76.46

```
TCCCATATGGTCTAGCGGTTAGGATTCCTGGTTTTCACCCAGGTGGCCCGGGTTCGACTC

CCGGTATGGGAA
```

(SEQ ID NO: 385)
*Homo_sapiens*_chr2.trna20-GluTTC (130811242-130811171)
Glu (TTC) 72 bp Sc: 76.46
```
TCCCATATGGTCTAGCGGTTAGGATTCCTGGTTTTCACCCAGGTGGCCCGGGTTCGACTC

CCGGTATGGGAA
```

(SEQ ID NO: 386)
*Homo_sapiens*_chr1.trna2-GlyCCC (16926367-16926437)
Gly (CCC) 71 bp Sc: 63.06
```
GCCTTGGTGGTGCAGTGGTAGAATTCTCGCCTCCCACGTGGGAGACCCGGGTTCAATTCC

CGGCCAATGCA
```

(SEQ ID NO: 387)
*Homo_sapiens*_chr1.trna130-GlyCCC (16877423-16877353)
Gly (CCC) 71 bp Sc: 69.75
```
GCGTTGGTGGTTTAGTGGTAGAATTCTCGCCTCCCATGCGGGAGACCCGGGTTCAATTCC

CGGCCACTGCA
```

(SEQ ID NO: 388)
*Homo_sapiens*_chr17.trna13-GlyCCC (19704767-19704837)
Gly (CCC) 71 bp Sc: 70.13
```
GCATTGGTGGTTCAATGGTAGAATTCTCGCCTCCCACGCAGGAGACCCAGGTTCGATTCC

TGGCCAATGCA
```

(SEQ ID NO: 389)
*Homo_sapiens*_chr16.trna34-GlyCCC (626807-626737)
Gly (CCC) 71 bp Sc: 76.98
```
GCGCCGCTGGTGTAGTGGTATCATGCAAGATTCCCATTCTTGCGACCCGGGTTCGATTCC

CGGGCGGCGCA
```

(SEQ ID NO: 390)
*Homo_sapiens*_chr2.trna27-GlyCCC (70329697-70329627)
Gly (CCC) 71 bp Sc: 76.98
```
GCGCCGCTGGTGTAGTGGTATCATGCAAGATTCCCATTCTTGCGACCCGGGTTCGATTCC

CGGGCGGCGCA
```

(SEQ ID NO: 391)
*Homo_sapiens*_chr1.trna132-GlyCCC (16745091-16745021)
Gly (CCC) 71 bp Sc: 78.31
```
GCATTGGTGGTTCAGTGGTAGAATTCTCGCCTCCCACGCGGGAGACCCGGGTTCAATTCC

CGGCCAATGCA
```

(SEQ ID NO: 392)
*Homo_sapiens*_chr1.trna4-GlyCCC (17061003-17061073)
Gly (CCC) 71 bp Sc: 78.31
```
GCATTGGTGGTTCAGTGGTAGAATTCTCGCCTCCCACGCGGGAGACCCGGGTTCAATTCC

CGGCCAATGCA
```

(SEQ ID NO: 393)
*Homo_sapiens*_chr6.trna82-GlyGCC (142620469-142620539)
Gly (GCC) 71 bp Sc: 46.73
```
GCATGGGTGATTCAGTGGTAGAATTTTCACCTGCCATGCAGGAGGTCCAGGTTCATTTCC

TGGCCTATGCA
```

(SEQ ID NO: 394)
*Homo_sapiens*_chr16.trna18-GlyGCC (69380098-69380168)
Gly (GCC) 71 bp Sc: 56.35
```
GCATTGGTGGTTCAGTGGTAGAATTCTCGCCTGCCATGCGGGCGGCCGGGCTTCGATTCC

TGGCCAATGCA
```

(SEQ ID NO: 395)
*Homo_sapiens*_chr1.trna43-GlyGCC (159716980-159717050)
Gly (GCC) 71 bp Sc: 69.02
```
GCATAGGTGGTTCAGTGGTAGAATTCTTGCCTGCCACGCAGGAGGCCCAGGTTTGATTCC

TGGCCCATGCA
```

-continued (SEQ ID NO: 396)
*Homo_sapiens*_chr16.trna25-GlyGCC (69369685-69369615)
Gly (GCC) 71 bp Sc: 73.97
GCATTGGTGGTTCAGTGGTAGAATTCTCGCCTGCCACGCGGGAGGCCCGGGTTTGATTCC

CGGCCAGTGCA (SEQ ID NO: 397)
*Homo_sapiens*_chr1.trna68-GlyGCC (159760331-159760261)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 398)
*Homo_sapiens*_chr16.trna19-GlyGCC (69380911-69380981)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 399)
*Homo_sapiens*_chr16.trna24-GlyGCC (69370513-69370443)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 400)
*Homo_sapiens*_chr17.trna5-GlyGCC (7969789-7969859)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 401)
*Homo_sapiens*_chr2.trna19-GlyGCC (156965975-156965905)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 402)
*Homo_sapiens*_chr6.trna128-GlyGCC (27978735-27978665)
Gly (GCC) 71 bp Sc: 81.62
GCATTGGTGGTTCAGTGGTAGAATTCTCGCCTGCCACGCGGGAGGCCCGGGTTCGATTCC

CGGCCAATGCA (SEQ ID NO: 403)
*Homo_sapiens*_chr1.trna35-GlyGCC (159679718-159679788)
Gly (GCC) 71 bp Sc: 82.15
GCATGGGTGGTTCAGTGGTAGAATTCTCGCCTGCCACGCGGGAGGCCCGGGTTCGATTCC

CGGCCCATGCA (SEQ ID NO: 404)
*Homo_sapiens*_chr1.trna37-GlyGCC (159687091-159687161)
Gly (GCC) 71 bp Sc: 82.15
GCATGGGTGGTTCAGTGGTAGAATTCTCGCCTGCCACGCGGGAGGCCCGGGTTCGATTCC

CGGCCCATGCA (SEQ ID NO: 405)
*Homo_sapiens*_chr1.trna39-GlyGCC (159694522-159694592)
Gly (GCC) 71 bp Sc: 82.15
GCATGGGTGGTTCAGTGGTAGAATTCTCGCCTGCCACGCGGGAGGCCCGGGTTCGATTCC

CGGCCCATGCA (SEQ ID NO: 406)
*Homo_sapiens*_chr1.trna41-GlyGCC (159701882-159701952)
Gly (GCC) 71 bp Sc: 82.15
GCATGGGTGGTTCAGTGGTAGAATTCTCGCCTGCCACGCGGGAGGCCCGGGTTCGATTCC

CGGCCCATGCA (SEQ ID NO: 407)
*Homo_sapiens*_chr21.trna2-GlyGCC (17749048-17748978)
Gly (GCC) 71 bp Sc: 82.15
GCATGGGTGGTTCAGTGGTAGAATTCTCGCCTGCCACGCGGGAGGCCCGGGTTCGATTCC

CGGCCCATGCA (SEQ ID NO: 408)
*Homo_sapiens*_chr1.trna82-GlyTCC (159676656-159676585)
Gly (TCC) 72 bp Sc: 55.96
GCGTTGGTGGTATAGTGGTGAGCATAGTTGCCTTCCAAGCAGTTGACCCGGGCTCGATTC

CCGCCCAACGCA (SEQ ID NO: 409)
*Homo_sapiens*_chr17.trna10-GlyTCC (8065591-8065662)
Gly (TCC) 72 bp Sc: 71.94
GCGTTGGTGGTATAGTGGTAAGCATAGCTGCCTTCCAAGCAGTTGACCCGGGTTCGATTC

CCGGCCAACGCA (SEQ ID NO: 410)
*Homo_sapiens*_chr1.trna117-GlyTCC (144109292-144109221)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 411)
*Homo_sapiens*_chr1.trna45-GlyTCC (159767527-159767598)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 412)
*Homo_sapiens*_chr1.trna70-GlyTCC (159706242-159706171)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 413)
*Homo_sapiens*_chr1.trna73-GlyTCC (159698861-159698790)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 414)
*Homo_sapiens*_chr1.trna76-GlyTCC (159691451-159691380)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 415)
*Homo_sapiens*_chr1.trna79-GlyTCC (159684070-159683999)
Gly (TCC) 72 bp Sc: 73.26
GCGTTGGTGGTATAGTGGTGAGCATAGCTGCCTTCCAAGCAGTTGACCCGGGTTCGATTC

CCGGCCAACGCA (SEQ ID NO: 416)
*Homo_sapiens*_chr19.trna2-GlyTCC (4675082-4675153)
Gly (TCC) 72 bp Sc: 76.83
GCGTTGGTGGTATAGTGGTTAGCATAGCTGCCTTCCAAGCAGTTGACCCGGGTTCGATTC

CCGGCCAACGCA (SEQ ID NO: 417)
*Homo_sapiens*_chr3.trna4-HisGTG (149799324-149799253)
His (GTG) 72 bp Sc: 22.51
GCAGTGACTGTATAGTGGTTAGCACTCTGTGTTGTGGCCACAGCAACCATGGTTCAAATC

TGAGTCATGACA (SEQ ID NO: 418)
*Homo_sapiens*_chr1.trna106-HisGTG (147422523-147422452)
His (GTG) 72 bp Sc: 61.09

```
GCCATGATCGTATAGTGGTTAGTACTCTGCGCTGTGGCCGCAGCAACCTCGGTTCGAATC

CGAGTCACGGCA
```

(SEQ ID NO: 419)
*Homo_sapiens*_chr1.trna111-HisGTG (146241540-146241469)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 420)
*Homo_sapiens*_chr1.trna118-HisGTG (144108309-144108238)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 421)
*Homo_sapiens*_chr1.trna16-HisGTG (145011397-145011468)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 422)
*Homo_sapiens*_chr1.trna21-HisGTG (146220095-146220166)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 423)
*Homo_sapiens*_chr15.trna1-HisGTG (43280641-43280712)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 424)
*Homo_sapiens*_chr15.trna8-HisGTG (43279974-43279903)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 425)
*Homo_sapiens*_chr15.trna9-HisGTG (43278167-43278096)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 426)
*Homo_sapiens*_chr6.trna33-HisGTG (27233885-27233956)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 427)
*Homo_sapiens*_chr9.trna7-HisGTG (14424009-14423938)
His (GTG) 72 bp Sc: 64.63
```
GCCGTGATCGTATAGTGGTTAGTACTCTGCGTTGTGGCCGCAGCAACCTCGGTTCGAATC

CGAGTCACGGCA
```

(SEQ ID NO: 428)
*Homo_sapiens*_chr6.trna38-IleAAT (27349718-27349791)
Ile (AAT) 74 bp Sc: 75.35
```
GGCTGGTTAGTTCAGTTGGTTAGAGCGTGGTGCTAATAACGCCAAGGTCGTGGGTTCGAT

CCCCATATCGGCCA
```

(SEQ ID NO: 429)
*Homo_sapiens*_chr6.trna57-IleAAT (27744341-27744414)
Ile (AAT) 74 bp Sc: 76.09
```
GGCCGGTTAGCTCAGTCGGTAGAGCGTGGTGCTAATAACGCCAAGGTCGCGGGTTCGAT

CCCCGTACGGGCCA
```

-continued (SEQ ID NO: 430)
*Homo_sapiens*_chr6.trna165-IleAAT (26829273-26829200)
Ile (AAT) 74 bp Sc: 78.57
GGCCGGTTAGCTCAGTTGGTCAGAGCGTGGTGCTAATAACGCCAAGGTCGCGGGTTCGAT

CCCCGTACGGGCCA (SEQ ID NO: 431)
*Homo_sapiens*_chr6.trna28-IleAAT (26888811-26888884)
Ile (AAT) 74 bp Sc: 78.57
GGCCGGTTAGCTCAGTTGGTCAGAGCGTGGTGCTAATAACGCCAAGGTCGCGGGTTCGAT

CCCCGTACGGGCCA (SEQ ID NO: 432)
*Homo_sapiens*_chr6.trna163-IleAAT (26853307-26853234)
Ile (AAT) 74 bp Sc: 79.57
GGCCGGTTAGCTCAGTTGGTTAGAGCGTGGTGCTAATAACGCTAAGGTCGCGGGTTCGAT

CCCCGTACGGGCCA (SEQ ID NO: 433)
*Homo_sapiens*_chr14.trna10-IleAAT (101853182-101853255)
Ile (AAT) 74 bp Sc: 80.66
GGCCGGTTAGCTCAGTTGGTTAGAGCGTGGTGCTAATAACGCCAAGGTCGCGGGTTCGAT

CCCCGTACGGGCCA (SEQ ID NO: 434)
*Homo_sapiens*_chr17.trna9-IleAAT (8031636-8031709)
Ile (AAT) 74 bp Sc: 80.66
GGCCGGTTAGCTCAGTTGGTTAGAGCGTGGTGCTAATAACGCCAAGGTCGCGGGTTCGAT

CCCCGTACGGGCCA (SEQ ID NO: 435)
*Homo_sapiens*_chr6.trna11-IleAAT (26662329-26662402)
Ile (AAT) 74 bp Sc: 80.66
GGCCGGTTAGCTCAGTTGGTTAGAGCGTGGTGCTAATAACGCCAAGGTCGCGGGTTCGAT

CCCCGTACGGGCCA (SEQ ID NO: 436)
*Homo_sapiens*_chr6.trna154-IleAAT (27313402-27313329)
Ile (AAT) 74 bp Sc: 80.66
GGCCGGTTAGCTCAGTTGGTTAGAGCGTGGTGCTAATAACGCCAAGGTCGCGGGTTCGAT

CCCCGTACGGGCCA (SEQ ID NO: 437)
*Homo_sapiens*_chr6.trna158-IleAAT (27253046-27252973)
Ile (AAT) 74 bp Sc: 80.66
GGCCGGTTAGCTCAGTTGGTTAGAGCGTGGTGCTAATAACGCCAAGGTCGCGGGTTCGAT

CCCCGTACGGGCCA (SEQ ID NO: 438)
*Homo_sapiens*_chr17.trna34-IleAAT (8071107-8071034)
Ile (AAT) 74 bp Sc: 80.89
GGCCGGTTAGCTCAGTTGGTTAGAGCGTGGTGCTAATAACGCCAAGGTCGCGGGTTCGAA

CCCCGTACGGGCCA (SEQ ID NO: 439)
*Homo_sapiens*_chr6.trna153-IleAAT (27351042-27350969)
Ile (AAT) 74 bp Sc: 82.10
GGCTGGTTAGCTCAGTTGGTTAGAGCGTGGTGCTAATAACGCCAAGGTCGCGGGTTCGAT

CCCCGTACTGGCCA (SEQ ID NO: 440)
*Homo_sapiens*_chr6.trna59-IleAAT (27763946-27764019)
Ile (AAT) 74 bp Sc: 83.32
GGCCGGTTAGCTCAGTTGGTTAGAGCGTGGTGCTAATAACGCCAAGGTCGCGGGTTCGAT

CCCCGTACTGGCCA (SEQ ID NO: 441)
*Homo_sapiens*_chr6.trna80-IleAAT (58257213-58257286)
Ile (AAT) 74 bp Sc: 83.55
GGCCGGTTAGCTCAGTTGGTTAGAGCGTGGCGCTAATAACGCCAAGGTCGCGGGTTCGAT

CCCCGTACGGGCCA (SEQ ID NO: 442)
*Homo_sapiens*_chrX.trna5-IleGAT (3843344-3843271)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 443)
*Homo_sapiens*_chrX.trna6-IleGAT (3804915-3804842)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 444)
*Homo_sapiens*_chrX.trna7-IleGAT (3766491-3766418)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 445)
*Homo_sapiens*_chrX_random.trna1-IleGAT (118398-118471)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 446)
*Homo_sapiens*_chrX random.trna2-IleGAT (406943-407016)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 447)
*Homo_sapiens*_chrX random.trna3-IleGAT (465544-465617)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 448)
*Homo_sapiens*_chrX random.trna4-IleGAT (399021-398948)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 449)
*Homo_sapiens*_chrX random.trna5-IleGAT (86496-86423)
Ile (GAT) 74 bp Sc: 72.42
GGCCGGTTAGCTCAGTTGGTAAGAGCGTGGTGCTGATAACACCAAGGTCGCGGGCTCGAC

TCCCGCACCGGCCA (SEQ ID NO: 450)
Homo_*sapiens*_chr6.trna29-IleTAT (27096104-27096197)
Ile (TAT) 94 bp Sc: 67.58
GCTCCAGTGGCGCAATCGGTTAGCGCGCGGTACTTATATGGCAGTATGTGTGCGAGTGAT

GCCGAGGTTGTGAGTTCGAGCCTCACCTGGAGCA (SEQ ID NO: 451)
Homo_*sapiens*_chr6.trna55-IleTAT (27707179-27707272)
Ile (TAT) 94 bp Sc: 68.23
GCTCCAGTGGCGCAATCGGTTAGCGCGCGGTACTTATACAACAGTATATGTGCGGGTGAT

GCCGAGGTTGTGAGTTCGAGCCTCACCTGGAGCA (SEQ ID NO: 452)
Homo_*sapiens*_chr6.trna63-IleTAT (28613346-28613439)
Ile (TAT) 94 bp Sc: 65.86

```
GCTCCAGTGGCGCAATCGGTTAGCGCGCGGTACTTATAAGACAGTGCACCTGTGAGCAAT

GCCGAGGTTGTGAGTTCAAGCCTCACCTGGAGCA
```

(SEQ ID NO: 453)
*Homo_sapiens*_chr2.trna5-IleTAT (42891180-42891272)
Ile (TAT) 93 bp Sc: 68.11
```
GCTCCAGTGGCGCAATCGGTTAGCGCGCGGTACTTATACAGCAGTACATGCAGAGCAATG

CCGAGGTTGTGAGTTCGAGCCTCACCTGGAGCA
```

(SEQ ID NO: 454)
*Homo_sapiens*_chr19.trna10-IleTAT (44594740-44594648)
Ile (TAT) 93 bp Sc: 68.39
```
GCTCCAGTGGCGCAATCGGTTAGCGCGCGGTACTTATATGACAGTGCGAGCGGAGCAATG

CCGAGGTTGTGAGTTCGATCCTCACCTGGAGCA
```

(SEQ ID NO: 455)
*Homo_sapiens*_chr3.trna5-LeuAAG (149703999-149703918)
Leu (AAG) 82 bp Sc: 20.79
```
GGTAGCATGGCTGAGTGGTCTAAGATTCTGAATTAAGTCTCCAGTCTCTTTGGGGCGTG

GTTTTCAATCCCACCGCTGCTA
```

(SEQ ID NO: 456)
*Homo_sapiens*_chr20.trna6-LeuAAG (48385830-48385749)
Leu (AAG) 82 bp Sc: 40.72
```
GGTAGGGTGGCCGAGCGGTCTAAGGCACTGTATTAAGACTCCAGTCTCTTCAGAGGCATG

GGTTTGAATCCCACTGCTGCCA
```

(SEQ ID NO: 457)
*Homo_sapiens*_chr2.trna4-LeuAAG (30131072-30131144)
Leu (AAG) 73 bp Sc: 46.12
```
GGGCCAGTGGCTCAATGGATAATGCGTCTGACTAAGAATCAGAAGATTCCAGCCTTGACT

CCTGGCTGGCTCA
```

(SEQ ID NO: 458)
*Homo_sapiens*_chr6.trna126-LeuAAG (28554460-28554379)
Leu (AAG) 82 bp Sc: 59.09
```
GGTAGCGTGGCCGAGTGGTCTAAGACGCTGGATTAAGGCTCCAGTCTCTTCGGGGCGTG

GGTTTGAATCCCACCGCTGCCA
```

(SEQ ID NO: 459)
*Homo_sapiens*_chr6.trna78-LeuAAG (29064758-29064839)
Leu (AAG) 82 bp Sc: 68.10
```
GGTAGCGTGGCCGAGCGGTCTAAGGCGCTGGATTAAGGCTCCAGTCTCTTCGGGGCGTG

GGTTCAAATCCCACCGCTGCCA
```

(SEQ ID NO: 460)
*Homo_sapiens*_chr14.trna1-LeuAAG (20148131-20148212)
Leu (AAG) 82 bp Sc: 69.84
```
GGTAGCGTGGCCGAGCGGTCTAAGGCGCTGGATTAAGGCTCCAGTCTCTTCGGGGCGTG

GGTTCGAATCCCACCGCTGCCA
```

(SEQ ID NO: 461)
*Homo_sapiens*_chr16.trna16-LeuAAG (22215962-22216043)
Leu (AAG) 82 bp Sc: 69.84
```
GGTAGCGTGGCCGAGCGGTCTAAGGCGCTGGATTAAGGCTCCAGTCTCTTCGGGGCGTG

GGTTCGAATCCCACCGCTGCCA
```

(SEQ ID NO: 462)
*Homo_sapiens*_chr5.trna7-LeuAAG (180547307-180547388)
Leu (AAG) 82 bp Sc: 69.84
```
GGTAGCGTGGCCGAGCGGTCTAAGGCGCTGGATTAAGGCTCCAGTCTCTTCGGGGCGTG

GGTTCGAATCCCACCGCTGCCA
```

(SEQ ID NO: 463)
*Homo_sapiens*_chr6.trna98-LeuAAG (29019459-29019378)
Leu (AAG) 82 bp Sc: 69.84
```
GGTAGCGTGGCCGAGCGGTCTAAGGCGCTGGATTAAGGCTCCAGTCTCTTCGGGGCGTG

GGTTCGAATCCCACCGCTGCCA
```

```
                                              (SEQ ID NO: 464)
Homo_sapiens_chr5.trna16-LeuAAG (180533731-180533650)
Leu (AAG) 82 bp Sc: 71.96
GGTAGCGTGGCCGAGCGGTCTAAGGCGCTGGATTAAGGCTCCAGTCTCTTCGGAGGCGTG

GGTTCGAATCCCACCGCTGCCA (SEQ ID NO: 465)
Homo_sapiens_chr5.trna19-LeuAAG (180457161-180457080)
Leu (AAG) 82 bp Sc: 71.96
GGTAGCGTGGCCGAGCGGTCTAAGGCGCTGGATTAAGGCTCCAGTCTCTTCGGAGGCGTG

GGTTCGAATCCCACCGCTGCCA (SEQ ID NO: 466)
Homo_sapiens_chr5.trna3-LeuAAG (180461446-180461527)
Leu (AAG) 82 bp Sc: 71.96
GGTAGCGTGGCCGAGCGGTCTAAGGCGCTGGATTAAGGCTCCAGTCTCTTCGGAGGCGTG

GGTTCGAATCCCACCGCTGCCA (SEQ ID NO: 467)
Homo_sapiens_chr1.trna66-LeuCAA (159848443-159848360)
Leu (CAA) 84 bp Sc: 59.01
GTCAGGATGGCCGAGCAGTCTTAAGGCGCTGCGTTCAAATCGCACCCTCCGCTGGAGGCG

TGGGTTCGAATCCCACTTTTGACA (SEQ ID NO: 468)
Homo_sapiens_chr11.trna1-LeuCAA (9253366-9253439)
Leu (CAA) 74 bp Sc: 60.99
GCCTCCTTAGTGCAGTAGGTAGCGCATCAGTCTCAAAATCTGAATGGTCCTGAGTTCAAG

CCTCAGAGGGGGCA (SEQ ID NO: 469)
Homo_sapiens_chr1.trna58-LeuCAA (247134677-247134782)
Leu (CAA) 106 bp Sc: 65.69
GTCAGGATGGCCGAGTGGTCTAAGGCGCCAGACTCAAGGTAAGCACCTTGCCTGCGGGCT

TTCTGGTCTCCGGATGGAGGCGTGGGTTCGAATCCCACTTCTGACA (SEQ ID NO: 470)
Homo_sapiens_chr6.trna141-LeuCAA (27678433-27678327)
Leu (CAA) 107 bp Sc: 68.19
GTCAGGATGGCCGAGTGGTCTAAGGCGCCAGACTCAAGTTGCTACTTCCCAGGTTTGGGG

CTTCTGGTCTCCGCATGGAGGCGTGGGTTCGAATCCCACTTCTGACA (SEQ ID NO: 471)
Homo_sapiens_chr6.trna140-LeuCAA (27681503-27681396)
Leu (CAA) 108 bp Sc: 68.53
GTCAGGATGGCCGAGTGGTCTAAGGCGCCAGACTCAAGCTTACTGCTTCCTGTGTTCGGG

TCTTCTGGTCTCCGTATGGAGGCGTGGGTTCGAATCCCACTTCTGACA (SEQ ID NO: 472)
Homo_sapiens_chr6.trna100-LeuCAA (28972084-28971979)
Leu (CAA) 106 bp Sc: 68.23
GTCAGGATGGCCGAGTGGTCTAAGGCGCCAGACTCAAGCTAAGCTTCCTCCGCGGTGGGG

ATTCTGGTCTCCAATGGAGGCGTGGGTTCGAATCCCACTTCTGACA (SEQ ID NO: 473)
Homo_sapiens_chr6.trna74-LeuCAA (29016809-29016913)
Leu (CAA) 105 bp Sc: 69.73
GTCAGGATGGCCGAGTGGTCTAAGGCGCCAGACTCAAGCTTGGCTTCCTCGTGTTGAGGA

TTCTGGTCTCCAATGGAGGCGTGGGTTCGAATCCCACTTCTGACA (SEQ ID NO: 474)
Homo_sapiens_chr5.trna20-LeuCAG (159324696-159324619)
Leu (CAG) 78 bp Sc: 20.45
GGCAGTGGAGTTTAGTGGTTAAGGACCTGCTCAGACATCACAGGTAGGTAGATCTGGGTT

CAAACCCTAGCCCTGGCA
```

(SEQ ID NO: 475)
*Homo_sapiens*_chr16.trna17-LeuCAG (55891364-55891446)
Leu (CAG) 83 bp Sc: 75.90
GTCAGGATGGCCGAGCGGTCTAAGGCGCTGCGTTCAGGTCGCAGTCTCCCCTGGAGGCGT

GGGTTCGAATCCCACTTCTGACA (SEQ ID NO: 476)
*Homo_sapiens*_chr16.trna26-LeuCAG (55891975-55891893)
Leu (CAG) 83 bp Sc: 75.90
GTCAGGATGGCCGAGCGGTCTAAGGCGCTGCGTTCAGGTCGCAGTCTCCCCTGGAGGCGT

GGGTTCGAATCCCACTTCTGACA (SEQ ID NO: 477)
*Homo_sapiens*_chr1.trna34-LeuCAG (159677947-159678029)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 478)
*Homo_sapiens*_chr1.trna36-LeuCAG (159685365-159685447)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 479)
*Homo_sapiens*_chr1.trna38-LeuCAG (159692746-159692828)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 480)
*Homo_sapiens*_chr1.trna40-LeuCAG (159700156-159700238)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 481)
*Homo_sapiens*_chr1.trna42-LeuCAG (159707537-159707619)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 482)
*Homo_sapiens*_chr1.trna67-LeuCAG (159766838-159766756)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 483)
*Homo_sapiens*_chr6.trna7-LeuCAG (26629415-26629497)
Leu (CAG) 83 bp Sc: 77.22
GTCAGGATGGCCGAGCGGTCTAAGGCGCTGCGTTCAGGTCGCAGTCTCCCCTGGAGGCGT

GGGTTCGAATCCCACTCCTGACA (SEQ ID NO: 484)
*Homo_sapiens*_chrX.trna2-LeuTAA (55224554-55224480)
Leu (TAA) 75 bp Sc: 28.07
GTTAAGATGGCAGAGCCCGGCAATTGCATAAGACTTAAAACTTTATAATCAGAGGTTCAA

CTCCTCTCATTAACA (SEQ ID NO: 485)
*Homo_sapiens*_chr6.trna81-LeuTAA (69971099-69971181)
Leu (TAA) 83 bp Sc: 34.00
ACTCATTTGGCTGAGTGGTTAAGGCATTGGACTTAAGATCCAATGGAGTAGTGGCTGTGT

GGGTTTAAACCCCACTACTGGTA (SEQ ID NO: 486)
*Homo_sapiens*_chr4.trna2-LeuTAA (156604502-156604428)
Leu (TAA) 75 bp Sc: 48.70

GTTAAGATGGCAGAGCCTGGTAATTGCATAAAACTTAAAATTTTATAATCAGAGGTTCAA

CTCCTCTTCTTAACA (SEQ ID NO: 487)
*Homo_sapiens*_chr6.trna155-LeuTAA (27306395-27306313)
Leu (TAA) 83 bp Sc: 74.34
ACCGGGATGGCTGAGTGGTTAAGGCGTTGGACTTAAGATCCAATGGACAGGTGTCCGCGT

GGGTTCGAGCCCCACTCCCGGTA (SEQ ID NO: 488)
*Homo_sapiens*_chr11.trna4-LeuTAA (59075804-59075886)
Leu (TAA) 83 bp Sc: 79.52
ACCAGAATGGCCGAGTGGTTAAGGCGTTGGACTTAAGATCCAATGGATTCATATCCGCGT

GGGTTCGAACCCCACTTCTGGTA (SEQ ID NO: 489)
*Homo_sapiens*_chr6.trna134-LeuTAA (27796959-27796877)
Leu (TAA) 83 bp Sc: 80.48
ACCGGGATGGCCGAGTGGTTAAGGCGTTGGACTTAAGATCCAATGGGCTGGTGCCCGCGT

GGGTTCGAACCCCACTCTCGGTA (SEQ ID NO: 490)
*Homo_sapiens*_chr6.trna83-LeuTAA (144579377-144579459)
Leu (TAA) 83 bp Sc: 80.77
ACCAGGATGGCCGAGTGGTTAAGGCGTTGGACTTAAGATCCAATGGACATATGTCCGCGT

GGGTTCGAACCCCACTCCTGGTA (SEQ ID NO: 491)
*Homo_sapiens*_chr16.trna27-LeuTAG (22114614-22114533)
Leu (TAG) 82 bp Sc: 68.14
GGTAGCGTGGCCGAGTGGTCTAAGGCGCTGGATTTAGGCTCCAGTCATTTCGATGGCGTG

GGTTCGAATCCCACCGCTGCCA (SEQ ID NO: 492)
*Homo_sapiens*_chr14.trna2-LeuTAG (20163369-20163450)
Leu (TAG) 82 bp Sc: 68.82
GGTAGTGTGGCCGAGCGGTCTAAGGCGCTGGATTTAGGCTCCAGTCTCTTCGGGGGCGTG

GGTTCGAATCCCACCACTGCCA (SEQ ID NO: 493)
*Homo_sapiens*_chr17.trna42-LeuTAG (7964438-7964357)
Leu (TAG) 82 bp Sc: 72.19
GGTAGCGTGGCCGAGCGGTCTAAGGCGCTGGATTTAGGCTCCAGTCTCTTCGGAGGCGTG

GGTTCGAATCCCACCGCTGCCA (SEQ ID NO: 494)
*Homo_sapiens*_chr11.trna2-LysCTT (51216476-51216548)
Lys (CTT) 73 bp Sc: 40.00
AACCGAATAGCTTAGTTGATGAAGCGTGAGACTCTTAATCTCAGGGTAGTGGGTTCAAGC

CCCACATTGGACA (SEQ ID NO: 495)
*Homo_sapiens*_chr19.trna6-LysCTT (57117280-57117208)
Lys (CTT) 73 bp Sc: 51.97
CTGCAGCTAGCTCAGTCGGTAGAGCATGAGACTCTTAATCTCAGGGTCATGGGTTCGTGC

CCCATGTTGGGTG (SEQ ID NO: 496)
*Homo_sapiens*_chr19.trna5-LysCTT (40758590-40758662)
Lys (CTT) 73 bp Sc: 52.67
GCCCAGCTAGCTCAGTCGGTAGAGCATAAGACTCTTAATCTCAGGGTTGTGGATTCGTGC

CCCATGCTGGGTG (SEQ ID NO: 497)
*Homo_sapiens*_chr5.trna24-LysCTT (26234368-26234296)
Lys (CTT) 73 bp Sc: 53.34
GCCCGACTACCTCAGTCGGTGGAGCATGGGACTCTTCATCCCAGGGTTGTGGGTTCGAGC

CCCACATTGGGCA

-continued (SEQ ID NO: 498)
*Homo_sapiens*_chr16.trna5-LysCTT (3154940-3155012)
Lys (CTT) 73 bp Sc: 54.80
GCCTGGCTAGCTCAGTCGGCAAAGCATGAGACTCTTAATCTCAGGGTCGTGGGCTCGAGC

TCCATGTTGGGCG (SEQ ID NO: 499)
*Homo_sapiens*_chr1.trna127-LysCTT (55196202-55196130)
Lys (CTT) 73 bp Sc: 58.75
GCCCAGCTAGCTCAGTCGGTAGAGCATGAGACTCTTAATCTCAGGGTCATGGGTTTGAGC

CCCACGTTTGGTG (SEQ ID NO: 500)
*Homo_sapiens*_chr18.trna4-LysCTT (41923341-41923269)
Lys (CTT) 73 bp Sc: 60.42
GACGAGCTAGCTCAGTCGGTAGAGCATGGGACTCTTAATCCCAGGGTCGTGGGTTTGAGC

CCCATGTTGGGCA (SEQ ID NO: 501)
*Homo_sapiens*_chr16.trna30-LysCTT (3170628-3170556)
Lys (CTT) 73 bp Sc: 64.91
GCCCGGCTAGCTCAGTCGATAGAGCATGAGACTCTTAATCTCAGGGTCGTGGGTTCGAGC

CGCACGTTGGGCG (SEQ ID NO: 502)
*Homo_sapiens*_chr16.trna10-LysCTT (3181502-3181574)
Lys (CTT) 73 bp Sc: 74.61
GCCCGGCTAGCTCAGTCGGTAGAGCATGGGACTCTTAATCTCAGGGTCGTGGGTTCGAGC

CCCACGTTGGGCG (SEQ ID NO: 503)
*Homo_sapiens*_chr16.trna32-LysCTT (3147479-3147407)
Lys (CTT) 73 bp Sc: 76.19
GCCCGGCTAGCTCAGTCGGTAGAGCATGAGACCCTTAATCTCAGGGTCGTGGGTTCGAGC

CCCACGTTGGGCG (SEQ ID NO: 504)
*Homo_sapiens*_chr1.trna119-LysCTT (144106951-144106879)
Lys (CTT) 73 bp Sc: 80.47
GCCCGGCTAGCTCAGTCGGTAGAGCATGAGACTCTTAATCTCAGGGTCGTGGGTTCGAGC

CCCACGTTGGGCG (SEQ ID NO: 505)
*Homo_sapiens*_chr16.trna7-LysCTT (3165693-3165765)
Lys (CPT) 73 bp Sc: 80.47
GCCCGGCTAGCTCAGTCGGTAGAGCATGAGACTCTTAATCTCAGGGTCGTGGGTTCGAGC

CCCACGTTGGGCG (SEQ ID NO: 506)
*Homo_sapiens*_chr5.trna11-LysCTT (180581657-180581585)
Lys (CTT) 73 bp Sc: 80.47
GCCCGGCTAGCTCAGTCGGTAGAGCATGAGACTCTTAATCTCAGGGTCGTGGGTTCGAGC

CCCACGTTGGGCG (SEQ ID NO: 507)
*Homo_sapiens*_chr5.trna9-LysCTT (180567361-180567433)
Lys (CTT) 73 bp Sc: 80.47
GCCCGGCTAGCTCAGTCGGTAGAGCATGAGACTCTTAATCTCAGGGTCGTGGGTTCGAGC

CCCACGTTGGGCG (SEQ ID NO: 508)
*Homo_sapiens*_chr6.trna13-LysCTT (26664753-26664825)
Lys (CTT) 73 bp Sc: 80.47
GCCCGGCTAGCTCAGTCGGTAGAGCATGAGACTCTTAATCTCAGGGTCGTGGGTTCGAGC

CCCACGTTGGGCG (SEQ ID NO: 509)
*Homo_sapiens*_chr14.trna13-LysCTT (57776438-57776366)
Lys (CPT) 73 bp Sc: 80.72
GCCCGGCTAGCTCAGTCGGTAGAGCATGGGACTCTTAATCCCAGGGTCGTGGGTTCGAGC

CCCACGTTGGGCG (SEQ ID NO: 510)
*Homo_sapiens*_chr15.trna2-LysCTT (76939959-76940031)
Lys (CTT) 73 bp Sc: 80.72
GCCCGGCTAGCTCAGTCGGTAGAGCATGGGACTCTTAATCCCAGGGTCGTGGGTTCGAGC

CCCACGTTGGGCG (SEQ ID NO: 511)
*Homo_sapiens*_chr19.trna3-LysTTT (19713207-19713277)
Lys (TTT) 71 bp Sc: 28.27
ACCCTGTGGTACAGGGGCTAATATGCTGGGCCTTTACCACTTCAGCCCAGGTTCGATTCC

TGGTCAGGGAA (SEQ ID NO: 512)
*Homo_sapiens*_chr19.trna7-LysTTT (54729817-54729745)
Lys (TTT) 73 bp Sc: 48.15
ACCTGGGTAGCTTAGTTGGTAGAGCATTGGACTTTTAATTTGAGGGCCCAGGTTTCAAGT

CCCTGTTTGGGTG (SEQ ID NO: 513)
*Homo_sapiens*_chr12.trna1-LysTTT (27734573-27734645)
Lys (TTT) 73 bp Sc: 49.92
ACCCAGATAGCTCAGTCAGTAGAGCATCAGACTTTTAATCTGAGGGTCCAAGGTTCATGT

CCCTTTTTGGGTG (SEQ ID NO: 514)
*Homo_sapiens*_chr6.trna53-LysTTT (27651825-27651897)
Lys (TTT) 73 bp Sc: 59.40
ACCTGGGTAGCTCAGTAGGTAGAACATCAGACTTTTAATCTGAGGGTCTAGGGTTCAAGT

CCCTGTCCAGGCG (SEQ ID NO: 515)
*Homo_sapiens*_chr1.trna55-LysTTT (203709894-203709966)
Lys (TTT) 73 bp Sc: 62.89
GCCCGGAGAGCTCAGTGGGTAGAGCATCAGACTTTTAATCTGAGGGTCCAGGGTTCAAGT

CCTCGTTCGGGCA (SEQ ID NO: 516)
*Homo_sapiens*_chr7_random.trna1-LysTTT (397621-397697)
Lys (TTT) 77 bp Sc: 68.40
GCCCACGTAGCTCAATGGTCAGAGCGTGCGGCTTTTAACCGCAAGGAAGGCTGCGAGTTC

GACCCTCGCCGTGGGCT (SEQ ID NO: 517)
*Homo_sapiens*_chr6.trna71-LysTTT (28823500-28823572)
Lys (TTT) 73 bp Sc: 72.00
GCCTGGATAGCTCAGTTGGTAGAACATCAGACTTTTAATCTGACGGTGCAGGGTTCAAGT

CCCTGTCCAGGCG (SEQ ID NO: 518)
*Homo_sapiens*_chr6.trna149-LysTTT (27410820-27410748)
Lys (TTT) 73 bp Sc: 81.41
GCCTGGGTAGCTCAGTCGGTAGAGCATCAGACTTTTAATCTGAGGGTCCAGGGTTCAAGT

CCCTGTCCAGGCG (SEQ ID NO: 519)
*Homo_sapiens*_chr11.trna5-LysTTT (59080478-59080550)
Lys (TTT) 73 bp Sc: 82.14
GCCCGGATAGCTCAGTCGGTAGAGCATCAGACTTTTAATCTGAGGGTCCGGGGTTCAAGT

CCCTGTTCGGGCG (SEQ ID NO: 520)
*Homo_sapiens*_chr6.trna143-LysTTT (27667644-27667572)
Lys (TTT) 73 bp Sc: 83.31

```
GCCTGGATAGCTCAGTCGGTAGAGCATCAGACTTTTAATCTGAGGGTCCAGGGTTCAAGT

CCCTGTTCAGGCG (SEQ ID NO: 521)
Homo_sapiens_chr1.trna54-LysTTT (202742278-202742350)
Lys (TTT) 73 bp Sc: 83.80
GCCCGGATAGCTCAGTCGGTAGAGCATCAGACTTTTAATCTGAGGGTCCAGGGTTCAAGT

CCCTGTTCGGGCG (SEQ ID NO: 522)
Homo_sapiens_chr1.trna62-LysTTT (202742853-202742781)
Lys (TTT) 73 bp Sc: 83.80
GCCCGGATAGCTCAGTCGGTAGAGCATCAGACTTTTAATCTGAGGGTCCAGGGTTCAAGT

CCCTGTTCGGGCG (SEQ ID NO: 523)
Homo_sapiens_chr11.trna14-LysTTT (59084456-59084384)
Lys (TTT) 73 bp Sc: 83.80
GCCCGGATAGCTCAGTCGGTAGAGCATCAGACTTTTAATCTGAGGGTCCAGGGTTCAAGT

CCCTGTTCGGGCG (SEQ ID NO: 524)
Homo_sapiens_chr17.trna2-LysTTT (7963198-7963270)
Lys (TTT) 73 bp Sc: 83.80
GCCCGGATAGCTCAGTCGGTAGAGCATCAGACTTTTAATCTGAGGGTCCAGGGTTCAAGT

CCCTGTTCGGGCG (SEQ ID NO: 525)
Homo_sapiens_chr6.trna76-LysTTT (29026785-29026857)
Lys (TTT) 73 bp Sc: 83.80
GCCCGGATAGCTCAGTCGGTAGAGCATCAGACTTTTAATCTGAGGGTCCAGGGTTCAAGT

CCCTGTTCGGGCG (SEQ ID NO: 526)
Homo_sapiens_chr11.trna11-LysTTT (121935865-121935937)
Lys (TTT) 73 bp Sc: 83.96
GCCTGGATAGCTCAGTTGGTAGAGCATCAGACTTTTAATCTGAGGGTCCAGGGTTCAAGT

CCCTGTTCAGGCG (SEQ ID NO: 527)
Homo_sapiens_chr16.trna23-LysTTT (72069789-72069717)
Lys (TTT) 73 bp Sc: 84.43
GCCTGGATAGCTCAGTTGGTAGAGCATCAGACTTTTAATCTGAGGGTCCAGGGTTCAAGT

CCCTGTTCAGGCA (SEQ ID NO: 528)
Homo_sapiens_chr9.trna1-MetCAT (19393996-19394070)
Met (CAT) 75 bp Sc: 43.49
AGCAGAGTGGTGCAGTGGAAGCATACCTATGGGCCCATAACCCAGAGGTTGATGGATGGA

AACCATCCTCTGCTA (SEQ ID NO: 529)
Homo_sapiens_chr6.trna61-MetCAT (27853643-27853714)
Met (CAT) 72 bp Sc: 62.43
AGCAGAGTGGCGCAGCGGAAGCGTGCTGGGCCCATAACCCAGAGGTCGATGGATCTAAAC

CATCCTCTGCTA (SEQ ID NO: 530)
Homo_sapiens_chr6.trna92-MetCAT (58276523-58276451)
Met (CAT) 73 bp Sc: 64.33
GCCCTCTTAGTGCAGCTGGCAGCGCGTCAGTTTCATAATCTGAAAGTCCTGAGTTCAAGC

CTCAGAGAGGGCA (SEQ ID NO: 531)
Homo_sapiens_chr1.trna32-MetCAT (151910350-151910421)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA
```

-continued (SEQ ID NO: 532)
*Homo_sapiens*_chr17.trna20-MetCAT (78045957-78045886)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 533)
*Homo_sapiens*_chr6.trna129-MetCAT (27978321-27978250)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 534)
*Homo_sapiens*_chr6.trna142-MetCAT (27668650-27668579)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 535)
*Homo_sapiens*_chr6.trna150-MetCAT (27408814-27408743)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 536)
*Homo_sapiens*_chr6.trna169-MetCAT (26438579-26438508)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 537)
*Homo_sapiens*_chr6.trna171-MetCAT (26421402-26421331)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 538)
*Homo_sapiens*_chr6.trna2-MetCAT (26394733-26394804)
Met (CAT) 72 bp Sc: 68.98
AGCAGAGTGGCGCAGCGGAAGCGTGCTGGGCCCATAACCCAGAGGTCGATGGATCGAAAC

CATCCTCTGCTA (SEQ ID NO: 539)
*Homo_sapiens*_chr16.trna22-MetCAT (85975201-85975129)
Met (CAT) 73 bp Sc: 74.51
GCCTCGTTAGCGCAGTAGGCAGCGCGTCAGTCTCATAATCTGAAGGTCGTGAGTTCGAGC

CTCACACGGGGCA (SEQ ID NO: 540)
*Homo_sapiens*_chr6.trna21-MetCAT (26809691-26809763)
Met (CAT) 73 bp Sc: 75.06
GCCCTCTTAGCGCAGCTGGCAGCGCGTCAGTCTCATAATCTGAAGGTCCTGAGTTCAAGC

CTCAGAGAGGGCA (SEQ ID NO: 541)
*Homo_sapiens*_chr6.trna162-MetCAT (26866601-26866529)
Met (CAT) 73 bp Sc: 75.76
GCCCTCTTAGCGCAGCGGGCAGCGCGTCAGTCTCATAATCTGAAGGTCCTGAGTTCGAGC

CTCAGAGAGGGCA (SEQ ID NO: 542)
*Homo_sapiens*_chr6.trna164-MetCAT (26843625-26843553)
Met (CAT) 73 bp Sc: 75.76
GCCCTCTTAGCGCAGCGGGCAGCGCGTCAGTCTCATAATCTGAAGGTCCTGAGTTCGAGC

CTCAGAGAGGGCA (SEQ ID NO: 543)
*Homo_sapiens*_chr6.trna27-MetCAT (26874423-26874495)
Met (CAT) 73 bp Sc: 75.76
GCCTCTTAGCGCAGCGGGCAGCGCGTCAGTCTCATAATCTGAAGGTCCTGAGTTCGAGC

CTCAGAGAGGGCA (SEQ ID NO: 544)
*Homo_sapiens*_chr6.trna75-MetCAT (29020331-29020403)
Met (CAT) 73 bp Sc: 76.58
GCCTCCTTAGCGCAGTAGGCAGCGCGTCAGTCTCATAATCTGAAGGTCCTGAGTTCGAAC

CTCAGAGGGGGCA (SEQ ID NO: 545)
*Homo_sapiens*_chr6.trna97-MetCAT (29029093-29029021)
Met (CAT) 73 bp Sc: 76.58
GCCTCCTTAGCGCAGTAGGCAGCGCGTCAGTCTCATAATCTGAAGGTCCTGAGTTCGAAC

CTCAGAGGGGGCA (SEQ ID NO: 546)
*Homo_sapiens*_chr16.trna20-MetCAT (70017897-70017969)
Met (CAT) 73 bp Sc: 78.21
GCCCTCTTAGCGCAGTGGGCAGCGCGTCAGTCTCATAATCTGAAGGTCCTGAGTTCGAGC

CTCAGAGAGGGCA (SEQ ID NO: 547)
*Homo_sapiens*_chr8.trna10-MetCAT (124238723-124238651)
Met (CAT) 73 bp Sc: 79.85
GCCTCGTTAGCGCAGTAGGTAGCGCGTCAGTCTCATAATCTGAAGGTCGTGAGTTCGATC

CTCACACGGGGCA (SEQ ID NO: 548)
*Homo_sapiens*_chr6.trna56-PheGAA (27740524-27740599)
Phe (GAA) 76 bp Sc: 53.54
GCCGAAATAGCTCAATTGGGAGAGTGTTAGACTGAAGATCTTCTGCAGGTCTCTGGTTCA

ATTCCGGGTTTCGACA (SEQ ID NO: 549)
*Homo_sapiens*_chr6.trna112-PheGAA (28839426-28839353)
Phe (GAA) 74 bp Sc: 56.32
GCTGAAATAGCTCAGTTGGGAGAGCGTTAGACTGAAGATCTTAAAGTTCCCTGGTTCAAC

CCTGGGTTTCAGCC (SEQ ID NO: 550)
*Homo_sapiens*_chr6.trna72-PheGAA (28840143-28840215)
Phe (GAA) 73 bp Sc: 59.98
GCCAAAATTGCTCAGTTGGGAGAGCGTTAGACTGAAGATCTAAAGGTCCCTGGTTCGATC

CCGGGTTTCACCA (SEQ ID NO: 551)
*Homo_sapiens*_chr6.trna103-PheGAA (28899145-28899072)
Phe (GAA) 74 bp Sc: 67.94
GCCGAAATAGCTCAGTTGGGAGAGCGTTAGACCGAAGATCTTAAAGGTCCCTGGTTCAAT

CCCGGGTTTCGGCA (SEQ ID NO: 552)
*Homo_sapiens*_chr6.trna106-PheGAA (28883661-28883589)
Phe (GAA) 73 bp Sc: 82.13
GCCGAGATAGCTCAGTTGGGAGAGCGTTAGACTGAAGATCTAAAGGTCCCTGGTTCAATC

CCGGGTTTCGGCA (SEQ ID NO: 553)
*Homo_sapiens*_chr11.trna13-PheGAA (59090501-59090429)
Phe (GAA) 73 bp Sc: 82.45
GCCGAAATAGCTCAGTTGGGAGAGCGTTAGACTGAAGATCTAAAGGTCCCTGGTTCAATC

CCGGGTTTCGGCA (SEQ ID NO: 554)
*Homo_sapiens*_chr11.trna15-PheGAA (59081618-59081546)
Phe (GAA) 73 bp Sc: 84.19

```
GCCGAAATAGCTCAGTTGGGAGAGCGTTAGACTGAAGATCTAAAGGTCCCTGGTTCGATC

CCGGGTTTCGGCA (SEQ ID NO: 555)
Homo_sapiens_chr12.trna11-PheGAA (123978414-123978342)
Phe (GAA) 73 bp Sc: 84.19
GCCGAAATAGCTCAGTTGGGAGAGCGTTAGACTGAAGATCTAAAGGTCCCTGGTTCGATC

CCGGGTTTCGGCA (SEQ ID NO: 556)
Homo_sapiens_chr13.trna1-PheGAA (93999977-93999905)
Phe (GAA) 73 bp Sc: 84.19
GCCGAAATAGCTCAGTTGGGAGAGCGTTAGACTGAAGATCTAAAGGTCCCTGGTTCGATC

CCGGGTTTCGGCA (SEQ ID NO: 557)
Homo_sapiens_chr19.trna14-PheGAA (1334433-1334361)
Phe (GAA) 73 bp Sc: 84.19
GCCGAAATAGCTCAGTTGGGAGAGCGTTAGACTGAAGATCTAAAGGTCCCTGGTTCGATC

CCGGGTTTCGGCA (SEQ ID NO: 558)
Homo_sapiens_chr6.trna109-PheGAA (28866550-28866478)
Phe (GAA) 73 bp Sc: 84.19
GCCGAAATAGCTCAGTTGGGAGAGCGTTAGACTGAAGATCTAAAGGTCCCTGGTTCGATC

CCGGGTTTCGGCA (SEQ ID NO: 559)
Homo_sapiens_chr6.trna96-PheGAA (29057500-29057428)
Phe (GAA) 73 bp Sc: 84.19
GCCGAAATAGCTCAGTTGGGAGAGCGTTAGACTGAAGATCTAAAGGTCCCTGGTTCGATC

CCGGGTTTCGGCA (SEQ ID NO: 560)
Homo_sapiens_chr1.trna65-ProAGG (165951420-165951349)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 561)
Homo_sapiens_chr11.trna9-ProAGG (75624205-75624276)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 562)
Homo_sapiens_chr14.trna22-ProAGG (20151471-20151400)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 563)
Homo_sapiens_chr14.trna23-ProAGG (20147406-20147335)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 564)
Homo_sapiens_chr16.trna29-ProAGG (3172707-3172636)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 565)
Homo_sapiens_chr16.trna9-ProAGG (3179635-3179706)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC
```

-continued (SEQ ID NO: 566)
*Homo_sapiens*_chr6.trna12-ProAGG (26663477-26663548)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 567)
*Homo_sapiens*_chr7.trna2-ProAGG (128210740-128210811)
Pro (AGG) 72 bp Sc: 75.92
GGCTCGTTGGTCTAGGGGTATGATTCTCGCTTAGGGTGCGAGAGGTCCCGGGTTCAAATC

CCGGACGAGCCC (SEQ ID NO: 568)
*Homo_sapiens*_chr16.trna11-ProAGG (3181990-3182061)
Pro (AGG) 72 bp Sc: 77.31
GGCTCGTTGGTCTAGGGGTATGATTCTCGCTTAGGATGCGAGAGGTCCCGGGTTCAAATC

CCGGACGAGCCC (SEQ ID NO: 569)
*Homo_sapiens*_chr16.trna4-ProAGG (3150387-3150481)
Pro (AGG) 95 bp Sc: 43.10
GGCTCGTTGGTCTAGGGGTGTGGTTCTCGCTTAGGGACCACAGGGACAAGCCCGGGAGAC

CCAAGAGGTCCCGGGTTCAAATCCCGGACGAGCCC (SEQ ID NO: 570)
*Homo_sapiens*_chr6.trna30-ProCGG (27167500-27167571)
Pro (CGG) 72 bp Sc: 71.93
GGCTCGTTGGTCTAGGGGTATGATTCTCGCTTCGGGTGTGAGAGGTCCCGGGTTCAAATC

CCGGACGAGCCC (SEQ ID NO: 571)
*Homo_sapiens*_chr1.trna52-ProCGG (165950586-165950657)
Pro (CGG) 72 bp Sc: 76.52
GGCTCGTTGGTCTAGGGGTATGATTCTCGCTTCGGGTGCGAGAGGTCCCGGGTTCAAATC

CCGGACGAGCCC (SEQ ID NO: 572)
*Homo_sapiens*_chr16.trna6-ProCGG (3162050-3162121)
Pro (CGG) 72 bp Sc: 76.52
GGCTCGTTGGTCTAGGGGTATGATTCTCGCTTCGGGTGCGAGAGGTCCCGGGTTCAAATC

CCGGACGAGCCC (SEQ ID NO: 573)
*Homo_sapiens*_chr17.trna37-ProCGG (8066947-8066876)
Pro (CGG) 72 bp Sc: 76.52
GGCTCGTTGGTCTAGGGGTATGATTCTCGCTTCGGGTGCGAGAGGTCCCGGGTTCAAATC

CCGGACGAGCCC (SEQ ID NO: 574)
*Homo_sapiens*_chr14.trna6-ProTGG (20222015-20222086)
Pro (TGG) 72 bp Sc: 76.15
GGCTCGTTGGTCTAGGGGTATGATTCTCGCTTTGGGTGCGAGAGGTCCCGGGTTCAAATC

CCGGACGAGCCC (SEQ ID NO: 575)
*Homo_sapiens*_chr16.trna28-ProTGG (3174205-3174134)
Pro (TGG) 72 bp Sc: 76.15
GGCTCGTTGGTCTAGGGGTATGATTCTCGCTTTGGGTGCGAGAGGTCCCGGGTTCAAATC

CCGGACGAGCCC (SEQ ID NO: 576)
*Homo_sapiens*_chr16.trna3-ProTGG (3148924-3148995)
Pro (TGG) 72 bp Sc: 76.15
GGCTCGTTGGTCTAGGGGTATGATTCTCGCTTTGGGTGCGAGAGGTCCCGGGTTCAAATC

CCGGACGAGCCC

```
                                                        (SEQ ID NO: 577)
Homo_sapiens_chr16.trna8-ProTGG (3178095-3178166)
Pro (TGG) 72 bp Sc: 76.15
GGCTCGTTGGTCTAGGGGTATGATTCTCGCTTTGGGTGCGAGAGGTCCCGGGTTCAAATC

CCGGACGAGCCC (SEQ ID NO: 578)
Homo_sapiens_chr5.trna14-ProTGG (180548531-180548460)
Pro (TGG) 72 bp Sc: 76.15
GGCTCGTTGGTCTAGGGGTATGATTCTCGCTTTGGGTGCGAGAGGTCCCGGGTTCAAATC

CCGGACGAGCCC (SEQ ID NO: 579)
Homo_sapiens_chr11.trna12-ProTGG (75624588-75624517)
Pro (TGG) 72 bp Sc: 76.24
GGCTCGTTGGTCTAGGGGTATGATTCTCGGTTTGGGTCCGAGAGGTCCCGGGTTCAAATC

CCGGACGAGCCC (SEQ ID NO: 580)
Homo_sapiens_chr14.trna3-ProTGG (20171005-20171076)
Pro (TGG) 72 bp Sc: 79.61
GGCTCGTTGGTCTAGTGGTATGATTCTCGCTTTGGGTGCGAGAGGTCCCGGGTTCAAATC

CCGGACGAGCCC (SEQ ID NO: 581)
Homo_sapiens_chr5.trna17-LeuAAG (180524251-180524170)
Leu (AAG) 82 bp Sc: 25.68
GATAGCAAGGCCGAGCGGTCTAAGGCTCCGGATTAAGGCGCCGGTGTCTTCGGAGGCATG

GGTTCGAATTCCACCTCTGCCA (SEQ ID NO: 582)
Homo_sapiens_chr20.trna5-IleAAT (50651822-50651745)
Ile (AAT) 78 bp Sc: 23.04
GACCAATTAGCAAGCACAGTTGGCTAGAACATGGTGCTAATAAGGCCACGGTCAGGGGTT

CAATTCCCTTATGGGCTG (SEQ ID NO: 583)
Homo_sapiens_chr12.trna9-IleAAT (128282151-128282225)
Ile (AAT) 75 bp Sc: 27.18
TGGCTGATGAGCTCAGCTGGTGGGAGCATGGTGTTAATGAGGCTGAGGTCGTGGGTTCAA

TCCCCACCGGGCTAT (SEQ ID NO: 584)
Homo_sapiens_chr6.trna39-IleAAT (27359843-27359916)
Ile (AAT) 74 bp Sc: 44.67
GGCCGGTTAACTTAATTGGTTAGAGCGTGGTGCTAATAATGTCAAGGTTGCGGGTTGGAT

CCCCGAACGGGCCA (SEQ ID NO: 585)
Homo_sapiens_chr5.trna1-CysACA (151968789-151968964)
Cys (ACA) 176 bp Sc: 29.48
GGCTGTATAGCTCAGTGGTAGAGCATTTGACTACAGAATCCTATACTCAGGGGAAGGAGA

ACTGGGGGTTTCTCAGTGGGTCAAAGGACTTGTAGTGGTAAATCAAAAGCAACTCTATAA

GCTATGTAACAAACTTTAAAGTCATATGTAGCTGGGTTCAAATCCTGTTTCTGCCA (SEQ ID NO: 586)
Homo_sapiens_chr6.trna41-SerACT (27369650-27369723)
Ser (ACT) 74 bp Sc: 49.68
GGCCGGTTAGCTCAGTTGGTTAGAGCGTGCTGCTACTAATGCCAGGGTCGAGGTTTCGAT

CCCCGTACGGGCCT (SEQ ID NO: 587)
Homo_sapiens_chr20.trna2-SerAGA (29552364-29552435)
Ser (AGA) 72 bp Sc: 20.36
GGTAATGTAGCCTCGTGGTTAGGGGCTGCATTCTAGAGCTATGCTGCCCAGGTTCAAATT

CTGGTGCCACTC
```

-continued (SEQ ID NO: 588)
*Homo_sapiens*_chr6.trna111-AlaAGC (28854594-28854523)
Ala (AGC) 72 bp Sc: 32.22
GGGGGTATAGCTCAGGGACAGAGCACGTGGTTAGCATGCGTGAGGTCCTGCGTTCAACTT

CCAGTATTTCCA (SEQ ID NO: 589)
*Homo_sapiens*_chr16.trna33-ProAGG (3142681-3142610)
Pro (AGG) 72 bp Sc: 23.16
CGCTCTTTGGTCTAGGGGTATGATCTTCGCTTAGGGTGCGAGAGGTGCCTGGATCAACTC

CTTCACAAGCCG (SEQ ID NO: 590)
*Homo_sapiens*_chr2.trna7-ProAGG (77749101-77749171)
Pro (AGG) 71 bp Sc: 30.29
GGCTGGTTGGTCTAGGGCTATGATTCTCACTTAGGGTGCAAGAGGTCCTGGTTCAAATCC

CAGAGGAGCCC (SEQ ID NO: 591)
*Homo_sapiens*_chr2.trna8-ProAGG (87193084-87193155)
Pro (AGG) 72 bp Sc: 37.07
GGCTGGTTGGTCTAGGGCTATGATTCTCACTTAGGGTGCAAAGGTCCTGGGTTCAAATC

CCAGAGGAGCCC (SEQ ID NO: 592)
*Homo_sapiens*_chr10.trna3-LeuCAA (34631489-34631422)
Leu (CAA) 68 bp Sc: 20.90
CATAGGGTAGTGGCTAAGAACCTAAACTCTAAATTTAGATGTCCTGAGTTCAAATCCCAG

CTGTATGC (SEQ ID NO: 593)
*Homo_sapiens*_chr20.trna3-ValCAC (43384415-43384487)
Val (CAC) 73 bp Sc: 29.18
GCTTCTGTAATGTAGTGGTTATCACATTCGCCTCACACATGAAAGGTCACCAGTTTGAGA

CCGGGCCAAAACA (SEQ ID NO: 594)
*Homo_sapiens*_chr1.trna1-ValCAC (16924648-16924720)
Val (CAC) 73 bp Sc: 30.83
GTTTCTGTAGTATAGTGGTTATCATGTTTGCCTCACATGTGAAAGACCCTTGGCTCGAGA

CTGGAGGGAAACA (SEQ ID NO: 595)
*Homo_sapiens*_chr1.trna131-ValCAC (16746819-16746747)
Val (CAC) 73 bp Sc: 41.96
GTTTCTGTGGTGTAGTGGTTATTATGTTCGCTTCACATATGAAAGGTCTCTGGTTCGAGA

CTGCGTGGGAACA (SEQ ID NO: 596)
*Homo_sapiens*_chr1.trna3-ValCAC (17059280-17059352)
Val (CAC) 73 bp Sc: 41.96
GTTTCTGTGGTGTAGTGGTTATTATGTTCGCTTCACATATGAAAGGTCTCTGGTTCGAGA

CTGCGTGGGAACA (SEQ ID NO: 597)
*Homo_sapiens*_chr2.trna1-GlyCCC (11609278-11609349)
Gly (CCC) 72 bp Sc: 43.42
TACTCAGTGGTCTAGTGGTTAGGATTCAGCGCTCCCACCGCCGCAGCCCGGGTTCGATTC

CCGGTCATGGAA (SEQ ID NO: 598)
*Homo_sapiens*_chr1.trna91-GlyCCC (147946904-147946834)
Gly (CCC) 71 bp Sc: 49.64
GCACTGGTGGTTCAGTGGTAGAATTCTCGCCTCCCACGCGGGAGACCCGGGTTTAATTCC

CGGTCAAGATA (SEQ ID NO: 599)
*Homo_sapiens*_chr11.trna7-ArgCCT (63418343-63418411)
Arg (CCT) 69 bp Sc: 21.47

```
GCATTCGTAGTTCAGCGGCAGAAATTTCGTCTCCTACGCGGGAGACTCGGGTTCGACTTC

GGCCATGCA
```

(SEQ ID NO: 600)
*Homo_sapiens*_chr1.trna88-ArgCCT (147994965-147994895)
Arg (CCT) 71 bp Sc: 21.62
```
GGATTTGTGGTCCAGTGGTAGAATTCTCACCGCCTGCATAGGAGACCCTGGTTTAATTCC

TGGCCAATGCA
```

(SEQ ID NO: 601)
*Homo_sapiens*_chr1.trna96-ArgCCT (147609775-147609705)
Arg (CCT) 71 bp Sc: 27.53
```
GGATTGGTGGTCCAGTGGTAGAATTCTCACCGCCTGCATAGGAGACCCTGGTTTAATTCC

TGGCCAATGCA
```

(SEQ ID NO: 602)
*Homo_sapiens*_chr1.trna14-ArgCCT (144652936-144653006)
Arg (CCT) 71 bp Sc: 34.62
```
GCATTGGTAGTTCAGCGGTGGCATTCTCCCCACCTACGCGGGAGACCTGGGTTCAACTCC

CGGCCAAAGCA
```

(SEQ ID NO: 603)
*Homo_sapiens*_chr1.trna18-ArgCCT (145949915-145949985)
Arg (CCT) 71 bp Sc: 34.62
```
GCATTGGTAGTTCAGCGGTGGCATTCTCCCCACCTACGCGGGAGACCTGGGTTCAACTCC

CGGCCAAAGCA
```

(SEQ ID NO: 604)
*Homo_sapiens*_chr14.trna11-SupCTA (77770663-77770591)
Sup (CTA) 73 bp Sc: 26.26
```
GGCGGGATAATGTAGTGGTTAAAGGCATGGGCTCTAGAGCCAGACTTCCTGGGTTCAAAT

CTCAGACCTGCTA
```

(SEQ ID NO: 605)
*Homo_sapiens*_chr3.trna1-SupCTA (13808887-13808954)
Sup (CTA) 68 bp Sc: 26.42
```
GGCAGGGTAGGGTAGAGGTTAAAACCATGGATTCTAGAGCCAGATGGGTTCAAATCCCGG

CTCTGCCG
```

(SEQ ID NO: 606)
*Homo_sapiens*_chrX.trna3-GluCTC (51322923-51322852)
Glu (CTC) 72 bp Sc: 20.35
```
TCCCTGGTGTTCCGGTGGTTAGGATTTGGCATTCTCACTGTTGTGGTGCGGATTCAATCC

TGGCTTAGGGTA
```

(SEQ ID NO: 607)
*Homo_sapiens*_chr12.trna14-GluCTC (112871000-112870928)
Glu (CTC) 73 bp Sc: 22.05
```
CCGTGGATAGCCCAGCGGCTATGGGAGCCGGGCTCTCACTCTGACGTCCTGGGTTCAAGT

CCCAGTGTGCACA
```

(SEQ ID NO: 608)
*Homo_sapiens*_chr2.trna25-GluCTC (71127068-71126996)
Glu (CTC) 73 bp Sc: 22.62
```
CCCCTGGCGGTCTAGTGGTTAGGATTCGGCGCTCTCATCCACCGCGGCCTGGGTTCGACT

CGTGGTCAGAGTG
```

(SEQ ID NO: 609)
*Homo_sapiens*_chr8.trna7-GluCTC (70234894-70234968)
Glu (CTC) 75 bp Sc: 22.64
```
CTCTGGTGGTTTAGTGGCTAGGATTCACCTCTCTCACTGCTGCAGCCCAGGGTTCCATTC

CCTGGGAGTCAGATG
```

(SEQ ID NO: 610)
*Homo_sapiens*_chr2.trna24-GluCTC (95580992-95580921)
Glu (CTC) 72 bp Sc: 23.39
```
CCCCTTGTAGTCTAGTGGTTAGAATTCTGCGGTCTCACAGCCGCGGCCCGGGTTCGATTC

CCATTCCGGGAA
```

-continued (SEQ ID NO: 611)
*Homo_sapiens*_chr3.trna10-GluCTC (105362285-105362214)
Glu (CTC) 72 bp Sc: 25.40
TTATTATTATACCTGTGGTTAGGATTCGGCGCTCTCACCGCCACGACCCGGGTTCAATTC

CCGGTCAGGGAA (SEQ ID NO: 612)
*Homo_sapiens*_chr8.trna1-GluCTC (11830789-11830860)
Glu (CTC) 72 bp Sc: 26.22
CCCCTGGTAGTCTAGTGGTTAGGCTTTGCCGCTCTCAGTGCCGCTGCCTGGGTTGGATTC

CCAGTCATGTGA (SEQ ID NO: 613)
*Homo_sapiens*_chr20.trna7-GluCTC (13918541-13918470)
Glu (CTC) 72 bp Sc: 27.08
TCCCTGCTTGTCTAGTGGTTAGAATTCAGCACTCTCACTGCCACAGCCCAGGTTCAATTC

CCTGTCAGAGAA (SEQ ID NO: 614)
*Homo_sapiens*_chr2.trna12-GluCTC (150927523-150927595)
Glu (CTC) 73 bp Sc: 29.78
TTCCCCTTGGTCTAGTGGTTAGGATTCAACACTCTCACCGCCGCAGCCCGGGTTTGATTC

CCAGGCAGGGAAG (SEQ ID NO: 615)
*Homo_sapiens*_chr2.trna18-GluCTC (159446488-159446417)
Glu (CTC) 72 bp Sc: 31.33
CCCCTGGTGGTCTAGTGCTTAGGATTTGGCACTCTCGCCACCGCAGCCTGCGTTCAATTC

CCGGTCAGGGAA (SEQ ID NO: 616)
*Homo_sapiens*_chr13.trna2-GluCTC (57356622-57356551)
Glu (CTC) 72 bp Sc: 34.44
TCCCTGGTGGTCTAATGGTTAGGAGTCGGCACTCTCACCGCCGCGGCTGGGGTTTGATTC

CCAGTCATGTAA (SEQ ID NO: 617)
*Homo_sapiens*_chr2.trna15-GlnCTG (219199376-219199451)
Gln (CTG) 76 bp Sc: 22.40
GTGAGACTGCACAGCCCAGTGGTGCAGGGCATGGCTCTGACACCTGGCGGCCTGGGTTCA

AATCCCAGCTTCTACA (SEQ ID NO: 618)
*Homo_sapiens*_chr1.trna128-GlnCTG (17053558-17053487)
Gln (CTG) 72 bp Sc: 25.51
GGTTCCATGATGTAATGGTGAGCGCTTTGGACTCTGAGTACGGTGATCAGCGTTCAAGTC

TCAGTGGGACCT (SEQ ID NO: 619)
*Homo_sapiens*_chr5.trna21-GlnCTG (151228338-151228267)
Gln (CTG) 72 bp Sc: 25.76
GGTAGTGTAGTCTACTGGTTAAACGCTTGGGCTCTGACATTAACGTCCTGGGTTCAAATC

CCAGCTTTGTCA (SEQ ID NO: 620)
*Homo_sapiens*_chr10.trna5-GlnCTG (20076688-20076614)
Gln (CTG) 75 bp Sc: 26.31
CTAGGACGTGGTGTAATAGGTAGCACAGAGAATTCTGGATTCTCAGGGGTAGGTTCAATT

CCTATAGAACCTAGG (SEQ ID NO: 621)
*Homo_sapiens*_chr1.trna27-GlnCTG (147345988-147346059)
Gln (CTG) 72 bp Sc: 39.31
GGTTCCATGGTGTAATGGTGAGGGCTTTGGACTCTGACTACAGTGATCAGAGTTCAAGTC

TCAGTGGGACCT (SEQ ID NO: 622)
*Homo_sapiens*_chr1.trna23-GlnCTG (146292313-146292384)
Gln (CTG) 72 bp Sc: 43.68
GGTTCCATGGGTTAATGGTGAGCACCCTGGACTCTGAATCAAGCGATCCGAGTTCAAATC

TCGGTGGTACCT (SEQ ID NO: 623)
*Homo_sapiens*_chr15.trna6-LysCTT (74461893-74461820)
Lys (CTT) 74 bp Sc: 37.12
GCCTGGCTACCTCAGTTGGTAGAGCATGGGACTCTTAATCCCAGAGTCAGTGGGTTCAAG

CCTCACATTGAGTG (SEQ ID NO: 624)
*Homo_sapiens*_chr16.trna13-LysCTT (3186154-3186226)
Lys (CPT) 73 bp Sc: 41.66
GCCCAGCTAGCTCAGCCGGTAGAGCACAAGACTCTTAATCTCAGGGTCGTGGGTTTGAGC

CCTGTGTTGAGCA (SEQ ID NO: 625)
*Homo_sapiens*_chr1.trna51-LysCTT (163832774-163832846)
Lys (CTT) 73 bp Sc: 42.42
GTCTAGCTAGATCAGTTGGTAGAGCATAAGACTCTTAATCTCAGGGTCATGGGTTTGAGC

CCTACGTTGGGCG (SEQ ID NO: 626)
*Homo_sapiens*_chr1.trna8-LysCTT (39742782-39742854)
Lys (CTT) 73 bp Sc: 46.90
ACCAGCATGTCTCAGTCGGTATAGTGTGAGACTCTTAATCTCAGGGTCGTGGGTTCAAGC

CCCACATTGGGCG (SEQ ID NO: 627)
*Homo_sapiens*_chr8.trna9-PheGAA (124339978-124339906)
Phe (GAA) 73 bp Sc: 20.84
GCCAAAATAGCTCAGCTGGGAGAGTATTAGGTTGAAGATACAAAGTTCCTTGGCTCAATC

CAGAGTTTGGGGG (SEQ ID NO: 628)
*Homo_sapiens*_chr6.trna116-PheGAA (28802906-28802834)
Phe (GAA) 73 bp Sc: 27.39
GCTGAGATAGCTCGGTTGGGAGGGCATCAGCCTGAAGATCTAAAGGAGACTGGTTCAATT

CTGGGTTTTGGCA (SEQ ID NO: 629)
*Homo_sapiens*_chr1.trna92-PheGAA (147939600-147939529)
Phe (GAA) 72 bp Sc: 32.31
TGCATGGTTGTCTAGTGGCTAGGATTCGGTGCTGAAAGCGTCACGGCCCGGGTTCGATTC

CCGGTCAGGGAA (SEQ ID NO: 630)
*Homo_sapiens*_chr1.trna100-PheGAA (147554054-147553983)
Phe (GAA) 72 bp Sc: 32.35
TGCATGGTTGTCTAGTGGCTAGGATTCGGTGCTGAAAGAGCCACGGCCCGGGTTCGATTC

CCGGTCAGGGAA (SEQ ID NO: 631)
*Homo_sapiens*_chr6.trna88-PheGAA (79724801-79724729)
Phe (GAA) 73 bp Sc: 43.56
GCCAAAATAGCTCAGCTGGGAGAGCATTAGACTGAAGATCTAAAGGTCTCTGGTTTGATC

CTGGGTTTCAGAA (SEQ ID NO: 632)
*Homo_sapiens*_chr3.trna12-CysGCA (17716468-17716396)
Cys (GCA) 73 bp Sc: 36.14
GGGGGTATATCTCAGGGGGCAGAGCATTTGACTGCAGATCAAGAGGTCCCCGGTTGAAAT

CCGGGTGCTGGAT (SEQ ID NO: 633)
*Homo_sapiens*_chr10.trna1-ProGGG (22892585-22892657)
Pro (GGG) 73 bp Sc: 34.81

GGCAGTGTGGCATAGTGGTTAGAAATGTGCGCTCTGGGGCTGCTGATCCCAGGCTCAAAC

CCTGGCGCTGTCA (SEQ ID NO: 634)
*Homo_sapiens*_chr15.trna5-TyrGTA (90055378-90055306)
Tyr (GTA) 73 bp Sc: 24.21
GTCAGTGTTGCACAACGGTTAAGTGAAGAGGCTGTAAACCCAGACTGGATGGGTTCAATT

CCCATCTCTGCCG (SEQ ID NO: 635)
*Homo_sapiens*_chr7.trna24-TyrGTA (148684753-148684678)
Tyr (GTA) 76 bp Sc: 33.50
TCAATTATAGCTCAGTGGTAGAGCATTTAACTGTAGATCAAGAGGTCCCTGGATCAACTC

TGGGTGCCCCCTTTAA (SEQ ID NO: 636)
*Homo_sapiens*_chr1.trna44-AspGTC (159759559-159759630)
Asp (GTC) 72 bp Sc: 27.96
TCCTTGTTACTATAGTGGTGAGTATCTCTGCCTGTCATGCGTGAGAGAGGGGGTCGATTC

CCCGACGGGGAG (SEQ ID NO: 637)
*Homo_sapiens*_chr1.trna109-AsnGTT (146317757-146317684)
Asn (GTT) 74 bp Sc: 34.29
GTCTCTGTGGCACAATCGGTTAGCTTGTTCGGCTGTTAATCTAGAGGTTGGTGGTTAGAG

CCCACTGAGGGATG (SEQ ID NO: 638)
*Homo_sapiens*_chr1.trna104-AsnGTT (147478645-147478572)
Asn (GTT) 74 bp Sc: 41.72
GTCTCTGTGGCACAATCGGTTAGAGCGTTCGGCTGTTAATCTAAAGGTTGGTGGCTAGAA

CCCACTGAGGGACG (SEQ ID NO: 639)
*Homo_sapiens*_chr1.trna124-AsnGTT (142455154-142455081)
Asn (GTT) 74 bp Sc: 43.05
GTCTCTGTGGCACAATCGGTTAGCGCGTTCGGCTGTTAATCTAGAGGTTGGTGGTTAGAG

CCCACTGAGGGATG (SEQ ID NO: 640)
*Homo_sapiens*_chr8.trna13-LeuTAA (47859277-47859203)
Leu (TAA) 75 bp Sc: 20.57
GTTAAGATGGCATAGCCCAGCAATTGCATAAAACTTAAGACTTTATAATTAGAAGTTCAA

CACCTCTTCTTAACA (SEQ ID NO: 641)
*Homo_sapiens*_chr20.trna4-LeuTAA (55366909-55366835)
Leu (TAA) 75 bp Sc: 25.92
GTTAAGATGGCAGAGCCCAGCGATTGCATAAAACTTAACACTTTATAATCAGAGGTTCAA

CTCCTCTTCTTAACA (SEQ ID NO: 642)
*Homo_sapiens*_chr1.trna60-LeuTAA (236173653-236173579)
Leu (TAA) 75 bp Sc: 29.87
GTTAAGATGGCAGAGCCCAGCAATTGCATAAAACTTAAAACTTTACAATCAGAGGTTCAA

CTCCTCTTCTTAACA (SEQ ID NO: 643)
*Homo_sapiens*_chr2.trna9-LeuTAA (117497887-117497961)
Leu (TAA) 75 bp Sc: 34.06
GTTAAGATGGCAGAGCCCAGCAATTGCATAAATCTTAAAACTTTATAATCAGAGGTTCGA

CTCCTCTTCTTAACA (SEQ ID NO: 644)
*Homo_sapiens*_chr6.trna86-ValTAC (156910812-156910738)
Val (TAC) 75 bp Sc: 31.66
GTTAAGACGGCAGAGCCCGGCAATTGCGTAAAATTTACAACTTTATGGGCAGAGGTTCAA

TTCCTCTTCTTAACA (SEQ ID NO: 645)
*Homo_sapiens*_chr14.trna15-LeuTAG (20215099-20215018)
Leu (TAG) 82 bp Sc: 32.18
GGTAGTGTGGTTGAATGGTCTAAGGCACTGAATTTAGGCTCCAGTCTCTTTGGGGACGTG

GGTTTAAATCCCACTGCTGCAA (SEQ ID NO: 646)
*Homo_sapiens*_chr18.trna3-GlyTCC (53497175-53497246)
Gly (TCC) 72 bp Sc: 32.27
GTGTTGATGGTATAGTGGTGAGCATAGCTGCCTTCCAAGCAATTGACCCGACTTCAATTC

CCAGCCAACGCA (SEQ ID NO: 647)
*Homo_sapiens*_chr18.trna2-GlyTCC (53496852-53496923)
Gly (TCC) 72 bp Sc: 33.06
GTGTTGATGGTATAGTGGTGAGCATAGCTGCCTTCCAAGCAATTGACCCGACTTCGATTC

CCAGCCAATGCA (SEQ ID NO: 648)
*Homo_sapiens*_chr17.trna32-SerTGA (21952374-21952306)
Ser (TGA) 69 bp Sc: 23.94
GAAAAAGTCATAGGGGTTATGAGGCTGGCTTGAAACCAGCCTTAGGAGGTTCAATTCCTT

CCTTTTTTG (SEQ ID NO: 649)
*Homo_sapiens*_chr2.trna10-SerTGA (131856612-131856681)
Ser (TGA) 70 bp Sc: 27.03
GAGAAGGTCATAGAGGTTATGGGATTGGCTTGAAACCAGTCTCTGGGGGGTTCGATTCCC

TCCTTTTTCA (SEQ ID NO: 650)
*Homo_sapiens*_chr11.trna6-AlaTGC (60520084-60520153)
Ala (TGC) 70 bp Sc: 20.74
GGGGGAGTGGTGTGGTTACGAATGTGGCCTCTGCAAGCAGACAGCCTGGGTTCAATTCCC

AGCTTGGCCA (SEQ ID NO: 651)
*Homo_sapiens*_chr6.trna122-AlaTGC (28709909-28709838)
Ala (TGC) 72 bp Sc: 42.75
GTGGATGTAGTTTAGTGGTAGAACGCGCGCTTTGCATGTATGAGGTCCCGGTTTCGATCC

CTGGCGTTTCCA (SEQ ID NO: 652)
*Homo_sapiens*_chr1.trna61-ProTGG (205244853-205244777)
Pro (TGG) 77 bp Sc: 23.61
GCCAGGAGAGCTCAGTGGTGATGGGATGAGATCTGGACTCACACCTCTAGGCCTGGGTTC

AAATCCCAGGTCTAGCG (SEQ ID NO: 653)
*Homo_sapiens*_chr1.trna57-ProTGG (236172485-236172556)
Pro (TGG) 72 bp Sc: 33.27
TAGGACTTGGTGTAATAGGTAGCACGAAGAGATTTGGATTCTCAGGGGTAGGTTCAATTC

CTATAGTTCTGG (SEQ ID NO: 654)
*Homo_sapiens*_chr16.trna31-ProTGG (3161032-3160962)
Pro (TGG) 71 bp Sc: 37.53
GGCCTGTTGGTCTAGAGGTATGATTCTCGCTTTGGGTGCGAGAGGCCCCGGTGCGAGTCC

CAGAGGAGCCC (SEQ ID NO: 655)
*Homo_sapiens*_chr4.trna5-SupTTA (7376810-7376739)
Sup (TTA) 72 bp Sc: 21.73
GGCAGCCTGGCTTAGTGGAAAGGGAATAGGCTTTAGAGCCAGACTGCCTGGGTTTGAATC

CCAGCCCCGCCA (SEQ ID NO: 656)
*Homo_sapiens*_chr6.trna85-GluTTC (163130072-163130004)
Glu (TTC) 69 bp Sc: 22.25
TCCCTGGTCTAGTGGTTAGGATTTATTATTTTCATGGCTGTGGCCTGAGTTCAATTTCCA

ATCAGGGAA (SEQ ID NO: 657)
*Homo_sapiens*_chr1.trna17-GluTTC (145016802-145016873)
Glu (TTC) 72 bp Sc: 23.38
TCCCTGGTGGTCTGGTGGCTAGAATTTAGCGCTTTCACCGCCGCAGCTCGGGTTGGATTA

CCAGTCAGGGAA (SEQ ID NO: 658)
*Homo_sapiens*_chr1.trna102-GluTTC (147545481-147545409)
Glu (TTC) 73 bp Sc: 35.32
TCCGTGGTGGTCTAGTGGCTAGGATTCGGCGCTTTCACCGCCTGCAGCTCGAGTTCGATT

CCTGGTCAGGGAA (SEQ ID NO: 659)
*Homo_sapiens*_chr2.trna17-GluTTC (203937446-203937376)
Glu (TTC) 71 bp Sc: 39.76
GCAATGGTGGTTCAGTGGTAGAATTCTCGCCTTTCACACAGGAGACCCGGGTTCAATTCC

TGACCCATGTA (SEQ ID NO: 660)
*Homo_sapiens*_chr1.trna105-GluTTC (147428323-147428252)
Glu (TTC) 72 bp Sc: 41.70
TGTCTGGTGGTCAAGTGGCTAGGATTTGGCGCTTTCACTGCCGCGGCCCGCGTTCGATTC

CCGGTCAGGGAA (SEQ ID NO: 661)
*Homo_sapiens*_chr1.trna110-GluTTC (146247725-146247654)
Glu (TTC) 72 bp Sc: 43.43
TCCTTGGTGGTCTAGTGGCTAGGATTCGGTGCTTTCACCTGTGCGGCCCGGGTTCAATTC

CCGATGAAGGAA (SEQ ID NO: 662)
*Homo_sapiens*_chr4.trna1-GlnTTG (156603338-156603409)
Gln (TTG) 72 bp Sc: 20.26
TAGGACGTGGTGTGATAGGTAGCACAGAGAATTTTGGATTCTCAGGGGTAGGTTAAATTC

CTATAGTACTAG (SEQ ID NO: 663)
*Homo_sapiens*_chr7.trna26-GlnTTG (57257993-57257922)
Gln (TTG) 72 bp Sc: 22.05
TAGGACGTGGTGTGATAGGTAGCATGGGGAATTTTGGATTCTCAGGGGTGGGTTCAATTC

CTATAGTTCTAG (SEQ ID NO: 664)
*Homo_sapiens*_chr12.trna15-GlnTTG (96014895-96014822)
Gln (TTG) 74 bp Sc: 22.16
GGCAATGTAGCATTGTGGCTAAGTGCACAGGCTTTGGAAACTGGCAGGCCTGGGTTCAAA

TCCCAGCTTATTCA (SEQ ID NO: 665)
*Homo_sapiens*_chr17.trna33-GlnTTG (19447250-19447179)
Gln (TTG) 72 bp Sc: 22.33
TAGGATGTGGTGTAATAGGTGGCATGGAGAATTTTGGATTATCAGGGGTAGGTTCAATTC

CTATAGTTCTAG (SEQ ID NO: 666)
*Homo_sapiens*_chr8.trna14-GlnTTG (32992259-32992188)
Gln (TTG) 72 bp Sc: 22.66
TAGTACATAGTGTAATAGGTAGCACAGATAATTTTGGATTCTCAGGGGTAGGTTCAATTC

TTATAGTTCTAG (SEQ ID NO: 667)
*Homo_sapiens*_chr19.trna12-GlnTTG (9011428-9011356)
Gln (TTG) 73 bp Sc: 23.15

```
AGCAGTGTAGCCTAGTGGCTAGGTCCTCTGACTTTGAAACCACGTGGTCTGGGTTTAAGT

CTCAGCTGTGCTA
```

(SEQ ID NO: 668)
*Homo_sapiens*_chr13.trna6-GlnTTG (35537818-35537747)
Gln (TTG) 72 bp Sc: 23.74
```
TAGGATGTGGTGTGACAGGTAGCATGGAGAATTTTGGATTCTCAGGGTTAGGTTCAATTC

CTATAGTTCTAG
```

(SEQ ID NO: 669)
*Homo_sapiens*_chr5.trna23-GlnTTG (77354604-77354532)
Gln (TTG) 73 bp Sc: 24.04
```
AGCTGTATATTATAGTGGAATAAATGTGGACTTTGAAGTTAGATACACCTGGGTTCAAAT

CCCAGTGCTGTCA
```

(SEQ ID NO: 670)
*Homo_sapiens*_chr2.trna11-GlnTTG (131859603-131859674)
Gln (TTG) 72 bp Sc: 25.61
```
TAGGACGTGGTGTGATAGGTAGCACGGAGAATTTTGGATTCTCAGGGATGGGTTCAATTC

CTGTAGTTCTAG
```

(SEQ ID NO: 671)
*Homo_sapiens*_chrY.trna1-GlnTTG (8300214-8300140)
Gln (TTG) 75 bp Sc: 27.14
```
TTTAGGACGTGGTGTAATAGGTAGCACAGAGAATTTTGGATTCTCAGGTGCAGGTTCAAT

TCCTATATTCTAGAG
```

(SEQ ID NO: 672)
*Homo_sapiens*_chr2.trna22-GlnTTG (130746452-130746381)
Gln (TTG) 72 bp Sc: 28.85
```
TAGGACGTGGTGTGATAGGTAGCATGGAGAATTTTGGATTCTCAGGGATGGGTTCAATTC

CTATAGTCCTAG
```

(SEQ ID NO: 673)
*Homo_sapiens*_chr12.trna16-GlnTTG (48497531-48497457)
Gln (TTG) 75 bp Sc: 29.85
```
TCTAGGATGTGGTGTGATAGGTAGCATGGAGAATTTTGGATTCTCAGGGGTAGGTTCAAT

TCCTATATTCTAGAA
```

(SEQ ID NO: 674)
*Homo_sapiens*_chr3.trna9-GlnTTG (108103639-108103568)
Gln (TTG) 72 bp Sc: 32.34
```
TAGGATGTGGTGTATTAGGTAGCACAGAGAATTTTGGATTCTCAGGGGTAGGTTCGATTC

CTATAATTCTAC
```

(SEQ ID NO: 675)
*Homo_sapiens*_chr7.trna4-GlnTTG (141149826-141149897)
Gln (TTG) 72 bp Sc: 34.30
```
TAGGACGTGGTGTAGTAGGTAGCATGGAGAATGTTGAATTCTCAGGGGTAGGTTCAATTC

CTATAGTTCTAG
```

(SEQ ID NO: 676)
*Homo_sapiens*_chrX.trna1-GlnTTG (55223391-55223462)
Gln (TTG) 72 bp Sc: 34.66
```
TAGGACATGGTGTGATAGGTAGCATGGAGAATTTTGGATTCTCAGGGGTAGGTTCAATTC

CTACAGTTCTAG
```

(SEQ ID NO: 677)
*Homo_sapiens*_chr2.trna28-GlnTTG (45791017-45790945)
Gln (TTG) 73 bp Sc: 35.83
```
GGCTGTGTACCTCAGTGGGCAAGGGTATGGACTTTGAAGCCAGACTATTTGGGTTCAAAT

CCCAGCTTGGCCT
```

(SEQ ID NO: 678)
*Homo_sapiens*_chr8.trna2-LysTTT (18164483-18164552)
Lys (TTT) 70 bp Sc: 20.79
```
TCCTATAGCCCAGTGATTAGGATTCTTTGCTTTTACTACCATGACCTGGGTTCAATACCC

AGTCAGGGAA
```

-continued (SEQ ID NO: 679)
*Homo_sapiens*_chr2.trna16-LysTTT (223894631-223894559)
Lys (TTT) 73 bp Sc: 34.01
GTTGGGGTAACTCAGTTGGTAGAGTAGCAGACTTTTCATCTGAGGGTCCAGGGTTTAAGT

CCATGTCCAGGCA (SEQ ID NO: 680)
*Homo_sapiens*_chr14.trna12-LysTTT (73125354-73125282)
Lys (TTT) 73 bp Sc: 38.73
ACCCAGATAGCTCAGTTGATAGAGCATCAGACTTTTAATCTGAGGGTCCAGGGTTCATGT

CCCTGTTCCTTAA (SEQ ID NO: 681)
*Homo_sapiens*_chr6.trna118-LysTTT (28769039-28768966)
Lys (TTT) 74 bp Sc: 44.65
GCCTGGGTAGCTCAGTCGGTAGAGCTATCAGACTTTTAGCCTGAGGATTCAGGGTTCAAT

CCCTTGCTGGGCG (SEQ ID NO: 682)
*Homo_sapiens*_chr19.trna9-LysTTT (46440054-46439982)
Lys (TTT) 73 bp Sc: 53.63
GCCAGGATAGTTCAGGTGGTAGAGCATCAGACTTTTAACCTGAGGGTTCAGGGTTCAAGT

CTCTGTTTGGGCG (SEQ ID NO: 683)
*Homo_sapiens*_chr17.trna25-SeCTCA (35527152-35527079)
SeC (TCA) 74 bp Sc: 47.88
GACCGTGTGGCCTTAATGGATAAGGTGTCTGACTTCAGATCAGAAGATTGAGGGTTTGAG

TCCCTTTGTGGTCA (SEQ ID NO: 684)
*Homo_sapiens*_chr22.trna1-SeC(e)TCA (42877870-42877955)
SeC(e) (TCA) 86 bp Sc: 62.60
GCTCGGATGATCCTCAGTGGTCTGGGGTGCAGGCTTCAAACCTGTAGCT

GTCTAGTGACA GAGTGGTTCAATTCCACCTTTGTAGG (SEQ ID NO: 685)
*Homo_sapiens*_chr19.trna8-SeC(e)TCA (50673785-50673700)
SeC(e) (TCA) 86 bp Sc: 75.99
GCCCGGATGATCCTCAGTGGTCTGGGGTGCAGGCTTCAAACCTGTAGCTGTCTAG

CGACAGAGTGGTTCAATTCCACCTTTCGGGC (SEQ ID NO: 686)
*Homo_sapiens*_chr11.trna10-SerAGA (108541249-108541330)
Ser (AGA) 82 bp Sc: 29.13
TGAGTTGTAGCTGAGTGGTTAAGGCAACGAGCTAGAAATTCGTTGGTTTCTCTCTGTGCA

GGTTTGAATCCTGCTAATTATG (SEQ ID NO: 687)
*Homo_sapiens*_chr7.trna12-SerAGA (148936400-148936471)
Ser (AGA) 72 bp Sc: 62.08
GGGTGTATGGCTCAGGGGTAGAGAATTTGACTAGAGATCAAGAGGTCCCTGGTTCAAATC

CAGGTGCCCCCT (SEQ ID NO: 688)
*Homo_sapiens*_chr6.trna145-SerAGA (27629252-27629171)
Ser (AGA) 82 bp Sc: 79.96
GTAGTCGTGGCCGAGTGGTTAAGGTGATGGACTAGAAACCCATTGGGTCTCCCCGCGCA

GGTTCGAATCCTGCCGACTACG (SEQ ID NO: 689)
*Homo_sapiens*_chr6.trna50-SerAGA (27607966-27608047)
Ser (AGA) 82 bp Sc: 86.61
GTAGTCGTGGCCGAGTGGTTAAGGCGATGGACTAGAAATCCATTGGGGTTTCCCCACGCA

GGTTCGAATCCTGCCGACTACG (SEQ ID NO: 690)
*Homo_sapiens*_chr17.trna35-SerAGA (8070734-8070653)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 691)
*Homo_sapiens*_chr6.trna44-SerAGA (27554570-27554651)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 692)
*Homo_sapiens*_chr6.trna46-SerAGA (27571572-27571653)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 693)
*Homo_sapiens*_chr6.trna47-SerAGA (27578797-27578878)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 694)
*Homo_sapiens*_chr6.trna5-SerAGA (26435796-26435877)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 695)
*Homo_sapiens*_chr8.trna11-SerAGA (96351142-96351061)
Ser (AGA) 82 bp Sc: 88.01
GTAGTCGTGGCCGAGTGGTTAAGGCGATGGACTAGAAATCCATTGGGGTCTCCCCGCGCA

GGTTCGAATCCTGCCGACTACG (SEQ ID NO: 696)
*Homo_sapiens*_chr6.trna147-SerAGA (27617614-27617533)
Ser (AGA) 82 bp Sc: 88.50
GTAGTCGTGGCCGAGTGGTTAAGGCGATGGACTAGAAATCCATTGGGGTTTCCCCGCGCA

GGTTCGAATCCTGCCGACTACG (SEQ ID NO: 697)
*Homo_sapiens*_chr12.trna2-SerCGA (54870415-54870496)
Ser (CGA) 82 bp Sc: 89.14
GTCACGGTGGCCGAGTGGTTAAGGCGTTGGACTCGAAATCCAATGGGGTTTCCCCGCACA

GGTTCGAATCCTGTTCGTGACG (SEQ ID NO: 698)
*Homo_sapiens*_chr6.trna137-SerCGA (27748289-27748208)
Ser (CGA) 82 bp Sc: 89.16
GCTGTGATGGCCGAGTGGTTAAGGTGTTGGACTCGAAATCCAATGGGGGTTCCCCGCGCA

GGTTCAAATCCTGCTCACAGCG (SEQ ID NO: 699)
*Homo_sapiens*_chr6.trna35-SerCGA (27285607-27285688)
Ser (CGA) 82 bp Sc: 90.35
GCTGTGATGGCCGAGTGGTTAAGGCGTTGGACTCGAAATCCAATGGGGTCTCCCCGCGCA

GGTTCAAATCCTGCTCACAGCG (SEQ ID NO: 700)
*Homo_sapiens*_chr17.trna41-SerCGA (7983005-7982924)
Ser (CGA) 82 bp Sc: 92.09
GCTGTGATGGCCGAGTGGTTAAGGCGTTGGACTCGAAATCCAATGGGGTCTCCCCGCGCA

GGTTCGAATCCTGCTCACAGCG (SEQ ID NO: 701)
*Homo_sapiens*_chr6.trna175-SerGCT (26413780-26413697)
Ser (GCT) 84 bp Sc: 67.16

```
GGAGAGGCCTGGCCGAGTGGTTAAGGCGATGGACTGCTAATCCATTGTGCTCTGCACGCG

TGGGTTCGAATCCCATCCTCGTCG (SEQ ID NO: 702)
Homo_sapiens_chr6.trna62-SerGCT (28288794-28288875)
Ser (GCT) 82 bp Sc: 83.46
GACGAGGTGGCCGAGTGGTTAAGGCGATGGACTGCTAATCCATTGTGCTCTGCACACGTG

GGTTCGAATCCCATCCTCGTCG (SEQ ID NO: 703)
Homo_sapiens_chr15.trna10-SerGCT (38673396-38673315)
Ser (GCT) 82 bp Sc: 85.34
GACGAGGTGGCCGAGTGGTTAAGGCGATGGACTGCTAATCCATTGTGCTCTGCACGCGTG

GGTTCGAATCCCATCCTCGTCG (SEQ ID NO: 704)
Homo_sapiens_chr17.trna7-SerGCT (8030909-8030990)
Ser (GCT) 82 bp Sc: 85.34
GACGAGGTGGCCGAGTGGTTAAGGCGATGGACTGCTAATCCATTGTGCTCTGCACGCGTG

GGTTCGAATCCCATCCTCGTCG (SEQ ID NO: 705)
Homo_sapiens_chr6.trna123-SerGCT (28673177-28673096)
Ser (GCT) 82 bp Sc: 85.34
GACGAGGTGGCCGAGTGGTTAAGGCGATGGACTGCTAATCCATTGTGCTCTGCACGCGTG

GGTTCGAATCCCATCCTCGTCG (SEQ ID NO: 706)
Homo_sapiens_chr11.trna8-SerGCT (65872167-65872248)
Ser (GCT) 82 bp Sc: 85.83
GACGAGGTGGCCGAGTGGTTAAGGCGATGGACTGCTAATCCATTGTGCTTTGCACGCGTG

GGTTCGAATCCCATCCTCGTCG (SEQ ID NO: 707)
Homo_sapiens_chr6.trna43-SerGCT (27373754-27373835)
Ser (GCT) 82 bp Sc: 86.80
GACGAGGTGGCCGAGTGGTTAAGGCGATGGACTGCTAATCCATTGTGCTCTGCACGCGTG

GGTTCGAATCCCACCTTCGTCG (SEQ ID NO: 708)
Homo_sapiens_chr6.trna31-SerGCT (27173064-27173145)
Ser (GCT) 82 bp Sc: 88.12
GACGAGGTGGCCGAGTGGTTAAGGCGATGGACTGCTAATCCATTGTGCTCTGCACGCGTG

GGTTCGAATCCCACCCTCGTCG (SEQ ID NO: 709)
Homo_sapiens_chr2.trna21-SerTGA (130749563-130749494)
Ser (TGA) 70 bp Sc: 31.73
GAGAAGGTCACAGAGGTTATGGGATTGGCTTGAAACCAGTCTGTGGGGGTTCGATTCCC

TCCTTTTTCA (SEQ ID NO: 710)
Homo_sapiens_chr6.trna148-SerTGA (27581667-27581586)
Ser (TGA) 82 bp Sc: 84.78
GTAGTCGTGGCCGAGTGGTTAAGGCGATGGACTTGAAATCCATTGGGGTTTCCCCGCGCA

GGTTCGAATCCTGTCGGCTACG (SEQ ID NO: 711)
Homo_sapiens_chr6.trna172-SerTGA (26420884-26420803)
Ser (TGA) 82 bp Sc: 88.25
GTAGTCGTGGCCGAGTGGTTAAGGCGATGGACTTGAAATCCATTGGGGTCTCCCCGCGCA

GGTTCGAATCCTGCCGACTACG (SEQ ID NO: 712)
Homo_sapiens_chr6.trna51-SerTGA (27621447-27621528)
Ser (TGA) 82 bp Sc: 88.73
GTAGTCGTGGCCGAGTGGTTAAGGCGATGGACTTGAAATCCATTGGGGTTTCCCCGCGCA

GGTTCGAATCCTGCCGACTACG
```

-continued (SEQ ID NO: 713)
*Homo_sapiens*_chr10.trna2-SerTGA (69194267-69194348)
Ser (TGA) 82 bp Sc: 90.86
GCAGCGATGGCCGAGTGGTTAAGGCGTTGGACTTGAAATCCAATGGGGTCTCCCCGCGCA

GGTTCGAACCCTGCTCGCTGCG (SEQ ID NO: 714)
*Homo_sapiens*_chr17.trna11-SupCTA (15349410-15349483)
Sup (CTA) 74 bp Sc: 28.00
GGCAGTGACGCCTACTGGTTTAGAGCACAGATTCTAGATCGAGACATTCCTGGGTTCAAA

TCCCAGCACTGTTG (SEQ ID NO: 715)
*Homo_sapiens*_chr21.trna1-SupTTA (14848387-14848457)
Sup (TTA) 71 bp Sc: 22.35
GGCAGTGACATGTAATGGTTATGAGGGTGGACTTTAACCACACTGCCTAGGTTCAAATCC

TGACTCTGTCA (SEQ ID NO: 716)
*Homo_sapiens*_chr17.trna17-SupTTA (56218375-56218445)
Sup (TTA) 71 bp Sc: 57.62
GCCCGGATAGTTCAGTTGGTAGAGCATCAGACTTAATCAGAGGGTCCAGGGTTCAAGTCC

CTGTTTGGGTG (SEQ ID NO: 717)
*Homo_sapiens*_chr17.trna24-ThrAGT (59957453-59957380)
Thr (AGT) 74 bp Sc: 43.90
AGCACCATGGCTTAGCTGGTTAAAGCACCTGTCTAGTAAACAGGAGATCCTGAGTTTCAA

TTCCAATGGTGCCT (SEQ ID NO: 718)
*Homo_sapiens*_chr6.trna34-ThrAGT (27238029-27238102)
Thr (AGT) 74 bp Sc: 80.30
GGCCCTGTGGCTTAGCTGGTCAAAGCGCCTGTCTAGTAAACAGGAGATCCTGGGTTCGAA

TCCCAGCGGGGCCT (SEQ ID NO: 719
*Homo_sapiens*_chr6.trna60-ThrAGT (27802452-27802525)
Thr (AGT) 74 bp Sc: 81.60
GGCTTCGTGGCTTAGCTGGTTAAAGCGCCTGTCTAGTAAACAGGAGATCCTGGGTTCGAA

TCCCAGCGAGGCCT (SEQ ID NO: 720)
*Homo_sapiens*_chr17.trna40-ThrAGT (7983568-7983495)
Thr (AGT) 74 bp Sc: 81.60
GGCGCCGTGGCTTAGCTGGTTAAAGCGCCTGTCTAGTAAACAGGAGATCCTGGGTTCGAA

TCCCAGCGGTGCCT (SEQ ID NO: 721)
*Homo_sapiens*_chr6.trna69-ThrAGT (28801774-28801847)
Thr (AGT) 74 bp Sc: 82.17
GGCTCCGTAGCTTAGTTGGTTAAAGCGCCTGTCTAGTAAACAGGAGATCCTGGGTTCGAC

TCCCAGCGGGGCCT (SEQ ID NO: 722)
*Homo_sapiens*_chr6.trna135-ThrAGT (27760526-27760453)
Thr (AGT) 74 bp Sc: 83.05
GGCTCCGTGGCTTAGCTGGTTAAAGCGCCTGTCTAGTAAACAGGAGATCCTGGGTTCGAA

TCCCAGCGGGGCCT (SEQ ID NO: 723)
*Homo_sapiens*_chr6.trna167-ThrAGT (26641197-26641124)
Thr (AGT) 74 bp Sc: 83.05
GGCTCCGTGGCTTAGCTGGTTAAAGCGCCTGTCTAGTAAACAGGAGATCCTGGGTTCGAA

TCCCAGCGGGGCCT (SEQ ID NO: 724)
*Homo_sapiens*_chr17.trna36-ThrAGT (8070351-8070278)
Thr (AGT) 74 bp Sc: 84.06
GGCGCCGTGGCTTAGTTGGTTAAAGCGCCTGTCTAGTAAACAGGAGATCCTGGGTTCGAA

TCCCAGCGGTGCCT (SEQ ID NO: 725)
*Homo_sapiens*_chr17.trna8-ThrAGT (8031203-8031276)
Thr (AGT) 74 bp Sc: 84.06
GGCGCCGTGGCTTAGTTGGTTAAAGCGCCTGTCTAGTAAACAGGAGATCCTGGGTTCGAA

TCCCAGCGGTGCCT (SEQ ID NO: 726)
*Homo_sapiens*_chr19.trna4-ThrAGT (38359803-38359876)
Thr (AGT) 74 bp Sc: 84.06
GGCGCCGTGGCTTAGTTGGTTAAAGCGCCTGTCTAGTAAACAGGAGATCCTGGGTTCGAA

TCCCAGCGGTGCCT (SEQ ID NO: 727)
*Homo_sapiens*_chr6.trna151-ThrCGT (27379618-27379547)
Thr (CGT) 72 bp Sc: 46.44
GGCAGAGTGGTGCAGCGGAAGCGTGCTGGGCCCGTAACCCAGAGGTCAATGGATCGAAGC

CATCCTTGGCTA (SEQ ID NO: 728)
*Homo_sapiens*_chr6.trna54-ThrCGT (27694114-27694187)
Thr (CGT) 74 bp Sc: 63.29
GGCCCTGTAGCTCAGCGGTTGGAGCGCTGGTCTCGTAAACCTAGGGGTCGTGAGTTCAAA

TCTCACCAGGGCCT (SEQ ID NO: 729)
*Homo_sapiens*_chr17.trna14-ThrCGT (26901213-26901284)
Thr (CGT) 72 bp Sc: 79.77
GGCGCGGTGGCCAAGTGGTAAGGCGTCGGTCTCGTAAACCGAAGATCGCGGGTTCGAACC

CCGTCCGTGCCT (SEQ ID NO: 730)
*Homo_sapiens*_chr6.trna121-ThrCGT (28724036-28723963)
Thr (CGT) 74 bp Sc: 80.30
GGCTCTGTGGCTTAGTTGGCTAAAGCGCCTGTCTCGTAAACAGGAGATCCTGGGTTCGAA

TCCCAGCGGGGCCT (SEQ ID NO: 731)
*Homo_sapiens*_chr16.trna15-ThrCGT (14287251-14287322)
Thr (CGT) 72 bp Sc: 80.42
GGCGCGGTGGCCAAGTGGTAAGGCGTCGGTCTCGTAAACCGAAGATCACGGGTTCGAACC

CCGTCCGTGCCT (SEQ ID NO: 732)
*Homo_sapiens*_chr6.trna125-ThrCGT (28564822-28564749)
Thr (CGT) 74 bp Sc: 80.88
GGCTCTATGGCTTAGTTGGTTAAAGCGCCTGTCTCGTAAACAGGAGATCCTGGGTTCGAC

TCCCAGTGGGGCCT (SEQ ID NO: 733)
*Homo_sapiens*_chr5.trna13-ThrTGT (180551364-180551293)
Thr (TGT) 72 bp Sc: 75.64
GGCTCCATAGCTCAGGGGTTAGAGCACTGGTCTTGTAAACCAGGGTCGCGAGTTCAAATC

TCGCTGGGGCCT (SEQ ID NO: 734)
*Homo_sapiens*_chr14.trna4-ThrTGT (20219689-20219761)
Thr (TGT) 73 bp Sc: 78.79
GGCCCTATAGCTCAGGGGTTAGAGCACTGGTCTTGTAAACCAGGGGTCGCGAGTTCAAAT

CTCGCTGGGGCCT (SEQ ID NO: 735)
*Homo_sapiens*_chr14.trna20-ThrTGT (20169231-20169159)
Thr (TGT) 73 bp Sc: 79.46

GGCTCCATAGCTCAGGGGTTAGAGCACTGGTCTTGTAAACCAGGGGTCGCGAGTTCAAAT

CTCGCTGGGGCCT (SEQ ID NO: 736)
*Homo_sapiens_*chr14.trna21-ThrTGT (20151861-20151789)
Thr (TGT) 73 bp Sc: 80.94
GGCTCCATAGCTCAGGGGTTAGAGCGCTGGTCTTGTAAACCAGGGGTCGCGAGTTCAATT

CTCGCTGGGGCCT (SEQ ID NO: 737)
*Homo_sapiens_*chr1.trna56-ThrTGT (220704970-220705042)
Thr (TGT) 73 bp Sc: 83.03
GGCTCCATAGCTCAGTGGTTAGAGCACTGGTCTTGTAAACCAGGGGTCGCGAGTTCGATC

CTCGCTGGGGCCT (SEQ ID NO: 738)
*Homo_sapiens_*chr6.trna127-ThrTGT (28550381-28550308)
Thr (TGT) 74 bp Sc: 84.82
GGCTCTATGGCTTAGTTGGTTAAAGCGCCTGTCTTGTAAACAGGAGATCCTGGGTTCGAA

TCCCAGTAGAGCCT (SEQ ID NO: 739)
*Homo_sapiens_*chr11.trna19-TrpCCA (45246849-45246776)
Trp (CCA) 74 bp Sc: 21.17
GGAAGGATGGGGCCAAGCTGGAAAGCCTGTGGGCTCCACAGTCATGTGCCTGGGTTCAAT

TCCCAGTTCTGCAT (SEQ ID NO: 740)
*Homo_sapiens_*chr7.trna1-TrpCCA (98905243-98905314)
Trp (CCA) 72 bp Sc: 70.08
GACCTCGTGGCGCAACGGCAGCGCGTCTGACTCCAGATCAGAAGGTTGCGTGTTCAAATC

ACGTCGGGGTCA (SEQ ID NO: 741)
*Homo_sapiens_*chr12.trna6-TrpCCA (97422161-97422232)
Trp (CCA) 72 bp Sc: 71.65
GACCTCGTGGCGCAACGGTAGCGCGTCTGACTCCAGATCAGAAGGCTGCGTGTTCGAATC

ACGTCGGGGTCA (SEQ ID NO: 742)
*Homo_sapiens_*chr17.trna6-TrpCCA (8030401-8030472)
Trp (CCA) 72 bp Sc: 74.00
GACCTCGTGGCGCAACGGTAGCGCGTCTGACTCCAGATCAGAAGGTTGCGTGTTCAAATC

ACGTCGGGGTCA (SEQ ID NO: 743)
*Homo_sapiens_*chr6.trna168-TrpCCA (26439722-26439651)
Trp (CCA) 72 bp Sc: 74.00
GACCTCGTGGCGCAACGGTAGCGCGTCTGACTCCAGATCAGAAGGTTGCGTGTTCAAATC

ACGTCGGGGTCA (SEQ ID NO: 744)
*Homo_sapiens_*chr6.trna170-TrpCCA (26427380-26427309)
Trp (CCA) 72 bp Sc: 74.00
GACCTCGTGGCGCAACGGTAGCGCGTCTGACTCCAGATCAGAAGGTTGCGTGTTCAAATC

ACGTCGGGGTCA (SEQ ID NO: 745)
*Homo_sapiens_*chr17.trna12-TrpCCA (19352086-19352157)
Trp (CCA) 72 bp Sc: 74.80
GACCTCGTGGCGCAATGGTAGCGCGTCTGACTCCAGATCAGAAGGTTGCGTGTTCAAGTC

ACGTCGGGGTCA (SEQ ID NO: 746)
*Homo_sapiens_*chr17.trna39-TrpCCA (8064983-8064912)
Trp (CCA) 72 bp Sc: 74.81
GGCCTCGTGGCGCAACGGTAGCGCGTCTGACTCCAGATCAGAAGGTTGCGTGTTCAAATC

ACGTCGGGGTCA

-continued (SEQ ID NO: 747)
Homo_sapiens_chr9.trna3-TrpCCA (114656810-114656908)
Trp (CCA) 99 bp Sc: 23.38
GGCAGAGGAGGGTGCAGTTGGCAGCCTGTCCAAGTCCAGCACGGTTGGAGCACAGGATTT

AGAATGGGATGGTCCTGGGTTCAAACCCCAGCTGCGCCC (SEQ ID NO: 748)
Homo_sapiens_chr2.trna14-TyrATA (218818794-218818886)
Tyr (ATA) 93 bp Sc: 55.93
CCTTCAATAGTTCAGCTGGTAGAGCAGAGGACTATAGCTACTTCCTCAGTAGGAGACGTC

CTTAGGTTGCTGGTTCGATTCCAGCTTGAAGGA (SEQ ID NO: 749)
Homo_sapiens_chr7.trna9-TyrGTA (148886066-148886138)
Tyr (GTA) 73 bp Sc: 49.38
GGGGGTATAGCTCAGGGCTAGAGCTTTTTGACTGTAGAGCAAGAGGTCCCTGGTTCAAAT

CCAGGTTCTCCCT (SEQ ID NO: 750)
Homo_sapiens_chr14.trna19-TyrGTA (20191191-20191098)
Tyr (GTA) 94 bp Sc: 74.71
CCTTCGATAGCTCAGCTGGTAGAGCGGAGGACTGTAGCCTGTAGAAACATTTGTGGACAT

CCTTAGGTCGCTGGTTCGATTCCGGCTCGAAGGA (SEQ ID NO: 751)
Homo_sapiens_chr14.trna18-TyrGTA (20195556-20195463)
Tyr (GTA) 94 bp Sc: 75.82
CCTTCGATAGCTCAGCTGGTAGAGCGGAGGACTGTAGATTGTATAGACATTTGCGGACAT

CCTTAGGTCGCTGGTTCGATTCCAGCTCGAAGGA (SEQ ID NO: 752)
Homo_sapiens_chr14.trna17-TyrGTA (20198050-20197957)
Tyr (GTA) 94 bp Sc: 71.83
CCTTCGATAGCTCAGCTGGTAGAGCGGAGGACTGTAGACTGCGGAAACGTTTGTGGACAT

CCTTAGGTCGCTGGTTCAATTCCGGCTCGAAGGA (SEQ ID NO: 753)
Homo_sapiens_chr14.trna16-TyrGTA (20201284-20201191)
Tyr (GTA) 94 bp Sc: 74.71
CCTTCGATAGCTCAGCTGGTAGAGCGGAGGACTGTAGATTGTACAGACATTTGCGGACAT

CCTTAGGTCGCTGGTTCGATTCCGGCTCGAAGGA (SEQ ID NO: 754)
Homo_sapiens_chr14.trna5-TyrGTA (20221272-20221360)
Tyr (GTA) 89 bp Sc: 75.42
CCTTCGATAGCTCAGCTGGTAGAGCGGAGGACTGTAGTACTTAATGTGTGGTCATCCTTA

GGTCGCTGGTTCGATTCCGGCTCGAAGGA (SEQ ID NO: 755)
Homo_sapiens_chr6.trna14-TyrGTA (26677065-26677155)
Tyr (GTA) 91 bp Sc: 76.45
CCTTCGATAGCTCAGTTGGTAGAGCGGAGGACTGTAGTTGGCTGTGTCCTTAGACATCCT

TAGGTCGCTGGTTCGAATCCGGCTCGAAGGA (SEQ ID NO: 756)
Homo_sapiens_chr6.trna15-TyrGTA (26683777-26683866)
Tyr (GTA) 90 bp Sc: 72.82
CTTTCGATAGCTCAGTTGGTAGAGCGGAGGACTGTAGGTTCATTAAACTAAGGCATCCTT

AGGTCGCTGGTTCGAATCCGGCTCGAAGGA (SEQ ID NO: 757)
Homo_sapiens_chr6.trna16-TyrGTA (26685311-26685399)
Tyr (GTA) 89 bp Sc: 77.01
CCTTCGATAGCTCAGTTGGTAGAGCGGAGGACTGTAGGCTCATTAAGCAAGGTATCCTTA

GGTCGCTGGTTCGAATCCGGCTCGGAGGA

-continued (SEQ ID NO: 758)
*Homo_sapiens*_chr6.trna17-TyrGTA (26703081-26703169)
Tyr (GTA) 89 bp Sc: 73.91
CCTTCGATAGCTCAGCTGGTAGAGCGGAGGACTGTAGGGGTTTGAATGTGGTCATCCTTA

GGTCGCTGGTTCGAATCCGGCTCGGAGGA (SEQ ID NO: 759)
*Homo_sapiens*_chr2.trna2-TyrGTA (27127154-27127242)
Tyr (GTA) 89 bp Sc: 75.87
CCTTCGATAGCTCAGTTGGTAGAGCGGAGGACTGTAGTGGATAGGGCGTGGCAATCCTTA

GGTCGCTGGTTCGATTCCGGCTCGAAGGA (SEQ ID NO: 760)
*Homo_sapiens*_chr8.trna12-TyrGTA (66772173-66772086)
Tyr (GTA) 88 bp Sc: 46.11
TCTTCAATAGCTCAGCTGGTAGAGCGGAGGACTGTAGGTGCACGCCCGTGGCCATTCTTA

GGTGCTGGTTTGATTCCGACTTGGAGAG (SEQ ID NO: 761)
*Homo_sapiens*_chr8.trna4-TyrGTA (67188156-67188248)
Tyr (GTA) 93 bp Sc: 73.04
CCTTCGATAGCTCAGCTGGTAGAGCGGAGGACTGTAGCTACTTCCTCAGCAGGAGACATC

CTTAGGTCGCTGGTTCGATTCCGGCTCGAAGGA (SEQ ID NO: 762)
*Homo_sapiens*_chr8.trna5-TyrGTA (67188777-67188865)
Tyr (GTA) 89 bp Sc: 69.69
CCTTCGATAGCTCAGCTGGTAGAGCGGAGGACTGTAGGCGCGCGCCCGTGGCCATCCTTA

GGTCGCTGGTTCGATTCCGGCTCGAAGGA (SEQ ID NO: 763)
*Homo_sapiens*_chr1.trna63-ValAAC (178450971-178450899)
Val (AAC) 73 bp Sc: 48.28
GTTTCCATAGTGTACTGGTTATCACATTCACCTAACACGCGAAAGGTCCTTGGTTTGAAA

CCAGGCAGAAACA (SEQ ID NO: 764)
*Homo_sapiens*_chr6.trna115-ValAAC (28811256-28811185)
Val (AAC) 72 bp Sc: 64.08
GGGGGTGTAGCTCAGTGGTAGAGCGTATGCTTAACATTCATGAGGCTCTGGGTTCGATCC

CCAGCACTTCCA (SEQ ID NO: 765)
*Homo_sapiens*_chr6.trna37-ValAAC (27311267-27311339)
Val (AAC) 73 bp Sc: 74.63
GTTTCCGTAGTGTAGTGGTTATCACGTTTGCCTAACACGCGAAAGGTCCCCGGTTCGAAA

CCGGGCAGAAACA (SEQ ID NO: 766)
*Homo_sapiens*_chr6.trna136-ValAAC (27756936-27756864)
Val (AAC) 73 bp Sc: 79.68
GTTTCCGTAGTGTAGTGGTTATCACGTTCGCCTAACACGCGAAAGGTCCGCGGTTCGAAA

CCGGGCGGAAACA (SEQ ID NO: 767)
*Homo_sapiens*_chr6.trna139-ValAAC (27726758-27726686)
Val (AAC) 73 bp Sc: 81.58
GTTTCCGTAGTGTAGTGGTTATCACGTTCGCCTAACACGCGAAAGGTCCCTGGATCAAAA

CCAGGCGGAAACA (SEQ ID NO: 768)
*Homo_sapiens*_chr5.trna15-ValAAC (180548094-180548022)
Val (AAC) 73 bp Sc: 84.70
GTTTCCGTAGTGTAGTGGTCATCACGTTCGCCTAACACGCGAAAGGTCCCCGGTTCGAAA

CCGGGCGGAAACA (SEQ ID NO: 769)
*Homo_sapiens*_chr3.trna2-ValAAC (170972712-170972784)
Val (AAC) 73 bp Sc: 86.79

-continued

GTTTCCGTAGTGTAGTGGTTATCACGTTCGCCTAACACGCGAAAGGTCCCCGGTTCGAAA

CCGGGCGGAAACA (SEQ ID NO: 770)
*Homo_sapiens*_chr5.trna12-ValAAC (180577948-180577876)
Val (AAC) 73 bp Sc: 86.79
GTTTCCGTAGTGTAGTGGTTATCACGTTCGCCTAACACGCGAAAGGTCCCCGGTTCGAAA

CCGGGCGGAAACA (SEQ ID NO: 771)
*Homo_sapiens*_chr5.trna4-ValAAC (180523760-180523832)
Val (AAC) 73 bp Sc: 86.79
GTTTCCGTAGTGTAGTGGTTATCACGTTCGCCTAACACGCGAAAGGTCCCCGGTTCGAAA

CCGGGCGGAAACA (SEQ ID NO: 772)
*Homo_sapiens*_chr5.trna5-ValAAC (180529216-180529288)
Val (AAC) 73 bp Sc: 86.79
GTTTCCGTAGTGTAGTGGTTATCACGTTCGCCTAACACGCGAAAGGTCCCCGGTTCGAAA

CCGGGCGGAAACA (SEQ ID NO: 773)
*Homo_sapiens*_chr6.trna132-ValAAC (27829230-27829158)
Val (AAC) 73 bp Sc: 86.79
GTTTCCGTAGTGTAGTGGTTATCACGTTCGCCTAACACGCGAAAGGTCCCCGGTTCGAAA

CCGGGCGGAAACA (SEQ ID NO: 774)
*Homo_sapiens*_chr6.trna58-ValCAC (27758467-27758540)
Val (CAC) 74 bp Sc: 33.44
TTTTCTGTAGTGTAGTTGTTAACACGTTCGCCTCACACGCTTAAAGTTCTCTGGTTGGAT

ACCAGATGGAAATG (SEQ ID NO: 775)
*Homo_sapiens*_chr1.trna129-ValCAC (16879160-16879088)
Val (CAC) 73 bp Sc: 52.98
GTTTCTGTGGTGTAGTGGTTATCATGTTCGCCTCACACGAGAAAAGTCCCTGATTCGAGA

CTGGGTGGGAACG (SEQ ID NO: 776)
*Homo_sapiens*_chr6.trna32-ValCAC (27226001-27226073)
Val (CAC) 73 bp Sc: 56.94
GTTTCTGTAGTATGGTGGTTATCACGTTAGTCTCACACGTGAAAGGTCCCTGGTTCGAAA

CCAGGTGGAAACA (SEQ ID NO: 777)
*Homo_sapiens*_chr1.trna99-ValCAC (147561360-147561290)
Val (CAC) 71 bp Sc: 60.62
GCACTGGTGGTTCAGTGGTAGAATTCTCGCCTCACACGCGGGACACCCGGGTTCAATTCC

CGGTCAAGGCA (SEQ ID NO: 778)
*Homo_sapiens*_chr6.trna133-ValCAC (27804378-27804306)
Val (CAC) 73 bp Sc: 64.50
GTTTCCGTAGTGTAGTGGTTATTATGTTCGCCTCACACGCGAAAAGTCCCCGGTTCGAAA

TCAGGCGGGAACA (SEQ ID NO: 779)
*Homo_sapiens*_chr6.trna157-ValCAC (27281918-27281846)
Val (CAC) 73 bp Sc: 73.23
GTTTCCGTAGTGGAGTGGTTATCACGTTCGCCTCACACGCGAAAGGTCCCCGGTTTGAAA

CCAGGCGGAAACA (SEQ ID NO: 780)
*Homo_sapiens*_chr1.trna90-ValCAC (147950785-147950712)
Val (CAC) 74 bp Sc: 77.15
GTTTCCGTAGTGTAGTGGTTATCACGTTCGCCTCACACGCGTAAAGGTCCCCGGTTCGAA

ACCGGGCGGAAACA (SEQ ID NO: 781)
*Homo_sapiens*_chr1.trna98-ValCAC (147565251-147565179)
Val (CAC) 73 bp Sc: 82.06
GTTTCCGTAGTGTAGTGGTTATCACGTTCGCCTCACACGCGAAAGGTCCCCGGTTCGAAA

CTGGGCGGAAACA (SEQ ID NO: 782)
*Homo_sapiens*_chr19.trna13-ValCAC (4675719-4675647)
Val (CAC) 73 bp Sc: 84.20
GTTTCCGTAGTGTAGCGGTTATCACATTCGCCTCACACGCGAAAGGTCCCCGGTTCGATC

CCGGGCGGAAACA (SEQ ID NO: 783)
*Homo_sapiens*_chr6.trna152-ValCAC (27356100-27356028)
Val (CAC) 73 bp Sc: 87.34
GCTTCTGTAGTGTAGTGGTTATCACGTTCGCCTCACACGCGAAAGGTCCCCGGTTCGAAA

CCGGGCAGAAGCA (SEQ ID NO: 784)
*Homo_sapiens*_chr1.trna85-ValCAC (159636186-159636114)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 785)
*Homo_sapiens*_chr5.trna10-ValCAC (180582073-180582001)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 786)
*Homo_sapiens*_chr5.trna18-ValCAC (180461931-180461859)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 787)
*Homo_sapiens*_chr5.trna2-ValCAC (180456676-180456748)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 788)
*Homo_sapiens*_chr5.trna6-ValCAC (180533256-180533328)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 789)
*Homo_sapiens*_chr6.trna9-ValCAC (26646261-26646333)
Val (CAC) 73 bp Sc: 87.39
GTTTCCGTAGTGTAGTGGTTATCACGTTCGCCTCACACGCGAAAGGTCCCCGGTTCGAAA

CCGGGCGGAAACA (SEQ ID NO: 790)
*Homo_sapiens*_chr6.trna40-ValTAC (27366384-27366456)
Val (TAC) 73 bp Sc: 76.42
GTTTCCGTGGTGTAGTGGTTATCACATTCGCCTTACACGCGAAAGGTCCTCGGGTCGAAA

CCGAGCGGAAACA (SEQ ID NO: 791)
*Homo_sapiens*_chr10.trna6-ValTAC (5935752-5935680)
Val (TAC) 73 bp Sc: 81.67
GGTTCCATAGTGTAGTGGTTATCACATCTGCTTTACACGCAGAAGGTCCTGGGTTCAAGC

CCCAGTGGAACCA

-continued (SEQ ID NO: 792)
*Homo_sapiens*_chr11.trna16-ValTAC (59075108-59075036)
Val (TAC) 73 bp Sc: 82.67
GGTTCCATAGTGTAGCGGTTATCACGTCTGCTTTACACGCAGAAGGTCCTGGGTTCGAGC

CCCAGTGGAACCA (SEQ ID NO: 793)
*Homo_sapiens*_chr11.trna17-ValTAC (59074750-59074678)
Val (TAC) 73 bp Sc: 85.12
GGTTCCATAGTGTAGTGGTTATCACGTCTGCTTTACACGCAGAAGGTCCTGGGTTCGAGC

CCCAGTGGAACCA (SEQ ID NO: 794)
*Homo_sapiens*_chrX.trna4-ValTAC (18603022-18602950)
Val (TAC) 73 bp Sc: 85.12
GGTTCCATAGTGTAGTGGTTATCACGTCTGCTTTACACGCAGAAGGTCCTGGGTTCGAGC

CCCAGTGGAACCA (SEQ ID NO: 795)
*Homo_sapiens*_chr9.trna8-GlnTTG (5085156-5085085)
Gln (TTG) 72 bp Sc: 21.75
TAGGATATGGTTTAATAGGTAGCATGGAGAATTTTGGAGTCTCAGGGATAGGTTCAATTC

CTATAGTTCCAG (SEQ ID NO: 796)
*Homo_sapiens*_chr6.trna64-GlnTTG (28665135-28665206)
Gln (TTG) 72 bp Sc: 71.88
GGTCCCATGGTGTAATGGTTAGCACTCTGGACTTTGAATCCAGCAATCCGAGTTCGAATC

TCGGTGGGACCT

What is claimed is:

1. A neuroprotective molecule consisting of:
   (i) a sequence of 25-35 contiguous nucleotides that is identical to a contiguous sequence between nucleotide 1 and nucleotide 50 of a mature human transfer ribonucleic acid (tRNA) having a sequence selected from the group consisting of SEQ ID NOs: 32, 37, 40-46 and 48-55, wherein a first nucleotide of the 25-35 contiguous nucleotides corresponds to nucleotide position 1 of the mature human tRNA sequence; at least part of the sequence of 25-35 contiguous nucleotides forms a D-loop stem structure; and at least part of the sequence of 25-35 contiguous nucleotides binds to YB-1;
   (ii) optionally a 5'-monophosphate, one or more modified nucleotides, and/or one or more modifications in a phosphate backbone in the nucleotide(s) in (i) of the neuroprotective molecule; and
   (ii) optionally a 5'-protective group and/or a 3-' protective group;
   wherein at least four contiguous nucleotides in (i) of the neuroprotective molecule at the 5' end are guanosine deoxyribonucleotides; the neuroprotective molecule binds YB-1; and the neuroprotective molecule is capable of decreasing protein translation in a rabbit reticulocyte assay.

2. The neuroprotective molecule of claim 1, wherein the neuroprotective molecule comprises a 5'-monophosphate, one or more modified nucleotides, and/or one or more modifications in a phosphate backbone of the nucleotide(s) in (i) and (ii) of the neuroprotective molecule.

3. The neuroprotective molecule of claim 2, wherein the at least one modified nucleotide contains a modified base or a modified sugar.

4. The neuroprotective molecule of claim 1, wherein the neuroprotective molecule comprises a 5'- and/or a 3'-protective group.

5. The neuroprotective molecule of claim 1, wherein the neuroprotective molecule has a total length of between 39 to 60 nucleotides.

6. A pharmaceutical composition comprising at least one neuroprotective molecule of claim 1.

7. A neuroprotective molecule consisting of:
   (i) a sequence of 25-35 contiguous nucleotides that is identical to a contiguous sequence between nucleotide 1 and nucleotide 50 of a mature human tRNA$^{Ala}$, wherein a first nucleotide of the 25-35 contiguous nucleotides corresponds to nucleotide position 1 of the mature human tRNA$^{Ala}$ sequence; at least part of the sequence of 25-35 contiguous nucleotides forms a D-loop stem structure; and at least part of the sequence of 25-35 contiguous nucleotides binds to YB-1;
   (ii) optionally a 5'-monophosphate, one or more modified nucleotides, and/or one or more modifications in a phosphate backbone in the nucleotide(s) in (i) of the neuroprotective molecule; and
   (ii) optionally a 5'-protective group and/or a 3'-protective group;
   wherein at least four contiguous nucleotides in (i) of the neuroprotective molecule at the 5' end are guanosine deoxyribonucleotides; the neuroprotective molecule binds YB-1; and the neuroprotective molecule is capable of decreasing protein translation in a rabbit reticulocyte assay.

8. The neuroprotective molecule of claim 7, wherein the neuroprotective molecule comprises a 5'-monophosphate, one or more modified nucleotides, and/or one or more modifications in a phosphate backbone of the nucleotide(s) in (i) and (ii) of the neuroprotective molecule.

9. The neuroprotective molecule of claim 8, wherein the at least one modified nucleotide contains a modified base or a modified sugar.

10. The neuroprotective molecule of claim 7, wherein the neuroprotective molecule comprises a 5'- and/or a 3'-protective group.

11. The neuroprotective molecule of claim 7, wherein the neuroprotective molecule has a total length of between 39 to 60 nucleotides.

12. A pharmaceutical composition comprising at least one neuroprotective molecule of claim 7.

* * * * *

UNITED STATES PATENT AND TRADEMARK OFFICE
CERTIFICATE OF CORRECTION

PATENT NO.        : 9,676,810 B2
APPLICATION NO.   : 13/808863
DATED             : June 13, 2017
INVENTOR(S)       : Paul Anderson et al.

It is certified that error appears in the above-identified patent and that said Letters Patent is hereby corrected as shown below:

In the Claims

In Column 389, Line 18, Claim 1, delete "3-' protective" and insert -- 3'-protective --

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,676,810 B2
APPLICATION NO. : 13/808863
DATED : June 13, 2017
INVENTOR(S) : Paul Anderson, Pavel Ivanov and Mohammed Emara It is certified that error appears in the above-identified patent and that said Letters Patent is hereby corrected as shown below:

In the Specification

Column 1, Lines 15, replace "STATEMENT AS TO FEDERALLY SPONSORED RESEARCH
This invention was made with government Support under federal research grant AI0658568 awarded by the National Institutes of Health. The government has certain rights in the invention."

With -- STATEMENT OF FEDERALLY SPONSORED RESEARCH
This invention was made with government support under Grant Nos. AI658568, CA168872, and AI033600 awarded by the National Institutes of Health. The government has certain rights in the invention. --

Signed and Sealed this
Sixteenth Day of May, 2023

Katherine Kelly Vidal
*Director of the United States Patent and Trademark Office*